US012054540B2

(12) United States Patent
de Smit et al.

(10) Patent No.: US 12,054,540 B2
(45) Date of Patent: Aug. 6, 2024

(54) SINGLE DOMAIN ANTIBODIES BINDING TO TETANUS NEUROTOXIN

(71) Applicant: Smivet B.V., Wijchen (NL)

(72) Inventors: Abraham Johannes de Smit, Wijchen (NL); Michaël Marie Harmsen, Weesp (NL)

(73) Assignee: Smivet B.V., Wijchen (NL)

( * ) Notice: Subject to any disclaimer, the term of this patent is extended or adjusted under 35 U.S.C. 154(b) by 986 days.

(21) Appl. No.: 16/978,714

(22) PCT Filed: Mar. 13, 2019

(86) PCT No.: PCT/EP2019/056299
§ 371 (c)(1),
(2) Date: Sep. 7, 2020

(87) PCT Pub. No.: WO2019/175250
PCT Pub. Date: Sep. 19, 2019

(65) Prior Publication Data
US 2022/0275066 A1  Sep. 1, 2022

(30) Foreign Application Priority Data

Mar. 13, 2018  (EP) ..................................... 18161521

(51) Int. Cl.
*C07K 16/12*  (2006.01)
*C07K 16/18*  (2006.01)
*C07K 16/42*  (2006.01)

(52) U.S. Cl.
CPC .......... *C07K 16/1282* (2013.01); *C07K 16/18* (2013.01); *C07K 16/4283* (2013.01); *C07K 2317/22* (2013.01); *C07K 2317/31* (2013.01); *C07K 2317/33* (2013.01); *C07K 2317/35* (2013.01); *C07K 2317/569* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 2015/0010546 A1* | 1/2015 | Kolkman | G01N 33/57488 435/69.6 |
| 2016/0159866 A1 | 6/2016 | Ichtchenko et al. | |
| 2016/0202245 A1 | 7/2016 | Brunn | |

FOREIGN PATENT DOCUMENTS

| | | |
|---|---|---|
| WO | WO96/34103 A1 | 10/1996 |
| WO | WO01/00839 A1 | 1/2001 |
| WO | WO2007096779 A2 | 8/2007 |
| WO | WO2009068627 A2 | 6/2009 |
| WO | WO2016187594 A1 | 11/2016 |

OTHER PUBLICATIONS

Arbabi Ghahroudi M et al: Selection and identification of single domain antibody fragments from camel heavy-chain antibodies, FEBS Lett, vol. 414, No. 3, Sep. 15, 1997, pp. 521-526.
Martin a Rossotti et al: Increasing the potency of neutralizing single-domain antibodies by functionalization with a CDIIb/CD18 binding domain, MABS vol. 7, No. 5, Jul. 20, 2015, pp. 820-828.
David J. Vance et al: Stepwise Engineering of Heterodimeric Single Domain Camelid VHH Antibodies That Passively Protect Mice from Ricin Toxin, Journal of Biological Chemistry, vol. 288, No. 51, Dec. 20, 2013, pp. 36538-36547.
Mehdi Yousefi et al:Comparative in vitro and in vivo assessment of toxin neutralization by anti-tetanus toxin monoclonal antibodies, Human Vaccines and Immunotherapeutics, vol. 10, No. 2, (Oct. 14, 2013), pp. 344-351.
Mehdi Yousefi et al: Characterization of neutralizing monoclonal antibodies directed against tetanus toxin fragment C, Journal of Immunotoxicology, vol. 11, No. 1, Feb. 1, 2013, pp. 28-34.
Kunik, Vered, Bjoern Peters, and Yanay Ofran. "Structural consensus among antibodies defines the antigen binding site." PLoS computational biology 8.2 (2012): e1002388.
Caldas, Cristina, et al. "Humanization of the anti-CD18 antibody 6.7: an unexpected effect of a framework residue in binding to antigen." Molecular Immunology 39.15 (2003): 941-952.
Du, Jiamu, et al. "Molecular basis of recognition of human osteopontin by 23C3, a potential therapeutic antibody for treatment of rheumatoid arthritis." Journal of molecular biology 382.4 (2008): 835-842.

* cited by examiner

*Primary Examiner* — Ilia I Ouspenski
(74) *Attorney, Agent, or Firm* — N.V. Nederlandsch Octrooibureau

(57) ABSTRACT

The present invention relates to single domain antibodies (SDAs) that are capable of binding to tetanus neurotoxin. The invention further relates to polypeptide constructs comprising such an SDA as well as an SDA that is capable of binding to a serum protein, preferably to serum albumin or immunoglobulin. The invention also relates to nucleic acids encoding such SDAs or polypeptide constructs, to pharmaceutical compositions comprising such SDAs or polypeptide constructs, the medical use thereof and to their use in the treatment of tetanus.

12 Claims, 7 Drawing Sheets

Specification includes a Sequence Listing.

| VHH | Subfamily | CDR3 Group | FR1 (1–25) | CDR1 (26–34) | FR2 (35–48) | CDR2 (49–63) |
|---|---|---|---|---|---|---|
| SVA16 | 1 | A | QVQLQESGGGVVQAGGSLRLSCAAS | GRTVSSAMG | WFRLAPGKEREF | VVGISRSGGST |
| SVA04 | 1 | B | QVQLQESGGGGLVQAGGSLRLSCAAS | GRTLSSYVMG | WFRQAPGKEREF | VAAISWSGGST |
| SVA06 | 1 | C | QVQLQESGGGGLVQAEDSLRLSCAAS | GRTFVSYDMG | WFRQAPGKEREF | VAAINWRGYTT |
| SVA12 | 1 | D | QVQLQQSGGGGLVQAGGSLRLSCAAS | GRTFSYPMA  | WFRQAPGKEREF | VAAILGADTT- |
| SVA02 | 1 | E | QVQLQQSGGGGLVQAGGSLRLSCAAS | GREFSRQVMG | WFRQAPGKDREF | VGVISWDNGVT |
| SVA07 | 1 | F | QVQL------VQAGDSLRLSCAAS   | GRAFNYYTMG | WFRQAPGKEREF | VAKIYWDGGST |

| VHH | FR3 (66–104) | CDR3 (105–117) | FR4 (118–128) |
|---|---|---|---|
| SVA16 | FYADSVKGRFTISRKNAKNTVDLQMNSLKPEDTAVYYCAA | GYRPGYGDYREDEYDD | WGQGTQVTVSS |
| SVA04 | YYADSVKGRFTISRDNSKNTVYLQMNSLKPEDTAVYYCAA | TLRGSNRYYSGRV--- | WGQGTQVTVSS |
| SVA06 | DYVDSVKGRFTISRDIAKSTVYLQMNSLKPEDTAVYYCAA | RQMSGSSRYSPPGRVG | YDFWGQGTQVTVSS |
| SVA12 | YYADSVKGRFTISRDNAKNMVYLQMNSLKPEDTAVYYCAA | RNTYWSDVYYRECQ-- | YTNWGQGTQVTVSS |
| SVA02 | FYSDSVKGRFTMSREIAKKTVHLQMNSLKPEDTAVYYCAA | GNALHSRYYSPSK--- | YDYWGPGTQVTVSS |
| SVA07 | IYADSVKGRFTISIDNAKNTVVLQMNSLKPEDTAVYYCAA | DPSFYPFR-------- | PKYWGQGTQVTVSS |

SEQUENCE LISTING

```
<160> NUMBER OF SEQ ID NOS: 78

<210> SEQ ID NO 1
<211> LENGTH: 54
<212> TYPE: DNA
<213> ORGANISM: Artificial sequence
<220> FEATURE:
<223> OTHER INFORMATION: Primer BOLI192

<400> SEQUENCE: 1
aacagttaag cttccgcttg cggccgctac ttcattcgtt cctgaggaga cggt         54

<210> SEQ ID NO 2
<211> LENGTH: 53
<212> TYPE: DNA
<213> ORGANISM: Artificial sequence
<220> FEATURE:
<223> OTHER INFORMATION: Primer lam07

<400> SEQUENCE: 2
aacagttaag cttccgcttg cggccgcgga gctggggtct tcgctgtggt gcg          53

<210> SEQ ID NO 3
<211> LENGTH: 53
<212> TYPE: DNA
<213> ORGANISM: Artificial sequence
<220> FEATURE:
<223> OTHER INFORMATION: Primer lam08

<400> SEQUENCE: 3
aacagttaag cttccgcttg cggccgctgg ttgtggtttt ggtgtcttgg gtt          53

<210> SEQ ID NO 4
<211> LENGTH: 53
<212> TYPE: DNA
<213> ORGANISM: Artificial sequence
<220> FEATURE:
<223> OTHER INFORMATION: Primer BOLI401

<400> SEQUENCE: 4
aacagttaag cttccgcttg cggccgctgg ttgtggttgt ggtatcttgg gtt          53

<210> SEQ ID NO 5
<211> LENGTH: 458
<212> TYPE: DNA
<213> ORGANISM: Artificial sequence
<220> FEATURE:
<223> OTHER INFORMATION: VHH
```

<400> SEQUENCE: 5

| | | | | | |
|---|---|---|---|---|---|
| gagctcatca | cacaaacaaa | caaaacaaaa | tgatgctttt | gcaagccttc | cttttcctttt | 60 |
| tggctggttt | tgcagccaaa | atatctgcgg | aagttcaatt | gcaagcatct | ggtggtggtt | 120 |
| cagttcaagc | aggtggttct | ttaagattgt | catgtactgc | tgcaaactac | gctttcgatt | 180 |
| ctaagacagt | tggttggttt | agacaagttc | ctggtaaaga | aagagaaggt | gttgctggta | 240 |
| tttctggtgg | ttcaactaca | gcatattctg | attcagttaa | gggtagatac | actgtttctt | 300 |
| tagaaaatgc | taaaaataca | gtttatttgt | tgatcgataa | tttgcaacca | gaagatactg | 360 |
| ctatctatta | ctgtgcaggt | gtttcaggtt | ggagaggtag | acaatggttg | ttattggcag | 420 |
| aaacttacag | attttggggt | caaggtacac | aggtcacc | | | 458 |

<210> SEQ ID NO 6
<211> LENGTH: 21
<212> TYPE: DNA
<213> ORGANISM: Artificial sequence
<220> FEATURE:
<223> OTHER INFORMATION: Primer MPE25

<400> SEQUENCE: 6
tttctgtatg gggttttgct a                                           21

<210> SEQ ID NO 7
<211> LENGTH: 21
<212> TYPE: DNA
<213> ORGANISM: Artificial sequence
<220> FEATURE:
<223> OTHER INFORMATION: Primer MPE26

<400> SEQUENCE: 7
ggataacaat ttcacacagg a                                           21

<210> SEQ ID NO 8
<211> LENGTH: 22
<212> TYPE: DNA
<213> ORGANISM: Artificial sequence
<220> FEATURE:
<223> OTHER INFORMATION: Primer RevSeq

<400> SEQUENCE: 8
tcacacagga aacagctatg ac                                          22

<210> SEQ ID NO 9
<211> LENGTH: 21
<212> TYPE: DNA
<213> ORGANISM: Artificial sequence
<220> FEATURE:
<223> OTHER INFORMATION: Primer BOLI166

<400> SEQUENCE: 9
atgatgcttt tgcaagcctt c                                           21

<210> SEQ ID NO 10
<211> LENGTH: 23
<212> TYPE: DNA
<213> ORGANISM: Artificial sequence
<220> FEATURE:
<223> OTHER INFORMATION: Primer BOLI188

<400> SEQUENCE: 10
ttcagatcct cttctgagat gag                                         23

<210> SEQ ID NO 11
<211> LENGTH: 15
<212> TYPE: DNA
<213> ORGANISM: Artificial sequence
<220> FEATURE:
<223> OTHER INFORMATION: pUR4585A

<400> SEQUENCE: 11
cctgtcgggc ctacg                                                    15

<210> SEQ ID NO 12
<211> LENGTH: 15
<212> TYPE: DNA
<213> ORGANISM: Artificial sequence
<220> FEATURE:
<223> OTHER INFORMATION: pUR4585G

<400> SEQUENCE: 12
cctgtcgggc ctacg                                                    15

<210> SEQ ID NO 13
<211> LENGTH: 126
<212> TYPE: PRT
<213> ORGANISM: Artificial sequence
<220> FEATURE:
<223> OTHER INFORMATION: VHH

<400> SEQUENCE: 13

Gln Val Gln Leu Gln Gln Ser Gly Gly Gly Leu Val Gln Ala Gly Gly
1               5                   10                  15

Ser Leu Arg Leu Ser Cys Ala Ala Ser Gly Arg Thr Met Ser Ser Tyr
            20                  25                  30

Ala Met Gly Trp Phe Arg Gln Ala Pro Gly Lys Gln Arg Glu Phe Val
        35                  40                  45

Ala Ala Ile Ser Arg Ser Gly Gly Asn Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Glu Thr Ala Val Tyr Tyr Cys
                85                  90                  95

Ala Ala Asp Pro Asn Leu Met Tyr Glu Ser Lys Trp Lys Tyr Arg Ala
            100                 105                 110

Leu Glu Ala Trp Gly Gln Gly Thr Leu Val Thr Val Ser Ser
        115                 120                 125

<210> SEQ ID NO 14
<211> LENGTH: 126
<212> TYPE: PRT
<213> ORGANISM: Artificial sequence
<220> FEATURE:
<223> OTHER INFORMATION: VHH

<400> SEQUENCE: 14

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Thr Ile Ser Ser Tyr
            20                  25                  30

Ala Met Gly Trp Phe Arg Gln Ala Pro Gly Lys Gln Arg Glu Phe Val
        35                  40                  45

Ala Ala Ile Ser Arg Ser Gly Gly Asn Thr Tyr Tyr Thr Asp Ser Val
    50                  55                  60

```
Lys Gly Arg Phe Ile Ile Ser Arg Asp Asn Ala Lys Asn Thr Leu Tyr
 65                  70                  75                  80

Leu Gln Met Asn Asn Leu Lys Pro Glu Glu Thr Ala Val Tyr Tyr Cys
             85                  90                  95

Ala Ala Asp Pro Asn Leu Met Tyr Glu Ser Lys Trp Lys Tyr Arg Ala
            100                 105                 110

Leu Glu Ala Trp Gly Gln Gly Thr Leu Val Thr Val Ser Ser
        115                 120                 125

<210> SEQ ID NO 15
<211> LENGTH: 125
<212> TYPE: PRT
<213> ORGANISM: Artificial sequence
<220> FEATURE:
<223> OTHER INFORMATION: VHH

<400> SEQUENCE: 15

Gln Val Gln Leu Gln Glu Ser Gly Gly Gly Ser Val Gln Ala Gly Asp
1               5                   10                  15

Ser Leu Arg Leu Ser Cys Ala Ala Ser Gly Arg Thr Ile Ser Asn Tyr
            20                  25                  30

Ala Met Gly Trp Phe Arg Gln Ala Pro Gly Lys Gln Arg Glu Phe Val
        35                  40                  45

Ala Ala Ile Ser Arg Ser Asp Asn Thr Tyr Tyr Thr Asp Ser Val Lys
    50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Glu Thr Ala Val Tyr Tyr Cys Ala
             85                  90                  95

Ala Asp Pro Asn Leu Met Tyr Glu Ser Lys Trp Lys Tyr Arg Ala Leu
            100                 105                 110

Glu Ala Trp Gly Gln Gly Thr Leu Val Thr Val Ser Ser
        115                 120                 125

<210> SEQ ID NO 16
<211> LENGTH: 125
<212> TYPE: PRT
<213> ORGANISM: Artificial sequence
<220> FEATURE:
<223> OTHER INFORMATION: VHH

<400> SEQUENCE: 16

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Ile Ser Val Tyr
            20                  25                  30

Ala Met Gly Trp Phe Arg Gln Ala Pro Gly Lys Gln Arg Glu Phe Val
        35                  40                  45

Ala Ala Ile Ser Arg Ser Asp Asn Thr Tyr Tyr Thr Asp Ser Val Lys
    50                  55                  60

Gly Arg Phe Thr Ile Ser Arg Asp Asn Val Lys Asn Thr Leu Tyr Leu
 65                  70                  75                  80

Gln Met Asn Ser Leu Lys Pro Glu Glu Thr Ala Val Tyr Tyr Cys Ala
             85                  90                  95

Ala Asp Pro Asn Leu Met Tyr Glu Thr Lys Trp Lys Tyr Arg Ala Leu
            100                 105                 110

Glu Ala Trp Gly Gln Gly Thr Leu Val Thr Val Ser Ser
```

<210> SEQ ID NO 17
<211> LENGTH: 138
<212> TYPE: PRT
<213> ORGANISM: Artificial sequence
<220> FEATURE:
<223> OTHER INFORMATION: VHH

<400> SEQUENCE: 17

Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
            20                  25                  30

Thr Ile Ala Trp Phe Arg Arg Ala Ala Gly Glu Gly Arg Val Glu Asp
        35                  40                  45

Gly Glu Gly Val Ala Ser Ile Thr Lys Ser Tyr Asp Arg Ala Tyr Asp
    50                  55                  60

Asn Lys Ile Asn Tyr Gly His Ser Val Lys Gly Arg Phe Thr Ile Ser
65                  70                  75                  80

Arg Asp Asn Ala Lys Asn Thr Val Tyr Leu Gln Met Thr Asp Leu Leu
                85                  90                  95

Pro Ser Asp Thr Ala Val Tyr Tyr Cys Ala Leu Asp Ile Thr Pro Pro
            100                 105                 110

Gly Gly Val Gly Ala Ser Leu Thr Glu Gly Phe Leu Phe Asp Tyr Trp
        115                 120                 125

Gly Gln Gly Thr Gln Val Thr Val Ser Ser
    130                 135

<210> SEQ ID NO 18
<211> LENGTH: 138
<212> TYPE: PRT
<213> ORGANISM: Artificial sequence
<220> FEATURE:
<223> OTHER INFORMATION: VHH

<400> SEQUENCE: 18

Gln Val Gln Leu Gln Glu Ser Gly Gly Gly Ser Val Gln Ala Gly Gly
1               5                   10                  15

Ser Leu Thr Leu Ser Cys Ala Ala Ser Glu Phe Ser Tyr Asn Asp Tyr
            20                  25                  30

Thr Ile Ala Trp Phe Arg Arg Ala Ala Gly Lys Gly Arg Val Glu Asp
        35                  40                  45

Gly Glu Gly Val Ala Ser Ile Thr Lys Ser Tyr Asp Arg Ala Tyr Asp
    50                  55                  60

Asn Arg Ile His Tyr Ala Asp Ser Val Lys Gly Arg Phe Thr Ile Ser
65                  70                  75                  80

Arg Asp Asn Ala Lys Asn Thr Val Tyr Leu Gln Met Thr Ser Leu Asn
                85                  90                  95

Pro Ser Asp Thr Ala Val Tyr Tyr Cys Ala Leu Asp Ile Thr Pro Pro
            100                 105                 110

Gly Gly Ile Gly Ala Ser Leu Thr Glu Gly Phe Leu Phe Asp Tyr Trp
        115                 120                 125

Gly Gln Gly Thr Gln Val Thr Val Ser Ser
    130                 135

<210> SEQ ID NO 19
<211> LENGTH: 138

<212> TYPE: PRT
<213> ORGANISM: Artificial sequence
<220> FEATURE:
<223> OTHER INFORMATION: VHH

<400> SEQUENCE: 19

Gln Val Gln Leu Gln Glu Ser Gly Gly Gly Ser Val Gln Ala Gly Gly
1               5                   10                  15

Ser Leu Arg Leu Ser Cys Thr Ala Ser Glu Phe Ser Tyr Asn Asp Tyr
            20                  25                  30

Thr Ile Ala Trp Phe Arg Arg Ala Ala Gly Lys Gly Arg Val Glu Asp
        35                  40                  45

Gly Glu Gly Val Ala Ser Ile Thr Thr Ser Tyr Asp Arg Ala Tyr Asp
50                  55                  60

Asn Arg Ile His Tyr Gly Asp Ser Val Lys Gly Arg Phe Thr Ile Ser
65                  70                  75                  80

Arg Asp Asn Ala Lys Asn Thr Val Tyr Leu Gln Met Thr Asn Leu Asn
                85                  90                  95

Pro Ser Asp Thr Ala Val Tyr Tyr Cys Gly Leu Asp Ile Thr Pro Pro
            100                 105                 110

Gly Gly Ile Gly Ala Ser Leu Thr Glu Gly Phe Leu Phe Asp Tyr Trp
        115                 120                 125

Gly Gln Gly Thr Gln Val Thr Val Ser Ser
130                 135

<210> SEQ ID NO 20
<211> LENGTH: 123
<212> TYPE: PRT
<213> ORGANISM: Artificial sequence
<220> FEATURE:
<223> OTHER INFORMATION: VHH

<400> SEQUENCE: 20

Gln Val Gln Leu Gln Glu Ser Gly Gly Gly Leu Val Gln Thr Gly Gly
1               5                   10                  15

Ser Leu Arg Leu Ser Cys Arg Ala Ser Arg Ala Phe Ala Asn Tyr
            20                  25                  30

His Phe Gly Trp Phe Arg Gln Ala Pro Gly Lys Asp Arg Glu Phe Val
        35                  40                  45

Ala Ser Ile Ser Trp Lys Gly Ser Thr Tyr Tyr Ala Asn Phe Ala
50                  55                  60

Leu Gly Arg Phe Thr Ser Ser Val Asp Arg Ala Glu Ser Ser Val Tyr
65                  70                  75                  80

Leu Gln Met Ser Gly Leu Thr Pro Glu Asp Thr Ala Thr Tyr Tyr Cys
                85                  90                  95

Ala Ala His Asp Gly Gly Asp Trp Asn Tyr His Thr Gly Met Asp Tyr
            100                 105                 110

Trp Gly Lys Gly Ile Leu Val Thr Val Ser Ser
        115                 120

<210> SEQ ID NO 21
<211> LENGTH: 123
<212> TYPE: PRT
<213> ORGANISM: Artificial sequence
<220> FEATURE:
<223> OTHER INFORMATION: VHH

<400> SEQUENCE: 21

Gln Val Gln Leu Gln Glu Ser Gly Gly Gly Leu Val Gln Thr Gly Gly

```
                1               5                  10                 15
            Ser Leu Thr Leu Ser Cys Arg Ala Tyr Gly Arg Ala Phe Asp Asn Tyr
                        20                  25                 30

His Phe Gly Trp Phe Arg Gln Ala Pro Gly Lys Asp Arg Glu Phe Val
                        35                  40                 45

Ala Ser Ile Ser Trp Lys Gly Gly Ser Thr Tyr Arg Ala Asn Phe Ala
                        50                  55                 60

Leu Gly Arg Phe Thr Ser Ser Val Asn Arg Gly Glu Ser Ser Val Tyr
             65                  70                  75                 80

Leu His Met Ser Gly Leu Thr Pro Glu Asp Thr Ala Thr Tyr Tyr Cys
                        85                  90                 95

Ala Ala His Asp Gly Gly Asp Trp Asn Tyr His Thr Gly Met Asp Tyr
                        100                 105                110

Trp Gly Lys Gly Ile Leu Val Thr Val Ser Ser
                        115                 120

<210> SEQ ID NO 22
<211> LENGTH: 123
<212> TYPE: PRT
<213> ORGANISM: Artificial sequence
<220> FEATURE:
<223> OTHER INFORMATION: VHH

<400> SEQUENCE: 22

Gln Val Gln Leu Gln Glu Ser Gly Gly Gly Leu Val Gln Ala Gly Gly
             1               5                  10                 15

Ser Leu Arg Leu Ser Cys Ala Val Ser Gly Thr Asn Phe Asp Asp Tyr
                        20                  25                 30

Ala Ile Gly Trp Phe Arg Gln Ala Pro Gly Lys Arg Arg Glu Ala Val
                        35                  40                 45

Ala Cys Ile Ser Lys Thr Asp Gly Val Thr Arg Tyr Gly Asn Gly Val
                        50                  55                 60

Lys Gly Arg Phe Thr Ile Ser Ser Asp Glu Ala Arg Asn Thr Val Phe
             65                  70                  75                 80

Leu Gln Met Asn Asp Leu Lys Asp Glu Asp Thr Ala Ile Tyr Tyr Cys
                        85                  90                 95

Ile Gly Asp Phe Lys Ser Cys Gly Met Gly Tyr Lys Pro Ile Asp His
                        100                 105                110

Trp Gly Arg Gly Ile Gln Val Thr Val Ser Ser
                        115                 120

<210> SEQ ID NO 23
<211> LENGTH: 123
<212> TYPE: PRT
<213> ORGANISM: Artificial sequence
<220> FEATURE:
<223> OTHER INFORMATION: VHH

<400> SEQUENCE: 23

Gln Val Gln Leu Gln Glu Ser Gly Gly Gly Leu Val Gln Ala Gly Glu
             1               5                  10                 15

Ser Leu Arg Leu Ser Cys Thr Ala Ser Gly Ile Ser Phe Asp Asp Tyr
                        20                  25                 30

Ala Ile Gly Trp Phe Arg Gln Ala Pro Gly Gln Gln Arg Lys Gly Val
                        35                  40                 45

Ala Cys Ile Ser Lys Ala Asp Gly Arg Thr Asp Tyr Leu Gly Ser Val
                        50                  55                 60
```

-continued

Lys Gly Arg Phe Thr Leu Ser Thr Asp Asn Thr Lys Asn Thr Val His
65                  70                  75                  80

Leu Gln Met Asn Asn Leu Lys Pro Glu Asp Thr Ala Leu Tyr Thr Cys
            85                  90                  95

Ala Ala Glu Tyr Lys Ser Cys Gly Met Gly Tyr Lys Pro Ile Asp Tyr
        100                 105                 110

Trp Gly Gln Gly Met Gln Val Thr Val Ser Ser
        115                 120

<210> SEQ ID NO 24
<211> LENGTH: 125
<212> TYPE: PRT
<213> ORGANISM: Artificial sequence
<220> FEATURE:
<223> OTHER INFORMATION: VHH

<400> SEQUENCE: 24

Gln Val Gln Leu Gln Gln Ser Gly Gly Gly Ser Val Gln Ala Gly Gly
1               5                   10                  15

Ser Leu Arg Leu Ser Cys Val Gly Pro Gln Arg Thr Phe Ser Thr Tyr
            20                  25                  30

Gly Met Gly Trp Phe Arg Gln Ala Pro Gly Lys Glu Arg Glu Phe Val
        35                  40                  45

Ala Gly Ile Asn Tyr Lys Gly Asp Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Arg Ala Val Tyr Gln Cys
            85                  90                  95

Ala Arg Lys Gly Gly Leu Gly Gly Asp Tyr Arg Asp Ala Gly Gln Tyr
        100                 105                 110

Arg Tyr Trp Gly Gln Gly Thr Gln Val Thr Val Ser Ser
        115                 120                 125

<210> SEQ ID NO 25
<211> LENGTH: 124
<212> TYPE: PRT
<213> ORGANISM: Artificial sequence
<220> FEATURE:
<223> OTHER INFORMATION: VHH

<400> SEQUENCE: 25

Gln Val Gln Leu Gln Gln Ser Gly Gly Gly Ser Val Gln Thr Gly Asp
1               5                   10                  15

Ser Leu Thr Leu Ser Cys Thr Ala Ser Gly Gly Ser Leu Asn Ser Tyr
            20                  25                  30

Phe Val Gly Trp Phe Arg Gln Ser Gly Gly Lys Glu Arg Glu Phe Val
        35                  40                  45

Ser Val Ile Ala Arg Thr Gly Arg Ser Thr Ser Tyr Ala Asp Ser Val
    50                  55                  60

Lys Gly Arg Phe Thr Ile Ser Arg Asp Asn Ala Ala Asn Thr Val Phe
65                  70                  75                  80

Leu Thr Met Asn Asn Leu Arg Pro Asp Asp Thr Ala Ile Tyr Tyr Cys
            85                  90                  95

Ala Ala Val Gly Arg Pro Gly Val Leu His Leu Thr Gln Ser Tyr Asp
        100                 105                 110

Tyr Trp Gly Gln Gly Thr Gln Val Thr Val Ser Ser
        115                 120

<210> SEQ ID NO 26
<211> LENGTH: 136
<212> TYPE: PRT
<213> ORGANISM: Artificial sequence
<220> FEATURE:
<223> OTHER INFORMATION: VHH

<400> SEQUENCE: 26

Gln Val Gln Leu Gln Glu Ser Gly Gly Gly Leu Val Gln Pro Gly Gly
1               5                   10                  15

Ser Leu Arg Leu Ser Cys Ser Ala Ser Gly Phe Ser Phe Thr Asp Asp
            20                  25                  30

Tyr Gly Ile Gly Trp Phe Arg Ser Gly Pro Gly Lys Gly Arg Glu Ala
        35                  40                  45

Val Ala Pro Ile Ala Asp Arg Glu Ala Val Ala Ile Ala Leu Ser
    50                  55                  60

Asp Gly Asn Thr Tyr Tyr Ser Ala Ser Ala Lys Gly Arg Phe Thr Ile
65                  70                  75                  80

Ser Arg Asp Asn Ala Lys Ser Thr Ala Tyr Leu Gln Met Asn Asn Leu
                85                  90                  95

Lys Pro Glu Asp Thr Ala Thr Tyr Tyr Cys Ala Ala Asp Phe Trp Gly
            100                 105                 110

Tyr Gly Met Ser Trp Pro Met Ala Thr Leu Trp Glu Tyr Trp Gly Gln
        115                 120                 125

Gly Ile Gln Val Thr Val Ser Ser
    130                 135

<210> SEQ ID NO 27
<211> LENGTH: 118
<212> TYPE: PRT
<213> ORGANISM: Artificial sequence
<220> FEATURE:
<223> OTHER INFORMATION: VHH

<400> SEQUENCE: 27

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Ser Leu Thr Pro Asn Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Lys Asn Ser Tyr Tyr Gly Ala Met Asp Tyr Trp Gly Lys Gly Thr
            100                 105                 110

Leu Val Thr Val Ser Ser
        115

<210> SEQ ID NO 28
<211> LENGTH: 121
<212> TYPE: PRT
<213> ORGANISM: Artificial sequence
<220> FEATURE:
<223> OTHER INFORMATION: VHH

```
<400> SEQUENCE: 28

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Asp Ile Ile Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Ser Pro Ile Val Arg Thr Tyr Gly Tyr Asp Tyr Trp Gly
            100                 105                 110

Gln Gly Thr Gln Val Thr Val Ser Ser
        115                 120

<210> SEQ ID NO 29
<211> LENGTH: 123
<212> TYPE: PRT
<213> ORGANISM: Artificial sequence
<220> FEATURE:
<223> OTHER INFORMATION: VHH

<400> SEQUENCE: 29

Gln Val Gln Leu Gln Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Asp Phe Asp Pro Trp Gly Val Gly Thr Gly Gly Tyr Asp Tyr
            100                 105                 110

Trp Gly Gln Gly Thr Gln Val Thr Val Ser Ser
        115                 120

<210> SEQ ID NO 30
<211> LENGTH: 126
<212> TYPE: PRT
<213> ORGANISM: Artificial sequence
<220> FEATURE:
<223> OTHER INFORMATION: VHH

<400> SEQUENCE: 30

Gln Val Gln Leu Gln Glu Ser Gly Gly Ala Leu Val Gln Pro Gly Gly
1               5                   10                  15

Ser Leu Arg Leu Ser Cys Ala Ala Ser Gly Phe Pro Phe Ser Ala Tyr
            20                  25                  30

Asp Met Thr Trp Val Arg Gln Ala Pro Gly Gln Gly Leu Glu Trp Val
        35                  40                  45
```

Ser Thr Ile His Lys Ser Gly Ile Thr Thr Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Leu Glu Ser Glu Asp Thr Ala Val Tyr Tyr Cys
                85                  90                  95

Ala Lys Ala Leu Arg Ala His Asn Ser Asp Tyr Val Gly Arg Asn Ala
            100                 105                 110

Leu Gly Ser Trp Gly Glu Gly Thr Leu Val Thr Val Ser Ser
            115                 120                 125

<210> SEQ ID NO 31
<211> LENGTH: 124
<212> TYPE: PRT
<213> ORGANISM: Artificial sequence
<220> FEATURE:
<223> OTHER INFORMATION: VHH

<400> SEQUENCE: 31

Gln Val Gln Leu Gln Glu Ser Gly Gly Gly Leu Val Gln Ala Gly Gly
 1               5                   10                  15

Ser Leu Arg Leu Ser Cys Ala Ala Ser Gly Arg Ala Phe Gly Ser Tyr
                20                  25                  30

Thr Met Asn Trp Phe Arg Gln Ala Pro Gly Lys Glu Arg Asp Phe Val
                35                  40                  45

Ala Gly Ile Met Ser Ser Gly Met Asn Thr Trp Tyr Ala Asp Ser Val
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ser Arg Pro Arg Ser Thr Met Thr Ser Gly Arg Tyr Leu Tyr Asp
            100                 105                 110

Tyr Trp Gly Gln Gly Thr Gln Val Thr Val Ser Ser
            115                 120

<210> SEQ ID NO 32
<211> LENGTH: 123
<212> TYPE: PRT
<213> ORGANISM: Artificial sequence
<220> FEATURE:
<223> OTHER INFORMATION: VHH

<400> SEQUENCE: 32

Gln Val Gln Leu Gln Gln Ser Gly Gly Gly Leu Val Gln Ala Gly Gly
 1               5                   10                  15

Ser Leu Arg Leu Ser Cys Ala Ala Ser Gly Arg Thr Phe Ser Thr Tyr
                20                  25                  30

Asn Ile Ala Trp Phe Arg Gln Ala Pro Gly Lys Glu Arg Glu Phe Val
                35                  40                  45

Thr Ala Ile Thr Trp Gly Ser Gly Asn Thr Tyr Tyr Ala Asp Ser Val
        50                  55                  60

Lys Gly Arg Phe Thr Ile Ser Arg Asp Asn Ala Lys Asn Thr Val Phe
 65                  70                  75                  80

Leu Gln Met Asn Ser Leu Lys Pro Asp Asp Thr Ala Val Tyr Tyr Cys
                85                  90                  95

Ala Ala Arg Arg Ser Leu Gly Pro Thr Met Ala Phe Ala Tyr Glu Tyr

```
                100             105             110
Trp Gly Gln Gly Thr Gln Val Thr Val Ser Ser
        115                 120

<210> SEQ ID NO 33
<211> LENGTH: 119
<212> TYPE: PRT
<213> ORGANISM: Artificial sequence
<220> FEATURE:
<223> OTHER INFORMATION: VHH

<400> SEQUENCE: 33

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Val Met Gly Trp Phe Arg Gln Ala Pro Gly Lys Glu Arg Glu Phe Val
        35                  40                  45

Ser Ala Ile Ser Trp Asn Gly Val Ser Thr Phe Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Glu Arg Phe Val Val Arg Tyr Asn Tyr Trp Gly Gln Gly
            100                 105                 110

Thr Gln Val Thr Val Ser Ser
        115

<210> SEQ ID NO 34
<211> LENGTH: 122
<212> TYPE: PRT
<213> ORGANISM: Artificial sequence
<220> FEATURE:
<223> OTHER INFORMATION: VHH

<400> SEQUENCE: 34

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Thr
            20                  25                  30

Ala Tyr Ala Trp Ser Trp Ile Arg Gln Pro Pro Gly Lys Gly Leu Glu
        35                  40                  45

Trp Met Gly Ala Ile Arg Phe Asp Gly Thr Thr Asp Tyr Ser Pro Ser
    50                  55                  60

Leu Lys Ser Arg Ile Ser Ile Ser Arg Asp Thr Ser Asn Asn Gln Phe
65                  70                  75                  80

Ser Leu Arg Met Ser Ser Val Thr Pro Glu Asp Thr Ala Val Tyr Tyr
                85                  90                  95

Cys Ala Arg Tyr Gly Val Val Ser Asp His Gly Gly Leu Asp Tyr Trp
            100                 105                 110

Gly Gln Gly Thr Gln Val Thr Val Ser Ser
        115                 120

<210> SEQ ID NO 35
<211> LENGTH: 124
<212> TYPE: PRT
<213> ORGANISM: Artificial sequence
<220> FEATURE:
```

<223> OTHER INFORMATION: VHH

<400> SEQUENCE: 35

Gln Val Gln Leu Val Glu Ser Gly Pro Gly Leu Val Lys Pro Ser Gln
1               5                   10                  15

Thr Leu Ser Leu Thr Cys Thr Val Ser Gly Ala Ser Ile Thr Thr Ala
            20                  25                  30

Asp Tyr Thr Trp Ser Trp Ile Arg Gln Pro Pro Gly Lys Ala Leu Glu
        35                  40                  45

Trp Met Gly Ala Thr Asp Tyr Ser Gly Tyr Asp Tyr Tyr Arg Pro His
    50                  55                  60

Leu Lys Ser Arg Ala Ser Ile Ser Arg Asp Thr Ser Lys Asn Gln Phe
65                  70                  75                  80

Thr Leu Gln Leu Thr Ser Val Thr Pro Glu Asp Thr Ala Val Tyr Tyr
                85                  90                  95

Cys Ala Arg Gly Arg Arg Ala Gly Ser Asn Arg Arg Ser Asp Tyr Asp
            100                 105                 110

Phe Trp Gly Gln Gly Thr Gln Val Thr Val Ser Ser
        115                 120

<210> SEQ ID NO 36
<211> LENGTH: 125
<212> TYPE: PRT
<213> ORGANISM: Artificial sequence
<220> FEATURE:
<223> OTHER INFORMATION: VHH

<400> SEQUENCE: 36

Gln Val Gln Leu Val Glu Ser Gly Pro Gly Leu Val Lys Pro Ser Gln
1               5                   10                  15

Thr Leu Ser Leu Ile Cys Thr Val Ser Gly Gly Ser Ile Thr Ser Ser
            20                  25                  30

Gly Tyr Tyr Trp Ser Trp Ile Arg Gln Ser Pro Gly Lys Gly Leu Glu
        35                  40                  45

Trp Ile Gly Thr Ile Gly Phe Asp Asp Phe His Tyr Tyr Ser Pro Ser
    50                  55                  60

Leu Lys Ser Arg Ser Ser Ile Ser Arg Asp Thr Ser Lys Asn Gln Ile
65                  70                  75                  80

Thr Leu Gln Leu Ser Ser Val Thr Pro Glu Asp Thr Ala Val Tyr Tyr
                85                  90                  95

Cys Ala Arg Asp Lys Leu Pro Leu Gly Gly Thr Arg Trp Ser Glu Tyr
            100                 105                 110

Asp Ser Trp Gly Gln Gly Thr Gln Val Thr Val Ser Ser
        115                 120                 125

<210> SEQ ID NO 37
<211> LENGTH: 130
<212> TYPE: PRT
<213> ORGANISM: Artificial sequence
<220> FEATURE:
<223> OTHER INFORMATION: VHH

<400> SEQUENCE: 37

Gln Val Gln Leu Gln Glu Ser Gly Gly Gly Val Val Gln Ala Gly Gly
1               5                   10                  15

Ser Leu Arg Leu Ser Cys Ala Ala Ser Gly Arg Thr Val Ser Ser Ser
            20                  25                  30

Ala Met Gly Trp Phe Arg Leu Ala Pro Gly Lys Glu Arg Glu Phe Val

-continued

```
                35                  40                  45
Val Gly Ile Ser Arg Ser Gly Gly Ser Ile Phe Tyr Ala Asp Ser Val
 50                  55                  60

Lys Gly Arg Phe Thr Ile Ser Arg Lys Asn Ala Lys Asn Thr Val Asp
 65                  70                  75                  80

Leu Gln Met Asn Ser Leu Lys Pro Glu Asp Thr Ala Val Tyr Tyr Cys
                 85                  90                  95

Ala Ala Gly Tyr Arg Pro Gly Tyr Gly Asp Tyr Gly Arg Val Phe Tyr
                100                 105                 110

Arg Glu Asp Glu Tyr Asp Asp Trp Gly Gln Gly Thr Gln Val Thr Val
                115                 120                 125

Ser Ser
    130

<210> SEQ ID NO 38
<211> LENGTH: 125
<212> TYPE: PRT
<213> ORGANISM: Artificial sequence
<220> FEATURE:
<223> OTHER INFORMATION: VHH

<400> SEQUENCE: 38

Gln Val Gln Leu Gln Gln Ser Gly Gly Gly Leu Val Gln Ala Gly Gly
 1               5                  10                  15

Ser Leu Arg Leu Ala Cys Ala Ala Ser Gly Arg Thr Leu Ser Ser Tyr
                 20                  25                  30

Val Met Gly Trp Phe Arg Gln Ala Pro Gly Lys Glu Arg Glu Phe Val
                 35                  40                  45

Ala Ala Ile Ser Trp Ser Gly Gly Ser Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Thr Leu Arg Gly Ser Asn Arg Tyr Tyr Ser Gly Arg Val Tyr
                100                 105                 110

Asp Tyr Trp Gly Gln Gly Thr Gln Val Thr Val Ser Ser
                115                 120                 125

<210> SEQ ID NO 39
<211> LENGTH: 128
<212> TYPE: PRT
<213> ORGANISM: Artificial sequence
<220> FEATURE:
<223> OTHER INFORMATION: VHH

<400> SEQUENCE: 39

Gln Val Gln Leu Gln Glu Ser Gly Gly Arg Leu Val Gln Ala Glu Asp
 1               5                  10                  15

Ser Leu Arg Leu Ser Cys Ala Ala Ser Gly Arg Thr Phe Val Ser Tyr
                 20                  25                  30

Asp Met Gly Trp Phe Arg Gln Ala Pro Gly Lys Glu Arg Glu Phe Val
                 35                  40                  45

Ala Ala Ile Asn Trp Arg Gly Tyr Thr Thr Asp Tyr Val Asp Ser Val
 50                  55                  60

Lys Gly Arg Phe Phe Ile Ser Arg Asp Ile Ala Lys Ser Thr Val Tyr
 65                  70                  75                  80
```

```
Leu Gln Met Asn Asn Leu Lys Pro Glu Asp Thr Ala Val Tyr Tyr Cys
                85                  90                  95

Ala Ala Arg Gln Met Ser Gly Ser Ser Arg Tyr Ser Pro Pro Gly Arg
            100                 105                 110

Val Gly Tyr Asp Phe Trp Gly Gln Gly Thr Gln Val Thr Val Ser Ser
        115                 120                 125

<210> SEQ ID NO 40
<211> LENGTH: 128
<212> TYPE: PRT
<213> ORGANISM: Artificial sequence
<220> FEATURE:
<223> OTHER INFORMATION: VHH

<400> SEQUENCE: 40

Gln Val Gln Leu Gln Glu Ser Gly Gly Arg Leu Val Gln Ala Glu Asp
1               5                   10                  15

Ser Leu Arg Leu Ser Cys Ala Ala Ser Gly Arg Thr Phe Val Ser Tyr
            20                  25                  30

Asp Met Gly Trp Phe Arg Gln Ala Pro Gly Lys Glu Arg Glu Phe Val
        35                  40                  45

Ala Ala Ile Asn Trp Arg Gly Tyr Thr Thr Asp Tyr Val Asp Ser Val
    50                  55                  60

Lys Gly Arg Phe Phe Ile Ser Arg Asp Ile Ala Lys Ser Thr Val Tyr
65                  70                  75                  80

Leu Gln Met Asn Asn Leu Lys Pro Glu Asp Thr Ala Val Tyr Tyr Cys
                85                  90                  95

Ala Ala Arg Gln Met Ser Gly Ser Ser Arg Tyr Ser Pro Pro Gly Arg
            100                 105                 110

Val Gly Tyr Asp Phe Trp Gly Gln Gly Thr Gln Val Thr Val Ser Ser
        115                 120                 125

<210> SEQ ID NO 41
<211> LENGTH: 125
<212> TYPE: PRT
<213> ORGANISM: Artificial sequence
<220> FEATURE:
<223> OTHER INFORMATION: VHH

<400> SEQUENCE: 41

Gln Val Gln Leu Gln Gln Ser Gly Gly Gly Leu Val Gln Ala Gly Gly
1               5                   10                  15

Ser Leu Arg Leu Ser Cys Ala Ala Ser Gly Arg Phe Phe Ser Arg Gln
            20                  25                  30

Val Met Gly Trp Phe Arg Gln Ala Pro Gly Lys Asp Arg Glu Phe Val
        35                  40                  45

Gly Val Ile Ser Trp Asp Asn Gly Val Thr Phe Tyr Ser Asp Ser Val
    50                  55                  60

Lys Gly Arg Phe Thr Met Ser Arg Glu Ile Ala Lys Lys Thr Val His
65                  70                  75                  80

Leu Gln Met Asn Ser Leu Lys Pro Glu Asp Thr Ala Val Tyr Tyr Cys
                85                  90                  95

Ala Ala Gly Asn Ala Leu His Ser Arg Tyr Tyr Ser Pro Ser Lys Tyr
            100                 105                 110

Asp Tyr Trp Gly Pro Gly Thr Gln Val Thr Val Ser Ser
        115                 120                 125

<210> SEQ ID NO 42
```

<211> LENGTH: 120
<212> TYPE: PRT
<213> ORGANISM: Artificial sequence
<220> FEATURE:
<223> OTHER INFORMATION: VHH

<400> SEQUENCE: 42

Gln Val Gln Leu Gln Gln Ser Gly Gly Gly Leu Val Gln Ala Gly Asp
1               5                   10                  15

Ser Leu Arg Leu Ser Cys Ala Ala Ser Gly Arg Ala Phe Asn Tyr Tyr
            20                  25                  30

Thr Met Gly Trp Phe Arg Gln Ala Pro Gly Lys Glu Arg Glu Phe Val
        35                  40                  45

Ala Lys Ile Tyr Trp Asp Gly Ser Thr Ile Tyr Ala Asp Ser Val
    50                  55                  60

Lys Gly Arg Phe Thr Ile Ser Ile Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Pro Ser Phe Tyr Pro Phe Arg Pro Lys Tyr Trp Gly Gln
            100                 105                 110

Gly Thr Gln Val Thr Val Ser Ser
            115                 120

<210> SEQ ID NO 43
<211> LENGTH: 266
<212> TYPE: PRT
<213> ORGANISM: Artificial sequence
<220> FEATURE:
<223> OTHER INFORMATION: VHH

<400> SEQUENCE: 43

Gln Val Gln Leu Gln Gln Ser Gly Gly Gly Ser Val Gln Ala Gly Gly
1               5                   10                  15

Ser Leu Arg Leu Ser Cys Val Gly Pro Gln Arg Thr Phe Ser Thr Tyr
            20                  25                  30

Gly Met Gly Trp Phe Arg Gln Ala Pro Gly Lys Glu Arg Glu Phe Val
        35                  40                  45

Ala Gly Ile Asn Tyr Lys Gly Asp Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Arg Ala Val Tyr Gln Cys
                85                  90                  95

Ala Arg Lys Gly Gly Leu Gly Gly Asp Tyr Arg Asp Ala Gly Gln Tyr
            100                 105                 110

Arg Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Ala
    130                 135                 140

Leu Val Gln Pro Gly Gly Ser Leu Arg Leu Ser Cys Ala Ala Ser Gly
145                 150                 155                 160

Phe Pro Phe Ser Ala Tyr Asp Met Thr Trp Val Arg Gln Ala Pro Gly
                165                 170                 175

Gln Gly Leu Glu Trp Val Ser Thr Ile His Lys Ser Gly Gly Ile Thr
            180                 185                 190

Thr Tyr Ala Asp Ser Val Lys Gly Arg Phe Thr Ile Ser Arg Asp Asn

```
            195                 200                 205
Ala Lys Asn Thr Leu Tyr Leu Gln Met Asn Leu Glu Ser Glu Asp
    210                 215                 220

Thr Ala Val Tyr Tyr Cys Ala Lys Ala Leu Arg Ala His Asn Ser Asp
225                 230                 235                 240

Tyr Val Gly Arg Asn Ala Leu Gly Ser Trp Gly Gln Gly Thr Gln Val
                245                 250                 255

Thr Val Ser Ser His His His His His His
            260                 265

<210> SEQ ID NO 44
<211> LENGTH: 279
<212> TYPE: PRT
<213> ORGANISM: Artificial sequence
<220> FEATURE:
<223> OTHER INFORMATION: VHH

<400> SEQUENCE: 44

Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
            20                  25                  30

Thr Ile Ala Trp Phe Arg Arg Ala Ala Gly Glu Gly Arg Val Glu Asp
        35                  40                  45

Gly Glu Gly Val Ala Ser Ile Thr Lys Ser Tyr Asp Arg Ala Tyr Asp
    50                  55                  60

Asn Lys Ile Asn Tyr Gly His Ser Val Lys Gly Arg Phe Thr Ile Ser
65                  70                  75                  80

Arg Asp Asn Ala Lys Asn Thr Val Tyr Leu Gln Met Thr Asp Leu Leu
                85                  90                  95

Pro Ser Asp Thr Ala Val Tyr Tyr Cys Ala Leu Asp Ile Thr Pro Pro
            100                 105                 110

Gly Gly Val Gly Ala Ser Leu Thr Glu Gly Phe Leu Phe Asp Tyr Trp
        115                 120                 125

Gly Gln Gly Thr Gln Val Thr Val Ser Ser Gly Gly Gly Gly Ser Gly
    130                 135                 140

Gly Gly Ser Glu Val Gln Leu Val Glu Ser Gly Gly Ala Leu Val Gln
145                 150                 155                 160

Pro Gly Gly Ser Leu Arg Leu Ser Cys Ala Ala Ser Gly Phe Pro Phe
                165                 170                 175

Ser Ala Tyr Asp Met Thr Trp Val Arg Gln Ala Pro Gly Gln Gly Leu
            180                 185                 190

Glu Trp Val Ser Thr Ile His Lys Ser Gly Gly Ile Thr Thr Tyr Ala
        195                 200                 205

Asp Ser Val Lys Gly Arg Phe Thr Ile Ser Arg Asp Asn Ala Lys Asn
    210                 215                 220

Thr Leu Tyr Leu Gln Met Asn Asn Leu Glu Ser Glu Asp Thr Ala Val
225                 230                 235                 240

Tyr Tyr Cys Ala Lys Ala Leu Arg Ala His Asn Ser Asp Tyr Val Gly
                245                 250                 255

Arg Asn Ala Leu Gly Ser Trp Gly Gln Gly Thr Gln Val Thr Val Ser
            260                 265                 270

Ser His His His His His His
        275
```

```
<210> SEQ ID NO 45
<211> LENGTH: 264
<212> TYPE: PRT
<213> ORGANISM: Artificial sequence
<220> FEATURE:
<223> OTHER INFORMATION: VHH

<400> SEQUENCE: 45
```

Gln Val Gln Leu Gln Glu Ser Gly Gly Gly Leu Val Gln Thr Gly
1               5                   10                  15

Ser Leu Arg Leu Ser Cys Arg Ala Ser Gly Arg Ala Phe Ala Asn Tyr
                20                  25                  30

His Phe Gly Trp Phe Arg Gln Ala Pro Gly Lys Asp Arg Glu Phe Val
            35                  40                  45

Ala Ser Ile Ser Trp Lys Gly Ser Thr Tyr Tyr Ala Asn Phe Ala
        50                  55                  60

Leu Gly Arg Phe Thr Ser Ser Val Asp Arg Ala Glu Ser Ser Val Tyr
65                  70                  75                  80

Leu Gln Met Ser Gly Leu Thr Pro Glu Asp Thr Ala Thr Tyr Tyr Cys
                85                  90                  95

Ala Ala His Asp Gly Asp Trp Asn Tyr His Thr Gly Met Asp Tyr
            100                 105                 110

Trp Gly Gln Gly Thr Gln Val Thr Val Ser Gly Gly Gly Gly Ser
        115                 120                 125

Gly Gly Gly Ser Glu Val Gln Leu Val Glu Ser Gly Ala Leu Val
        130                 135                 140

Gln Pro Gly Gly Ser Leu Arg Leu Ser Cys Ala Ala Ser Gly Phe Pro
145                 150                 155                 160

Phe Ser Ala Tyr Asp Met Thr Trp Val Arg Gln Ala Pro Gly Gln Gly
                165                 170                 175

Leu Glu Trp Val Ser Thr Ile His Lys Ser Gly Gly Ile Thr Thr Tyr
                180                 185                 190

Ala Asp Ser Val Lys Gly Arg Phe Thr Ile Ser Arg Asp Asn Ala Lys
                195                 200                 205

Asn Thr Leu Tyr Leu Gln Met Asn Asn Leu Glu Ser Glu Asp Thr Ala
210                 215                 220

Val Tyr Tyr Cys Ala Lys Ala Leu Arg Ala His Asn Ser Asp Tyr Val
225                 230                 235                 240

Gly Arg Asn Ala Leu Gly Ser Trp Gly Gln Gly Thr Gln Val Thr Val
                245                 250                 255

Ser Ser His His His His His His
        260

```
<210> SEQ ID NO 46
<211> LENGTH: 266
<212> TYPE: PRT
<213> ORGANISM: Artificial sequence
<220> FEATURE:
<223> OTHER INFORMATION: VHH

<400> SEQUENCE: 46
```

Gln Val Gln Leu Gln Glu Ser Gly Gly Gly Ser Val Gln Ala Gly Asp
1               5                   10                  15

Ser Leu Arg Leu Ser Cys Ala Ala Ser Gly Arg Thr Ile Ser Asn Tyr
                20                  25                  30

Ala Met Gly Trp Phe Arg Gln Ala Pro Gly Lys Gln Arg Glu Phe Val
            35                  40                  45

Ala Ala Ile Ser Arg Ser Asp Asn Thr Tyr Tyr Thr Asp Ser Val Lys
    50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Glu Thr Ala Val Tyr Tyr Cys Ala
                 85                  90                  95

Ala Asp Pro Asn Leu Met Tyr Glu Ser Lys Trp Lys Tyr Arg Ala Leu
            100                 105                 110

Glu Ala Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Ala
    130                 135                 140

Leu Val Gln Pro Gly Gly Ser Leu Arg Leu Ser Cys Ala Ala Ser Gly
145                 150                 155                 160

Phe Pro Phe Ser Ala Tyr Asp Met Thr Trp Val Arg Gln Ala Pro Gly
                165                 170                 175

Gln Gly Leu Glu Trp Val Ser Thr Ile His Lys Ser Gly Gly Ile Thr
            180                 185                 190

Thr Tyr Ala Asp Ser Val Lys Gly Arg Phe Thr Ile Ser Arg Asp Asn
        195                 200                 205

Ala Lys Asn Thr Leu Tyr Leu Gln Met Asn Asn Leu Glu Ser Glu Asp
    210                 215                 220

Thr Ala Val Tyr Tyr Cys Ala Lys Ala Leu Arg Ala His Asn Ser Asp
225                 230                 235                 240

Tyr Val Gly Arg Asn Ala Leu Gly Ser Trp Gly Gln Gly Thr Gln Val
                245                 250                 255

Thr Val Ser Ser His His His His His His
            260                 265

<210> SEQ ID NO 47
<211> LENGTH: 419
<212> TYPE: PRT
<213> ORGANISM: Artificial sequence
<220> FEATURE:
<223> OTHER INFORMATION: VHH

<400> SEQUENCE: 47

Gln Val Gln Leu Gln Glu Ser Gly Gly Gly Ser Val Gln Ala Gly Gly
 1               5                  10                  15

Ser Leu Arg Leu Ser Cys Thr Ala Ser Glu Leu Ser Tyr Asp Asp Tyr
             20                  25                  30

Thr Ile Ala Trp Phe Arg Arg Ala Ala Gly Glu Gly Arg Val Glu Asp
         35                  40                  45

Gly Glu Gly Val Ala Ser Ile Thr Lys Ser Tyr Asp Arg Ala Tyr Asp
     50                  55                  60

Asn Lys Ile Asn Tyr Gly His Ser Val Lys Gly Arg Phe Thr Ile Ser
 65                  70                  75                  80

Arg Asp Asn Ala Lys Asn Thr Val Tyr Leu Gln Met Thr Asp Leu Leu
             85                  90                  95

Pro Ser Asp Thr Ala Val Tyr Tyr Cys Ala Leu Asp Ile Thr Pro Pro
            100                 105                 110

Gly Gly Val Gly Ala Ser Leu Thr Glu Gly Phe Leu Phe Asp Tyr Trp
        115                 120                 125

Gly Gln Gly Thr Gln Val Thr Val Ser Ser Gly Gly Gly Gly Ser Gly
    130                 135                 140

```
Gly Gly Gly Ser Gly Gly Gly Ser Gln Val Gln Leu Gln Glu Ser
145                 150                 155                 160

Gly Gly Gly Ser Val Gln Ala Gly Asp Ser Leu Arg Leu Ser Cys Ala
                165                 170                 175

Ala Ser Gly Arg Thr Ile Ser Asn Tyr Ala Met Gly Trp Phe Arg Gln
            180                 185                 190

Ala Pro Gly Lys Gln Arg Glu Phe Val Ala Ala Ile Ser Arg Ser Asp
            195                 200                 205

Asn Thr Tyr Tyr Thr Asp Ser Val Lys Gly Arg Phe Thr Ile Ser Arg
        210                 215                 220

Asp Asn Ala Lys Asn Thr Leu Tyr Leu Gln Met Asn Ser Leu Lys Pro
225                 230                 235                 240

Glu Glu Thr Ala Val Tyr Tyr Cys Ala Ala Asp Pro Asn Leu Met Tyr
                245                 250                 255

Glu Ser Lys Trp Lys Tyr Arg Ala Leu Glu Ala Trp Gly Gln Gly Thr
            260                 265                 270

Gln Val Thr Val Ser Ser Gly Gly Gly Ser Gly Gly Gly Ser Glu
        275                 280                 285

Val Gln Leu Val Glu Ser Gly Gly Ala Leu Val Gln Pro Gly Gly Ser
290                 295                 300

Leu Arg Leu Ser Cys Ala Ala Ser Gly Phe Pro Phe Ser Ala Tyr Asp
305                 310                 315                 320

Met Thr Trp Val Arg Gln Ala Pro Gly Gln Gly Leu Glu Trp Val Ser
                325                 330                 335

Thr Ile His Lys Ser Gly Gly Ile Thr Thr Tyr Ala Asp Ser Val Lys
            340                 345                 350

Gly Arg Phe Thr Ile Ser Arg Asp Asn Ala Lys Asn Thr Leu Tyr Leu
        355                 360                 365

Gln Met Asn Asn Leu Glu Ser Glu Asp Thr Ala Val Tyr Tyr Cys Ala
370                 375                 380

Lys Ala Leu Arg Ala His Asn Ser Asp Tyr Val Gly Arg Asn Ala Leu
385                 390                 395                 400

Gly Ser Trp Gly Gln Gly Thr Gln Val Thr Val Ser Ser His His His
                405                 410                 415

His His His

<210> SEQ ID NO 48
<211> LENGTH: 419
<212> TYPE: PRT
<213> ORGANISM: Artificial sequence
<220> FEATURE:
<223> OTHER INFORMATION: VHH

<400> SEQUENCE: 48

Gln Val Gln Leu Gln Gln Ser Gly Gly Ser Val Gln Ala Gly Gly
1               5                   10                  15

Ser Leu Arg Leu Ser Cys Val Gly Pro Gln Arg Thr Phe Ser Thr Tyr
            20                  25                  30

Gly Met Gly Trp Phe Arg Gln Ala Pro Gly Lys Glu Arg Glu Phe Val
        35                  40                  45

Ala Gly Ile Asn Tyr Lys Gly Asp Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Arg Ala Val Tyr Gln Cys
```

85                  90                  95
Ala Arg Lys Gly Gly Leu Gly Gly Asp Tyr Arg Asp Ala Gly Gln Tyr
                100                 105                 110

Arg Tyr Trp Gly Gln Gly Thr Gln Val Thr Val Ser Ser Gly Gly Gly
            115                 120                 125

Gly Ser Gly Gly Gly Gly Ser Gly Gly Gly Gly Ser Gln Val Gln Leu
        130                 135                 140

Gln Glu Ser Gly Gly Gly Ser Val Gln Ala Gly Gly Ser Leu Arg Leu
145                 150                 155                 160

Ser Cys Thr Ala Ser Glu Leu Ser Tyr Asp Asp Tyr Thr Ile Ala Trp
                165                 170                 175

Phe Arg Arg Ala Ala Gly Glu Gly Arg Val Glu Asp Gly Glu Gly Val
                180                 185                 190

Ala Ser Ile Thr Lys Ser Tyr Asp Arg Ala Tyr Asp Asn Lys Ile Asn
                195                 200                 205

Tyr Gly His Ser Val Lys Gly Arg Phe Thr Ile Ser Arg Asp Asn Ala
        210                 215                 220

Lys Asn Thr Val Tyr Leu Gln Met Thr Asp Leu Leu Pro Ser Asp Thr
225                 230                 235                 240

Ala Val Tyr Tyr Cys Ala Leu Asp Ile Thr Pro Pro Gly Gly Val Gly
                245                 250                 255

Ala Ser Leu Thr Glu Gly Phe Leu Phe Asp Tyr Trp Gly Gln Gly Thr
                260                 265                 270

Gln Val Thr Val Ser Ser Gly Gly Gly Gly Ser Gly Gly Gly Gly Ser Glu
                275                 280                 285

Val Gln Leu Val Glu Ser Gly Gly Ala Leu Val Gln Pro Gly Gly Ser
        290                 295                 300

Leu Arg Leu Ser Cys Ala Ala Ser Gly Phe Pro Phe Ser Ala Tyr Asp
305                 310                 315                 320

Met Thr Trp Val Arg Gln Ala Pro Gly Gln Gly Leu Glu Trp Val Ser
                325                 330                 335

Thr Ile His Lys Ser Gly Gly Ile Thr Thr Tyr Ala Asp Ser Val Lys
                340                 345                 350

Gly Arg Phe Thr Ile Ser Arg Asp Asn Ala Lys Asn Thr Leu Tyr Leu
            355                 360                 365

Gln Met Asn Asn Leu Glu Ser Glu Asp Thr Ala Val Tyr Tyr Cys Ala
        370                 375                 380

Lys Ala Leu Arg Ala His Asn Ser Asp Tyr Val Gly Arg Asn Ala Leu
385                 390                 395                 400

Gly Ser Trp Gly Gln Gly Thr Gln Val Thr Val Ser Ser His His His
                405                 410                 415

His His His

<210> SEQ ID NO 49
<211> LENGTH: 417
<212> TYPE: PRT
<213> ORGANISM: Artificial sequence
<220> FEATURE:
<223> OTHER INFORMATION: VHH

<400> SEQUENCE: 49

Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
            20                  25                  30

Thr Ile Ala Trp Phe Arg Arg Ala Gly Glu Gly Arg Val Glu Asp
        35                  40                  45

Gly Glu Gly Val Ala Ser Ile Thr Lys Ser Tyr Asp Arg Ala Tyr Asp
50                  55                  60

Asn Lys Ile Asn Tyr Gly His Ser Val Lys Gly Arg Phe Thr Ile Ser
65                  70                  75                  80

Arg Asp Asn Ala Lys Asn Thr Val Tyr Leu Gln Met Thr Asp Leu Leu
                85                  90                  95

Pro Ser Asp Thr Ala Val Tyr Tyr Cys Ala Leu Asp Ile Thr Pro Pro
            100                 105                 110

Gly Gly Val Gly Ala Ser Leu Thr Glu Gly Phe Leu Phe Asp Tyr Trp
        115                 120                 125

Gly Gln Gly Thr Gln Val Thr Val Ser Ser Gly Gly Gly Ser Gly
    130                 135                 140

Gly Gly Gly Ser Gly Gly Gly Ser Gln Val Gln Leu Gln Glu Ser
145                 150                 155                 160

Gly Gly Gly Leu Val Gln Thr Gly Gly Ser Leu Arg Leu Ser Cys Arg
                165                 170                 175

Ala Ser Gly Arg Ala Phe Ala Asn Tyr His Phe Gly Trp Phe Arg Gln
            180                 185                 190

Ala Pro Gly Lys Asp Arg Glu Phe Val Ala Ser Ile Ser Trp Lys Gly
        195                 200                 205

Gly Ser Thr Tyr Tyr Ala Asn Phe Ala Leu Gly Arg Phe Thr Ser Ser
    210                 215                 220

Val Asp Arg Ala Glu Ser Ser Val Tyr Leu Gln Met Ser Gly Leu Thr
225                 230                 235                 240

Pro Glu Asp Thr Ala Thr Tyr Tyr Cys Ala Ala His Asp Gly Gly Asp
                245                 250                 255

Trp Asn Tyr His Thr Gly Met Asp Tyr Trp Gly Gln Gly Thr Gln Val
            260                 265                 270

Thr Val Ser Ser Gly Gly Gly Ser Gly Gly Gly Ser Glu Val Gln
        275                 280                 285

Leu Val Glu Ser Gly Gly Ala Leu Val Gln Pro Gly Gly Ser Leu Arg
    290                 295                 300

Leu Ser Cys Ala Ala Ser Gly Phe Pro Phe Ser Ala Tyr Asp Met Thr
305                 310                 315                 320

Trp Val Arg Gln Ala Pro Gly Gln Gly Leu Glu Trp Val Ser Thr Ile
                325                 330                 335

His Lys Ser Gly Gly Ile Thr Thr Tyr Ala Asp Ser Val Lys Gly Arg
            340                 345                 350

Phe Thr Ile Ser Arg Asp Asn Ala Lys Asn Thr Leu Tyr Leu Gln Met
        355                 360                 365

Asn Asn Leu Glu Ser Glu Asp Thr Ala Val Tyr Tyr Cys Ala Lys Ala
    370                 375                 380

Leu Arg Ala His Asn Ser Asp Tyr Val Gly Arg Asn Ala Leu Gly Ser
385                 390                 395                 400

Trp Gly Gln Gly Thr Gln Val Thr Val Ser Ser His His His His
                405                 410                 415

His

<210> SEQ ID NO 50
<211> LENGTH: 278
<212> TYPE: PRT

<213> ORGANISM: Artificial sequence
<220> FEATURE:
<223> OTHER INFORMATION: VHH

<400> SEQUENCE: 50

Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
            20                  25                  30

Thr Ile Ala Trp Phe Arg Arg Ala Ala Gly Glu Gly Arg Val Glu Asp
        35                  40                  45

Gly Glu Gly Val Ala Ser Ile Thr Lys Ser Tyr Asp Arg Ala Tyr Asp
50                  55                  60

Asn Lys Ile Asn Tyr Gly His Ser Val Lys Gly Arg Phe Thr Ile Ser
65                  70                  75                  80

Arg Asp Asn Ala Lys Asn Thr Val Tyr Leu Gln Met Thr Asp Leu Leu
                85                  90                  95

Pro Ser Asp Thr Ala Val Tyr Tyr Cys Ala Leu Asp Ile Thr Pro Pro
            100                 105                 110

Gly Gly Val Gly Ala Ser Leu Thr Glu Gly Phe Leu Phe Asp Tyr Trp
        115                 120                 125

Gly Gln Gly Thr Gln Val Thr Val Ser Ser Gly Gly Gly Ser Gly
130                 135                 140

Gly Gly Ser Glu Val Gln Leu Val Glu Ser Gly Gly Leu Val Gln
145                 150                 155                 160

Ala Gly Gly Ser Leu Arg Leu Ser Cys Ala Ala Ser Gly Arg Thr Phe
                165                 170                 175

Ser Tyr Tyr Pro Met Ala Trp Phe Arg Gln Ala Pro Gly Gln Glu Arg
            180                 185                 190

Glu Phe Val Ala Ala Ile Ile Gly Ala Asp Thr Thr Tyr Tyr Ala Asp
        195                 200                 205

Ser Leu Lys Gly Arg Phe Thr Ile Ser Arg Asp Asn Ala Lys Asn Met
    210                 215                 220

Val Tyr Leu Gln Met Asn Ser Leu Lys Pro Glu Asp Thr Ala Val Tyr
225                 230                 235                 240

Tyr Cys Ala Ala Arg Asn Thr Tyr Trp Ser Asp Val Tyr Tyr Arg Glu
                245                 250                 255

Gly Gln Tyr Thr Asn Trp Gly Gln Gly Thr Gln Val Thr Val Ser Ser
            260                 265                 270

His His His His His His
        275

<210> SEQ ID NO 51
<211> LENGTH: 418
<212> TYPE: PRT
<213> ORGANISM: Artificial sequence
<220> FEATURE:
<223> OTHER INFORMATION: VHH

<400> SEQUENCE: 51

Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
            20                  25                  30

Thr Ile Ala Trp Phe Arg Arg Ala Ala Gly Glu Gly Arg Val Glu Asp
        35                  40                  45

```
Gly Glu Gly Val Ala Ser Ile Thr Lys Ser Tyr Asp Arg Ala Tyr Asp
 50                  55                  60

Asn Lys Ile Asn Tyr Gly His Ser Val Lys Gly Arg Phe Thr Ile Ser
 65                  70                  75                  80

Arg Asp Asn Ala Lys Asn Thr Val Tyr Leu Gln Met Thr Asp Leu Leu
                 85                  90                  95

Pro Ser Asp Thr Ala Val Tyr Tyr Cys Ala Leu Asp Ile Thr Pro Pro
            100                 105                 110

Gly Val Gly Ala Ser Leu Thr Glu Gly Phe Leu Phe Asp Tyr Trp
        115                 120                 125

Gly Gln Gly Thr Gln Val Thr Val Ser Gly Gly Gly Ser Gly
130                 135                 140

Gly Gly Ser Gly Gly Gly Ser Gln Val Gln Leu Gln Glu Ser
145                 150                 155                 160

Gly Gly Gly Ser Val Gln Ala Gly Asp Ser Leu Arg Leu Ser Cys Ala
                165                 170                 175

Ala Ser Gly Arg Thr Ile Ser Asn Tyr Ala Met Gly Trp Phe Arg Gln
            180                 185                 190

Ala Pro Gly Lys Gln Arg Glu Phe Val Ala Ala Ile Ser Arg Ser Asp
        195                 200                 205

Asn Thr Tyr Tyr Thr Asp Ser Val Lys Gly Arg Phe Thr Ile Ser Arg
210                 215                 220

Asp Asn Ala Lys Asn Thr Leu Tyr Leu Gln Met Asn Ser Leu Lys Pro
225                 230                 235                 240

Glu Glu Thr Ala Val Tyr Tyr Cys Ala Ala Asp Pro Asn Leu Met Tyr
                245                 250                 255

Glu Ser Lys Trp Lys Tyr Arg Ala Leu Glu Ala Trp Gly Gln Gly Thr
            260                 265                 270

Gln Val Thr Val Ser Ser Gly Gly Gly Ser Gly Gly Gly Ser Glu
        275                 280                 285

Val Gln Leu Val Glu Ser Gly Gly Gly Leu Val Gln Ala Gly Gly Ser
290                 295                 300

Leu Arg Leu Ser Cys Ala Ala Ser Gly Arg Thr Phe Ser Tyr Tyr Pro
305                 310                 315                 320

Met Ala Trp Phe Arg Gln Ala Pro Gly Gln Glu Arg Glu Phe Val Ala
                325                 330                 335

Ala Ile Ile Gly Ala Asp Thr Thr Tyr Tyr Ala Asp Ser Leu Lys Gly
            340                 345                 350

Arg Phe Thr Ile Ser Arg Asp Asn Ala Lys Asn Met Val Tyr Leu Gln
        355                 360                 365

Met Asn Ser Leu Lys Pro Glu Asp Thr Ala Val Tyr Tyr Cys Ala Ala
370                 375                 380

Arg Asn Thr Tyr Trp Ser Asp Val Tyr Tyr Arg Glu Gly Gln Tyr Thr
385                 390                 395                 400

Asn Trp Gly Gln Gly Thr Gln Val Thr Val Ser Ser His His His His
                405                 410                 415

His His

<210> SEQ ID NO 52
<211> LENGTH: 419
<212> TYPE: PRT
<213> ORGANISM: Artificial sequence
<220> FEATURE:
<223> OTHER INFORMATION: VHH
```

```
<400> SEQUENCE: 52

Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
            20                  25                  30

Thr Ile Ala Trp Phe Arg Arg Ala Ala Gly Glu Gly Arg Val Glu Asp
        35                  40                  45

Gly Glu Gly Val Ala Ser Ile Thr Lys Ser Tyr Asp Arg Ala Tyr Asp
    50                  55                  60

Asn Lys Ile Asn Tyr Gly His Ser Val Lys Gly Arg Phe Thr Ile Ser
65                  70                  75                  80

Arg Asp Asn Ala Lys Asn Thr Val Tyr Leu Gln Met Thr Asp Leu Leu
                85                  90                  95

Pro Ser Asp Thr Ala Val Tyr Tyr Cys Ala Leu Asp Ile Thr Pro Pro
            100                 105                 110

Gly Gly Val Gly Ala Ser Leu Thr Glu Gly Phe Leu Phe Asp Tyr Trp
        115                 120                 125

Gly Gln Gly Thr Gln Val Thr Val Ser Ser Gly Gly Gly Gly Ser Gly
    130                 135                 140

Gly Gly Gly Ser Gly Gly Gly Gly Ser Gln Val Gln Leu Gln Gln Ser
145                 150                 155                 160

Gly Gly Gly Ser Val Gln Ala Gly Gly Ser Leu Arg Leu Ser Cys Val
                165                 170                 175

Gly Pro Gln Arg Thr Phe Ser Thr Tyr Gly Met Gly Trp Phe Arg Gln
            180                 185                 190

Ala Pro Gly Lys Glu Arg Glu Phe Val Ala Gly Ile Asn Tyr Lys Gly
        195                 200                 205

Asp Thr Thr Tyr Tyr Ala Asp Ser Val Lys Gly Arg Phe Thr Ile Ser
    210                 215                 220

Arg Asp Asn Ala Lys Asn Thr Leu Tyr Leu Gln Met Asp Ser Leu Lys
225                 230                 235                 240

Pro Glu Asp Arg Ala Val Tyr Gln Cys Ala Arg Lys Gly Gly Leu Gly
                245                 250                 255

Gly Asp Tyr Arg Asp Ala Gly Gln Tyr Arg Tyr Trp Gly Gln Gly Thr
            260                 265                 270

Gln Val Thr Val Ser Ser Gly Gly Gly Ser Gly Gly Gly Ser Glu
    275                 280                 285

Val Gln Leu Val Glu Ser Gly Gly Ala Leu Val Gln Pro Gly Gly Ser
290                 295                 300

Leu Arg Leu Ser Cys Ala Ala Ser Gly Phe Pro Phe Ser Ala Tyr Asp
305                 310                 315                 320

Met Thr Trp Val Arg Gln Ala Pro Gly Gln Gly Leu Glu Trp Val Ser
                325                 330                 335

Thr Ile His Lys Ser Gly Gly Ile Thr Thr Tyr Ala Asp Ser Val Lys
            340                 345                 350

Gly Arg Phe Thr Ile Ser Arg Asp Asn Ala Lys Asn Thr Leu Tyr Leu
        355                 360                 365

Gln Met Asn Asn Leu Glu Ser Glu Asp Thr Ala Val Tyr Tyr Cys Ala
    370                 375                 380

Lys Ala Leu Arg Ala His Asn Ser Asp Tyr Val Gly Arg Asn Ala Leu
385                 390                 395                 400

Gly Ser Trp Gly Gln Gly Thr Gln Val Thr Val Ser Ser His His His
                405                 410                 415
```

His His His

<210> SEQ ID NO 53
<211> LENGTH: 406
<212> TYPE: PRT
<213> ORGANISM: Artificial sequence
<220> FEATURE:
<223> OTHER INFORMATION: VHH

<400> SEQUENCE: 53

```
Gln Val Gln Leu Gln Gln Ser Gly Gly Gly Ser Val Gln Ala Gly Gly
 1               5                  10                  15

Ser Leu Arg Leu Ser Cys Val Gly Pro Gln Arg Thr Phe Ser Thr Tyr
            20                  25                  30

Gly Met Gly Trp Phe Arg Gln Ala Pro Gly Lys Glu Arg Glu Phe Val
        35                  40                  45

Ala Gly Ile Asn Tyr Lys Gly Asp Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Arg Ala Val Tyr Gln Cys
                85                  90                  95

Ala Arg Lys Gly Gly Leu Gly Gly Asp Tyr Arg Asp Ala Gly Gln Tyr
            100                 105                 110

Arg Tyr Trp Gly Gln Gly Thr Gln Val Thr Val Ser Ser Gly Gly Gly
        115                 120                 125

Gly Ser Gly Gly Gly Gly Ser Gly Gly Gly Gly Ser Gln Val Gln Leu
    130                 135                 140

Gln Glu Ser Gly Gly Gly Ser Val Gln Ala Gly Asp Ser Leu Arg Leu
145                 150                 155                 160

Ser Cys Ala Ala Ser Gly Arg Thr Ile Ser Asn Tyr Ala Met Gly Trp
                165                 170                 175

Phe Arg Gln Ala Pro Gly Lys Gln Arg Glu Phe Val Ala Ala Ile Ser
            180                 185                 190

Arg Ser Asp Asn Thr Tyr Tyr Thr Asp Ser Val Lys Gly Arg Phe Thr
        195                 200                 205

Ile Ser Arg Asp Asn Ala Lys Asn Thr Leu Tyr Leu Gln Met Asn Ser
    210                 215                 220

Leu Lys Pro Glu Glu Thr Ala Val Tyr Tyr Cys Ala Ala Asp Pro Asn
225                 230                 235                 240

Leu Met Tyr Glu Ser Lys Trp Lys Tyr Arg Ala Leu Glu Ala Trp Gly
                245                 250                 255

Gln Gly Thr Gln Val Thr Val Ser Ser Gly Gly Gly Gly Ser Gly Gly
            260                 265                 270

Gly Ser Glu Val Gln Leu Val Glu Ser Gly Gly Ala Leu Val Gln Pro
        275                 280                 285

Gly Gly Ser Leu Arg Leu Ser Cys Ala Ala Ser Gly Phe Pro Phe Ser
    290                 295                 300

Ala Tyr Asp Met Thr Trp Val Arg Gln Ala Pro Gly Gln Gly Leu Glu
305                 310                 315                 320

Trp Val Ser Thr Ile His Lys Ser Gly Gly Ile Thr Thr Tyr Ala Asp
                325                 330                 335

Ser Val Lys Gly Arg Phe Thr Ile Ser Arg Asp Asn Ala Lys Asn Thr
            340                 345                 350
```

Leu Tyr Leu Gln Met Asn Asn Leu Glu Ser Glu Asp Thr Ala Val Tyr
            355                 360                 365

Tyr Cys Ala Lys Ala Leu Arg Ala His Asn Ser Asp Tyr Val Gly Arg
370                 375                 380

Asn Ala Leu Gly Ser Trp Gly Gln Gly Thr Gln Val Thr Val Ser Ser
385                 390                 395                 400

His His His His His His
            405

<210> SEQ ID NO 54
<211> LENGTH: 894
<212> TYPE: DNA
<213> ORGANISM: Artificial sequence
<220> FEATURE:
<223> OTHER INFORMATION: VHH

<400> SEQUENCE: 54

```
gagctcatca cacaaacaaa caaaacaaaa tgatgctttt gcaagccttc cttttccttt    60
tggctggttt tgcagccaaa atatctgcgc aggtgcagct gcagcagtct ggcggaggat   120
cggtgcaggc tggggctct ctgaggctct cctgtgtagg acctcaacgc accttcagca    180
cctatggcat gggttggttc cgccaggcgc ggggaagga gcgtgagttt gtagcaggga    240
ttaattataa aggggatacc acatatatg cggactccgt gaagggccga ttcaccatct    300
ccagagacaa cgccaagaac acctgtatc tgcaaatgga cagtctgaaa cctgaagaca    360
gggccgtgta tcagtgtgca cgtaaaggag gcttgggtgg tgattaccgc gacgccggcc    420
agtatcgcta ctggggtcag gggacccagg tcaccgtctc ctcaggcgga ggtggctctg    480
gtggcggaag tgaggtgcag ctggtggagt ctggggagg attggtgcag ctgggggct     540
ctctgagact ctcctgtgca gcctctggac gcaccttcag ttactatccc atggcctggt   600
tccgccaggc tccagggcag gagcgtgagt ttgtagcagc tattattggt gccgatacca    660
catactatgc agactctctg aagggccgat tcaccatctc cagagacaac gccaagaaca    720
tggtgtatct gcaaatgaac agcctgaaac ctgaggacac ggccgtttat tactgtgcag    780
cgaggaatac atactggagt gatgtctact accgagaagg ccagtatacg aactggggcc    840
aggggaccca ggtcaccgtc tcctcacatc accatcacca tcactgataa gctt          894
```

<210> SEQ ID NO 55
<211> LENGTH: 888
<212> TYPE: DNA
<213> ORGANISM: Artificial sequence
<220> FEATURE:
<223> OTHER INFORMATION: VHH

<400> SEQUENCE: 55

```
gagctcatca cacaaacaaa caaaacaaaa tgatgctttt gcaagccttc cttttccttt    60
tggctggttt tgcagccaaa atatctgcgc aggtgcagct gcaggagtct gggggaggat   120
tggtgcagac tggggctct ctgagactct cctgtcgagc tctggacgc gccttcgcta     180
actatcactt cggctggttc cgccaggctc caggaaagga ccgagagttt gtagcttcta    240
ttagctggaa aggtggtagt acatatatcg caaatttcgc gctcggccgc ttcaccagct    300
ccgtggatag ggccgaaagc tcggtgtatc tgcaaatgag cggcctgaca cctgaggaca    360
cggccactta ttactgtgca gcccacgacg tggggactg aactaccac accggcatgg     420
actattgggg ccaggggacc caggtcaccg tctcctcagg cggaggtggc tctggtggcg    480
gaagtgaggt gcagctggtg gagtctgggg gaggattggt gcaggctggg ggctctctga    540
```

```
gactctcctg tgcagcctct ggacgcacct tcagttacta tcccatggcc tggttccgcc    600
aggctccagg gcaggagcgt gagtttgtag cagctattat tggtgccgat accacatact    660
atgcagactc tctgaagggc cgattcacca tctccagaga caacgccaag aacatggtgt    720
atctgcaaat gaacagcctg aaacctgagg acacggccgt ttattactgt gcagcgagga    780
atacatactg gagtgatgtc tactaccgag aaggccagta tacgaactgg ggccagggga    840
cccaggtcac cgtctcctca catcaccatc accatcactg ataagctt                888
```

<210> SEQ ID NO 56
<211> LENGTH: 894
<212> TYPE: DNA
<213> ORGANISM: Artificial sequence
<220> FEATURE:
<223> OTHER INFORMATION: VHH

<400> SEQUENCE: 56

```
gagctcatca cacaaacaaa caaaacaaaa tgatgctttt gcaagccttc cttttccttt     60
tggctggttt tgcagccaaa atatctgcgc aggtgcagct gcaggagtca ggggagggt    120 cggtgcaggc tggggactct ctgagactct cctgtgcagc ctctggacgc accatcagta    180
attatgccat gggctggttc cgccaggctc cagggaagca gcgtgagttt gtagcagcta    240
ttagccggag tgataataca tactacacag actccgtgaa gggccgattc accatctcca    300
gagacaacgc caagaacacg ctgtatctgc aaatgaacag cctgaaacct gaggagacgg    360
ccgtttatta ctgtgcagca gacccgaatt taatgtacga gagtaaatgg aagtatagag    420
cttttggaag catggggcag gggacccagg tcaccgtctc ctcaggcgga ggtggctctg    480
gtggcggaag tgaggtgcag ctggtggagt ctggggagg attggtgcag gctgggggct    540
ctctgagact ctcctgtgca gcctctggac gcaccttcag ttactatccc atggcctggt    600
tccgccaggc tccagggcag gagcgtgagt ttgtagcagc tattattggt gccgatacca    660
catactatgc agactctctg aagggccgat tcaccatctc cagagacaac gccaagaaca    720
tggtgtatct gcaaatgaac agcctgaaac tgaggacac ggccgtttat tactgtgcag    780
cgaggaatac atactggagt gatgtctact accgagaagg ccagtatacg aactggggcc    840
agggacccca ggtcaccgtc tcctcacatc accatcacca tcactgataa gctt          894
```

<210> SEQ ID NO 57
<211> LENGTH: 873
<212> TYPE: DNA
<213> ORGANISM: Artificial sequence
<220> FEATURE:
<223> OTHER INFORMATION: VHH

<400> SEQUENCE: 57

```
gagctcatca cacaaacaaa caaaacaaaa tgatgctttt gcaagccttc cttttccttt     60
tggctggttt tgcagccaaa atatctgcgc aggtgcagct gcagcagtct ggcggaggat    120
cggtgcaggc tgggggctct ctgaggctct cctgtgtagg acctcaacgc accttcagca    180
cctatggcat gggttggttc cgccaggcgc cggggaagga gcgtgagttt gtagcaggga    240
ttaattataa agggatacc acatatatg cggactccgt gaagggccga ttcaccatct    300
ccagagacaa cgccaagaac accctgtatc tgcaaatgga cagtctgaaa cctgaagaca    360
gggccgtgta tcagtgtgca cgtaaaggag gcttgggtgg tgattaccgc gacgccggcc    420
agtatcgcta ctggggtcag gggacccagg tcaccgtctc ctcaggcgga ggtggctctg    480
```

| | |
|---|---|
| gtggcggaag tgaggtgcag ctggtggagt ctggggggagg cttggtgcag cctgggggt | 540 |
| ctctgagact ctcctgtgaa gcctctggat tcacttttga tgactatggc atgagctggg | 600 |
| tccgacaggc tccagggaag gggctggagt gggtctcatc tcttaccccg aatggtggtt | 660 |
| cgacatacta tgcagactcc gtgaagggcc gattcaccat ctccagagac aacgccaaga | 720 |
| acacgctgta tctgcaaatg aacagtttga acctgagga cacggccctg tattattgtg | 780 |
| caaagaactc ttattacggt gccatggact actggggcca agggacccag gtcaccgtct | 840 |
| cctcacatca ccatcaccat cactgataag ctt | 873 |

<210> SEQ ID NO 58
<211> LENGTH: 912
<212> TYPE: DNA
<213> ORGANISM: Artificial sequence
<220> FEATURE:
<223> OTHER INFORMATION: VHH

<400> SEQUENCE: 58

| | |
|---|---|
| gagctcatca cacaaacaaa caaaacaaaa tgatgctttt gcaagccttc cttttccttt | 60 |
| tggctggttt tgcagccaaa atatctgcgc aggtgcagct gcaggagtca gggggaggct | 120 |
| cggtgcaggc tggggggtcg ctgagactct cctgtacagc ctctgaactc agttacgatg | 180 |
| attataccat agcatggttc cgccgggccg caggagaggg gcgtgtggag acggtgaggg | 240 |
| gggtcgcctc tattacgaaa agttatgaca gggcctacga taacaagatc aactatggtc | 300 |
| actctgtgaa gggccggttc accatctcca gagacaacgc caagaacacg gtgtatttgc | 360 |
| agatgaccga tctgcttcca tctgacacgg ccgtttacta ttgtgcactg gatattacgc | 420 |
| cgccgggtgg agtaggagca agtttgactg agggattttt atttgactac tggggccagg | 480 |
| ggacccaggt caccgtctcc tcaggcgagg tggctctgg tggcggaagt gaggtgcagc | 540 |
| tggtggagtc tgggggaggc ttggtgcagc tggggggtc tctgagactc tcctgtgaag | 600 |
| cctctggatt cacttttgat gactatgca tgagctgggt ccgacaggct cagggaagg | 660 |
| ggctggagtg ggtctcatct cttaccccga atggtggttc gacatactat gcagactccg | 720 |
| tgaagggccg attcaccatc tccagagaca acgccaagaa cacgctgtat ctgcaaatga | 780 |
| acagtttgaa acctgaggac acggccctgt attattgtgc aaagaactct tattacggtg | 840 |
| ccatggacta ctggggccaa gggacccagg tcaccgtctc ctcacatcac catcaccatc | 900 |
| actgataagc tt | 912 |

<210> SEQ ID NO 59
<211> LENGTH: 867
<212> TYPE: DNA
<213> ORGANISM: Artificial sequence
<220> FEATURE:
<223> OTHER INFORMATION: VHH

<400> SEQUENCE: 59

| | |
|---|---|
| gagctcatca cacaaacaaa caaaacaaaa tgatgctttt gcaagccttc cttttccttt | 60 |
| tggctggttt tgcagccaaa atatctgcgc aggtgcagct gcaggagtct gggggaggat | 120 |
| tggtgcagac tggggctct ctgagactct cctgtgagc ctctgacgc gccttcgcta | 180 |
| actatcactt cggctggttc cgccaggctc aggaaagga ccgagagttt gtagcttcta | 240 |
| ttagctggaa aggtggtagt acatattacg caaatttcgc gctcggccgc ttcaccagct | 300 |
| ccgtggatag ggccgaaagc tcggtgtatc tgcaaatgag cggcctgaca cctgaggaca | 360 |
| cggccactta ttactgtgca gcccacgacg gtggggactg gaactaccac accggcatgg | 420 |

```
actattgggg ccaggggacc caggtcaccg tctcctcagg cggaggtggc tctggtggcg    480
gaagtgaggt gcagctggtg gagtctgggg gaggcttggt gcagcctggg gggtctctga    540
gactctcctg tgaagcctct ggattcactt ttgatgacta tggcatgagc tgggtccgac    600
aggctccagg aaggggctg gagtgggtct catctcttac cccgaatggt ggttcgacat     660
actatgcaga ctccgtgaag gccgattca ccatctccag agacaacgcc aagaacacgc     720
tgtatctgca aatgaacagt ttgaaacctg aggacacggc cctgtattat tgtgcaaaga    780
actcttatta cggtgccatg gactactggg ccaagggac ccaggtcacc gtctcctcac     840
atcaccatca ccatcactga taagctt                                        867
```

<210> SEQ ID NO 60
<211> LENGTH: 873
<212> TYPE: DNA
<213> ORGANISM: Artificial sequence
<220> FEATURE:
<223> OTHER INFORMATION: VHH

<400> SEQUENCE: 60

```
gagctcatca cacaaacaaa caaaacaaaa tgatgctttt gcaagccttc cttttccttt     60
tggctggttt tgcagccaaa atatctgcgc aggtgcagct gcaggagtca gggggagggt    120
cggtgcaggc tggggactct ctgagactct cctgtgcagc ctctggacgc accatcagta    180
attatgccat gggctggttc cgccaggctc agggaagca gcgtgagttt gtagcagcta    240
ttagccggag tgataataca tactacacag actccgtgaa gggccgattc accatctcca    300
gagacaacgc caagaacacg ctgtatctgc aaatgaacag cctgaaacct gaggagacgg    360
ccgtttatta ctgtgcagca gacccgaatt taatgtacga gagtaaatgg aagtatagag    420 cttttggaagc atgggccag gggacccagg tcaccgtctc ctcaggcgga ggtggctctg    480
gtggcggaag tgaggtgcag ctggtggagt ctggggagg cttggtgcag cctggggggt    540
ctctgagact ctcctgtgaa gcctctggat tcacttttga tgactatggc atgagctggg    600
tccgacaggc tccagggaag gggctggagt gggtctcatc tcttacccg aatggtggtt    660 cgacatacta tgcagactcc gtgaagggcc gattcaccat ctccagagac aacgccaaga    720
acacgctgta tctgcaaatg aacagtttga aacctgagga cacggccctg tattattgtg    780
caaagaactc ttattacggt gccatggact actgggccca agggacccag gtcaccgtct    840
cctcacatca ccatcaccat cactgataag ctt                                 873
```

<210> SEQ ID NO 61
<211> LENGTH: 1242
<212> TYPE: DNA
<213> ORGANISM: Artificial sequence
<220> FEATURE:
<223> OTHER INFORMATION: VHH

<400> SEQUENCE: 61

```
gagctcatca cacaaacaaa caaaacaaaa tgatgctttt gcaagccttc cttttccttt     60
tggctggttt tgcagccaaa atatctgcgc aggtgcagct gcagcagtct ggcggaggat    120
cggtgcaggc tgggggctct ctgaggctct cctgtgtagg acctcaacgc accttcagca    180
cctatggcat gggttggttc cgccaggcgc ggggaagga gcgtgagttt gtagcaggga    240
ttaattataa aggggatacc acatattatg cggactccgt gaagggccga ttcaccatct    300
ccagagacaa cgccaagaac accctgtatc tgcaaatgga cagtctgaaa cctgaagaca    360
```

| | |
|---|---:|
| gggccgtgta tcagtgtgca cgtaaaggag gcttgggtgg tgattaccgc gacgccggcc | 420 |
| agtatcgcta ctggggtcag ggacccaggt caccgtctcc ctcacaggtg cagctgcagg | 480 |
| agtctggggg aggattggtg cagactgggg gctctctgag actctcctgt cgagcctctg | 540 |
| gacgcgcctt cgctaactat cacttcggct ggttccgcca ggctccagga aaggaccgag | 600 |
| agtttgtagc ttctattagc tggaaaggtg gtagtacata ttacgcaaat ttcgcgctcg | 660 |
| gccgcttcac cagctccgtg gatagggccg aaagctcggt gtatctgcaa atgagcggcc | 720 |
| tgacacctga ggacacggcc acttattact gtgcagccca cgacggtggg gactggaact | 780 |
| accacaccgg catggactat tggggccagg ggacccaggt caccgtctcc tcaggcggag | 840 |
| gtggctctgg tggcggaagt gaggtgcagc tggtggagtc tgggggaggc ttggtgcagc | 900 |
| ctggggggtc tctgagactc tcctgtgaag cctctggatt cacttttgat gactatggca | 960 |
| tgagctgggt ccgacaggct ccaggaaggg gctggagtgg gtctcatct cttaccccga | 1020 |
| atggtggttc gacatactat gcagactccg tgaagggccg attcaccatc tccagagaca | 1080 |
| acgccaagaa cacgctgtat ctgcaaatga acagtttgaa acctgaggac acggccctgt | 1140 |
| attattgtgc aaagaactct tattacggtg ccatggacta ctggggccaa gggacccagg | 1200 |
| tcaccgtctc ctcacatcac catcaccatc actgataagc tt | 1242 |

<210> SEQ ID NO 62
<211> LENGTH: 1287
<212> TYPE: DNA
<213> ORGANISM: Artificial sequence
<220> FEATURE:
<223> OTHER INFORMATION: VHH

<400> SEQUENCE: 62

| | |
|---|---:|
| gagctcatca cacaaacaaa caaaacaaaa tgatgctttt gcaagccttc ctttcctttt | 60 |
| tggctggttt tgcagccaaa atatctgcgc aggtgcagct gcaggagtca gggggaggct | 120 |
| cggtgcaggc tggggggtcg ctgagactct cctgtacagc ctctgaactc agttacgatg | 180 |
| attataccat agcatggttc cgccgggccg caggagaggg gcgtgtggag gacggtgagg | 240 |
| gggtcgcctc tattacgaaa agttatgaca gggcctacga taacaagatc aactatggtc | 300 |
| actctgtgaa gggccggttc accatctcca gagacaacgc caagaacacg gtgtatttgc | 360 |
| agatgaccga tctgcttcca tctgacacgg ccgtttacta ttgtgcactg gatattacgc | 420 |
| cgccgggtgg agtaggagca gtttgactg agggattttt atttgactac tggggccagg | 480 |
| ggacccaggt caccgtctcc tcacaggtgc agctgcagga gtcaggggga gggtcggtgc | 540 |
| aggctgggga ctctctgaga ctctcctgtg cagcctctgg acgcaccatc agtaattatg | 600 |
| ccatgggctg gttccgccag gctccaggga agcagcgtga gtttgtagca gctattagcc | 660 |
| ggagtgataa tacatactac acagactccg tgaagggccg attcaccatc tccagagaca | 720 |
| acgccaagaa cacgctgtat ctgcaaatga acagcctgaa acctgaggag acggccgttt | 780 |
| attactgtgc agcagacccg aatttaatgt acgagagtaa atggaagtat agagctttgg | 840 |
| aagcatgggg ccaggggacc caggtcaccg tctcctcagg cggaggtggc tctggtggcg | 900 |
| gaagtgaggt gcagctggtg gagtctgggg gaggcttggt gcagcctggg gggtctctga | 960 |
| gactctcctg tgaagcctct ggattcactt ttgatgacta tggcatgagc tgggtccgac | 1020 |
| aggctccagg aaggggctg gagtgggtct catctcttac cccgaatggt ggttcgacat | 1080 |
| actatgcaga ctccgtgaag ggccgattca ccatctccag agacaacgcc aagaacacgc | 1140 |
| tgtatctgca aatgaacagt ttgaaacctg aggacacggc cctgtattat tgtgcaaaga | 1200 |

-continued

```
actcttatta cggtgccatg gactactggg gccaagggac ccaggtcacc gtctcctcac    1260
atcaccatca ccatcactga taagctt                                        1287
```

<210> SEQ ID NO 63
<211> LENGTH: 912
<212> TYPE: DNA
<213> ORGANISM: Artificial sequence
<220> FEATURE:
<223> OTHER INFORMATION: VHH

<400> SEQUENCE: 63

```
gagctcatca cacaaacaaa caaaacaaaa tgatgctttt gcaagccttc ctttccttt      60 tggctggttt tgcagccaaa atatctgcgc aggtgcagct gcaggagtct ggggagg ct    120 cggtgcaggc tggggggtct ctgagactct cctgtacagc ctctgaattc agttacaatg   180
attataccat agcgtggttc cgccgggccg caggaaaggg gcgtgtggag gacggtgagg   240
gggtcgcctc tattacgaca agttatgaca gcctacga taacaggatt cactatggtg     300
actctgtgaa gggccgattc accatctcca gagacaacgc caagaacacg gtgtatttgc   360
agatgaccaa cctgaatcca tctgacacgg ccgtttatta ttgtggacta gatattacgc   420
cgccgggtgg aataggagca agtttgactg agggattttt atttgactac tggggccagg   480
ggacccaggt caccgtctcc tcaggcggag gtggctctgg tggcggaagt gaggtgcagc   540
tggtggagtc tgggggaggc ttggtgcagc ctggggggtc tctgagactc tcctgtgaag   600
cctctggatt cacttttgat gactatggca tgagctgggt ccgacaggct ccagggaagg   660
ggctggagtg ggtctcatct cttacccccga atggtggttc gacatactat gcagactccg   720
tgaagggccg attcaccatc tccagagaca acgccaagaa cacgctgtat ctgcaaatga   780
acagtttgaa acctgaggac acggccctgt attattgtgc aaagaactct tattacggtg   840
ccatggacta ctggggccaa gggacccagg tcaccgtctc ctcacatcac catcaccatc   900
actgataagc tt                                                        912
```

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64

```
aggtsmarct gcagsagtcw gg                                              22
```

<210> SEQ ID NO 65
<211> LENGTH: 265
<212> TYPE: PRT
<213> ORGANISM: Artificial sequence
<220> FEATURE:
<223> OTHER INFORMATION: RL493

<400> SEQUENCE: 65

```
Gln Val Gln Leu Gln Gln Ser Gly Gly Gly Ser Val Gln Ala Gly Gly
1               5                   10                  15

Ser Leu Arg Leu Ser Cys Val Gly Pro Gln Arg Thr Phe Ser Thr Tyr
            20                  25                  30

Gly Met Gly Trp Phe Arg Gln Ala Pro Gly Lys Glu Arg Glu Phe Val
        35                  40                  45

Ala Gly Ile Asn Tyr Lys Gly Asp Thr Thr Tyr Tyr Ala Asp Ser Val
```

```
                  50                  55                  60
Lys Gly Arg Phe Thr Ile Ser Arg Asp Asn Ala Lys Asn Thr Leu Tyr
 65                  70                  75                  80

Leu Gln Met Asp Ser Leu Lys Pro Glu Asp Arg Ala Val Tyr Gln Cys
                     85                  90                  95

Ala Arg Lys Gly Gly Leu Gly Gly Asp Tyr Arg Asp Ala Gly Gln Tyr
                100                 105                 110

Arg Tyr Trp Gly Gln Gly Thr Gln Val Thr Val Ser Ser Gly Gly Gly
                115                 120                 125

Gly Ser Gly Gly Gly Ser Glu Val Gln Leu Val Glu Ser Gly Gly Gly
                130                 135                 140

Leu Val Gln Ala Gly Gly Ser Leu Arg Leu Ser Cys Ala Ala Ser Gly
145                 150                 155                 160

Arg Thr Phe Ser Tyr Tyr Pro Met Ala Trp Phe Arg Gln Ala Pro Gly
                165                 170                 175

Gln Glu Arg Glu Phe Val Ala Ala Ile Gly Ala Asp Thr Thr Tyr Tyr
                180                 185                 190

Tyr Ala Asp Ser Leu Lys Gly Arg Phe Thr Ile Ser Arg Asp Asn Ala
                195                 200                 205

Lys Asn Met Val Tyr Leu Gln Met Asn Ser Leu Lys Pro Glu Asp Thr
                210                 215                 220

Ala Val Tyr Tyr Cys Ala Ala Arg Asn Thr Tyr Trp Ser Asp Val Tyr
225                 230                 235                 240

Tyr Arg Glu Gly Gln Tyr Thr Asn Trp Gly Gln Gly Thr Gln Val Thr
                245                 250                 255

Val Ser Ser His His His His His His
                260                 265

<210> SEQ ID NO 66
<211> LENGTH: 263
<212> TYPE: PRT
<213> ORGANISM: Artificial sequence
<220> FEATURE:
<223> OTHER INFORMATION: RL494

<400> SEQUENCE: 66

Gln Val Gln Leu Gln Glu Ser Gly Gly Gly Leu Val Gln Thr Gly Gly
 1                   5                  10                  15

Ser Leu Arg Leu Ser Cys Arg Ala Ser Gly Arg Ala Phe Ala Asn Tyr
                 20                  25                  30

His Phe Gly Trp Phe Arg Gln Ala Pro Gly Lys Asp Arg Glu Phe Val
                 35                  40                  45

Ala Ser Ile Ser Trp Lys Gly Gly Ser Thr Tyr Tyr Ala Asn Phe Ala
                 50                  55                  60

Leu Gly Arg Phe Thr Ser Ser Val Asp Arg Ala Glu Ser Ser Val Tyr
 65                  70                  75                  80

Leu Gln Met Ser Gly Leu Thr Pro Glu Asp Thr Ala Thr Tyr Tyr Cys
                 85                  90                  95

Ala Ala His Asp Gly Gly Asp Trp Asn Tyr His Thr Gly Met Asp Tyr
                100                 105                 110

Trp Gly Gln Gly Thr Gln Val Thr Val Ser Ser Gly Gly Gly Gly Ser
                115                 120                 125

Gly Gly Gly Ser Glu Val Gln Leu Val Glu Ser Gly Gly Gly Leu Val
                130                 135                 140

Gln Ala Gly Gly Ser Leu Arg Leu Ser Cys Ala Ala Ser Gly Arg Thr
```

```
                145                 150                 155                 160
Phe Ser Tyr Tyr Pro Met Ala Trp Phe Arg Gln Ala Pro Gly Gln Glu
                    165                 170                 175

Arg Glu Phe Val Ala Ala Ile Ile Gly Ala Asp Thr Thr Tyr Tyr Ala
                180                 185                 190

Asp Ser Leu Lys Gly Arg Phe Thr Ile Ser Arg Asp Asn Ala Lys Asn
                195                 200                 205

Met Val Tyr Leu Gln Met Asn Ser Leu Lys Pro Glu Asp Thr Ala Val
210                 215                 220

Tyr Tyr Cys Ala Ala Arg Asn Thr Tyr Trp Ser Asp Val Tyr Tyr Arg
225                 230                 235                 240

Glu Gly Gln Tyr Thr Asn Trp Gly Gln Gly Thr Gln Val Thr Val Ser
                245                 250                 255

Ser His His His His His His
                260

<210> SEQ ID NO 67
<211> LENGTH: 265
<212> TYPE: PRT
<213> ORGANISM: Artificial sequence
<220> FEATURE:
<223> OTHER INFORMATION: RL495

<400> SEQUENCE: 67

Gln Val Gln Leu Gln Glu Ser Gly Gly Gly Ser Val Gln Ala Gly Asp
1               5                   10                  15

Ser Leu Arg Leu Ser Cys Ala Ala Ser Gly Arg Thr Ile Ser Asn Tyr
                20                  25                  30

Ala Met Gly Trp Phe Arg Gln Ala Pro Gly Lys Gln Arg Glu Phe Val
            35                  40                  45

Ala Ala Ile Ser Arg Ser Asp Asn Thr Tyr Tyr Thr Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Ala
                85                  90                  95

Ala Asp Pro Asn Leu Met Tyr Glu Ser Lys Trp Lys Tyr Arg Ala Leu
                100                 105                 110

Glu Ala Trp Gly Gln Gly Thr Gln Val Thr Val Ser Ser Gly Gly Gly
            115                 120                 125

Gly Ser Gly Gly Gly Ser Glu Val Gln Leu Val Glu Ser Gly Gly Gly
        130                 135                 140

Leu Val Gln Ala Gly Gly Ser Leu Arg Leu Ser Cys Ala Ala Ser Gly
145                 150                 155                 160

Arg Thr Phe Ser Tyr Tyr Pro Met Ala Trp Phe Arg Gln Ala Pro Gly
                165                 170                 175

Gln Glu Arg Glu Phe Val Ala Ala Ile Ile Gly Ala Asp Thr Thr Tyr
            180                 185                 190

Tyr Ala Asp Ser Leu Lys Gly Arg Phe Thr Ile Ser Arg Asp Asn Ala
        195                 200                 205

Lys Asn Met Val Tyr Leu Gln Met Asn Ser Leu Lys Pro Glu Asp Thr
            210                 215                 220

Ala Val Tyr Tyr Cys Ala Ala Arg Asn Thr Tyr Trp Ser Asp Val Tyr
225                 230                 235                 240

Tyr Arg Glu Gly Gln Tyr Thr Asn Trp Gly Gln Gly Thr Gln Val Thr
```

```
                        245                 250                 255

Val Ser His His His His His His
            260                 265

<210> SEQ ID NO 68
<211> LENGTH: 258
<212> TYPE: PRT
<213> ORGANISM: Artificial sequence
<220> FEATURE:
<223> OTHER INFORMATION: RL496

<400> SEQUENCE: 68

Gln Val Gln Leu Gln Gln Ser Gly Gly Gly Ser Val Gln Ala Gly Gly
1               5                   10                  15

Ser Leu Arg Leu Ser Cys Val Gly Pro Gln Arg Thr Phe Ser Thr Tyr
            20                  25                  30

Gly Met Gly Trp Phe Arg Gln Ala Pro Gly Lys Glu Arg Glu Phe Val
        35                  40                  45

Ala Gly Ile Asn Tyr Lys Gly Asp Thr Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Arg Ala Val Tyr Gln Cys
                85                  90                  95

Ala Arg Lys Gly Gly Leu Gly Gly Asp Tyr Arg Asp Ala Gly Gln Tyr
            100                 105                 110

Arg Tyr Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Gly Ser Leu Arg Leu Ser Cys Glu Ala Ser Gly
145                 150                 155                 160

Phe Thr Phe Asp Asp Tyr Gly Met Ser Trp Val Arg Gln Ala Pro Gly
                165                 170                 175

Lys Gly Leu Glu Trp Val Ser Ser Leu Thr Pro Asn Gly Gly Ser Thr
            180                 185                 190

Tyr Tyr Ala Asp Ser Val Lys Gly Arg Phe Thr Ile Ser Arg Asp Asn
        195                 200                 205

Ala Lys Asn Thr Leu Tyr Leu Gln Met Asn Ser Leu Lys Pro Glu Asp
    210                 215                 220

Thr Ala Leu Tyr Tyr Cys Ala Lys Asn Ser Tyr Tyr Gly Ala Met Asp
225                 230                 235                 240

Tyr Trp Gly Gln Gly Thr Gln Val Thr Val Ser Ser His His His His
                245                 250                 255

His His

<210> SEQ ID NO 69
<211> LENGTH: 271
<212> TYPE: PRT
<213> ORGANISM: Artificial sequence
<220> FEATURE:
<223> OTHER INFORMATION: RL497

<400> SEQUENCE: 69

Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
```

```
            20                  25                  30
Thr Ile Ala Trp Phe Arg Arg Ala Gly Glu Gly Arg Val Glu Asp
            35                  40                  45
Gly Glu Gly Val Ala Ser Ile Thr Lys Ser Tyr Asp Arg Ala Tyr Asp
 50                  55                  60
Asn Lys Ile Asn Tyr Gly His Ser Val Lys Gly Arg Phe Thr Ile Ser
 65                  70                  75                  80
Arg Asp Asn Ala Lys Asn Thr Val Tyr Leu Gln Met Thr Asp Leu Leu
                 85                  90                  95
Pro Ser Asp Thr Ala Val Tyr Tyr Cys Ala Leu Asp Ile Thr Pro Pro
                100                 105                 110
Gly Gly Val Gly Ala Ser Leu Thr Glu Gly Phe Leu Phe Asp Tyr Trp
                115                 120                 125
Gly Gln Gly Thr Gln Val Thr Val Ser Ser Gly Gly Gly Ser Gly
                130                 135                 140
Gly Gly Ser Glu Val Gln Leu Val Glu Ser Gly Gly Gly Leu Val Gln
145                 150                 155                 160
Pro Gly Gly Ser Leu Arg Leu Ser Cys Glu Ala Ser Gly Phe Thr Phe
                165                 170                 175
Asp Asp Tyr Gly Met Ser Trp Val Arg Gln Ala Pro Gly Lys Gly Leu
                180                 185                 190
Glu Trp Val Ser Ser Leu Thr Pro Asn Gly Gly Ser Thr Tyr Tyr Ala
                195                 200                 205
Asp Ser Val Lys Gly Arg Phe Thr Ile Ser Arg Asp Asn Ala Lys Asn
                210                 215                 220
Thr Leu Tyr Leu Gln Met Asn Ser Leu Lys Pro Glu Asp Thr Ala Leu
225                 230                 235                 240
Tyr Tyr Cys Ala Lys Asn Ser Tyr Gly Ala Met Asp Tyr Trp Gly
                245                 250                 255
Gln Gly Thr Gln Val Thr Val Ser Ser His His His His His His
                260                 265                 270

<210> SEQ ID NO 70
<211> LENGTH: 256
<212> TYPE: PRT
<213> ORGANISM: Artificial sequence
<220> FEATURE:
<223> OTHER INFORMATION: RL498

<400> SEQUENCE: 70

Gln Val Gln Leu Gln Glu Ser Gly Gly Gly Leu Val Gln Thr Gly Gly
 1                   5                  10                  15
Ser Leu Arg Leu Ser Cys Arg Ala Ser Gly Arg Ala Phe Ala Asn Tyr
                 20                  25                  30
His Phe Gly Trp Phe Arg Gln Ala Pro Gly Lys Asp Arg Glu Phe Val
                 35                  40                  45
Ala Ser Ile Ser Trp Lys Gly Gly Ser Thr Tyr Tyr Ala Asn Phe Ala
                 50                  55                  60
Leu Gly Arg Phe Thr Ser Ser Val Asp Arg Ala Glu Ser Ser Val Tyr
 65                  70                  75                  80
Leu Gln Met Ser Gly Leu Thr Pro Glu Asp Thr Ala Thr Tyr Tyr Cys
                 85                  90                  95
Ala Ala His Asp Gly Asp Trp Asn Tyr His Thr Gly Met Asp Tyr
                100                 105                 110
Trp Gly Gln Gly Thr Gln Val Thr Val Ser Ser Gly Gly Gly Gly Ser
```

```
            115                 120                 125
Gly Gly Gly Ser Glu Val Gln Leu Val Glu Ser Gly Gly Leu Val
        130                 135                 140

Gln Pro Gly Gly Ser Leu Arg Leu Ser Cys Glu Ala Ser Gly Phe Thr
145                 150                 155                 160

Phe Asp Asp Tyr Gly Met Ser Trp Val Arg Gln Ala Pro Gly Lys Gly
                165                 170                 175

Leu Glu Trp Val Ser Ser Leu Thr Pro Asn Gly Gly Ser Thr Tyr Tyr
            180                 185                 190

Ala Asp Ser Val Lys Gly Arg Phe Thr Ile Ser Arg Asp Asn Ala Lys
        195                 200                 205

Asn Thr Leu Tyr Leu Gln Met Asn Ser Leu Lys Pro Glu Asp Thr Ala
    210                 215                 220

Leu Tyr Tyr Cys Ala Lys Asn Ser Tyr Tyr Gly Ala Met Asp Tyr Trp
225                 230                 235                 240

Gly Gln Gly Thr Gln Val Thr Val Ser His His His His His
                245                 250                 255

<210> SEQ ID NO 71
<211> LENGTH: 258
<212> TYPE: PRT
<213> ORGANISM: Artificial sequence
<220> FEATURE:
<223> OTHER INFORMATION: RL499

<400> SEQUENCE: 71

Gln Val Gln Leu Gln Glu Ser Gly Gly Gly Ser Val Gln Ala Gly Asp
1               5                   10                  15

Ser Leu Arg Leu Ser Cys Ala Ala Ser Gly Arg Thr Ile Ser Asn Tyr
            20                  25                  30

Ala Met Gly Trp Phe Arg Gln Ala Pro Gly Lys Gln Arg Glu Phe Val
        35                  40                  45

Ala Ala Ile Ser Arg Ser Asp Asn Thr Tyr Tyr Thr Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Glu Thr Ala Val Tyr Tyr Cys Ala
                85                  90                  95

Ala Asp Pro Asn Leu Met Tyr Glu Ser Lys Trp Lys Tyr Arg Ala Leu
            100                 105                 110

Glu Ala Trp Gly Gln Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Gly Ser Leu Arg Leu Ser Cys Glu Ala Ser Gly
145                 150                 155                 160

Phe Thr Phe Asp Asp Tyr Gly Met Ser Trp Val Arg Gln Ala Pro Gly
                165                 170                 175

Lys Gly Leu Glu Trp Val Ser Ser Leu Thr Pro Asn Gly Gly Ser Thr
            180                 185                 190

Tyr Tyr Ala Asp Ser Val Lys Gly Arg Phe Thr Ile Ser Arg Asp Asn
        195                 200                 205

Ala Lys Asn Thr Leu Tyr Leu Gln Met Asn Ser Leu Lys Pro Glu Asp
    210                 215                 220

Thr Ala Leu Tyr Tyr Cys Ala Lys Asn Ser Tyr Tyr Gly Ala Met Asp
```

-continued

```
                225                 230                 235                 240
Tyr Trp Gly Gln Gly Thr Gln Val Thr Val Ser Ser His His His His
                    245                 250                 255

His His

<210> SEQ ID NO 72
<211> LENGTH: 381
<212> TYPE: PRT
<213> ORGANISM: Artificial sequence
<220> FEATURE:
<223> OTHER INFORMATION: RL500

<400> SEQUENCE: 72

Gln Val Gln Leu Gln Gln Ser Gly Gly Gly Ser Val Gln Ala Gly Gly
1               5                   10                  15

Ser Leu Arg Leu Ser Cys Val Gly Pro Gln Arg Thr Phe Ser Thr Tyr
                20                  25                  30

Gly Met Gly Trp Phe Arg Gln Ala Pro Gly Lys Glu Arg Glu Phe Val
            35                  40                  45

Ala Gly Ile Asn Tyr Lys Gly Asp Thr Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asp Ser Leu Lys Pro Glu Asp Arg Ala Val Tyr Gln Cys
                85                  90                  95

Ala Arg Lys Gly Gly Leu Gly Gly Asp Tyr Arg Asp Ala Gly Gln Tyr
            100                 105                 110

Arg Tyr Trp Gly Gln Gly Thr Gln Val Thr Val Ser Ser Gln Val Gln
        115                 120                 125

Leu Gln Glu Ser Gly Gly Gly Leu Val Gln Thr Gly Gly Ser Leu Arg
    130                 135                 140

Leu Ser Cys Arg Ala Ser Gly Arg Ala Phe Ala Asn Tyr His Phe Gly
145                 150                 155                 160

Trp Phe Arg Gln Ala Pro Gly Lys Asp Arg Glu Phe Val Ala Ser Ile
                165                 170                 175

Ser Trp Lys Gly Gly Ser Thr Tyr Tyr Ala Asn Phe Ala Leu Gly Arg
            180                 185                 190

Phe Thr Ser Ser Val Asp Arg Ala Glu Ser Ser Val Tyr Leu Gln Met
        195                 200                 205

Ser Gly Leu Thr Pro Glu Asp Thr Ala Thr Tyr Tyr Cys Ala Ala His
    210                 215                 220

Asp Gly Gly Asp Trp Asn Tyr His Thr Gly Met Asp Tyr Trp Gly Gln
225                 230                 235                 240

Gly Thr Gln Val Thr Val Ser Ser Gly Gly Gly Ser Gly Gly Gly Gly
                245                 250                 255

Ser Glu Val Gln Leu Val Glu Ser Gly Gly Leu Val Gln Pro Gly
            260                 265                 270

Gly Ser Leu Arg Leu Ser Cys Glu Ala Ser Gly Phe Thr Phe Asp Asp
        275                 280                 285

Tyr Gly Met Ser Trp Val Arg Gln Ala Pro Gly Lys Gly Leu Glu Trp
    290                 295                 300

Val Ser Ser Leu Thr Pro Asn Gly Gly Ser Thr Tyr Tyr Ala Asp Ser
305                 310                 315                 320

Val Lys Gly Arg Phe Thr Ile Ser Arg Asp Asn Ala Lys Asn Thr Leu
                325                 330                 335
```

```
Tyr Leu Gln Met Asn Ser Leu Lys Pro Glu Asp Thr Ala Leu Tyr Tyr
                340                 345                 350

Cys Ala Lys Asn Ser Tyr Tyr Gly Ala Met Asp Tyr Trp Gly Gln Gly
            355                 360                 365

Thr Gln Val Thr Val Ser His His His His His
        370                 375             380
```

<210> SEQ ID NO 73
<211> LENGTH: 396
<212> TYPE: PRT
<213> ORGANISM: Artificial sequence
<220> FEATURE:
<223> OTHER INFORMATION: RL501

<400> SEQUENCE: 73

```
Gln Val Gln Leu Gln Glu Ser Gly Gly Gly Ser Val Gln Ala Gly Gly
1               5                   10                  15

Ser Leu Arg Leu Ser Cys Thr Ala Ser Glu Leu Ser Tyr Asp Asp Tyr
            20                  25                  30

Thr Ile Ala Trp Phe Arg Arg Ala Ala Gly Glu Gly Arg Val Glu Asp
        35                  40                  45

Gly Glu Gly Val Ala Ser Ile Thr Lys Ser Tyr Asp Arg Ala Tyr Asp
    50                  55                  60

Asn Lys Ile Asn Tyr Gly His Ser Val Lys Gly Arg Phe Thr Ile Ser
65                  70                  75                  80

Arg Asp Asn Ala Lys Asn Thr Val Tyr Leu Gln Met Thr Asp Leu Leu
                85                  90                  95

Pro Ser Asp Thr Ala Val Tyr Tyr Cys Ala Leu Asp Ile Thr Pro Pro
            100                 105                 110

Gly Gly Val Gly Ala Ser Leu Thr Glu Gly Phe Leu Phe Asp Tyr Trp
        115                 120                 125

Gly Gln Gly Thr Gln Val Thr Val Ser Ser Gln Val Gln Leu Gln Glu
    130                 135                 140

Ser Gly Gly Gly Ser Val Gln Ala Gly Asp Ser Leu Arg Leu Ser Cys
145                 150                 155                 160

Ala Ala Ser Gly Arg Thr Ile Ser Asn Tyr Ala Met Gly Trp Phe Arg
                165                 170                 175

Gln Ala Pro Gly Lys Gln Arg Glu Phe Val Ala Ala Ile Ser Arg Ser
            180                 185                 190

Asp Asn Thr Tyr Tyr Thr Asp Ser Val Lys Gly Arg Phe Thr Ile Ser
        195                 200                 205

Arg Asp Asn Ala Lys Asn Thr Leu Tyr Leu Gln Met Asn Ser Leu Lys
    210                 215                 220

Pro Glu Glu Thr Ala Val Tyr Tyr Cys Ala Ala Asp Pro Asn Leu Met
225                 230                 235                 240

Tyr Glu Ser Lys Trp Lys Tyr Arg Ala Leu Glu Ala Trp Gly Gln Gly
                245                 250                 255

Thr Gln Val Thr Val Ser Ser Gly Gly Gly Ser Gly Gly Gly Ser
            260                 265                 270

Glu Val Gln Leu Val Glu Ser Gly Gly Gly Leu Val Gln Pro Gly Gly
        275                 280                 285

Ser Leu Arg Leu Ser Cys Glu Ala Ser Gly Phe Thr Phe Asp Asp Tyr
    290                 295                 300

Gly Met Ser Trp Val Arg Gln Ala Pro Gly Lys Gly Leu Glu Trp Val
305                 310                 315                 320
```

Ser Ser Leu Thr Pro Asn Gly Gly Ser Thr Tyr Tyr Ala Asp Ser Val
            325                 330                 335

Lys Gly Arg Phe Thr Ile Ser Arg Asp Asn Ala Lys Asn Thr Leu Tyr
        340                 345                 350

Leu Gln Met Asn Ser Leu Lys Pro Glu Asp Thr Ala Leu Tyr Tyr Cys
    355                 360                 365

Ala Lys Asn Ser Tyr Tyr Gly Ala Met Asp Tyr Trp Gly Gln Gly Thr
370                 375                 380

Gln Val Thr Val Ser Ser His His His His His
385                 390                 395

<210> SEQ ID NO 74
<211> LENGTH: 271
<212> TYPE: PRT
<213> ORGANISM: Artificial sequence
<220> FEATURE:
<223> OTHER INFORMATION: RL502

<400> SEQUENCE: 74

Gln Val Gln Leu Gln Glu Ser Gly Gly Gly Val Gln Ala Gly Gly
1               5                   10                  15

Ser Leu Arg Leu Ser Cys Thr Ala Ser Glu Phe Ser Tyr Asn Asp Tyr
            20                  25                  30

Thr Ile Ala Trp Phe Arg Arg Ala Ala Gly Lys Gly Arg Val Glu Asp
        35                  40                  45

Gly Glu Gly Val Ala Ser Ile Thr Thr Ser Tyr Asp Arg Ala Tyr Asp
    50                  55                  60

Asn Arg Ile His Tyr Gly Asp Ser Val Lys Gly Arg Phe Thr Ile Ser
65                  70                  75                  80

Arg Asp Asn Ala Lys Asn Thr Val Tyr Leu Gln Met Thr Asn Leu Asn
                85                  90                  95

Pro Ser Asp Thr Ala Val Tyr Tyr Cys Gly Leu Asp Ile Thr Pro Pro
            100                 105                 110

Gly Gly Ile Gly Ala Ser Leu Thr Glu Gly Phe Leu Phe Asp Tyr Trp
        115                 120                 125

Gly Gln Gly Thr Gln Val Thr Val Ser Ser Gly Gly Gly Gly Ser Gly
    130                 135                 140

Gly Gly Ser Glu Val Gln Leu Val Glu Ser Gly Gly Gly Leu Val Gln
145                 150                 155                 160

Pro Gly Gly Ser Leu Arg Leu Ser Cys Glu Ala Ser Gly Phe Thr Phe
                165                 170                 175

Asp Asp Tyr Gly Met Ser Trp Val Arg Gln Ala Pro Gly Lys Gly Leu
            180                 185                 190

Glu Trp Val Ser Ser Leu Thr Pro Asn Gly Gly Ser Thr Tyr Tyr Ala
        195                 200                 205

Asp Ser Val Lys Gly Arg Phe Thr Ile Ser Arg Asp Asn Ala Lys Asn
    210                 215                 220

Thr Leu Tyr Leu Gln Met Asn Ser Leu Lys Pro Glu Asp Thr Ala Leu
225                 230                 235                 240

Tyr Tyr Cys Ala Lys Asn Ser Tyr Tyr Gly Ala Met Asp Tyr Trp Gly
                245                 250                 255

Gln Gly Thr Gln Val Thr Val Ser Ser His His His His His His
            260                 265                 270

<210> SEQ ID NO 75

<211> LENGTH: 1311
<212> TYPE: DNA
<213> ORGANISM: Artificial sequence
<220> FEATURE:
<223> OTHER INFORMATION: pRL505

<400> SEQUENCE: 75

| | |
|---|---|
| atgatgcttt tgcaagcctt ccttttcctt ttggctggtt ttgcagccaa aatatctgcg | 60 |
| caggtgcagc tgcaggagtc aggggggaggc tcggtgcagg ctgggggggtc gctgagactc | 120 |
| tcctgtacag cctctgaact cagttacgat gattatacca tagcatggtt ccgccgggcc | 180 |
| gcaggagagg ggcgtgtgga ggacggtgag ggggtcgcct ctattacgaa aagttatgac | 240 |
| agggcctacg ataacaagat caactatggt cactctgtga agggccggtt caccatctcc | 300 |
| agagacaacg ccaagaacac ggtgtatttg cagatgaccg atctgcttcc atctgacacg | 360 |
| gccgtttact attgtgcact ggatattacg ccgccgggtg gagtaggagc aagtttgact | 420 |
| gagggatttt tatttgacta ctggggccag gggacccagg tcaccgtctc ctcaggtggc | 480 |
| ggtggctcgg gcggtggtgg gtcggtggcc ggcggatctc aggtgcagct gcaggagtct | 540 |
| gggggaggat tggtgcagac tggggggctct ctgagactct cctgtcgagc ctctggacgc | 600 |
| gccttcgcta actatcactt cggctggttc cgccaggctc aggaaaagga ccgagagttt | 660 |
| gtagcttcta ttagctggaa aggtggtagt acatattacg caaatttcgc gctcggccgc | 720 |
| ttcaccagct ccgtggatag ggccgaaagc tcggtgtatc tgcaaatgag cggcctgaca | 780 |
| cctgaggaca cggccactta ttactgtgca gcccacgacg gtggggactg gaactaccac | 840 |
| accggcatgg actattgggg ccaggggacc caggtcaccg tctcctcagg cggaggtggc | 900 |
| tctggtggcg gaagtgaggt gcagctggtg gagtctgggg gaggattggt gcaggctggg | 960 |
| ggctctctga actctcctg tgcagcctct ggacgcacct tcagttacta tcccatggcc | 1020 |
| tggttccgcc aggctccagg gcaggagcgt gagtttgtag cagctattat tggtgccgat | 1080 |
| accacatact atgcagactc tctgaagggc cgattcacca tctccagaga caacgccaag | 1140 |
| aacatggtgt atctgcaaat gaacagcctg aaacctgagg acacggccgt ttattactgt | 1200 |
| gcagcgagga atacatactg gagtgatgtc tactaccgag aaggccagta tacgaactgg | 1260 |
| ggccagggga cccaggtcac cgtctcctca catcaccatc accatcactg a | 1311 |

<210> SEQ ID NO 76
<211> LENGTH: 1290
<212> TYPE: DNA
<213> ORGANISM: Artificial sequence
<220> FEATURE:
<223> OTHER INFORMATION: pRL506

<400> SEQUENCE: 76

| | |
|---|---|
| atgatgcttt tgcaagcctt ccttttcctt ttggctggtt ttgcagccaa aatatctgcg | 60 |
| caggtgcagc tgcaggagtc tggggggagga ttggtgcaga ctgggggctc tctgagactc | 120 |
| tcctgtcgag cctctggacg cgccttcgct aactatcact tcggctggtt ccgccaggct | 180 |
| ccaggaaagg accgagagtt tgtagcttct attagctgga aaggtggtag tacatattac | 240 |
| gcaaatttcg cgctcggccg cttcaccagc tccgtggata gggccgaaag ctcggtgtat | 300 |
| ctgcaaatga gcggcctgac acctgaggac acggccactt attactgtgc agcccacgac | 360 |
| ggtggggact ggaactacca caccggcatg gactattggg gccaggggac ccaggtcacc | 420 |
| gtctcctcag gtggcggtgg ctcggggcggt ggtgggtcgg tggcggcgg atctcaggtg | 480 |
| cagctgcagg agtcaggggg aggctcggtg caggctgggg ggtcgctgag actctcctgt | 540 |

-continued

```
acagcctctg aactcagtta cgatgattat accatagcat ggttccgccg ggccgcagga    600
gagggggcgtg tggaggacgg tgaggggggtc gcctctatta cgaaaagtta tgacagggcc   660
tacgataaca agatcaacta tggtcactct gtgaagggcc ggttcaccat ctccagagac    720
aacgccaaga acacggtgta tttgcagatg accgatctgc ttccatctga cacggccgtt    780
tactattgtg cactggatat tacgccgccg ggtggagtag gagcaagttt gactgaggga    840
tttttatttg actactgggg ccaggggacc caggtcaccg tctcctcagg cggaggtggc    900
tctggtggcg gaagtgaggt gcagctggtg gagtctgggg gaggcttggt gcagcctggg   960
gggtctctga gactctcctg tgaagcctct ggattcactt ttgatgacta tgcatgagc    1020
tgggtccgac aggctccagg gaaggggctg gagtgggtct catctcttac cccgaatggt   1080
ggttcgacat actatgcaga ctccgtgaag ggccgattca ccatctccag agacaacgcc   1140
aagaacacgc tgtatctgca aatgaacagt ttgaaacctg aggacacggc cctgtattat   1200
tgtgcaaaga actcttatta cggtgccatg gactaccggg gccaagggac ccaggtcacc   1260
gtctcctcac atcaccatca ccatcactga                                    1290
```

<210> SEQ ID NO 77
<211> LENGTH: 436
<212> TYPE: PRT
<213> ORGANISM: Artificial sequence
<220> FEATURE:
<223> OTHER INFORMATION: RL505

<400> SEQUENCE: 77

```
Met Met Leu Leu Gln Ala Phe Leu Phe Leu Leu Ala Gly Phe Ala Ala
1               5                   10                  15
Lys Ile Ser Ala Gln Val Gln Leu Gln Glu Ser Gly Gly Gly Ser Val
            20                  25                  30
Gln Ala Gly Gly Ser Leu Arg Leu Ser Cys Thr Ala Ser Glu Leu Ser
        35                  40                  45
Tyr Asp Asp Tyr Thr Ile Ala Trp Phe Arg Arg Ala Ala Gly Glu Gly
    50                  55                  60
Arg Val Glu Asp Gly Glu Gly Val Ala Ser Ile Thr Lys Ser Tyr Asp
65                  70                  75                  80
Arg Ala Tyr Asp Asn Lys Ile Asn Tyr Gly His Ser Val Lys Gly Arg
                85                  90                  95
Phe Thr Ile Ser Arg Asp Asn Ala Lys Asn Thr Val Tyr Leu Gln Met
            100                 105                 110
Thr Asp Leu Leu Pro Ser Asp Thr Ala Val Tyr Tyr Cys Ala Leu Asp
        115                 120                 125
Ile Thr Pro Pro Gly Gly Val Gly Ala Ser Leu Thr Glu Gly Phe Leu
    130                 135                 140
Phe Asp Tyr Trp Gly Gln Gly Thr Gln Val Thr Val Ser Ser Gly Gly
145                 150                 155                 160
Gly Gly Ser Gly Gly Gly Gly Ser Gly Gly Gly Ser Gln Val Gln
                165                 170                 175
Leu Gln Glu Ser Gly Gly Gly Leu Val Gln Thr Gly Gly Ser Leu Arg
            180                 185                 190
Leu Ser Cys Arg Ala Ser Gly Arg Ala Phe Ala Asn Tyr His Phe Gly
        195                 200                 205
Trp Phe Arg Gln Ala Pro Gly Lys Asp Arg Glu Phe Val Ala Ser Ile
    210                 215                 220
```

```
Ser Trp Lys Gly Gly Ser Thr Tyr Tyr Ala Asn Phe Ala Leu Gly Arg
225                 230                 235                 240

Phe Thr Ser Ser Val Asp Arg Ala Glu Ser Ser Val Tyr Leu Gln Met
            245                 250                 255

Ser Gly Leu Thr Pro Glu Asp Thr Ala Thr Tyr Tyr Cys Ala Ala His
        260                 265                 270

Asp Gly Gly Asp Trp Asn Tyr His Thr Gly Met Asp Tyr Trp Gly Gln
    275                 280                 285

Gly Thr Gln Val Thr Val Ser Ser Gly Gly Gly Ser Gly Gly Gly
290                 295                 300

Ser Glu Val Gln Leu Val Glu Ser Gly Gly Leu Val Gln Ala Gly
305                 310                 315                 320

Gly Ser Leu Arg Leu Ser Cys Ala Ala Ser Gly Arg Thr Phe Ser Tyr
            325                 330                 335

Tyr Pro Met Ala Trp Phe Arg Gln Ala Pro Gly Gln Glu Arg Glu Phe
        340                 345                 350

Val Ala Ala Ile Ile Gly Ala Asp Thr Thr Tyr Tyr Ala Asp Ser Leu
            355                 360                 365

Lys Gly Arg Phe Thr Ile Ser Arg Asp Asn Ala Lys Asn Met Val Tyr
370                 375                 380

Leu Gln Met Asn Ser Leu Lys Pro Glu Asp Thr Ala Val Tyr Tyr Cys
385                 390                 395                 400

Ala Ala Arg Asn Thr Tyr Trp Ser Asp Val Tyr Tyr Arg Glu Gly Gln
                405                 410                 415

Tyr Thr Asn Trp Gly Gln Gly Thr Gln Val Thr Val Ser Ser His His
            420                 425                 430

His His His His
        435

<210> SEQ ID NO 78
<211> LENGTH: 429
<212> TYPE: PRT
<213> ORGANISM: Artificial sequence
<220> FEATURE:
<223> OTHER INFORMATION: RL506

<400> SEQUENCE: 78

Met Met Leu Leu Gln Ala Phe Leu Phe Leu Leu Ala Gly Phe Ala Ala
1               5                   10                  15

Lys Ile Ser Ala Gln Val Gln Leu Gln Glu Ser Gly Gly Gly Leu Val
                20                  25                  30

Gln Thr Gly Gly Ser Leu Arg Leu Ser Cys Arg Ala Ser Gly Arg Ala
            35                  40                  45

Phe Ala Asn Tyr His Phe Gly Trp Phe Arg Gln Ala Pro Gly Lys Asp
        50                  55                  60

Arg Glu Phe Val Ala Ser Ile Ser Trp Lys Gly Gly Ser Thr Tyr Tyr
65                  70                  75                  80

Ala Asn Phe Ala Leu Gly Arg Phe Thr Ser Ser Val Asp Arg Ala Glu
                85                  90                  95

Ser Ser Val Tyr Leu Gln Met Ser Gly Leu Thr Pro Glu Asp Thr Ala
            100                 105                 110

Thr Tyr Tyr Cys Ala Ala His Asp Gly Gly Asp Trp Asn Tyr His Thr
        115                 120                 125

Gly Met Asp Tyr Trp Gly Gln Gly Thr Gln Val Thr Val Ser Ser Gly
    130                 135                 140
```

```
Gly Gly Gly Ser Gly Gly Gly Ser Gly Gly Gly Ser Gln Val
145                 150                 155                 160

Gln Leu Gln Glu Ser Gly Gly Ser Val Gln Ala Gly Gly Ser Leu
                165                 170                 175

Arg Leu Ser Cys Thr Ala Ser Glu Leu Ser Tyr Asp Asp Tyr Thr Ile
                180                 185                 190

Ala Trp Phe Arg Arg Ala Ala Gly Glu Gly Arg Val Glu Asp Gly Glu
            195                 200                 205

Gly Val Ala Ser Ile Thr Lys Ser Tyr Asp Arg Ala Tyr Asp Asn Lys
                210                 215                 220

Ile Asn Tyr Gly His Ser Val Lys Gly Arg Phe Thr Ile Ser Arg Asp
225                 230                 235                 240

Asn Ala Lys Asn Thr Val Tyr Leu Gln Met Thr Asp Leu Leu Pro Ser
                245                 250                 255

Asp Thr Ala Val Tyr Tyr Cys Ala Leu Asp Ile Thr Pro Pro Gly Gly
                260                 265                 270

Val Gly Ala Ser Leu Thr Glu Gly Phe Leu Phe Asp Tyr Trp Gly Gln
                275                 280                 285

Gly Thr Gln Val Thr Val Ser Ser Gly Gly Gly Gly Ser Gly Gly Gly
                290                 295                 300

Ser Glu Val Gln Leu Val Glu Ser Gly Gly Gly Leu Val Gln Pro Gly
305                 310                 315                 320

Gly Ser Leu Arg Leu Ser Cys Glu Ala Ser Gly Phe Thr Phe Asp Asp
                325                 330                 335

Tyr Gly Met Ser Trp Val Arg Gln Ala Pro Gly Lys Gly Leu Glu Trp
                340                 345                 350

Val Ser Ser Leu Thr Pro Asn Gly Gly Ser Thr Tyr Tyr Ala Asp Ser
                355                 360                 365

Val Lys Gly Arg Phe Thr Ile Ser Arg Asp Asn Ala Lys Asn Thr Leu
                370                 375                 380

Tyr Leu Gln Met Asn Ser Leu Lys Pro Glu Asp Thr Ala Leu Tyr Tyr
385                 390                 395                 400

Cys Ala Lys Asn Ser Tyr Tyr Gly Ala Met Asp Tyr Arg Gly Gln Gly
                405                 410                 415

Thr Gln Val Thr Val Ser Ser His His His His His His
                420                 425
```

SINGLE DOMAIN ANTIBODIES BINDING TO TETANUS NEUROTOXIN

FIELD OF THE INVENTION

The present invention i.a. relates to single domain antibodies (SDA) capable of binding to tetanus neurotoxin, polypeptide constructs comprising such SDAs, compositions comprising such SDAs and/or polypeptide constructs and to DNA fragments encoding such SDA and/or polypeptide constructs. Furthermore, the invention relates to host cells comprising such DNA fragments, methods for the production of such SDAs and/or polypeptide constructs and to the use of such SDAs and/or polypeptide constructs and/or compositions in the treatment or prevention of disease after *Clostridium tetani* infection.

BACKGROUND OF THE INVENTION

Tetanus, a disease caused by the bacterium *Clostridium tetani*, was first described in Egypt about 3000 years ago.

Tetanus toxaemia is caused by a specific neurotoxin; tetanus neurotoxin (TeNT) produced by the bacterium *Clostridium tetani*. Almost all mammals including humans, are susceptible. Humans, horses and lambs are amongst the most sensitive of all species. Dogs and cats are relatively more resistant. Tetanus is found worldwide but the occurrence of *C. tetani* in the soil and the incidence of tetanus in people, horses, and lambs are higher in the warmer parts of the various continents. In most cases, the bacterium *C. tetani* is introduced into the tissues through wounds. Tetanus typically follows deep penetrating wounds where anaerobic bacterial growth is facilitated. In lambs, however, and sometimes in other species, tetanus may also follow docking or castration.

Tetanus neurotoxin is a zinc-binding protease that cleaves synaptobrevin, a vesicle-associated membrane protein. The cleavage of this protein leads to the inhibition of neurotransmitter release. The toxin is absorbed by the motor nerves in the area of infection and travels retrograde up the nerve tract to the spinal cord, where it causes ascending tetanus.

TeNT is synthesized as a 150 kDa single polypeptide chain. This polypeptide is cleaved into a heavy chain (H) of 100 kDa and a light chain (L) of 50 kDa which are held together by a disulfide bond and form the active toxin. Digestion of the holotoxin with papain results in fragment B which is comprised of the TeNT light chain and the amino terminal half of the TeNT heavy chain (HN), and fragment C (Hc or TTC) which contains the carboxy terminal half of the heavy chain. In vitro experiments have suggested that Hc is responsible for binding to neurons through gangliosides while the HN fragment plays a role in internalization and membrane translocation.

The incubation period (the time from infection to the first symptom) can be as short as 24 hours or as long as many months after inoculation with *C. tetani*. This interval is a reflection of the distance the toxin must travel within the nervous system, and may be related to the quantity of toxin released. The period of onset is the time between the first symptom and the start of spastic paralysis. The incubation period usually averages $10^{-14}$ days. Localized stiffness, often involving the masseter muscles and muscles of the neck, the hindlimbs, and the region of the infected wound, is seen first; general stiffness becomes pronounced ~1 day later, and tonic spasms and hyperesthesia become evident. Because of their relatively high resistance to tetanus toxin, dogs and cats often have a long incubation period and frequently develop localized tetanus; however, generalized tetanus does develop in these species. A comprehensive description of tetanus neurotoxin (and the related botulinum neurotoxin) can be found in BOTULINUM AND TETANUS NEUROTOXINS, ISBN 978-1-4757-9544-8, © 1993 Springer Science & Business Media New York. Originally published by Plenum Press, New York in 1993. A review relating to tetanus, its cause and the effects, as well as methods of treatment can e.g. be found in Farrar, J. J. et al., in the J. Neurol Neurosurg Psychiatry 69:292-301 (2000).

Passive immunisation with polyclonal human or for example equine tetanus antitoxin shortens the course and may reduce the severity of tetanus. The equine antiserum (Fab) is prepared from a pool of serum collected from immunized equines, and has a half-life of 12-20 hrs in humans (Flanagan R J, Jones A L. Drug Saf. 2004; 27(14): 1115-33). The equine (or bovine) form, used throughout the developing world, causes incidentally anaphylactic reactions but is much cheaper and easier to produce than the human donor serum.

Treatment of tetanus disease consists of administration of antibiotics or metronidazole, by treatment of the site of infection (e.g. flushed, drained and debrided), antitoxin administration and supportive care (e.g. muscle relaxant, sedative, hydration etc.). Passive immunisation with preparations containing immunoglobulins (e.g. purified and fragmented) obtained from actively immunized sheep or horses provides effective protection in unimmunized animals and humans.

Tetanus antitoxin (e.g. in the form of SDAs or immune sera) can be used in at least 3 different scenarios: as part of a pre-operative standard procedure, in animals that are injured but not diseased yet and thirdly in a therapeutic scenario when the animal is suffering from tetanus. There is a difference in antitoxin dose used, depending on prophylactic or therapeutic treatment, the latter being at 2-20 fold higher dose depending on the species. In cases of tetanus daily treatments may be necessary.

Up till today, administration of antiserum raised in e.g. horses and human volunteers is the only treatment for acute tetanus disease. In principle, a possible alternative could be offered by purified antibodies and their engineered variants such as antigen-binding fragments (Fab) and single-chain variable fragments (scFv). In vitro produced tetanus antitoxin SDAs, avoiding animal and human donors, are not yet commercially available as human or veterinary medicinal products. An example of anti-tetanus toxin single-chain variable fragments is described by Nathan Scott et al., in Molecular Immunology 47: 1931-1941 (2010).

However, although useful, common antibodies and their engineered variants Fab and scFv have several limitations. Examples of such limitations are low solubility, low stability and high costs and animal usage (Doshi, R. et al., Scientific Reports 4:6760 DOI; 10.1030/srep06760). Such regular antibodies and their fragments have relatively large molecular weight: the average MW of regular antibodies is about 160 kDa, Fabs have a MW of 65 kDa and even the relatively small scFv have a MW of 28 kDa.

On top of this, there is the problem of poor production feasibility: production of larger proteins is sometimes problematic and in any case expensive.

The monomeric, hyper-variable, antigen-binding regions of homodimeric, heavy-chain-only antibodies (HCAbs) naturally found in camelids and some species of sharks lack many of the disadvantages of common antibodies and their engineered variants Fab and scFv. For clarity reasons, this variable domain derived from a heavy chain molecule naturally devoid of light chain is referred to also as a VHH when derived from camelids and $V_{NAR}$ when derived from sharks to distinguish it from the conventional VH of four chain immunoglobulins. For convenience, the anti-TeNT VHHs will further be referred to herein as single domain antibodies (SDAs).

An early patent family relating to the structure, composition, preparation and uses of heavy chain antibodies devoid of light chains and the isolated antigen binding fragments thereof is the patent family comprising EP 0656946. Such single domain molecules are i.a. also described by Hamers-Casterman, C. et al., Nature 363: 446-448 (1993). They can be derived from Camelid species, for example in camel, llama, dromedary, alpaca and guanaco. Compared to regular antibodies and their fragments, the molecular size of SDAs is the smallest (about 15 kDa). SDA are also very robust, highly resistant to denaturation/thermal degradation, have high aqueous solubility, and in general, are highly and functionally expressed using standard microbial expression systems. Furthermore, SDA also have superior body distribution and tissue penetration. This makes them attractive for clinical use.

An example of SDAs capable of binding to tetanus toxoid is described in Arbabi Ghahroudi (M. Arbabi Ghahroudi, A. Desmyter, L. Wyns, R. Hamers, S. Muyldermans. Selection and identification of single domain antibody fragments from camel heavy-chain antibodies. FEBS Letters 414 (1997) 521-526). WO 96/34103 discloses SDAs capable of binding to tetanus toxoid. Mouse studies show that at low toxin doses administration of the SDAs allowed survival of about 40-50% of treated mice after 2 to 4 days. These results are also reported in Arbabi Ghahroudi et al., FEBS LETTERS (1997), 414, 521-526. Rossotti et al. (MABS, DOI: 10.1080/19420862.2015.1068491) describe SDAs binding to tetanus toxin.

A specific problem seen with the clostridial neurotoxins is their extremely high toxicity. TeNT is toxic in humans already in concentrations as low 0.1-2.5 ng/kg and in other animals already in concentrations as low 0.1-5 ng/kg. In horses, the lethal dose is e.g. between 0.1 and 0.3 ng/kg. This means that only high-affinity antibodies capable of binding to TeNT, and subsequently preventing uptake in the neuron, will be capable of bringing the level of free TeNT down to a level that suppresses or even avoids the fatal symptoms of tetanus once infection with *Clostridium tetani* has taken place.

The direct measurement of biomolecular interactions plays an important role in biotherapeutic drug discovery and development. Accurate information about the rate of biomolecular complex formation and complex stability, are key components of a drug-target interaction. The affinity of an interaction directly affects the dose at which a biopharmaceutical is effective. The affinity of an antibody for an antigen can be determined experimentally using any suitable method see, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein, Lad, L. et al., Journal of Biomolecular Screening 2015, Vol. 20(4) 498-507, Yang, D. et al., doi:10.3791/55659). The measured affinity of a particular antibody-target protein interaction can vary if measured under different conditions (e.g., salt concentration, pH). Thus, measurements of affinity, or avidity in case of multimeric SDAs, (e.g., $K_D, k_a, k_{dis}$) are preferably made with standardized solutions of antibody and antigen, and a standardized buffer.

Up till now, however, anti-TeNT SDAs do have a $K_D$ that exceeds 1-10 nM or even 35 nM, indicating a lower affinity. This can be seen i.a. in Rossotti et al. (2015, mAbs, 7:5, 820-828, DOI: 10.1080/19420862.2015.1068491) and in Arbabi Ghahroudi, referred to above.

SUMMARY OF THE INVENTION

In an aspect, the present invention relates to a single domain antibody (SDA) capable of binding to tetanus neurotoxin (TeNT), wherein the SDA has an overall amino acid sequence identity of at least 70% with a sequence selected from the group consisting of SEQ ID NO: 17, 13, 14, 15, 16, 18, 19, 20, 21, 22, 23, 24, 25 and 26 with the proviso that the amino acid sequence identities of CDR1, CDR2 and CDR3 are at least 75%.

In a preferred embodiment, the SDA has an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or preferably 100% with a sequence selected from the group consisting of SEQ ID NO: 17, 13, 14, 15, 16, 18, 19, 20, 21, 22, 23, 24, 25 and 26, with the proviso that the amino acid sequence identities of CDR1, CDR2 and CDR3 are at least 75%.

Alternatively, or in combination with a previous embodiment, in a further preferred embodiment, the amino acid sequence identities of CDR1, CDR2 and CDR3 are at least 76, 77, 78, 79, 80, 81, 82, 83, 84, 85, 86, 87, 88, 89, 90, 91, 92, 93, 94, 95, 96, 97, 98, 99 or preferably 100%.

In a further aspect, the present invention relates to a polypeptide construct comprising at least one SDA capable of binding to TeNT according to the invention and at least one SDA capable of binding to a serum protein. Preferably, the serum protein is serum albumin or an immunoglobulin. More preferably the immunoglobulin is immunoglobulin G (IgG). In a preferred embodiment, the SDA capable of binding to serum albumin has an overall amino acid sequence identity of at least 70% with a sequence selected from the group consisting of SEQ ID NO: 40, 37, 38, 39, 41 and 42, with the proviso that the amino acid sequence identities of CDR1, CDR2 and CDR3 are at least 75%. In a preferred embodiment, the SDA capable of binding to the immunoglobulin has an overall amino acid sequence identity of at least 70% with a sequence selected from the group consisting of SEQ ID NO: 30, 27, 28, 29, 31, 32, 33 and 34, with the proviso that the amino acid sequence identities of CDR1, CDR2 and CDR3 are at least 75%.

In a preferred embodiment, the polypeptide construct comprises at least two SDAs capable of binding to TeNT wherein each of the at least two SDAs capable of binding to TeNT has an overall amino acid sequence identity of at least 70% with a sequence selected from selection A; SEQ ID NO: 24, or selection B; SEQ ID NO: 25, or selection C; SEQ ID NO: 20, or selection D; SEQ ID NO: 17 or 19 or selection E; SEQ ID NO: 22, 15, 23 or 14, with the proviso that the at least two SDAs do not comprise a sequence from the same selection and with the proviso that the amino acid sequence identities of CDR1, CDR2 and CDR3 are at least 75%.

In a further aspect, the present invention relates to a pharmaceutical composition comprising at least one SDA capable of binding to TeNT according to the invention and/or at least one polypeptide construct according to the invention, and a pharmaceutically acceptable carrier. Preferably, the composition comprises at least two SDAs capable of binding to TeNT according to the invention and/or at least one polypeptide construct according to the invention.

In a further aspect, the present invention relates to an SDA capable of binding to TeNT according to the invention or a polypeptide construct according to the invention for use as a medicament.

In yet another aspect, the present invention relates to an SDA capable of binding to TeNT according to the invention, a polypeptide construct according to the invention or a pharmaceutical composition according to the invention, for use in the prevention or treatment of Clostridium tetani disease/symptoms.

In a further aspect, the present invention relates to a DNA fragment encoding an SDA capable of binding to TeNT according to the invention or a polypeptide construct according to the invention.

In another aspect, the present invention relates to a nucleic acid comprising a DNA fragment according to the invention, wherein the DNA fragment is operably linked to a promoter and optionally other regulatory elements.

In a further aspect, the present invention relates to a host cell comprising a nucleic acid according to the invention.

In yet a further aspect, the present invention relates to a method for the production of an SDA according to the invention or a polypeptide construct according to the invention, wherein the method comprises the steps of a) culturing of a host cell according to the invention under conditions allowing the expression of the SDA or polypeptide construct; and optionally b) recovering the SDA or polypeptide construct from at least one of the host cell and the culture medium.

In an aspect, the present invention relates to a diagnostic kit, comprising at least one SDA capable of binding to TeNT according to the invention.

DESCRIPTION OF THE INVENTION

Surprisingly, it was found now that anti-TeNT SDAs can be obtained that possess a $K_D$ that is significantly lower than that of known anti-TeNT SDAs and that possess in vivo tetanus toxin neutralising activity. Such novel anti-TeNT SDAs have the advantage that they are capable of binding to TeNT with an extremely high affinity. This shifts the balance between free and bound TeNT molecules extremely far to the bound TeNT molecules, which in turn sufficiently suppresses the fatal symptoms of tetanus after infection with Clostridium tetani.

Several groups of anti-TeNT SDAs have now been identified that have $K_D$ values of below 1 nM. FIG. 1 shows the sequences of seven groups or examples of members of groups (Group A, B, C, D, and one member of each of groups E, F and G) of SDAs. The three shaded regions indicate where the hypervariable regions or complementarity-determining regions (CDRs) are located. As can be seen from FIG. 1, some natural variation does exist between individual SDAs. These variations may be due to (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in "The Proteins" Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M.D., Atlas of protein sequence and structure, Nat. Biomed. Res. Found., Washington D.C., 1978, vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (Science 227, 1435-1441, 1985) and determining the functional similarity between homologous proteins. Amino acid substitutions of the exemplary embodiments of this invention, as well as variations having deletions and/or insertions are within the scope of the invention as long as the resulting proteins are not essentially affected in their antigenic or immunogenic properties.

This explains why SDAs according to the invention may have overall amino acid sequence identity levels of about 70%, while still representing the same protein in the sense that the protein still has a $K_D$ value of <1 nM. Those variations in the amino acid sequence of a certain SDA according to the invention that still provide an SDA having a Ko value of <1 nM are considered as "not essentially affecting the antigenic or immunogenic properties of said protein".

In a first aspect the present invention relates to an antigen-binding protein, preferably a single domain antibody (SDA), capable of binding to tetanus neurotoxin (TeNT), wherein the antigen-binding domain has an overall amino acid sequence identity of at least 70% with a sequence selected from the group consisting of SEQ ID NO: 17, 13, 14, 15, 16, 18, 19, 20, 21, 22, 23, 24, 25 and 26 with the proviso that the amino acid sequence identities of CDR1, CDR2 and CDR3 region are at least 75%.

Alternatively said, in this aspect, the present invention relates to an antigen-binding protein that specifically binds to tetanus neurotoxin (TeNT). Preferably, the antigen-binding protein comprises an amino acid sequence that comprises 4 framework regions, FR1 to FR4, and 3 complementarity-determining regions, CDR1 to CDR3, that are operably linked in the order FR1-CDR1-FR2-CDR2-FR3-CDR3-FR4. Preferably, the CDR1 has an amino acid sequence selected from the group consisting of the CDR1 sequences of the VHH sequences SEQ ID NOs: 13-26, as shown in FIG. 1 or an amino acid sequence that differs from the CDR1 in one or two of the amino acid residues; b) the CDR2 has an amino acid sequence selected from the group consisting of the CDR2 sequences of the VHH sequences SEQ ID NOs: 13-26, as shown in FIG. 1 or an amino acid sequence that differs from the CDR2 in one, two, three or four of the amino acid residues; and, c) the CDR3 has an amino acid sequence selected from the group consisting of the CDR3 sequences of the VHH sequences SEQ ID NOs: 13-26, as shown in FIG. 1 or an amino acid sequence that differs from the CDR3 in one, two, three, four or five of the amino acid residues; and, wherein each of the framework regions has at least 50, 55, 60, 65, 70, 75, 80, 85, 90, 95 or 100% amino acid identity with the framework amino acid sequence of any one of SEQ ID NOs: 13-26, as shown in FIG. 1. Preferably, CDR1, CDR2 and CDR3 are from the same SEQ ID NO. More preferably, the framework region is from the same SEQ ID NO as the complementarity-determining regions.

An overall amino acid sequence identity level of a certain percentage as used herein, such as about 70%, means that the level of amino acid sequence identity of the whole antigen-binding protein—in other words: when the two sequences are aligned over their entire length FR1-CDR1-FR2-CDR2-FR3-CDR3-FR4—is about 70%. Thus, "overall" in this context is used to include CDRs 1-3. "Sequence identity" or "identity" is herein defined as a relationship between two or more amino acid (polypeptide or protein) sequences or two or more nucleic acid (polynucleotide) sequences, as determined by comparing the sequences. In the art, "identity"

also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods. The terms "sequence identity" or "sequence similarity" means that two (poly)peptide or two nucleotide sequences, when optimally aligned, preferably over the entire length (of at least the shortest sequence in the comparison) and maximizing the number of matches and minimizes the number of gaps such as by the programs ClustalW (1.83), GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 is ClustalW (1.83) using a blosum matrix and default settings (Gap opening penalty:10; Gap extension penalty: 0.05). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). A preferred multiple alignment program for aligning protein sequences of the invention EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

Alignment of rearranged antibody variable domains may require extensive gap introductions at the end of CDR regions. Especially the CDR3 region sometimes requires such long gap extensions. Without wishing to be bound by any theory, this is probably due to the specific molecular process of VDJ recombination that forms CDR3. As a result standard software programs for DNA or protein alignment may fail to properly align rearranged SDA domains. The program IMGTN-QUEST (Brochet, X. et al., Nucl. Acids Res. 36, W503-508 (2008) was especially developed for sequence analysis, including alignment, of antibody variable domains, including SDAs and is therefore a preferred program to determine alignment. It can be accessed from the internet at www.imgt.org/IMGT_vquest/vquest (IMGT/V-QUEST program version: 3.4.9 dated 9 Jan. 2018—AMGT/V-QUEST reference directory release: 201807-3 dated 14 Feb. 2018). This results in alignment of SDA according to the IMGT numbering system and identification of the three CDR and four FR regions. The program also has an option for identification of unusual insertions and deletions. Subsequently, sequence identity of the CDRs and FR can be determined.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acid substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to Ile or Val; Lys to Arg; Gln or Glu; Met to Leu or Ile; Phe to Met, Leu or Tyr; Ser to Thr; Thr to Ser; Trp to Tyr; Tyr to Trp or Phe; and, Val to Ile or Leu.

Preferred SDAs according to the invention comprise the amino acid sequence VEDG at position 50a-50d. This is in the middle of the FR2 region, adjacent to residue Arg 50 (Kabat position 45) that is often mentioned in SDA literature as the most typical amino acid substitution of SDAs. Conventional SDAs normally contain a Leu at IMGT position 50 that makes hydrophobic contact with the VL domain. SDAs most often have an Arg at IMGT position 50. This substitution renders the former VL interface more hydrophilic. The insertion of VEDG renders the FR2 region more hydrophilic, and lowers its isoelectric point, increasing its solubility and reducing the chance of aggregation.

In a preferred embodiment, an antigen-binding protein according to the invention comprises one or more single binding domains, whereby a single binding domain does not comprise a light chain and whereby the single binding domain comprises the full antigen-binding capacity. Preferably, an antigen-binding protein of the invention is selected from the group consisting of an antibody comprising heavy chains and being devoid of light chains, a fragment thereof, an affibody (Nord et al. (1997) Nature Biotechnology 15:772-777), a single domain antibody and a fragment thereof. Examples of antigen-binding proteins according to the invention are SDA derived from camelid or shark heavy chain only antibodies that are naturally devoid of light chains and affibodies. Preferably an antigen-binding protein is an antibody that comprises heavy chains only and that is naturally devoid of light chains or antibody fragment thereof, such as for example a VHH (derived from camelids) or VNAR (derived from sharks). Alternatively, (and also preferred) antigen-binding protein of the invention can be derived from an antibody naturally devoid of light chains or a fragment thereof, e.g. by modification such as mutation. Antibodies naturally devoid of light chains may be obtained e.g. by immunisation of camelids (e.g. llamas, camels, dromedaries, bactrian camels, alpacas, vicu5 as and guanacos) or sharks (see further below). These antibodies comprise heavy chains only and are devoid of light chains. The advantage of these single domain heavy chain antibodies is that they are exceptionally stable, small and are easily produced in host organisms such as *Saccharomyces cerevisiae*.

Thus, an antigen-binding protein of the invention preferably comprises an immunoglobulin-derived variable domain that comprises a complete antigen-binding site for the epitope on a target molecule in a single polypeptide chain. Such antigen-binding proteins specifically include but are not limited to:

1) antibodies obtainable from camelids and sharks that consist of only heavy chains and that are naturally devoid of light chains;
2) variable domains of the antibodies defined in 1), usually referred to as VHH domains or $V_{NAR}$ fragments, collectively referred to herein as single domain antibodies (SDAs);
3) engineered forms of the antibodies defined in 1) or domains in 2) such as e.g. "camelidised" or "(camelised)" antibodies in which frame work sequences of a camelid (or shark) VHH domain are grafted with CDRs obtained from other sources;
4) engineered forms of immunoglobulin-like variable domains in which framework sequences from a variety of immunoglobulin-like molecules are combined with CDRs specific for a given target molecule as e.g. described in WO 04/108749.

In a preferred antigen-binding protein of the invention, the single polypeptide chain of the variable domain that comprises the full antigen-binding capacity preferably has an amino acid sequence and structure that can be considered to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementarity-determining regions or "CDR's", which are referred to in the art as "Complementarity-Determining Region 1" or "CDR1"; as "Complementarity-Determining Region 2" or "CDR2"; and as "Complementarity-Determining Region 3" or "CDR3", respectively. These framework regions and complementarity-determining regions are preferably are operably linked in the order FR1-CDR1-FR2-CDR2-FR3-CDR3-FR4 (from amino terminus to carboxy terminus).

The total number of amino acid residues in the variable domain with full antigen-binding capacity can be in the region of $110^{-135}$, and preferably is in the region of 115-129. However, a variable domain with full antigen-binding capacity in accordance with the invention is not particularly limited as to its length and/or size, as the domain meets the further functional requirements outlined herein and/or is suitable for the purposes described herein. The amino acid residues of a variable domain with full antigen-binding capacity are numbered according to the general numbering for VH domains given by Kabat et al. (Sequences of Proteins of Immunological Interest (5th Edition), NIH Publication No. 91-3242, U.S. Department of Health and Human Services, Public Health Service, National Institutes of Health (1991)), as applied to VHH domains from camelids by Riechmann and Muyldermans (1999, J. Immunol. Methods 231 (1-2): 25-38, see for example FIG. 2 of said reference) and by Harmsen et al. (2000, Molecular Immunology 37: 579-590, see for example FIG. 1 of said reference).

In this respect, it should be noted that—as is well known in the art for VH domains and for VHH domains—the total number of amino acid residues in each of the CDR's may vary and may not correspond to the total number of amino acid residues indicated by the Kabat numbering. However, based on the conserved amino acids of the frame work region a skilled person will be able to align the respective frame work and complementarity-determining regions in accordance with the Kabat definitions for those variable domains with full antigen-binding. Examples thereof are given in the definition of the complementarity determining regions in the amino acid sequences of the VHH binding to TeNT, immunoglobulin and serum albumin as depicted in FIGS. 1 to 3, respectively. Alternative methods for numbering the amino acid residues of VH domains, which methods can also be applied in an analogous manner to VHH domains from camelids and to variable domains with full antigen-binding capacity, are the method described by Chothia et al. (Nature 342, 877-883 (1989)), the so-called "AbM definition" and the so-called "contact definition", or the IMGT numbering system (Lefranc et al., 1999, Nucl. Acids Res. 27: 209-212).

It is known that the three hypervariable regions or complementarity-determining regions (CDR1, 2 and 3) are the regions that play a main role in actually determining the specificity and the binding characteristics of SDAs.

It is noted that the amino acid sequence variation in the CDR1 region and the CDR2 region within the various groups shown in FIG. 1 is relatively low, i.e. lower than in the not CDR-related parts of the various SDAs. The CDR1 region comprises on the average 8 or 9 amino acids and the variation within the groups relates to only 1 or 2 amino acids, i.e. about 25%. The CDR2 region shows about the same levels of variation. It can be assumed that the level of identity in this region will not be below 75%. In most cases the level of identity will be even higher, i.e. 76, 77, 78, 79, 80, 81, 82, 83, 84, 85, 86, 87, 88, 89, 90, 91, 92, 93, 94, 95, 96, 97, 98, 99 or even 100%.It is also noted that the amino acid sequence variation in the CDR3 region, which is generally considered to be the most important region involved in binding, is lower than in the not CDR-related parts of the various SDAs. Merely as an example: the level of identity in the CDR3 region between the four members of SDA group A identified so far and shown in FIG. 1 is about 95%. The level of identity in that region between the three members of group B is about 92% and in group C it is 94%. The two SDAs of group D have a CDR3 level of identity of about 75%. As for the CDR1 and CDR2 region, it can be assumed that the level of identity in this region will not be below 75%. In most cases the level of identity will be even higher, i.e. at least 76, 77, 78, 79, 80, 81, 82, 83, 84, 85, 86, 87, 88, 89, 90, 91, 92, 93, 94, 95, 96, 97, 98, 99 or even 100%.

The proviso that the amino acid sequence identities of the CDR1, 2 and 3 regions are at least 75% implies that an antigen-binding protein falling within the scope of the invention has a CDR1, 2 and 3 region that has an amino acid sequence identity of at least 75% with that of any of the CDR1, 2 and 3 regions within the amino acid sequences selected from the group of SEQ ID NO: 13, 14, 15, 16, 17, 18, 19, 20, 21, 22, 23, 24, 25 and 26.

Preferably, the antigen-binding protein capable of binding to TeNT has an overall sequence identity with a sequence selected from the group consisting of SEQ ID NO: 13, 14, 15, 16, 17, 18, 19, 20, 21, 22, 23, 24, 25 and 26 that exceeds 70%, e.g. at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% in that order of preference.

Alternatively or in combination with a previous embodiment, in a preferred embodiment, the sequence identities of the CDR1, CDR2 and CDR3 regions are at least 76, 77, 78, 79, 80, 81, 82, 83, 84, 85, 86, 87, 88, 89, 90, 91, 92, 93, 94, 95, 96, 97, 98, 99 or even 100% in that order of preference. These sequence identities can be determined independently from one another.

Thus, a preferred form of this embodiment relates to an antigen-binding protein according to the invention, wherein the antigen-binding protein has an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or preferably 100% with a sequence selected from the group consisting of SEQ ID NO: 13, 14, 15, 16, 17, 18, 19, 20, 21, 22, 23, 24, 25 and 26, with the proviso that the amino acid sequence identities of CDR1, CDR2 and CDR3 are at least 75%. Thus, a more preferred form of this embodiment relates to an antigen-binding protein according to the invention, wherein the antigen-binding protein has an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% with a sequence selected from the group consisting of SEQ ID NO: 13, 14, 15, 16, 17, 18, 19, 20, 21, 22, 23, 24, 25 and 26, with the proviso that the amino acid sequence identities of CDR1, CDR2 and CDR3 regions are at least 76, 77, 78, 79, 80, 81, 82, 83, 84, 85, 86, 87, 88, 89, 90, 91, 92, 93, 94, 95, 96, 97, 98, 99 or even 100%.

An antigen-binding protein of the invention, that can bind to, that has affinity for, that is capable of binding to and/or that has specificity for a specific antigen, such as TeNT, may be said to be "against" or "directed against" said antigen (e.g. TeNT). The term "specificity" refers to the number of different types of antigens or antigenic determinants to which a particular antigen-binding protein molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein. Alternatively, the affinity can also be expressed as the affinity constant ($K_A$), which is $1/K_D$. Affinity can be determined in a manner known per se, depending on the specific combination of antigen binding protein and antigen of interest. Avidity is herein understood to refer to the strength of binding of a target molecule with multiple binding sites by a larger complex of binding agents, i.e. the strength of binding of multivalent binding. Avidity is related to both the affinity between an antigenic determinant and its antigen binding site on the antigen-binding molecule and the number of binding sites present on the antigen-binding molecule. Affinity, on the other hand refers to simple monovalent receptor ligand systems.

Typically, antigen-binding proteins of the invention that are capable of binding to TeNT will bind TeNT with a dissociation constant (Ko) of about $10^{-5}$ to $10^{-12}$ M or less, and preferably $10^{-7}$ to $10^{-12}$ M or less and more preferably $10^{-8}$ to $10^{-12}$ M or less, and/or with a binding affinity of at least $10^{-7}$ M, preferably at least $10^{-8}$ M, more preferably at least $10^{-9}$ M, such as at least $10^{-10}$, $10^{-11}$, $10^{-12}$ M or more. Any Ko value greater than $10^{-4}$ M (i.e. less than 100 μM) is generally considered to indicate non-specific binding. Preferably, a polypeptide of the invention will bind to TeNT with an affinity less than 500 nM, preferably less than 200 nM, more preferably less than 10 nM, such as less than 500 μM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

Tetanus toxoid is an attenuated form of TeNT, for example a formaldehyde-treated TeNT. Preferred antigen-binding proteins of the invention that are capable of binding to a bacterial toxin such as TeNT are also capable of binding tetanus toxoid. Toxoid binding capacity is advantageous because it allows assessment of antigen-binding proteins according to the invention without requiring use of TeNT.

Above, the advantages of SDAs over classical antibodies such as binding characteristics, resistance to denaturation/thermal degradation, aqueous solubility, body distribution and tissue penetration have been addressed.

However, a disadvantage of SDA fragments is their relatively short serum half-life once administered to the body; their rate of clearance from the blood is high. A typical half-life of a monovalent VHH can be about 2 hours and clearance takes place in 1 day (Harmsen, M. M. et al, Vaccine 23: 4926-4934 (2005)). This disadvantage is due to their relatively small molecular weight. Merely as a rule of thumb: a molecule with a minimal M.W. of 50-60 kDa, more preferably of 60-70 kDa, would have a significantly longer half-life.

This disadvantage could e.g. be overcome through continuous intravenous administration of SDA fragments. This approach is from a point of view of animal welfare, practicality and as well as from an economical point of view however not a preferred method. For this reason, other ways have been tried and found to overcome this problem. A widely used approach to reduce the rate of clearance is direct conjugation to a second molecule that has an inherent long serum half-life. One such method is to increase the hydrodynamic size of the protein by chemical attachment of polyethylene glycol (PEG), which can produce a drug with a terminal half-life in humans of up to 14 days. Another approach is to express the therapeutic protein as a genetic fusion with a natural protein that has a long serum half-life; either 67 kDa serum albumin (SA) or the Fc portion of an antibody, which adds an additional 60-70 kDa in its natural dimeric form, depending on glycosylation. This provides compounds that have terminal half-lives in humans of several days.

In the present invention, another approach is chosen. The solution provided in the present invention and discussed in more detail below relates to a combination of at least one SDA capable of binding to TeNT according to the invention that is coupled through a linker with at least another SDA that is directed to another (a non-TeNT) protein. As used herein said another protein, which is not a TeNT protein, is a protein that is present in the human or animal body, preferably in the blood, preferably a serum protein. Examples of such proteins will be given below, where the concept is explained in more detail.

An example of such a combination is a combination comprising an SDA according to the invention, capable of binding to TeNT, a linker and an SDA that is directed to another (a non-TeNT) protein.

It goes without saying that combinations that e.g. comprise two or more SDAs capable of binding to TeNT connected through a linker, and further connected through a linker with e.g. at least one SDA that is directed to another (a non-TeNT) protein, preferably a serum protein, may even be more efficient in neutralising TeNT. Preferably, the two or more SDAs capable of binding to TeNT would be directed against different epitopes of TeNT.

As used herein, any such combinations of at least one SDA capable of binding to TeNT, at least one linker and at least one other SDAs that is directed to another (a non-TeNT) protein are further also referred to as a polypeptide construct. The Examples section below provides ample examples of such polypeptide constructs.

The concept of a linker is discussed below in more detail. Basically, the function of a linker is to connect SDAs. The linker is a relatively short peptide that adopts an unstructured, flexible conformation. In principle, the linker peptide should not, or as little as possible, interfere with assembly and binding activity of the domains it connects.

A polypeptide construct according to the invention would e.g. have a size of about 2×15 kDa for a polypeptide construct comprising one SDA capable of binding to a TeNT epitope, a linker and a second SDA capable of binding to another protein. It would e.g. have a size of about 3×15 kDa for a polypeptide construct comprising one SDA capable of binding to a first TeNT epitope, a second SDA capable of binding to a second TeNT epitope and a third SDA capable of binding to another protein.

The advantage of such polypeptide constructs is, that their relatively short length makes it easily possible to synthesise it chemically or to express a DNA fragment encoding the polypeptide construct in a suitable expression system in an economically feasible way.

Arguably such polypeptide constructs as such would in principle still have a relatively short half-life (their M.W. would still be below 50-60 kDa, or below 60-70 kDa), but they differ significantly from the monomeric constructs described above in that once administered to the body, they bind through their "SDA capable of binding to another protein" to said another protein, thereby leading to a molecule that has a considerably larger size than the polypeptide construct as such. The resulting bound polypeptide constructs would have M.W.s that significantly exceed 60 kDa.

This approach has the advantage that the polypeptide constructs can easily be produced (vide supra) and at the same time it solves the problem of the short half-life of small molecules: once administered, large molecules will form that overcome this problem.

The said another (the non-TeNT) protein would preferably be a serum protein, so that the SDA capable of binding to said another (the non-TeNT) protein would easily come into close contact with that protein after parenteral administration.

Thus, in one embodiment, the invention pertains to a particular form of an antigen-binding protein of the invention: a multivalent antigen-binding protein. The multivalent antigen-binding protein comprises the amino acid sequences of at least one antigen-binding protein capable of binding to TeNT as defined herein above and of at least one antigen-binding protein that is capable of binding to a serum protein. The amino acid sequences of the at least two antigen-binding proteins will usually be fused head-to tail, i.e. the C-terminus of the most N-terminal sequence fused to the N-terminus of the second sequence and so on. The amino acid sequences of at least two antigen-binding proteins may be fused directly linked or via a linker or spacer. Multivalent antigen-binding proteins of the invention may be produced by expression of a nucleotide sequence encoding the multivalent protein wherein two or more coding sequences of the antigen-binding proteins are operably linked together in the same reading frame. The skilled person will know how to operably fuse protein coding sequences.

Thus, in another aspect the present invention relates to a polypeptide construct (or fusion protein) comprising at least one antigen-binding protein capable of binding to TeNT according to the invention and at least one antigen-binding protein capable of binding to a serum protein. The two or more amino acid sequences are preferably linked together by a genetic fusion wherein nucleotide sequences encoding the respective amino acid sequences are operably linked together in frame by means known per se in the art. The amino acid sequences may be linked directly or optionally through a spacer or linker amino acid sequence.

Furthermore this serum protein would preferably be a relatively large protein: the size of the product formed after binding of the polypeptide construct to the serum protein should preferably exceed 60 kDa in order to provide a longer half-life. Examples of large serum proteins are i.a. serum albumin and serum immunoglobulin (Ig), e.g. immunoglobulin G (IgG).

Therefore, a preferred form of this embodiment of the present invention relates to a polypeptide construct comprising at least one antigen-binding protein capable of binding to TeNT according to the invention and at least one antigen-binding protein capable of binding to a serum protein wherein said serum protein is serum albumin, preferably Equine, Porcine, Feline or Canine serum albumin.

In preferred embodiments the polypeptide construct comprising at least one SDA capable of binding to a serum protein according to the invention and at least one SDA capable of binding to TeNT has at least one SDA that binds to a linear epitope and at least a second SDA that binds to a conformational epitope. More preferably, the construct has one SDA that binds to a linear epitope and two SDAs that bind to a conformational epitope.

Therefore, a highly preferred embodiment relates to a polypeptide construct comprising at least one antigen-binding protein, preferably an SDA, capable of binding to a serum protein and at least a first and a second antigen-binding protein, preferably each an SDA, capable of binding to a bacterial toxin, preferably a Clostridial toxin, more preferably a Cl. *tetani*, Cl. *botuli* or Cl. *Difficile* toxin, most preferably TeNT, wherein the first toxin-binding protein binds a linear epitope, more preferably wherein the first toxin-binding protein binds a linear epitope and the second toxin-binding protein binds a conformational epitope.

Another highly preferred embodiment relates to a polypeptide construct comprising at least a first and a second antigen-binding protein, preferably each an SDA, capable of binding to a bacterial toxin, preferably a Clostridial toxin, more preferably a Cl. *tetani*, Cl. *botuli* or Cl. *Difficile* toxin, most preferably TeNT, wherein the first toxin-binding protein binds a linear epitope, more preferably wherein the first toxin-binding protein binds a linear epitope and the second toxin-binding protein binds a conformational epitope.

Serum albumin is present in the body in relatively high concentrations. This means that a polypeptide construct according to the invention comprising at least one antigen-binding protein capable of binding to serum albumin, once administrated to the body, would easily form a large product through the binding with serum albumin. Nevertheless, also for the antigen-binding protein capable of binding to serum albumin, a low Kovalue, e.g. below 1 microM would be preferred. The present invention provides antigen-binding proteins capable of binding to serum albumin. Six examples of such antigen-binding proteins and their sequences are provided in FIG. 3. The three shaded regions indicate where the hypervariable regions or complementarity-determining regions (CDRs) are located. The present invention indeed provides SDAs that bind to serum albumin with a low Ko (0.5-300 nM) as can be seen in Table 28.

Table 18 and FIG. 6 in the Example section shows i.a. the results of the half-life in pigs of various polypeptide constructs where an SDA capable of binding TeNT according to the invention is coupled to an SDA capable of binding to serum albumin according to the invention. As becomes immediately evident from the table, such polypeptide constructs have a surprisingly high average half-life of between 100 and 150 hours. A similar half-life (117 hrs) was reported (Hoefman et al., 2015) for other albumin half-life extended single domain antibodies. Table 33 in the Example section (example 23) show the surprising finding that a polypeptide construct, where an SDA capable of binding TeNT according to the invention is coupled to an SDA capable of binding to serum albumin according to the invention, when administered to Equines, had an average half-life of between 396 and 609 hrs. Preferred polypeptide constructs according to the invention, comprising at least one SDA according to the invention capable of binding TeNT, and at least one SDA according to the invention capable of binding to a serum protein (such as SVA12), have an average half-life of at least 200 hours, preferably of at least 250 hours, more preferably of at least 300 hours, even more preferably of at least 350 hours, even more preferably of at least 375 hours, even more preferably of at least 380 hours, even more preferably of at least 390 hours, even more preferably of at least 395 hours, even more preferably of at least 450 hours, even more preferably of at least 475 hours, more preferably still of at least 500 hours, even more preferably of at least 550 hours, most preferably of at least 600 hours; wherein the half-life is preferably half-life in horses, more preferably as determined in example 23.

Even more surprising, the present invention i.a. provides SDAs that show a large extent of cross-species binding. Cross-species binding is understood to be binding to serum albumin of more than one species. Six examples of SDAs capable of binding to serum albumin according to the invention and their sequences are provided in Table 6 and are discussed below.

A clear advantage of SDAs having cross-species binding, i.e. capable of binding to serum albumin of more than one animal species would have the advantage that they can be used in a polypeptide construct according to the invention that can be used in more than one animal species.

Thus, in another aspect, the present invention relates to an antigen-binding protein that specifically binds serum albumin, wherein the antigen-binding protein preferably comprises an amino acid sequence that comprises 4 framework regions, FR1 to FR4, and 3 complementarity-determining regions, CDR1 to CDR3, that are operably linked in the order FR1-CDR1-FR2-CDR2-FR3-CDR3-FR4. Preferably, the CDR1 has an amino acid sequence selected from the group consisting of the CDR1 sequences of the VHH sequences SEQ ID NOs: 37-42, as shown in FIG. 2 or an amino acid sequence that differs from the CDR1 in one or two of the amino acid residues; b) the CDR2 has an amino acid sequence selected from the group consisting of the CDR2 sequences of the VHH sequences SEQ ID NOs: 37-42, as shown in FIG. 2 or an amino acid sequence that differs from the CDR2 in one, two, three or four of the amino acid residues; and, c) the CDR3 has an amino acid sequence selected from the group consisting of the CDR3 sequences of the VHH sequences SEQ ID NOs: 37-42, as shown in FIG. 2 or an amino acid sequence that differs from the CDR3 in one, two, three, four or five of the amino acid residues; and, wherein each of the framework regions has at least 50, 55, 60, 65, 70, 75, 80, 85, 90, 95 or 100% amino acid identity with the framework amino acid sequence of any one of SEQ ID NOs: 37-42, as shown in FIG. 2. Preferably, CDR1, CDR2 and CDR3 are from the same SEQ ID NO. More preferably, the framework region is from the same SEQ ID NO as the complementarity-determining regions. Alternatively said, in this aspect the invention relates to an antigen-binding protein, preferably an SDA, capable of binding to serum albumin, wherein the antigen-binding protein has an overall amino acid sequence identity of at least 70% with a sequence selected from the group consisting of SEQ ID NO: 40, 37, 38, 39, 41 or 42, with the proviso that the amino acid sequence identities of the CDR1, CDR2 and CDR3 are at least 75%. Preferably, the antigen-binding protein is capable of binding Equine, Porcine, Feline or Canine serum albumin.

Preferably, an antigen-binding protein capable of binding to serum albumin according to the invention has an overall sequence identity with a sequence selected from the group consisting of SEQ ID NO: 37, 38, 39, 40, 41 and 42 that exceeds 70%, e.g. at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% in that order of preference. Preferably, the level of identity of the CDR1, CDR2 and CDR3 regions is at least 75%.

Alternatively or in combination with a previous embodiment, in a preferred embodiment, the sequence identities of the CDR1, CDR2 and CDR3 regions are at least 76, 77, 78, 79, 80, 81, 82, 83, 84, 85, 86, 87, 88, 89, 90, 91, 92, 93, 94, 95, 96, 97, 98, 99 or even 100%, in that order of preference. These sequence identities can be determined independently from one another.

Thus, a preferred form of this embodiment relates to an antigen-binding protein capable of binding to serum albumin according to the invention having an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or preferably 100% with a sequence selected from the group consisting of SEQ ID NO: 37, 38, 39, 40, 41 and 42, with the proviso that the amino acid sequence identities of CDR1, CDR2 and CDR3 are at least 75%. Thus a more preferred form of this embodiment relates to an antigen-binding protein capable of binding to serum albumin according to the invention, wherein the antigen-binding protein has an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% with a sequence selected from the group consisting of SEQ ID NO: 37, 38, 39, 40, 41 and 42, with the proviso that the amino acid sequence identities of the CDR1, CDR2 and CDR3 regions are at least 76, 77, 78, 79, 80, 81, 82, 83, 84, 85, 86, 87, 88, 89, 90, 91, 92, 93, 94, 95, 96, 97, 98, 99 or even 100%.

As mentioned above, antigen-binding proteins capable of binding to serum albumin of more than one animal species would have the advantage that they can be used in a polypeptide construct according to the invention that can be used in more than one animal species. The present invention provides several antigen-binding proteins capable of binding to serum albumin showing such cross-species binding. As can be seen in Table 6, especially SVA12L (SEQ ID NO: 40) and SVA06L (SEQ ID NO: 39) provide strong cross-species binding in the sense that it binds to serum albumin of canines, equines, felines and porcine. As can also be seen in Tables 6 and 28, especially SVA16L (SEQ ID NO: 37) provides strong cross-species binding in the sense that it binds to serum albumin of both canines, equines and felines.

Therefore, a more preferred form of this embodiment relates to an antigen-binding protein capable of binding to serum albumin according to the invention having an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% with a sequence selected from the group consisting of SEQ ID NO: 37, 39 and 40 with the proviso that the amino acid sequence identities of the CDR1, CDR2 and CDR3 are at least 75%, preferably at least 76, 77, 78, 79, 80, 81, 82, 83, 84, 85, 86, 87, 88, 89, 90, 91, 92, 93, 94, 95, 96, 97, 98, 99 or 100%.

Therefore, a more preferred form of an embodiment of the present invention relates to a polypeptide construct (or fusion protein) comprising at least one antigen-binding protein capable of binding to TeNT according to the invention and at least one antigen-binding protein capable of binding to serum albumin, wherein said at least one antigen-binding protein capable of binding to serum albumin preferably is an antigen-binding protein according to the invention as referred to above.

Another preferred form of an embodiment of the present invention relates to a polypeptide construct (or fusion protein) comprising at least one antigen-binding protein capable of binding to TeNT according to the invention and at least one antigen-binding protein capable of binding to a serum protein wherein said serum protein is an immunoglobulin.

A more preferred form of this embodiment relates to a polypeptide construct according to the invention comprising at least one antigen-binding protein capable of binding to TeNT and at least one antigen-binding protein capable of binding to a serum protein wherein said serum protein is an IgG immunoglobulin, preferably equine, porcine, mouse, guinea-pig, human, bovine, feline or canine.

Immunoglobulins, like serum albumin, are present in the body in relatively high concentrations. This means that a polypeptide construct according to the invention comprising at least one antigen-binding protein capable of binding to immunoglobulin, once administrated to the body, would easily form a large product through the binding with serum immunoglobulin. Nevertheless, also for the antigen-binding protein capable of binding to immunoglobulin, a low Ko value, e.g. below 1 µM would be preferred.

The present invention provides antigen-binding proteins that bind to Ig with a suitable Ko. Eight examples of antigen-binding proteins according to the invention that bind to immunoglobulin with a low Ko and their sequences are provided in FIG. 2. The three shaded regions indicate where the hypervariable regions or complementarity-determining regions (CDRs) are located.

Thus, in another aspect, the present invention relates to an antigen-binding protein that specifically binds immunoglobulin (Ig), wherein the antigen-binding protein preferably comprises an amino acid sequence that comprises 4 framework regions, FR1 to FR4, and 3 complementarity-determining regions, CDR1 to CDR3, that are operably linked in the order FR1-CDR1-FR2-CDR2-FR3-CDR3-FR4. Preferably, the CDR1 has an amino acid sequence selected from the group consisting of the CDR1 sequences of the VHH sequences SEQ ID NOs: 27-34, as shown in FIG. 3 or an amino acid sequence that differs from the CDR1 in one or two of the amino acid residues; b) the CDR2 has an amino acid sequence selected from the group consisting of the CDR2 sequences of the VHH sequences SEQ ID NOs: 27-34, as shown in FIG. 3 or an amino acid sequence that differs from the CDR2 in one, two, three or four of the amino acid residues; and, c) the CDR3 has an amino acid sequence selected from the group consisting of the CDR3 sequences of the VHH sequences SEQ ID NOs: 27-34, as shown in FIG. 3 or an amino acid sequence that differs from the CDR3 in one, two, three, four or five of the amino acid residues; and, wherein each of the framework regions has at least 50, 55, 60, 65, 70, 75, 80, 85, 90, 95 or 100% amino acid identity with the framework amino acid sequence of any one of SEQ ID NOs: 27-34, as shown in FIG. 3. Preferably, CDR1, CDR2 and CDR3 are from the same SEQ ID NO. More preferably, the framework region is from the same SEQ ID NO as the complementarity-determining regions. Alternatively said, in this aspect the invention relates to an antigen-binding protein, preferably a single domain antibody (SDA), capable of binding to immunoglobulin (Ig), wherein the antigen-binding protein has an overall amino acid sequence identity of at least 70% with a sequence selected from the group consisting of SEQ ID NO: 30, 27, 28, 29, 31, 32, 33 or 34, with the proviso that the amino acid sequence identities of CDR1, CDR2 and CDR3 are at least 75%.

Preferably, an antigen-binding protein capable of binding to Ig has an overall sequence identity with a sequence selected from the group consisting of SEQ ID NO: 27, 28, 29, 30, 31, 32, 33 and 34, that exceeds 70%, e.g. at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% in that order of preference. Preferably, the sequence identities of the CDR1, CDR2 and CDR3 regions are at least 75%.

Thus, a preferred form of this embodiment relates to an antigen-binding protein capable of binding to Ig according to the invention having an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% with a sequence selected from the group consisting of SEQ ID NO: 27, 28, 29, 30, 31, 32, 33 and 34, with the proviso that the amino acid sequence identities of the CDR1, CDR2 and CDR3 regions are at least 75%.

More preferably, an SDA capable of binding to Ig will have an overall homology level with a sequence selected from the group of SEQ ID NO: 27, 28, 29, 30, 31, 32, 33 or 34, that exceeds 70%, e.g. 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% in that order of preference, where preferably, the level of identity of the CDR1, CDR2 and CDR3 region will be 76, 77, 78, 79, 80, 81, 82, 83, 84, 85, 86, 87, 88, 89, 90, 91, 92, 93, 94, 95, 96, 97, 98, 99 or even 100% in that order of preference.

Thus, a more preferred form of this embodiment relates to an antigen-binding protein capable of binding to Ig according to the invention having an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% with a sequence selected from the group consisting of SEQ ID NO: 27, 28, 29, 30, 31, 32, 33 and 34, with the proviso that the amino acid sequence identities of the CDR1, CDR2 and CDR3 regions are at least 76, 77, 78, 79, 80, 81, 82, 83, 84, 85, 86, 87, 88, 89, 90, 91, 92, 93, 94, 95, 96, 97, 98, 99 or preferably 100%.

According to Table 7, SVG 23 is specific for canines, whereas SVG03 is specific for equines.

Even more surprisingly, the present invention provides SDAs capable of binding to Ig that show a large extent of cross-species binding. As can also be seen in Table 7, especially SVG06 and SVG13 provide very strong cross-species binding in the sense that they bind to Ig (Fab fragment) of e.g. felines, canines, equines, humans and porcine. Also according to Table 7, especially SVG24 provides very strong cross-species binding in the sense that it binds to Ig (Fc fragment) of both canines and equines.

Therefore, an even more preferred form of this embodiment relates to an antigen-binding protein capable of binding to Ig according to the invention having an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% with a sequence selected from the group consisting of SEQ ID NO: 27, 30, 31, 32 and 33 with the proviso that the amino acid sequence identities of the CDR1, CDR2 and CDR3 regions are at least 75%.

A still even more preferred form of this embodiment relates to an antigen-binding protein capable of binding to Ig according to the invention having an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or preferably 100% with a sequence selected from the group consisting of SEQ ID NO: 27, 30, 31, 32 and 33 with the proviso that the amino acid sequence identities of the CDR1, CDR2 and CDR3 regions are at least 76, 77, 78, 79, 80, 81, 82, 83, 84, 85, 86, 87, 88, 89, 90, 91, 92, 93, 94, 95, 96, 97, 98, 99 or preferably 100%.

Therefore, another more preferred form of an embodiment of the present invention relates to a polypeptide construct (or fusion protein) comprising at least one antigen-binding protein capable of binding to TeNT according to the invention and at least one antigen-binding protein capable of binding to a serum protein wherein said serum protein is an Ig, wherein said at least one antigen-binding protein capable of binding to Ig preferably is an antigen-binding protein according to the invention as referred to above.

It should be noticed that generally spoken the order of the various antigen-binding proteins in the polypeptide construct according to the invention (their location relative to the N-terminus and C-terminus of the polypeptide construct) can vary. This is due to the fact that the hinge(s) adopt an unstructured and flexible conformation; their main function is to connect the various antigen-binding proteins.

As indicated above, in an aspect the present invention relates to a polypeptide construct (or fusion protein) comprising at least one antigen-binding protein capable of binding to TeNT according to the invention and at least one antigen-binding protein capable of binding to a serum protein. Even more surprisingly, an unexpected synergistic effect was found for polypeptide constructs according to the invention that comprise two or more SDAs capable of binding to TeNT.

Bivalent constructs provide an even stronger level of binding to TeNT in the mouse toxin neutralisation test than for example a mixture of two single valent constructs. This effect is even more significant when the polypeptide construct comprises two or more SDAs capable of binding to TeNT that bind to different epitopes of TeNT. This can be seen from Table 15, where an overview is shown of the epitope binding characteristics of various SDAs capable of binding to TeNT according to the invention.

As is immediately clear from Table 12, five different selections SDAs capable of binding to TeNT were identified: selection A; SVT02, selection B; SVT03, selection C; SVT15, selection D; SVT06/08 and selection E; SVT13/16/22/34.

It was e.g. found that a polypeptide construct comprising two SDAs: (i) an SDA capable of binding to TeNT and having the amino acid sequence according to SEQ ID NO:17 and (ii) an SDA capable of binding to TeNT and having the amino acid sequence according to SEQ ID NO:15, provides a strong synergistic effect. The TeNT neutralisation capacity of such a construct is significantly stronger than that of the single SVT-06 and SVT-16 SDAs (see Table 19 and 20 example 17).

For this reason, in an even more preferred embodiment a polypeptide construct according to the invention comprises at least two antigen-binding proteins capable of binding to TeNT according ot the invention. Preferably, each of the at least two antigen-binding proteins capable of binding to TeNT has an overall amino acid sequence identity of at least 70% with a sequence selected from selection A; SEQ ID NO: 24, or selection B; SEQ ID NO: 25, or selection C; SEQ ID NO: 20, or selection D; SEQ ID NO: 17 or 19 or selection E; SEQ ID NO: 22, 15, 23 or 14, with the proviso that the at least two SDAs do not comprise a sequence from the same selection and with the proviso that the amino acid sequence identities of the CDR1, CDR2 and CDR3 regions are at least 75%. Thus, alternatively said, each of the at least two antigen-binding proteins capable of binding to TeNT have an overall amino acid sequence identity of at least 70% with a sequence selected from the group consisting of:

(i) SEQ ID NO:24;
(ii) SEQ ID NO:25;
(iii) SEQ ID NO:20;
(iv) SEQ ID NO:17 or SEQ ID NO:19; and
(v) SEQ ID NO: 22, SEQ ID NO:15, SEQ ID NO:23 or SEQ ID NO:14;
with the proviso that the amino acid sequences identities of the CDR1, CDR2 and CDR3 regions are at least 75%.

A polypeptide construct according to the invention preferably comprises 2, 3 or 4 antigen-binding proteins capable of binding to TeNT according to the invention, more preferably 2 or 3, most preferably 2 antigen-binding proteins capable of binding TeNT. In a preferred embodiment, a polypeptide construct according to the invention comprises two antigen-binding proteins capable of binding to TeNT and having an overall amino acid sequence identity of at least 70% with the sequences:

(i) SEQ ID NO:15 and SEQ ID NO:17;
(ii) SEQ ID NO: 24 and SEQ ID NO:17;
(iii) SEQ ID NO:20 and SEQ ID NO:17;
(iv) SEQ ID NO:15 and SEQ ID NO:24; or
(v) SEQ ID NO:24 and SEQ ID NO:20;
with the proviso that the amino acid sequences identities of the CDR1, CDR2 and CDR3 regions are at least 75%.

A polypeptide construct according to the invention, preferably comprises one antigen-binding protein capable of binding to a serum protein.

Merely as an example: such a polypeptide construct according to the invention could e.g. comprise an SDA capable of binding to TeNT has an overall amino acid sequence identity of at least 70% with selection C; SEQ ID NO: 20 with the proviso that the amino acid sequence identity of the CDR1, CDR2 and CDR3 region has an amino acid sequence identity of at least 75%, and an SDA capable of binding to TeNT has an overall amino acid sequence identity of at least 70% with selection D; SEQ ID NO: 17 with the proviso that the amino acid sequence identity of the CDR1, CDR2 and CDR3 region has an amino acid sequence identity of at least 75%.

Preferably, the antigen-binding proteins capable of binding TeNT of such constructs have an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or preferably 100% with the sequence selected from selection A; SEQ ID NO: 24, or selection B;

SEQ ID NO: 25, or selection C; SEQ ID NO: 20, or selection D; SEQ ID NO: 17 or 19 or selection E; SEQ ID NO: 22, 15, 23 or 14.

More preferably, the antigen-binding proteins of such constructs have an overall amino acid sequence identity of at least 71, 72, 73, 74, 75, 76, 77, 78, 79, 80, 81, 82, 83, 84, 85, 86, 87, 88, 89, 90, 91, 92, 93, 94, 95, 96, 97, 98, 99 or preferably 100% with the sequence selected from selection A; SEQ ID NO: 24, or selection B; SEQ ID NO: 25, or selection C; SEQ ID NO: 20, or selection D; SEQ ID NO: 17 or 19 or selection E; SEQ ID NO: 22, 15, 23 or 14, and the amino acid sequence identities of the CDR1, CDR2 and CDR3 regions are at least 76, 77, 78, 79, 80, 81, 82, 83, 84, 85, 86, 87, 88, 89, 90, 91, 92, 93, 94, 95, 96, 97, 98, 99 or preferably 100%.

In a more preferred embodiment a polypeptide construct according to the invention comprises the antigen-binding protein having the sequence as depicted in SEQ ID NO: 15, the antigen-binding protein having the sequence as depicted in SEQ ID NO: 17 and the antigen-binding protein having the sequence as depicted in SEQ ID NO: 40. More preferably, the polypeptide construct comprises the SDA having the sequence as depicted in SEQ ID NO: 17 (SVT-06), the SDA having the sequence as depicted in SEQ ID NO: 15 (SVT16) and the SDA having the sequence as depicted in SEQ ID NO: 40 (SVA12) in the specific order N-terminus-SEQ ID NO: 17-SEQ ID NO: 15-SEQ ID NO: 40-C-terminus. Even more preferably, the polypeptide construct has the amino acid sequence as depicted in SEQ ID NO: 51, 77, or 78, preferably 51, or an amino acid sequence with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or preferably 100% sequence identity with SEQ ID NO: 51, 77, or 78, preferably 51, wherein the sequence identities of the CDR1, CDR2 and CDR3 regions are at least 75, 76, 77, 78, 79, 80, 81, 82, 83, 84, 85, 86, 87, 88, 89, 90, 91, 92, 93, 94, 95, 96, 97, 98, 99 or preferably 100%. The polypeptide construct can for example be altered by deleting the His6 tag and/or altering or replacing the linker sequences as depicted in SEQ ID NO:51, 77, or 78, preferably 51.

In highly preferred embodiments, the polypeptide construct has the amino acid sequence as depicted in SEQ ID NO: 51, or an amino acid sequence with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, preferably 80%, more preferably 90%, even more preferably 95%, even more preferably 98%, most preferably 100% sequence identity with SEQ ID NO: 51, wherein the sequence identities of the CDR1, CDR2 and CDR3 regions are at least 75, 76, 77, 78, 79, 80, 81, 82, 83, 84, 85, 86, 87, 88, 89, 90, 91, 92, 93, 94, 95, 96, 97, 98, 99 or 100%, preferably 80%, more preferably 90%, even more preferably 95%, even more preferably 98%, most preferably 100%. The polypeptide construct can for example be altered by deleting the His6 tag and/or altering or replacing the linker sequences as depicted in SEQ ID NO:51.

In highly preferred embodiments, the polypeptide construct has the amino acid sequence as depicted in SEQ ID NO: 77, or an amino acid sequence with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, preferably 80%, more preferably 90%, even more preferably 95%, even more preferably 98%, most preferably 100% sequence identity with SEQ ID NO: 77 wherein the sequence identities of the CDR1, CDR2 and CDR3 regions are at least 75, 76, 77, 78, 79, 80, 81, 82, 83, 84, 85, 86, 87, 88, 89, 90, 91, 92, 93, 94, 95, 96, 97, 98, 99 or 100%, preferably 80%, more preferably 90%, even more preferably 95%, even more preferably 98%, most preferably 100%. The polypeptide construct can for example be altered by deleting the His6 tag and/or altering or replacing the linker sequences as depicted in SEQ ID NO:77.

In highly preferred embodiments, the polypeptide construct has the amino acid sequence as depicted in SEQ ID NO: 78, or an amino acid sequence with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, preferably 80%, more preferably 90%, even more preferably 95%, even more preferably 98%, most preferably 100% sequence identity with SEQ ID NO: 78, wherein the sequence identities of the CDR1, CDR2 and CDR3 regions are at least 75, 76, 77, 78, 79, 80, 81, 82, 83, 84, 85, 86, 87, 88, 89, 90, 91, 92, 93, 94, 95, 96, 97, 98, 99 or 100%, preferably 80%, more preferably 90%, even more preferably 95%, even more preferably 98%, most preferably 100%. The polypeptide construct can for example be altered by deleting the His6 tag and/or altering or replacing the linker sequences as depicted in SEQ ID NO:78.

In a most preferred form, the polypeptide construct according to the invention has the sequence as depicted in SEQ ID NO: 51, 47, 48, 52, 53, 61, 62, 49, 50, 77, or 78, preferably as depicted in SEQ ID NO: 51, 47, 48, 52, 53, 61, 62, 49, 77, or 78, more preferably as depicted in SEQ ID NO: 51, 47, 48, 52, 53, 61, 62, or 49, most preferably as depicted in SEQ ID NO: 51, wherein the sequence identities of CDR1, CDR2 and CDR3 regions are at least 75, 76, 77, 78, 79, 80, 81, 82, 83, 84, 85, 86, 87, 88, 89, 90, 91, 92, 93, 94, 95, 96, 97, 98, 99 or preferably 100%.

It was also surprisingly noticed that combinations of different SDAs according to the invention, when mixed together, show a stronger toxin neutralizing effect in a mouse tetanus toxin neutralisation test (TNT). This is shown in Table 21-23 of the Examples section. Table 21 and 24 show the various combinations tested. Table 24 shows that the single SDA SVT06-GS3-SVT16-L123Q-GS2-SVA12M2-H6 provides 50% protection in mice at a certain dilution, whereas the combination of SDA SVT06-GS3-SVT16-L123Q-GS2-SVA12M2-H6 and SVT15-3FW4M-GS2-SVG13M4-H6 provides a 100% protection in mice at the same dilution.

As mentioned above, the various SDAs in polypeptide constructs according to the invention are preferably connected to each other through linker peptides. Linker peptides are sequences of amino acids that are commonly used to physically connect polypeptide domains.

Such a linker can be any linker known to the skilled artisan. For instance, the linker can be a biocompatible polymer with a length of 1 to 100 atoms. This can e.g. be a polymer existing of poly-lysine, poly-glycine, poly-glutamate, poly-isoleucine, poly-serine, or poly-arginine residues, or a combination thereof. Most linker peptides are composed of repetitive modules of one or more of the amino acids glycine and serine. Merely as an example: such linkers may e.g. have the following sequences: Gly4-Ser-Gly3-Ser or (Gly4-Ser) where n is 2, 3, 4, 5, or 6, preferably 4, 5, or 6.

Preferably the 15 amino acid $(G4S)_3$ linker that is composed of three consecutive repeats of the amino acid sequence $(Gly)_4$-Ser is used. This linker was initially used for production of single-chain Fvs [27], but has also often been used for fusion of VHHs [28]. It is a flexible linker that facilitates independent binding to different antigenic sites. This linker peptide has been well-characterized in the art (e.g., within the context of an antibody single-chain Fv (scFv) domain) and has been shown to adopt an unstructured, flexible conformation. In addition, this linker peptide does not interfere with assembly and binding activity of the domains it connects. (Freund, C. et al.,. FEBS 320: 97 (1993)). Other examples of suitable hinges are provided i.a. in EP2655624.

Other more rigid linkers for fusion of protein domains are also known. Huston J S, et al., Proc Natl Acad Sci. 1988; 85:5879-83, [28] Mukherjee J, et al., PLoS ONE. 2012; 7:e29941, [29] Sepulveda J, et al., Infect Immun. 2010; 78:756-63, [30] Vance D J, et al., J Biol Chem. 2013; 288:36538-47, [31] Klein J S, et al., Protein Eng Des Sel. 2014; 27:325-30, Trinh R, et al., Mol Immunol. 2004; 40:717-22.

The Examples section (vide infra) presents examples of linkers used in the present invention.

In a further aspect, the present invention relates to a DNA fragment encoding an antigen-binding protein according to the invention or encoding a polypeptide construct according to the invention. Such DNA fragments comprise the genetic information encoding the SDA or polypeptide construct.

In another aspect, the invention relates to a nucleic acid comprising a DNA fragment encoding an antigen-binding protein according to the invention or a polypeptide construct according to the invention as defined herein above. A preferred nucleic acid according to the invention is a nucleic acid construct, such as for example a plasmid, wherein the DNA fragment is operably linked to a promoter and optionally other regulatory elements such as e.g. terminators, enhancers, polyadenylation signals, signal sequences for secretion and the like. Such nucleic acid constructs are particularly useful for the production of the antigen-binding proteins or polypeptide constructs of the invention using recombinant techniques in which a nucleotide sequence (DNA fragment) encoding the antigen-binding protein of interest is expressed in suitable host cells such as described in Ausubel et al., "Current Protocols in Molecular Biology", Greene Publishing and Wiley Interscience, New York (1987) and in Sambrook and Russell (2001) "Molecular Cloning: A Laboratory Manual (3rd edition), Cold Spring Harbor Laboratory, Cold Spring Harbor Laboratory Press, New York). As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A suitable promoter is a promoter that is recognised in a host cell and drives in that host cell the expression of the genetic information that it controls. Suitable promoter/host cell combinations are known already for decades in the art.

Such nucleic acids can be inserted in a suitable host cell allowing the expression of the antigen-binding protein or the polypeptide construct under the control of the suitable promoter.

The expression of DNA fragments comprising a nucleic acid encoding any of the SDAs according to the invention or any of the polypeptide constructs according to the invention van be done in prokaryotic and eukaryotic host cells. Expression systems in all these host cells are known in the art since decades.

A classical text book describing numerous expression systems is "Production of Recombinant Proteins: Novel Microbial and Eukaryotic Expression Systems" by Gerd Gellissen (Editor). ISBN: 978-3-527-31036-4, December 2004, Publisher Wiley-Blackwell.

An overview of methods for the expression of heterologous proteins in insect cells is given in "Opportunities and challenges for the baculovirus expression system", (Monique M. van Oers, Journal of Invertebrate Pathology, Volume 107, Supplement, July 2011, Pages S3-S15). Specific methods for the expression of camelid SDAs in lower eukaryotic hosts such as moulds and yeasts are presented i.a. in EP0698097. Additionally, the Example section, more specifically Example 6 and 14 (vide infra) provides detailed examples of the expression of SDAs in yeast.

Thus, in a further aspect, the present invention relates to a host cell comprising a nucleic acid as defined above. Preferably, the host cell is a host cell for production of an antigen-binding protein according to the invention or a polypeptide construct according to the invention.

The host cell may be any host cell capable of producing an antigen-binding protein of the invention, including e.g. a prokaryotic host cell, such as e.g., *E. coli*, or a (cultured) mammalian, plant, insect, fungal or yeast host cell, including e.g. CHO-cells, BHK-cells, human cell lines (including HeLa, COS and PER.C6), Sf9 cells and Sf+cells. A preferred host cell for production of an antigen-binding protein of the invention is however a cell of an eukaryotic microorganism such as yeasts and filamentous fungi. Preferred yeast host cell e.g. include e.g. *Saccharomyces cerevisiae, Pichia pastoris, Hansenula polymorpha, Pichia angusta*, and *Kluyveromyces lactis*. Preferred strains, constructs and fermentation conditions for production of the antigen-binding protein of the invention are described by van de Laar, et al., (2007, Biotechnology and Bioengineering, Vol. 96, No. 3: 483-494). For example, production of the antigen-binding proteins can be performed in standard bioreactors with a working volume between 10 and 10,000 litres.

In another aspect, the present invention relates to a method for the production of an antigen-binding protein according to the invention or a polypeptide construct according to the invention wherein said method comprises the steps of a) culturing of a host cell comprising an antigen-binding protein according to the invention or a polypeptide construct according to the invention under conditions allowing the expression of the antigen-binding protein or polypeptide construct; and optionally b) recovering, harvesting or purifying the antigen-binding protein or polypeptide construct from at least one of the host cell and the culture medium. Suitable conditions may include the use of a suitable medium, the presence of a suitable source of food and/or suitable nutrients, a suitable temperature, and optionally the presence of a suitable inducing factor or compound (e.g. when the nucleotide sequences of the invention are under the control of an inducible promoter); all of which may be selected by the skilled person. Under such conditions, the amino acid sequences of the invention may be expressed in a constitutive manner, in a transient manner, or only when suitably induced. The antigen-binding proteins of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence of the invention) and/or preparative immunological techniques (i.e. using antibodies against the antigen-binding protein to be isolated). In an embodiment, the antigen-binding protein or polypeptide construct produced and optionally recovered is further mixed with a pharmaceutically acceptable carrier.

In another aspect, the present invention relates to a pharmaceutical composition comprising at least one antigen-binding protein capable of binding to TeNT according to the invention and/or at least one polypeptide construct according to the invention comprising at least one antigen-binding protein capable of binding to TeNT according to the invention, and a pharmaceutically acceptable carrier. In a further preferred embodiment, the pharmaceutical composition comprises at least two antigen-binding proteins capable of binding to TeNT according to the invention and/or at least one polypeptide construct according to the invention comprising at least two antigen-binding proteins capable of binding to TeNT according to the invention.

A pharmaceutically acceptable carrier as used herein can be as simple as e.g. sterile water, a physiological salt solution or a buffer, e.g. a buffered aqueous solution at physiological ionic strength and/or osmolarity (such as e.g. PBS).

Formulation of medicaments, ways of administration and the use of pharmaceutically acceptable excipients are known and customary in the art and for instance described in Remington; The Science and Practice of Pharmacy, 21st Edition 2005, University of Sciences in Philadelphia. Pharmaceutical compositions and medicaments according to the invention are preferably formulated to be suitable for intravenous or subcutaneous, or intramuscular administration, although other administration routes can be envisaged, such as mucosal administration or intradermal and/or intracutaneous administration, e.g. by injection.

Such compositions, as well as an antigen-binding protein according to the invention and/or the polypeptide construct according to the invention can successfully be used for use in the treatment or prevention of clinical disease after *Clostridium tetani* infection.

Therefore, in a further aspect, the present invention relates to an antigen-binding protein according to the invention or a polypeptide construct according to the invention for use as a medicament.

In a further aspect, the present invention relates to an antigen-binding protein according to the invention and/or a polypeptide construct according to the invention and/or a pharmaceutical composition according to the invention, for use in the prevention or treatment of disease after *Clostridium tetani* infection. Alternatively said, in this aspect, the invention relates to use of an antigen-binding protein according to the invention and/or a polypeptide construct according to the invention for the manufacture of a medicament for prevention or treatment of disease after *Clostridium tetani* infection. Alternatively, in this aspect, the invention relates to a method of preventing or treating disease after *Clostridium tetani* infection, wherein a subject in need thereof is administered with a therapeutically sufficient amount of an antigen-binding protein according to the invention and/or a polypeptide construct of the invention. Thus, in this aspect an antigen-binding protein, a polypeptide construct and/or a pharmaceutical composition according to the invention is used to prevent tetanus or to treat tetanus.

As used herein, the terms "treat", "treatment", or "treating" refer to application or administration of an antigen-binding protein, polypeptide construct and/or pharmaceutical composition of the invention to a subject who has tetanus, wherein the object is to cure, partially or completely reverse, alleviate, ameliorate, inhibit, delay, suppress, slow down or stop the progression or severity of tetanus, or of the symptoms associated with tetanus. The term "treating" includes reducing or alleviating at least one adverse effect or symptom of tetanus. Treatment is generally "effective" if one or more symptoms or clinical markers are reduced. Alternatively, treatment is "effective" if the progression of tetanus is reduced or halted. That is, "treatment" includes not just the improvement of symptoms or markers, but also a cessation or at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of tetanus also includes providing relief from the symptoms or side-effects of tetanus (including palliative treatment). As used herein, the term "prevent", "prevention", or "preventative" (also referred to as prophylactic) refer to application or administration of an antigen-binding protein, polypeptide construct and/or pharmaceutical composition according to the invention to a subject who is at risk of developing tetanus, with the purpose to prevent onset of, alleviate, ameliorate, relieve, inhibit progression of, reduce severity of, and/or reduce incidence of one or more symptoms or features of a future tetanus disease. Thus, an antigen-binding protein, polypeptide construct or pharmaceutical composition according to the invention may be administered to a subject who does not exhibit signs of tetanus and/or to a subject who exhibits only early signs of tetanus, preferably for the purpose of decreasing the risk of developing pathology associated with tetanus.

In an embodiment, the subject is an animal, including humans, preferably a mammal, more preferably a non-human mammal, even more preferably an Equine, Canine, Feline, Porcine or a member of the ruminant family Bovidae (for example Bovine, Caprine). Preferred subjects according to the invention are for example *Equus ferus, Equus africanus, Canis familiaris, Felis catus, Sus scrofa domesticus, Bos taurus, Ovis aries* and *Capra aegagrus hircus*, most preferably *Equus ferus*.

Passive immunisation with an antigen-binding protein against TeNT or polypeptide construct according to the invention can be used in at least 3 different scenarios. For example in a prophylactic scenario as part of a pre-operative standard procedure, or in subjects that are injured and possibly are infected with *Clostridium tetani*, but not diseased yet. Thirdly, in a therapeutic scenario when the subject is suffering from tetanus. There is a difference in dosage depending on prophylactic or therapeutic treatment, for example the latter at 2-20 fold higher dose depending on the species. A small amount of the antitoxin dose (e.g. 1000 IU) can also be administered locally around the wound site. Several routes of administration can be applied such as the intramuscular, subcutaneous, intravenous, epidural, subarachnoidal or intrathecal route. Antigen-binding proteins according to the invention and/or polypeptide constructs according to the invention that are able to effectively neutralise tetanus toxin can be utilised in the following manner. The to be administered preparation should preferably result in a blood concentration of at least 0.01-0.1 IU/ml. Therefore, the dosage is preferably based on body mass/blood volume.

Merely as an example: in established human cases patients should receive 500-1000 IU/kg intravenously or intramuscularly. For SDA SVT06-SVT16-SVA12 (SEQ ID NO.: 51) this would result in a dosage of maximally 0.5-1 mg/kg. The dose of the classic equine antitoxin product for established cases in small animals (feline and canine) is 100-1000 IU/kg given intravenously. For SDA SVT06-SVT16-SVA12 this would result in a dosage of maximally 0.1-1 mg/kg. Larger animals receive a proportionally smaller dose than smaller animals. For example horses may as a preoperative treatment receive 7500-11000 IU intramuscular or subcutaneous, a foal up to a 100 kg 3000-4000 IU via either route. Injured horses (not suffering from tetanus) may as a preventive treatment receive 15000-20000 IU intramuscular or subcutaneous, a foal up to a 100 kg 6500-8000 IU via either route. Horses suffering from tetanus should receive at least 50000-60000 IU via one route (if the preparation allows) or via the combination of several routes.

In clinical cases, tetanus treatment may be repeated on a daily basis depending on the effect seen.

All recommended dosages usually provide passive protection for as long as at least 3 weeks. Again, merely as an example: the half-life of construct SVT06-SVT16-SVA12 (SEQ ID NO:51) was shown to be such that after administration of 0.3 mg/kg to swine at 21 days later a serum level of 0.1 microgram/ml (equalling more than 0.1 IU (Example 17, Table 25)) was still detectable as can be seen in Example 16, FIG. 6. The same construct, SVT06-SVT16-SVA12 (SEQ ID NO:51), when administered (0.17 mg/kg, intramuscular) to Equines lead to a serum level of 0.4-0.6 microgram/ml (Example 23) at 21 days later, a level that is fully protective.

The amount of antitoxin (also referred to as "potency" or "neutralizing capacity") is given in International Units (IU). The first milestone in the global standardization of tetanus toxoid was the establishment of the International Standard for tetanus antitoxin of equine origin in 1928, which was replaced in 1969 (WHO Expert Committee on Biological Standardization. Twenty-second report. Geneva, World Health Organization, 1970 (WHO Technical Report Series, No. 444). The availability and use of this preparation enabled toxoids to be assessed in terms of their ability to produce tetanus antitoxin in humans, and allowed protective units for antitoxin to be defined in International Units (IUs). The neutralizing capacity can for example be determined as shown in Example 17 ("Analysis of SDA for tetanus toxin neutralizing capacity in a mouse model").

The commercially recommended antitoxin dosages for species differ and are mainly based on empirical data. Several routes of administration can be applied such as the intramuscular, subcutaneous, intravenous, epidural, subarachnoidal or intrathecal route. Antigen-binding proteins that are capable of binding to TeNT according to the invention and that are able to effectively neutralise tetanus toxin can be utilised in the same manner. A dose of antitoxin should preferably result in a blood concentration of at least 0.01-0.1 IU/ml. In established human cases patients preferably are administered 500-1000 IU/kg equine antitoxin intravenously or intramuscularly. Up to 5000-8000 IU human anti tetanus immunoglobulin can be given intramuscularly depending on the preparation used. The preferred dose of the classic equine antitoxin product for established cases in small animals (such as for example feline and canine) is 100-1000 units/kg given intravenously. Larger animals receive a proportionally smaller dose than smaller animals. For example horses may as a preoperative treatment receive 7500-8500 IU intramuscular or subcutaneous, a foal up to a 100 kg 3000-4000 IU via either route. Injured horses (not suffering from tetanus) may as a preventive treatment receive 15000-17000 IU intramuscular or subcutaneous, a foal up to a 100 kg 6500-8000 IU via either route. Horses suffering from tetanus is preferably administered at least 50000 IU via any route (if the preparation allows) or via the combination of several routes. In clinical cases of tetanus treatment may be repeated on a daily basis depending on the effect seen. All recommended dosages usually provide passive protection for as long as 1-3 weeks depending on the species and treatment given. In addition to passive immunisation, active vaccination should preferably be administered to a subject, so called passive-active immunisation. This provides both short term immunity (passive), and long term humoral immunity (active). As the first is declining the second appears and thus avoids a window of non-protection. Active immunization can be accomplished with formulated tetanus toxoid. Such tetanus based toxoid vaccines are commercially available. Toxoid based vaccines can be given concurrently with the SDA based antitoxin and are preferably repeated in 21 days.

In a further aspect, the present invention relates to diagnostic tests for the detection of TeNT or anti-TeNT antibodies in e.g. body fluids. Such diagnostic tests, aiming at the in vitro detection of toxin or anti-TeNT antibodies in e.g. the blood of a human or animal are currently quite complicated and time-consuming. This has to do i.a. with the fact that even very low TeNT levels in the blood are highly toxic, and as a consequence such tests have to be very sensitive. The present invention now provides antigen-binding proteins that show a very high affinity (i.e. low $K_D$ value) for TeNT. Diagnostic tests based upon such antigen-binding proteins are by definition very sensitive and thus such antigen-binding proteins are highly suitable for use in diagnostic tests.

Merely as an example of such a test: in a classical sandwich ELISA test, well-known for decades in the art, a 96-well plate or micro-well plate, lateral flow device carrier material or even a chip, can be coated with one or more antigen-binding proteins according to the invention. Again; merely as an example: SDA SVT06 could be used for the coating step. Due to its excellent affinity characteristics, SDA SVT06 will strongly bind even minute amounts of TeNT, if present. In a second step, the body fluid to be screened for the presence of TeNT can be added to the well. If TeNT is present this will bind to SDA SVT06. After a washing step, e.g. conjugated SDA SVT15 can be added to the wells. If TeNT was present in the body fluid and thus bound to SDA SVT06, conjugated SDA SVT15 can bind to another epitope of the bound TeNT and in a subsequent colour step a colour reaction will take place, thus indicating the presence of even minute amounts of TeNT.

Equally, the antigen-binding proteins capable of binding to TeNT according to the invention are suitable in tests for the detection of antibodies against TeNT in body fluids. In such tests, the body fluid to be tested can be mixed with a small amount of toxin. If anti-TeNT antibodies are present they will bind the toxin. Thereafter (preferably after removal of the antibody-TeNT complexes), the body fluid can be subjected to the sandwich ELISA described above, in order to see if any toxin is still present. If that is the case, this demonstrates that the body fluid was free of anti-TeNT antibodies.

Equally, the SDAs capable of binding to TeNT according to the invention are suitable in tests where the proteolytic cleavage activity of the TeNT L-chain is used for detection of TeNT that is captured using a receptor binding to the TeNT H-chain. Currently, such a binding-and-cleavage (BI-NACLE) assay is being developed (Behrensdorf-Nicol et al., 2015, ALTEX 32, 137-142). The above mentioned monovalent VHHs could serve as binding domains in such assays. The multivalent TeNT binding SDA SVT06-SVT16-SVA12 is even more preferred for such an application since it shows higher affinity and binds to two separate TeNT antigenic sites which increases the chance it only binds active TeNT forms.

Thus, still another embodiment of the present invention relates to diagnostic kits that comprise an antigen-binding protein capable of binding to TeNT according to the invention. Such diagnostic kits could e.g. further comprise a 96-wells plate, a micro-well plate or a chip that is pre-coated with one or more of the antigen-binding proteins capable of binding to TeNT according to the invention. It could e.g. also, or instead, comprise one or more of the antigen-binding proteins capable of binding to TeNT according to the invention in a conjugated form. Such a diagnostic kit could further comprise instructions for performing the diagnostic test.

The present invention also relates to diagnostic kits for the detection of specific species albumin in processed meat e.g. grinded cattle meat. Such diagnostic kits, aiming at the detection of Equine albumin in e.g. the ground meat in sausages, is currently quite complicated and time-consuming. The present invention now provides antigen-binding proteins that show a high binding capacity to Equine albumin. Accordingly, the invention provides a method for detecting albumin, the method comprising the steps of:
 i) providing an SDA capable of binding to serum albumin, preferably having an overall amino acid sequence identity of at least 70% with a sequence selected from the group consisting of SEQ ID NO: 40, 37, 38, 39, 41 and 42, with the proviso that the amino acid sequence identities of CDR1, CDR2 and CDR3 are at least 75%;
 ii) contacting the SDA of step i) with a test sample; and
 iii) detecting possible binding between the SDA of step i) and albumin present in the sample of step ii).

Features and definitions of the SDA of step i) are as described elsewhere herein. The sample of step ii) is preferably a sample comprising processed meat, more preferably processed meat suspected of comprising meat from more than one species. The albumin that is detected is preferably equine albumin. The detection in step iii) can be performed using any method as known in the art, such as ELISA, surface plasmon resonance, or isothermal titration calorimetry. The method is preferably an in vitro method. Accordingly, the invention also relates to the use of an SDA of step i) for the detection of an albumin.

Merely as an example of such a test: in a classical sandwich ELISA test, well-known for decades in the art, a 96-well plate or micro-well plate, sensor or e.g. a microchip can be coated with one or more antigen-binding proteins according to the invention. Again; merely as an example: SDA SVA12 or SVA16 could be used for the coating step. Due to their very high binding characteristics, these SDA will capture even minute amounts of albumin, if present. In a second step, the grinded meat dissolved in a fluid to be screened for the presence of albumin can be added to the well. If albumin is present this will bind to e.g. SDA SVA12 or SVA16. After a washing step, conjugated SDA SVA06 or SVA07 can be added to the wells. If albumin is present in the body fluid and thus bound to SDA SVA12 or SVA16, conjugated SDA SVA06 or SVA07 binds to another epitope of the albumin and in a subsequent colour step a colour reaction takes place, thus indicating the presence of even minute amounts of albumin.

The present invention also relates to biosensor platforms for the determination of affinity characterisation of e.g. Equine monoclonal antibodies. Such platforms could use e.g. the SDA SVG24L to capture Equine Ig on to sensors or microchips after which interaction with target proteins can be analysed.

Use of low SDAs concentrations is highly preferred. For this, it is preferred that as well a fast association to the toxin and even more so a much delayed dissociation of the toxin, to prevent it from exerting its activity, and that can recirculate for prolonged period in (intoxicated) animals (see examples 16 and 22).

TABLE 1

Relation between the name of the various SDAs, primers etc. and constructs as used herein and their SEQ ID NO in the sequence listing. When two SEQ ID NOs are provided, the number in parentheses is the polynucleotide that encodes the polypeptide of the other SEQ ID NO.

| Name | Plasmid | SEQ ID NO |
|---|---|---|
| BOLI192 | | 1 |
| LAM07 | | 2 |
| LAM08 | | 3 |
| BOLI401 | | 4 |
| Sacl-BstEII | | 5 |
| MPE25 | | 6 |
| MPE26 | | 7 |
| RevSeq | | 8 |
| BOLI166 | | 9 |
| BOLI188 | | 10 |
| pUR4585A | | 11 |
| pUR4585G | | 12 |
| SVT20 | | 13 |
| SVT34 | | 14 |
| SVT16 | | 15 |
| SVT25 | | 16 |
| SVT06 | | 17 |
| SVT31 | | 18 |
| SVT08 | | 19 |
| SVT15 | | 20 |
| SVT29 | | 21 |
| SVT13 | | 22 |
| SVT22 | | 23 |
| SVT02 | | 24 |
| SVT03 | | 25 |
| SVT05 | | 26 |
| SVG13 | | 27 |
| SVG18 | | 28 |
| SVG19 | | 29 |
| SVG06 | | 30 |
| SVG23 | | 31 |
| SVG24 | | 32 |
| SVG03 | | 33 |
| SVG07 | | 34 |
| sdAb-31 | | 35 |
| sdAb-32 | | 36 |
| SVA16 | | 37 |
| SVA04 | | 38 |
| SVA06 | | 39 |
| SVA12 | | 40 |
| SVA02 | | 41 |
| SVA07 | | 42 |
| SVT02-GS2-SVG06M4-H6 | pRL482 | 43 |
| SVT06-GS2-SVG06M4-H6 | pRL483 | 44 |
| SVT15-3FW4M-GS2-SVG6M4-H6 | pRL484 | 45 |
| SVT16-L123Q-GS2-SVG06M4-H6 | pRL485 | 46 |
| SVT06-GS3-SVT16-L123Q-GS2-SVG-06M4-H6 | pRL486 | 47 |
| SVT02-GS3-SVT06-GS2-SVG06M4-H6 | pRL487 | 48 |
| SVT06-GS3-SVT15-3FW4M-GS2-SVG06M4-H6 | pRL488 | 49 |
| SVT06-GS2-SVA12M2-H6 | pRL489 | 50 |
| SVT06-GS3-SVT16-L123Q-GS2-SVA12M2-H6* | pRL490 | 51 |
| SVT06-GS3-SVT02-GS2-SVG06M4-H6 | pRL491 | 52 |
| SVT02-GS3-SVT16-L123Q-GS2-SVG06M4-H6 | pRL492 | 53 |
| SVT02-GS2-SVA12M2-H6 | pRL493 | (54) 65 |
| SVT15-3FW4M-GS2-SVA12M2-H6 | pRL494 | (55) 66 |
| SVT16-L123Q-GS2-SVA12M2-H6 | pRL495 | (56) 67 |
| SVT02-GS2-SVG13M4-H6 | pRL496 | (57) 68 |
| SVT06-GS2-SVG13M4-H6 | pRL497 | (58) 69 |
| SVT15-3FW4M-GS2-SVG13M4-H6 | pRL498 | (59) 70 |
| SVT16-L123Q-GS2-SVG13M4-H6 | pRL499 | (60) 71 |

TABLE 1-continued

Relation between the name of the various SDAs, primers etc. and constructs as used herein and their SEQ ID NO in the sequence listing. When two SEQ ID NOs are provided, the number in parentheses is the polynucleotide that encodes the polypeptide of the other SEQ ID NO.

| Name | Plasmid | SEQ ID NO |
|---|---|---|
| SVT02-SVT15-3FW4M-GS2-SVG13M4-H6 | pRL500 | (61) 72 |
| SVT06-SVT16-L123Q-GS2-SVG13M4-H6 | pRL501 | (62) 73 |
| SVT08-GS2-SVG13M4-H6 | pRL502 | (63) 74 |
| VH2B primer | | 64 |
| SVT06-GS3-SVT15-3FW4M-GS2-SVA12M2-H6 | pRL505 | (75) 77 |
| SVT15-3FW4M-GS3-SVT06-GS2-SVG13M5-H6 | pRL506 | (76) 78 |

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

Unless stated otherwise, the practice of the invention will employ standard conventional methods of molecular biology, virology, microbiology or biochemistry. Such techniques are described in Sambrook et al. (1989) Molecular Cloning, A Laboratory Manual (2nd edition), Cold Spring Harbor Laboratory, Cold Spring Harbor Laboratory Press; in Sambrook and Russell (2001) Molecular Cloning: A Laboratory Manual, Third Edition, Cold Spring Harbor Laboratory Press, NY; in Volumes 1 and 2 of Ausubel et al. (1994) Current Protocols in Molecular Biology, Current Protocols, USA; and in Volumes I and II of Brown (1998) Molecular Biology LabFax, Second Edition, Academic Press (UK); Oligonucleotide Synthesis (N. Gait editor); Nucleic Acid Hybridization (Hames and Higgins, eds.).

The following examples are offered for illustrative purposes only, and are not intended to limit the scope of the present invention in any way.

DESCRIPTION OF THE FIGURES

FIG. 1—Sequences of TeNT binding SDAs isolated (SVT clones) that were later yeast-produced. SDAs are aligned and numbered according to the IMGT system. Dashes indicate gaps introduced for sequence alignment. The definitions of the different complementarity-determining regions (CDRs) and framework regions (FR) are also according to the IMGT system. The three CDR regions are indicated in grey background. Additional positions 50a to 50d were inserted in FR2 to accommodate the unusual insertion of 4 amino acids in this region of SVT06, SVT08 and SVT31. Additional residues were also introduced in CDR2 to accommodate the long CDR2 of SVT05. An additional gap was introduced at IMGT position 60 of SVT16 and SVT25 to align residues 62 and 63 of these SDAs with identical residues in SVT20 and SVT34. The classification of SDAs into subfamilies and classification into CDR3 groups is indicated for each SDA [52]

FIG. 2—Sequences of IgG binding SDAs isolated (SVG clones) that were later yeast-produced and two reference SDAs (sdAb-31 and sdAb-32). SDAs are aligned and numbered according to the IMGT system. Dashes indicate gaps introduced for sequence alignment. The definitions of the different complementarity-determining regions (CDRs) and framework regions (FR) are also according to the IMGT system. The three CDR regions are indicated in grey background. The classification of SDAs into subfamilies and classification into CDR3 groups is indicated for each SDA [52].

FIG. 3—Sequences of Alb binding SDAs isolated (SVA clones) that were later yeast-produced. SDAs are aligned and numbered according to the IMGT system. Dashes indicate gaps introduced for sequence alignment. The definitions of the different complementarity-determining regions (CDRs) and framework regions (FR) are also according to the IMGT system. The three CDR regions are indicated in grey background. The classification of SDAs into subfamilies and classification into CDR3 groups is indicated for each SDA[52].

FIG. 4—Western blot analysis of SVT SDAs binding to TeNT. Blot strips of TeNT separated by reducing SDS-PAGE were incubated with biotinylated VHHs indicated on top. The position of relevant molecular weight markers is indicated. The TeNT heavy chain is expected to migrate at about 100 kDa and the light chain at about 50 kDa.

FIG. 5A—SDS PAGE analysis of monomeric and multimeric SDAs. The SDA loaded is indicated above each lane. In case of multimeric SDAs the pRL plasmid that encodes the SDA is also indicated. The position of monomeric SDA, and multimeric SDAs is indicated by arrows at the right of each panel. The molecular weight of the marker proteins is indicated at the right. Panel A, multimeric SDAs containing SVG06 and three reference monomeric SDAs.

FIG. 5B—Panel B, multimeric SDAs containing SVA12 or SVG13 and their corresponding monomeric SDAs. The order of the TeNT binding SDAs in this gel is always SVT02, SVT16, SVT06 and SVT15-3FW4M in both monomeric and multimeric SDAs.

FIG. 6A—Serum half-life of multimeric SDAs injected (i.m.) into piglets. SDAs were injected at time is 0 h and sera were collected at 1, 2, 4, 8, 11, 14, 21 and 28 days. The amount of SDA present in serum samples was measured by ELISA. Mean and standard deviation of 6 piglets (panels A-D) are given. Panel A: SVT06-GS2-SVA12M2-H6 (0.2 mg/kg).

FIG. 6B—Panel B: SVT06-GS3-SVT16-L123Q-GS2-SVA12M2-H6 (0.3 mg/kg).

FIG. 6C—Panel C: SVT16-L123Q-GS2-SVA12M2-H6 (0.5 mg/kg).

FIG. 6D—Panel D: SVT16-L123Q-GS2-SVG13M4-H6 (0.5 mg/kg). Curve fitting for measurement of serum half-life was done with data from 24 to 96 h (predicted 48 h) or from 96 to 504 h (predicted 96 h).

EXAMPLES

1. Llama Immunization and Phage Display Library Generation

Llamas (*Lama glama*) (no. 9236 and 9237) were immunized in an identical manner. A commercially available tetanus vaccine (ready to use, tetanus toxoid based) was injected intramuscularly without further adjuvant addition, 1 ml per llama, in the right thigh at 0, 21 and 42 days post primary immunization (DPI). An target antigen mixture of 0.5 mg chrompure horse IgG (Jackson Immunoresearch Laboratories, West Grove, PA), 0.5 mg chrompure dog IgG (Jackson Immunoresearch Laboratories), 0.5 mg horse Alb (Rockland Immunochemicals, Limerick, PA), 0.5 mg dog Alb (Molecular Innovations, Novi, MI) and 8 µg recombinant tetanus toxin fragment C (rTTC; Reagent Proteins, San Diego, CA) was prepared. In vitro experiments [5] have indicated that fragment C (also designated as Hc or TTC) is responsible for the binding of the tetanus toxin to neurons. The antigen mixture was emulsified with Stimune adjuvant (Thermofisher Scientific, Lelystad, the Netherlands) and injected intramuscularly in the left thigh of each llama at 0 and 21 DPI. An identical mixture of antigens adjuvanted with IMS1312 adjuvant (Seppic, France) was injected intramuscularly in the left thigh of each llama at 42 DPI. Heparinized blood samples (150 ml) were taken at 28 and 49 DPI and peripheral blood lymphocytes (PBLs) were immediately isolated. Blood samples for serum preparation were taken at 0, 28 and 49 DPI.

Figure 4:
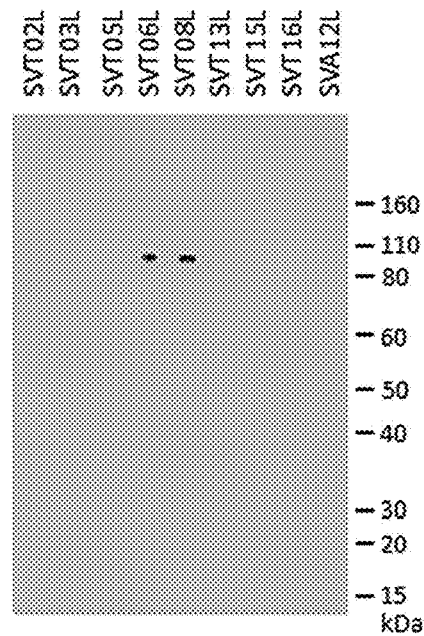
Figure 5A:
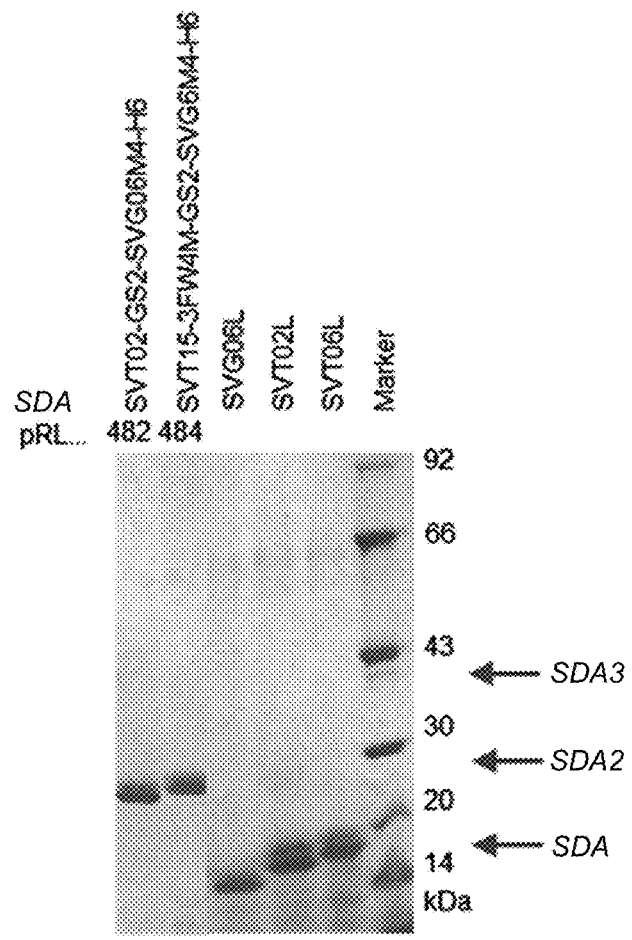
Figure 5B:
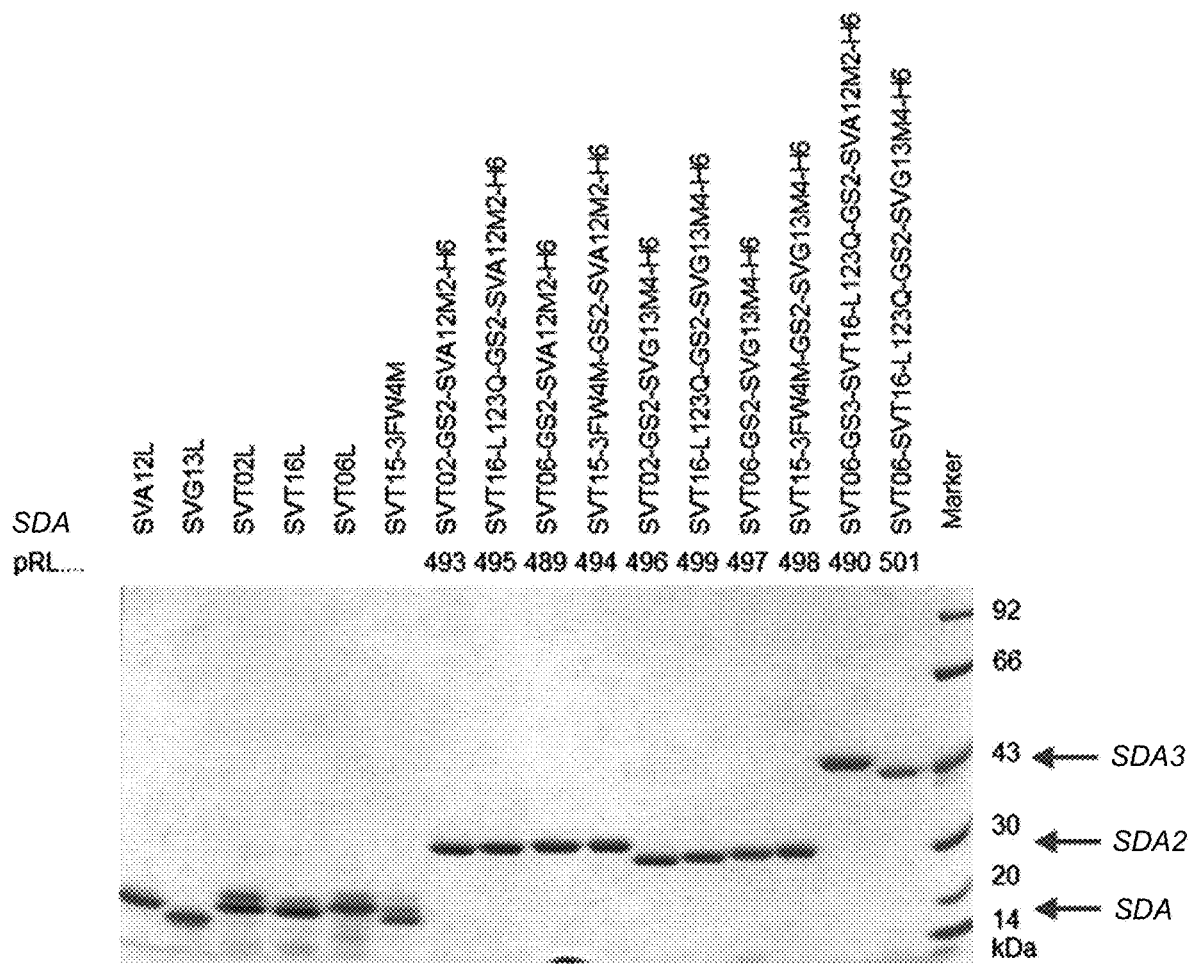
Figure 6A:
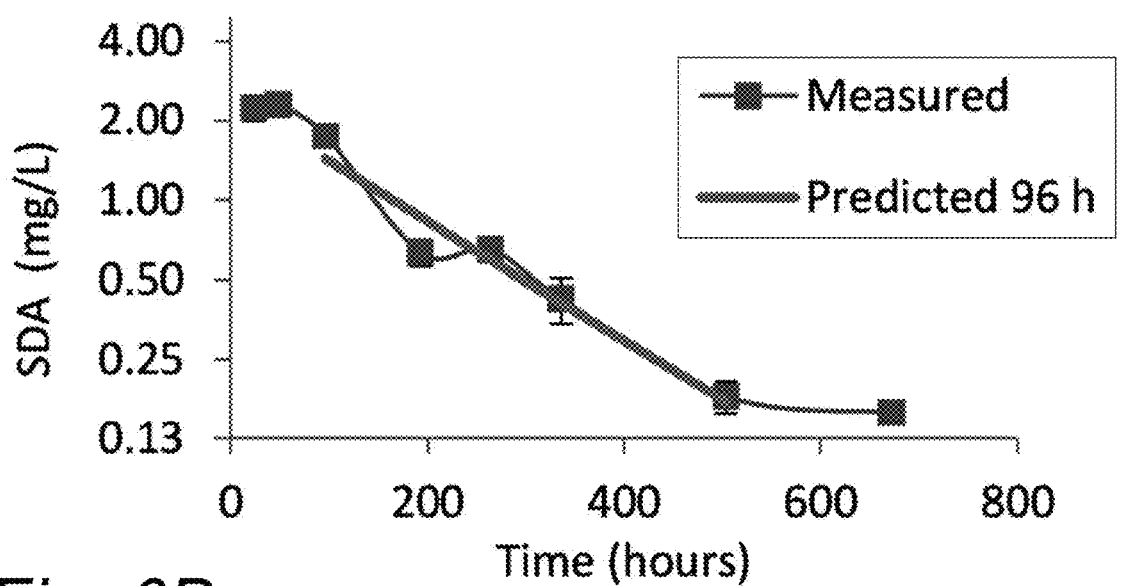
Figure 6B:
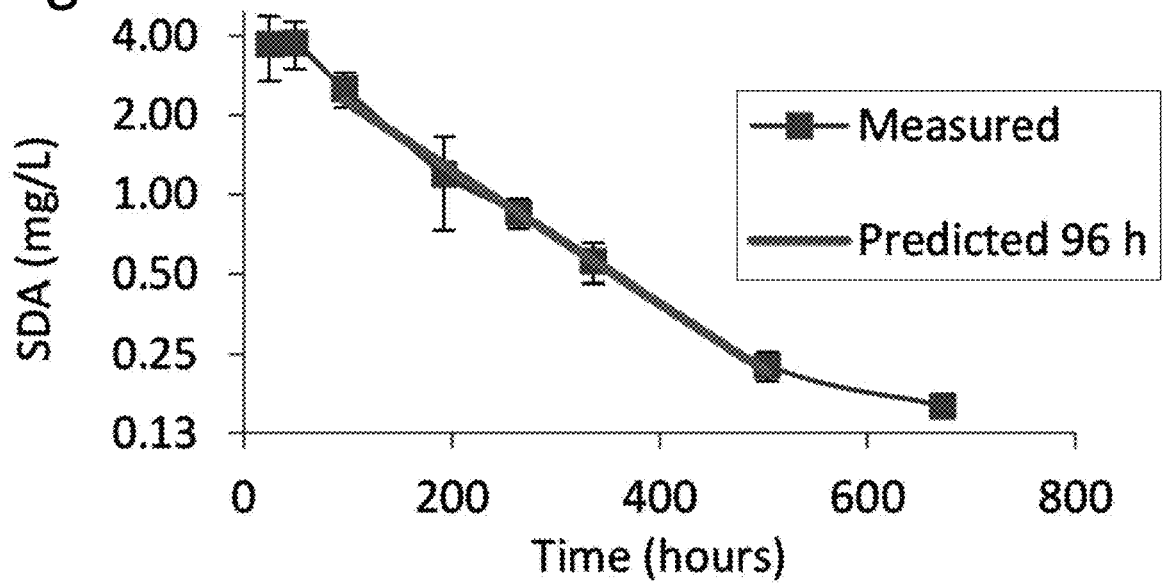
Figure 6C:
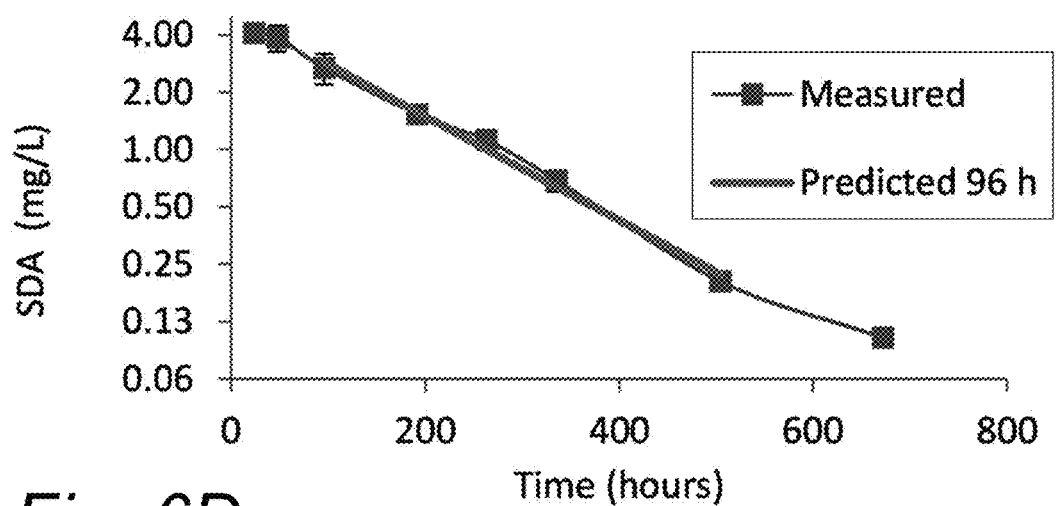
Figure 6D:
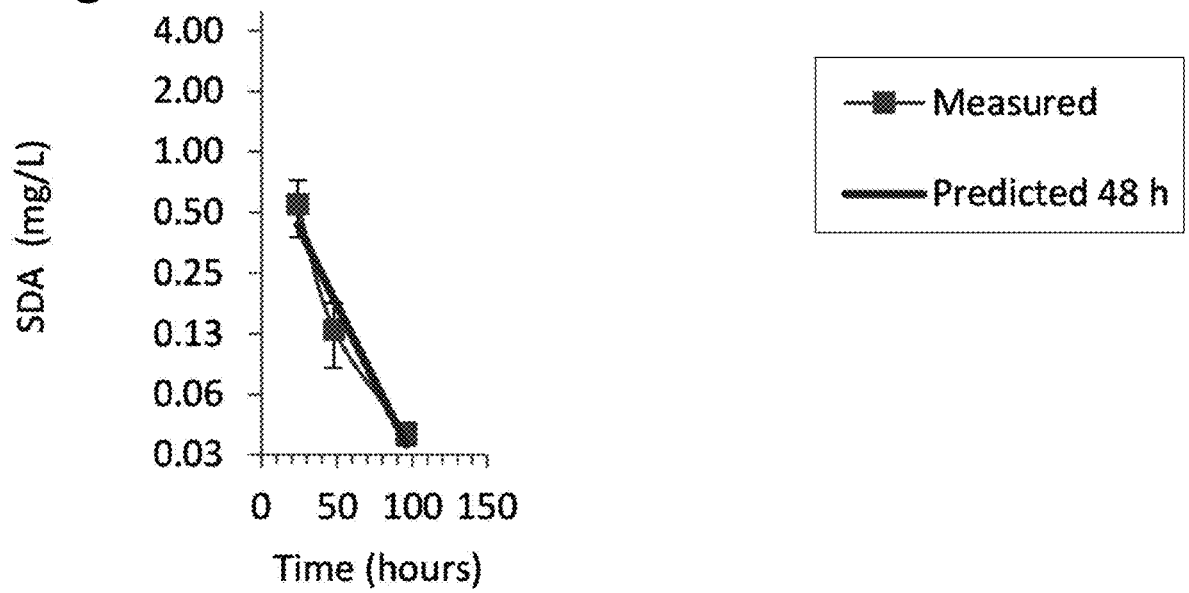

Total RNA was extracted from PBLs using the RNeasy Maxi kit (Qiagen) and used for preparation of cDNA using dT18 priming and Superscript III reverse transcriptase (Invitrogen, Carlsbad, CA). Three PCRs specific for SDAs were performed using primers BOL1192 (AACAGTTAAG CTTCCGCTTG CGGCCGCTAC TTCATTCGTT CCTGAGGAGA CGGT, SEQ ID NO: 1), lam07 (AACAGTTAAG CTTCCGCTTG CGGCCGCGGA GCTGGGGTCT TCGCTGTGGT GCG, SEQ ID NO: 2), and a mixture of primers lam08 (AACAGTTAAG CTTCCGCTTG CGGCCGCTGG TTGTGGTTTT GGTGTCTTGG GTT, SEQ ID NO: 3) and BOL1401 (AACAGTTAAG CTTCCGCTTG CGGCCGCTGG TTGTGGTTGT GGTATCTTGG GTT, SEQ ID NO: 4), all three in combination with primer VH2B (SEQ ID NO: 64) [45]. The resulting PCR fragments were digested with PstI and NotI and inserted into phage display plasmid pRL144 [19]. The ligations were used to transform $E.$ $coli$ TG1 cells (Lucigen, Middleton, WI, USA) by electroporation, resulting in twelve libraries (designated pAL808 to pAL819).

2. Yeast Production of cAb-TT2 Single Domain Antibody

A single domain antibody (SDA) cAb-TT2 [46] binding to the tetanus holotoxin but not to rTTC was produced in baker's yeast for use in subsequent phage display selection of TeNT binding SDAs. A synthetic gene encoding this SDA as fusion to the yeast invertase signal sequence and 5'-leader was generated as SacI-BstEII fragment. It was inserted into plasmid pRL188, resulting in production of the SDA linked to the llama long hinge region, containing a single cysteine and a his6-tag [2]. Such an expression format is especially suitable for SDA immobilization to solid surfaces [3]. The cAb-TT2 SDA was produced in baker's yeast strain SU51 at 150-ml scale, purified by immobilized-metal affinity chromatography (IMAC), and part of the isolated SDA was biotinylated as described earlier [3].

3. Phage Display Selection of TeNT Binding SDAs

The following reagents were used for phage display selection. Yeast-produced cAb-TT2 is described in the previous example. A tetanus toxin neutralizing mAb TT10 [47, 48] was purchased from the National Institute for Biological Standards and Control (NIBSC; Potters Bar, United Kingdom). Authentic tetanus holotoxin (TeNT) was purchased from List Biological Laboratories (Campbell, CA), rTTC is described in example 1.

The twelve libraries were used for phage rescue using helper phage VCSM13 and phage display selections were performed as described earlier [49]. However, a procedure was used that was modified in the following ways:

96-well ELISA plates were used for selection rather than immunotubes [50]
  lower phage amounts of about $10^{-10}$ transducing units (TU) were used in each panning
  trypsin was used for elution of phage [74]
  phage libraries of the three isotypes (hinge primers) were pooled.

Furthermore, selections were done with simultaneous phage ELISAs to monitor the different panning procedures and decide which panning tests should be further used.

The phage display libraries were screened in two rounds of phage display selection of SDAs binding to directly coated TeNT or rTTC.

Furthermore selections were done on TeNT captured with cAb-TT2 SDA or with mAb TT10.

Occasionally, different antigens were used in the second phage display round as compared to the first round.

ELISAs to detect binding to directly coated antigens of soluble SDAs present in tenfold diluted $E.$ $coli$ culture supernatants employing a mouse mAb anti-myc tag PO-conjugate for SDA detection were done as described earlier [19]. However, TeNT and rTTC were coated at 1 µg/ml using PBS buffer whereas cAb-TT2 was coated at 1 µg/ml in 50 mM carbonate/bicarbonate buffer (pH 9.6). Only the absorbance values of the SDA clones that were finally also expressed in yeast are reported.

For identifying individual TeNT binders eight 96-well plates were inoculated with individual clones from the second panning round and induced for production of soluble SDA in 96-well plates as described earlier [49]. Different antigens and 10-fold dilutions of $E.$ $coli$ supernatants containing the soluble SDA were used in the ELISAs. All clones were screened in ELISAs on directly coated TeNT and rTTC, on cAb-TT2 captured TeNT.

In addition, all clones were screened in a GT1b-TeNT binding inhibition ELISA to detect SDAs inhibiting toxin—receptor interaction. The TeNT-GT1b inhibition ELISA is most suitable for comparing the toxin binding and neuron binding blocking capacity of different SDAs, because it is not dependent on for example biotinylation efficiency, accessibility of epitope tags and denaturation due to coating procedure.

The GT1b-TeNT inhibition ELISA was done according to [8]. 96-well polystyrene plates were coated with 10 µg/ml GT1b ganglioside from bovine brain (Sigma Aldrich, St Louis, MO) in methanol at 100 µl/well by overnight incubation at room temperature (RT). During the overnight incubation the methanol evaporates completely. All subsequent incubations were done in PBS containing 0.5% BSA and 0.05% Tween-20 for 1 hr at RT after manual washing plates with PBS. 1 µg/ml TeNT (List Biological Laboratories) was pre-incubated with SDAs, $E.$ $coli$ culture supernatants or mAbs in 100 µl/well in a separate 96-well polystyrene ELISA plate and incubated for 1 hr at RT. Then 90 µl of these samples was transferred to the GT1b-coated plates and incubated for 1 hr at RT. Plates were then incubated with 100 µl/well 1000-fold diluted llama 9237 serum of 49 DPI. Bound llama IgG was detected with goat anti-llama IgG-PO conjugate (Bethyl Laboratories, Montgomery, TX). Bound PO was detected by staining with TMB. The reaction was stopped with sulfuric acid and the absorbance at 450 nm was measured with a spectrophotometer.

For the determination of the SDA (purified by streaking, single colony picked) sequence DNA fragments for sequence analysis were obtained by PCR on *E. coli* TG1 cells with primers MPE25 (TTTCTGTATGGGGTTTTGCTA, SEQ ID NO: 6) and MPE26 (GGATAACAATTTCACACAGGA, SEQ ID NO: 7). Sequence analysis was done using the BigDye Terminator v1.1 Cycle Sequencing Kit and an automated AB13130 DNA sequencer (Applied Biosystems, Nieuwerkerk a/d IJssel, The Netherlands). Purified PCR fragment was used as template in combination with primers MPE25 and RevSeq (TCACACAGGAAACAGCTATGAC, SEQ ID NO: 8). All sequences were determined from two reactions. All sequence interpretation was done based on the translated SDA sequence. The PstI site used for SDA cloning overlaps with amino acids 4 and 5 of the mature SDA. Therefore, the sequence QVQ (amino acids 1-3) that is encoded by the phage display vector used was appended to the SDA N-terminus. SDAs were aligned according to IMGT numbering system [51] of the mature SDA encoding region, ending at sequence VTVSS. SDAs were classified into subfamilies as done earlier [52]. Subfamily C indicates conventional like SDA, lacking the FR2 residues that are typical of SDAs. Such SDAs are often produced at lower levels. Subfamily 1, 2 and 3 designated SDAs indicate three genuine SDA subfamilies. Subfamily X indicates SDAs that are not classifiable. SDAs were also classified into CDR3 groups based on having identical CDR3 length and at least 65% sequence identity in CDR3. SDA sequences were also inspected for the presence of potential N-glycosylation sites (Asn-X-Ser/Thr, where X is any amino acid except Pro). Clones selected for yeast expression lacked such N-glycosylation sites.

Table 2 shows fourteen TeNT binding SDA clones that start with "SVT" followed by a number. Two SDAs, SVT02 and SVT03, that were selected on cAb-TT2 or mAb TT10 captured TeNT, respectively, did bind to cAb-TT2 captured TeNT but did not bind to directly coated TeNT or rTTC and did not inhibit GT1b-TeNT interaction as the absorbance measured was comparable to that observed with *E. coli* culture supernatants that do not contain a SDA (Table 2). These SDAs probably bind to a TeNT epitope whose conformation is affected by passive adsorption to polystyrene, resulting in reduced antigenicity as is earlier observed with other antigens [3, 53]. A further twelve SDAs, of which eleven SDAs were selected on directly coated TeNT or rTTC, did bind to both directly coated and captured TeNT, to directly coated rTTC and did inhibit TeNT-GT1b interaction (Table 2). Three SDAs, SVT05, SVT06 and SVT08 only show partial inhibition of GT1b-TeNT interaction as the absorbance values are decreased from about 1.3 in samples without SDA to 0.72-0.99.

Figure 1:
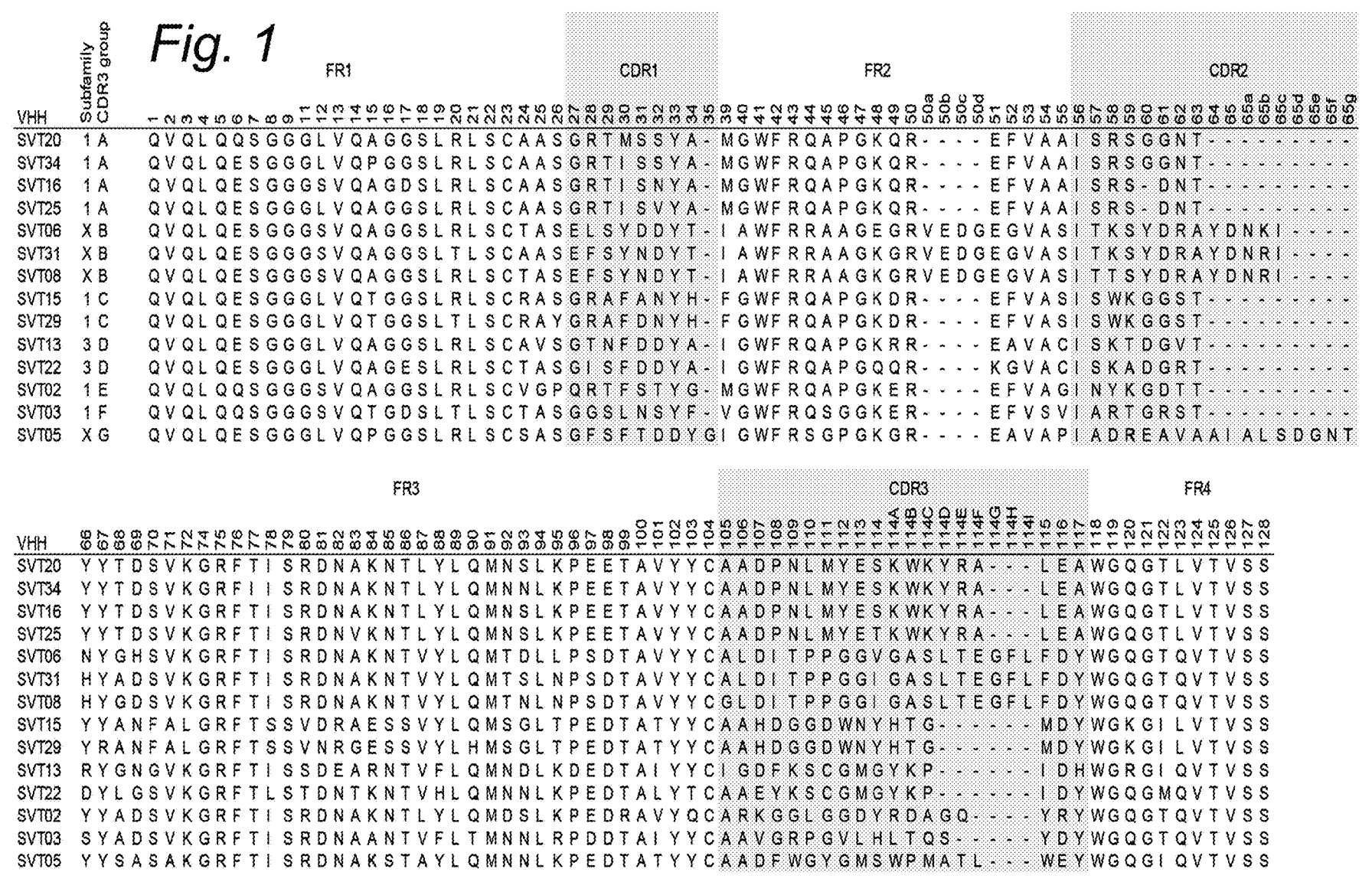

The sequences of the fourteen SVT SDAs form seven CDR3 groups indicated by letters A to G (FIG. 1). Clones from the same CDR3 groups generally behave similar in ELISA (Table 2). The twelve clones from CDR3 groups A, B, C, D and G all inhibit GT1b-TeNT interaction and bind to directly coated TeNT and rTTC as well as to cAb-TT2 captured TeNT. Clones SVT02 and SVT03 forming CDR3 groups E and F do not inhibit GT1b-TeNT interaction and do not bind to directly coated TeNT or rTTC, although they do bind to cAb-TT2 captured TeNT. Several remarkable sequence features are observed with the various SDAs that are discussed per CDR3 group. The four SDA clones from CDR3 group A and the two SDA clones forming CDR3 group C contain a Leu at IMGT position 123, which is associated with lower production level in yeast [11]. The two SDA clones from CDR3 group C also have Lys120 and I1e122 which is typical of the J7 segment encoding FR4 that is associated with reduced SDA production level in yeast [11]. This suggests that these SDAs are more highly produced with mutations K120Q, 1122T and L123Q.

All three SDA clones from CDR3 group B contain an unusual insertion of the amino acid sequence VEDG at position 50a-50d. This is in the middle of the FR2 region, adjacent to residue Arg 50 (Kabat position 45) that is often mentioned in SDA literature as the most typical amino acid substitution of SDAs. Conventional SDAs normally contain a Leu at IMGT position 50 that makes hydrophobic contact with the VL domain. SDAs most often have an Arg at IMGT position 50. This substitution renders the former VL interface more hydrophilic [1]. It is most likely that the insertion of the hydrophilic residues D (Asp) and E (Glu) of the VEDG insertion also render the FR2 region more hydrophilic. Partly because of these acidic residues the predicted isoelectric point (IEP) of these clones is low. A low IEP is more often observed with SDAs and is associated with increased solubility of SDAs [54]. Of note is also that the CDR2 and CDR3 regions are quite long. A long CDR3 is quite commonly observed with SDAs [1, 52]. A long CDR2 is less common, and presumably arises due to somatic hypermutation [55].

Clones SVT13 and SVT22 that form CDR3 group D have a Cys at IMGT position 55 and a Cys in CDR3 that most likely form an additional disulphide bond that is typical of subfamily 3 SDAs [52].

Although the CDR3 sequences are clearly homologous, SVT13 and SVT22 are highly diverse and show 32 amino acid differences.

The single clone SVT05 from CDR3 group G has a very long CDR2 of 17 residues (see discussion above for CDR3 group B) and a low IEP.

4. Phage Display Selection of IgG Binding SDAs Phage display selection of IgG binding SDAs was essentially done as described in the previous example using directly coated IgG from dog or horse. To select for SDAs binding to both dog and horse IgG the second round panning was not only done on IgG of the same species origin, but also on IgG of the other species.

For identifying individual IgG binders six 96-well plates were inoculated with individual clones from the second panning round and induced for production of soluble SDA in 96-well plates [49]. All clones were screened for binding to directly coated IgG of different species and Fab and Fc fragments in ELISA as previously described [19]. Horse and dog IgG antigens are described in example 1. Horse IgG Fc was from Fitzgerald Industries (Tompkinsville, KY) and dog Fab was from Rockland Immunochemicals.

Only the absorbance values of the SDA clones that were finally also expressed in yeast are reported. For this purpose IgG binding clones that bind to the respective antigens of both dog and horse, and preferably even more species were preferentially selected. Furthermore, clones that bind to Fab fragments were preferentially selected. These SDAs are most suited for therapeutic applications since interference with binding to the neonatal Fc (Brambell) receptor involved in IgG half-life is not expected for Fab binding SDAs and since the multispecies recognition makes it unlikely that allotypic IgG variation could cause failure to recognize the IgG in a particular individual animal.

Table 3 shows eight IgG binding SDA clones that start with “SVG” followed by a number. The background absorbance value using *E. coli* culture supernatant without SDA on horse IgG is 0.26, which is considerably higher than on other IgG samples. This could indicate binding of horse IgG to the peroxidase-conjugate used. The maximal absorbance in the ELISA between the different SDAs is also highly variable, presumably because the antigen used for coating is not a pure protein but a mixture of different IgGs of different isotypes and with different variable domains. SDAs SVG03 and SVG24 bind to Fc fragment from horse but not to Fab fragment from dog or horse. SDA SVG23 binds only to dog IgG. Since it does not bind dog Fab it presumably binds dog Fc. SVG03 binds to IgG from horse but not to IgG from dog, human, swine, bovine or guinea pig. SVG24 binds to dog, horse and swine IgG but not to human, bovine and guinea pig IgG. Thus, the three Fc specific SDAs also have a species specificity. SDAs SVG06, SVG07, SVG13, SVG18 and SVG19 bind to Fab fragment from dog and horse but not to horse Fc fragment. They bind to IgG of all six aforementioned species. Thus, the five Fab specific SDAs also have much broader species specificity.

Sequence analysis was done as described in the previous example. The eight clones selected for yeast production (FIG. 2) all belong to different CDR3 groups. All three SDAs bind to Fab fragments of dog and horse IgG and to IgG of all six species tested. All three SDAs and SVG06 are conventional-like SDAs (subfamily C). They all lack the substitution of Trp 118 (residue 103 according to Kabat numbering scheme) for a hydrophilic residue, often Lys, that is often observed with such SDAs [56]. SVG13 in addition has a Lys at position 120 and Leu at position 123 whereas SVG06 has mutations Glu at position 120 and Leu at position 123 that are all typical of J7 segment use in FR4 associated with reduced SDA production level in yeast [11].

Figure 2:
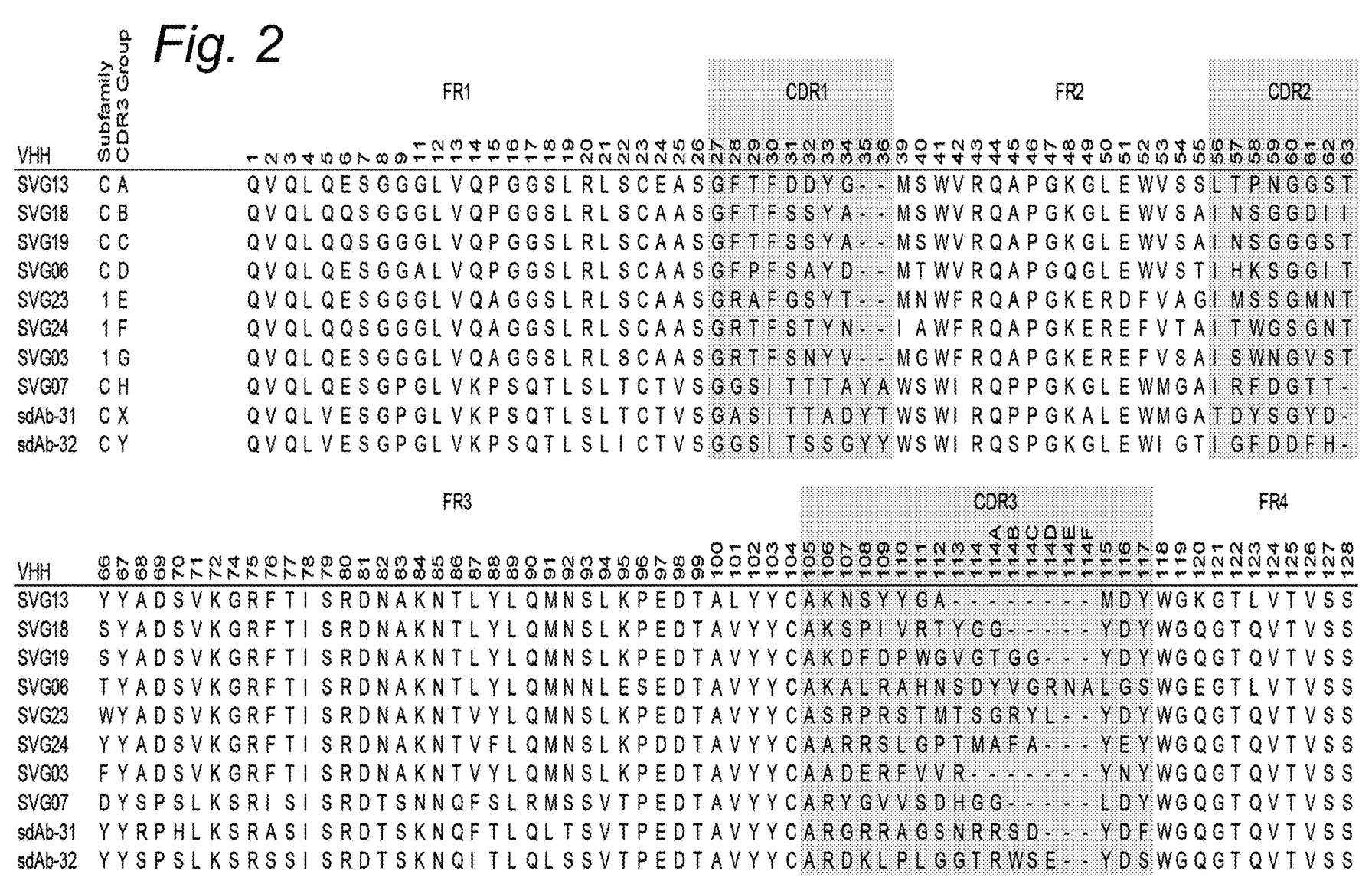

Most SDAs are similar to human VH3 family VHs. However SVG07 is more similar to human VH4 family VHs. Such SDAs were earlier observed [57]. For reference two VH4 family SDAs isolated from camels (sdAb-31 and sdAb-32) are included in the SDA alignment (FIG. 2). The amino acid sequence of FR1, FR2 and FR3 of SVG07 is identical to that of sdAb31 and/or sdAb32 and different from other SDAs at IMGT positions 9, 14, 16, 17, 18, 20, 22, 24, 25, 39, 42, 45, 53, 54, 68, 69, 71, 74, 77, 82, 83, 86, 87, 92, 94 and 95.

5. Phage Display Selection of Alb Binding SDAs

Phage display selection of Alb binding SDAs was essentially done as described in the previous examples using directly coated Alb from dog or horse described in example 1. To select for SDAs binding to both dog and horse Alb the second round panning was not only done on Alb of the same species origin, but also on Alb of the other species.

For identifying individual Alb binders two 96-well plates were inoculated with individual clones from the second panning round and induced for production of soluble SDA in 96-well plates [49]. All clones were screened for binding to directly coated Alb of dog, horse and human in ELISA as previously described [19]. Human Alb was from a commercial supplier (Jackson Immunoresearch Laboratories).

Only the absorbance values of the SDA clones that were finally also expressed in yeast are shown. For this purpose Alb binding clones that bind to the respective antigens of both dog and horse were preferentially selected. Table 4 shows six Alb binding clones that start with "SVA" followed by a number. None of the SDAs bind to human Alb. All SDAs bind to horse Alb. SDA SVA07 does not bind to dog Alb whereas SDAs SVA02, SVA04, SVA06, SVA12 and SVA16 do bind to dog Alb. Thus five SDAs binding both dog and horse Alb were obtained.

Sequence analysis was done as described in the previous examples. The six clones selected for yeast production (FIG. 3) all belong to different CDR3 groups. They are all genuine SDAs of subfamily 1 [52]. They all lack peculiar protein sequence features such as long insertions or FR4 residues associated with reduced SDA production in yeast [11].

6. Yeast Production of Novel SDAs Isolated by Phage Display

Fourteen SVT SDAs (Table 2), eight SVG SDAs (Table 3) and six SVA SDAs (Table 4) were produced by secretory yeast expression. For this purpose the SDA encoding regions were amplified by PCR from the phage display plasmids (examples 3-5) and cut with PstI and BstEII for ligation with similarly cut pUR4585 plasmid. pUR4585 is a yeast—*E. coli* shuttle vector suitable for expression of SDAs C-terminally fused to the c-myc and his6 tags. SDAs produced in this manner are indicated by the suffix "L". Plasmids derived from pUR4585 encoding such SDAs are indicated by the name of the SDA and the prefix "p" in addition to the suffix "L". In addition three mutant SVT SDAs with mutations in the FR4 region to increase yeast production level were produced (see example 3 and [11]):

SDA SVT15L-3FW4M is a derivative of SVT15L containing mutations K120Q, I122T and L123Q SDA SVT20L-L123Q is a derivative of SVT20L containing mutation L123Q SDA SVT34L-L123Q is a derivative of SVT34L containing mutation L123Q These mutations were introduced by producing synthetic PstI-BstEII fragments containing these mutations and subsequent insertion into plasmid pUR4585. The BstEII site used for subcloning is a site that is highly conserved in FR4, but lacking in some SDAs. This was the case with SVT16, SVT20, SVT25 and SVT34. Therefore this site was silently introduced into these four authentic SDAs as well as SVT20L-L123Q and SVT34L-L123Q by producing synthetic PstI-BstEII fragments and subsequent insertion into pUR4585. All yeast expression plasmids were sequence verified as described in example 3, but using purified plasmid DNA as template in combination with primers BOL1166 (ATGATGCTTTTGCAAGCTTC, SEQ ID NO: 9) and BOL1188 (TTCA-GATCCTCTTCTGAGATGAG, SEQ ID NO: 10). The pUR4585-derived plasmid encoding SVT29 encoded a silent A to G mutation on position 60 after the PstI site (CCTGTCGAGCCTACG (SEQ ID NO: 11) mutated to CCTGTCGGGCCTACG (SEQ ID NO: 12)) that was ignored since it was silent.

pUR4585-derived plasmids were introduced into *Saccharomyces cerevisiae* strain W303-1a (ATCC number 208352; MATa, ade2-1, ura3-1, his3-11, trp1-1, leu2-3, leu2-112, can1-100) by selection for the auxotrophic leu2 marker. Plasmids pSVT13L, pSVT15L, pSVT20L and pSVT34L were also introduced into strain SU51, which is more commonly used for SDA production [19, 58]. Yeast culture for SDA production and purification of SDA from spent culture supernatant by IMAC was done as described earlier [19, 58]. Purified SDAs were concentrated and the buffer exchanged to phosphate buffered saline (PBS) by use of Amicon Ultra 3-kDa molecular weight cut off centrifugal concentration devices (Millipore, Bedford, MA). The SDA concentration was determined using the Biorad (Hercules, CA) protein assay and a bovine IgG standard. From these stocks a sample was biotinylated with Sulfo-NHS-LC-biotin (Pierce, Rockford, IL) with a weight ratio of protein to biotin of 5. Mouse mAbs, horse and dog Alb and IgG and TeNT were biotinylated in a similar manner.

Based on the yield of purified SDA the yeast secreted SDA production level per liter culture volume was also determined (Table 5). SDAs were primarily produced in baker's yeast strain W303-1a, however, for comparison of yeast production levels four SVT SDAs were also produced in strain SU51 [58]. The increase in production level using strain SU51 varied from 2.5-fold to 13.6-fold dependent on the nature of the SDA. The mutant SDAs containing various FR4 mutations were produced at 2.6-fold to 5.2-fold higher levels as compared to the wildtype SDAs (Table 5), consistent with earlier findings [11].

The low production level of SVG07L of 0.15 mg/L could be related to this SDA being similar to human VH4 gene family SDAs. It was earlier suggested that conventional-like SDAs (subfamily C in Table 5) are produced at low levels [61]. However, three conventional-like SDAs, SVG06L, SVG13L and SVG19L are produced at reasonably high levels of at least 1.59 mg/L (Table 5).

7. Antigen Binding of Yeast-Produced SVA SDAs Binding of SVA SDAs to Alb from different species was analysed in ELISA by coating antigens to plates and detecting them primarily with unlabelled SDAs employing the myc tag for SDA detection. ELISAs were essentially performed as described in example 3. Purified serum albumins were coated at a concentration of 5 μg/ml. The source of horse and dog Alb is described in example 1. Bovine Alb and chicken ovalbumin were from Sigma Aldrich, human albumin from Jackson Immunoresearch Laboratories and mouse, sheep and swine albumin from Antibodies Online (Beijing, CN). Cat albumin was captured from 500-fold diluted normal cat serum (Agrisera Antibodies, Vännäs, Sweden) on plates coated with 1000-fold diluted immunoaffinity adsorbed goat anti-cat Alb IgG (Antibodies Online). Then plates were incubated with twofold SDA dilution series starting at 1 μg/ml SDA concentration over twelve wells. SDAs were detected using 0.5 μg/ml of anti-myc clone 9E10 mAb peroxidase conjugate (Roche Applied Science). Absorbance data were evaluated using an Excel® spreadsheet template (Microsoft Corporation, Redmond, USA to calculate the maximal A450 value. A four-parameter logistic curve was fitted to absorbance and SDA concentrations to interpolate the Effective Concentration (EC) resulting in an absorbance value of 0.2 for each SDA in each ELISA.

Negative controls without antigen coating, without SDA or with an aspecific SDA (SVT06L) all resulted in absorbance values below 0.15 (Table 6). Absorbance values above 0.15 were considered indicative of Alb binding. Clones SVA12L and SVA16L bind to horse and dog Alb with high (>1) absorbance values. SVA12L also binds swine Alb with high and cat Alb with lower absorbance values. Cat Alb was captured from normal serum with a coated polyclonal antibody. As a result the observed lower absorbance value does not necessarily indicate less efficient binding to cat Alb as compared to Alb from other species. Indeed in example 18 (Table 28), it is shown that SVA12L and SVA06L bind with very similar affinity to Feline Alb (commercially available). Furthermore, there (example 18) it is shown that SVA12L and SVA06L bind with similar affinity to Equine and Canine Alb. A competition assay (ELISA) showed that SVA06L and SVA12L recognize different epitopes (data not shown).

Both SVA12L and SVA16L titrate in ELISA to low SDA concentrations of about 10 ng/ml. SVA02L, SVA04L, SVA06L and SVA07L also bind to several Alb species, but often with lower absorbance values and higher SDA titres than SVA12L and SVA16L. SVA02L and SVA06L also bind to mouse Alb.

None of the SDAs bind to human, sheep, bovine or chicken Alb. The ELISA binding of the yeast-produced SVA SDAs is consistent with the binding of the corresponding SDA produced in *E. coli* (Example 5; Table 4) with one notable exception: clone SVA04L does not bind dog Alb whereas its *E. coli* produced counterpart bound dog Alb with the high absorbance value of 1.533. This could be due to the *E. coli* produced clone not being monoclonal but rather representing a mixture of two clones producing different SDAs. Since the yeast-produced SDA is clonal and more elaborately tested as SDA dilution series rather than in a single well results based on yeast-produced SDA are more reliable.

Clone SVA12L was selected for development of multimeric SDAs (see example 14, 15, 16, 17 and 18) since it binds to both horse, dog, swine and cat Alb and is efficiently produced in yeast (3.85 mg/L using strain W303-1a). SVA12L does not bind to mouse Alb in ELISA and therefore is unlikely to confer half-life elongation in mice (example 17). SVA06L is the candidate suitable for SDA half-life elongation in mice.

8. Antigen Binding of Yeast-Produced SVG SDAs

Binding of eight yeast-produced SVG SDAs to IgG of different species origin and antibody fragments Fab, $F(ab')_2$ and Fc of some species was analysed in a similar manner as described in the previous example. The source of several IgGs and fragments thereof is described in example 4. Mouse, cat, sheep, bovine and guinea pig gamma globulin (GG) as well as horse $F(ab')_2$ fragment was obtained from Jackson Immunoresearch Laboratories. Dog Fc fragment was obtained from Rockland Immunochemicals. The results are described in Table 7. Three ELISAs contained a relatively high background presumably due to cross reaction of the mouse anti-myc mAb PO-conjugate with the coated antigens (footnote b in Table 7). Therefore, the absorbance values in these ELISAs were background subtracted (footnote b in Table 7). Background subtracted absorbance values above 0.2 were considered indicative of antigen binding.

The ELISA binding of the yeast produced SVG SDAs is consistent with the binding of the corresponding SDA produced in *E. coli* (example 4) with two exceptions. Firstly, yeast-produced SDA SVG07L binds only to dog IgG whereas the corresponding *E. coli* produced SDA bound to IgG of all species analysed. Possibly this can partly be explained by the arbitrary cut off value of A450=0.2 chosen for binding being too high. Secondly, the yeast-produced clone SVG24L does not bind to swine IgG whereas its *E. coli* produced counterpart did. This could again be due to the arbitrary cut off value of A450=0.2 chosen for binding being too high. Alternatively, such binding of *E. coli* produced clones could also result from these clones not being monoclonal. Such an artefact is not likely for the yeast-produced SDAs. Thus, the data of the ELISA binding of the yeast-produced SDAs are more reliable.

SDAs SVG06L and SVG13L bind to Fab fragments and IgG of all species analysed except chicken when a background subtracted absorbance value above 0.2 is taken as indicative of antigen binding. The absorbance value of 0.164 on chicken IgG of SVG13 probably represents binding to chicken IgG since most other SDAs have absorbance values below 0.08 in this ELISA. SDA SVG19L shows considerable sequence similarity to SDA SVG13L (Example 4) and shows a binding pattern similar to SVG13L, but it does not bind with 0.2 absorbance values above background to mouse, sheep and swine IgG. SVG03L is specific for horse Fc and SVG23L for dog Fc fragment. SVG24L recognizes predominantly horse and dog Fc.

SDA SVG13L is most suitable for development of multimeric SDAs since it binds to Fab and IgG of all species analysed and is well produced (non-optimised) in yeast (1.6 mg/L).

SDA SVG06L is also suitable for development of multimeric SDAs since it binds to Fab and IgG of all species analysed except chicken and is also well produced (non-optimised) in yeast (1.8 mg/L).

9. Species Specificity of IqG Binding SDAs

The binding in ELISA to IgGs from various species of four porcine IgG-binding SDAs (VI-clones) isolated earlier [19] was compared with SDA SVG13L that reacts with IgGs of most species. ELISAs were done as described in example 8. The results (Table 8) show that SDAs VI-4L, VI-8L, VI-11L and VI-14L do not bind to bovine, cat, dog, mouse and human IgG. Possibly they do bind to sheep IgG since the maximal absorbance is slightly increased above background without SDA. SDA VI-11L in addition binds to horse IgG. However, in all instances, SVG13L yields much higher absorbance values on IgG from all species except swine IgG. On swine IgG on the contrary, all VI clones yield higher absorbance values than SVG13L.

10. Antigen Binding of Yeast-Produced SVT SDAs

Several yeast-produced SDAs and six anti-TeNT mAbs were analysed for antigen binding in ELISA in a similar manner as described for SVA and SVG SDAs. The anti-TeNT mAbs were obtained from different suppliers. Their origin and information provided by the supplier about TeNT neutralization in mouse bioassay or antigen binding in Western blot is described in Table 9. Part of these mAbs was biotinylated as described in example 6.

The binding of unlabelled SDAs or mAbs to directly coated TeNT, rTTC or polystyrene plates without antigen coating as well as to TeNT that was captured by passively adsorbed cAb-TT2 SDA was analysed. See examples 1 and 3 for such antigen coating procedures. These plates were then incubated with dilution series of unlabelled SDAs or mAbs and further processed as described in example 7, but using a 2000-fold diluted rabbit anti-mouse immunoglobulin PO conjugate (Dako, Glostrup, Denmark) for detection of mouse mAbs and without titrating the SDAs on rTTC-coated plates. Furthermore the binding of biotinylated SDAs or mAbs to directly coated TeNT and cAb-TT2 captured TeNT was analysed in a similar manner using 0.5 µg/ml streptavidin-PO conjugate (Jackson Immunoresearch Laboratories) for SDA detection. Finally, the GT1b-TeNT interaction inhibition of unlabelled SDAs or mAbs was analysed as described in example 3 using twofold dilution series of SDAs or mAbs over 11 wells starting at a concentration of 1 µg/ml SDA or 10 µg/ml mAb.

The results are described in Table 10. Absorbance values on plates without specific TeNT antigen coating were below 0.07. Also in ELISAs with control SDA SVA12L—with exception of the GT1b-TeNT inhibition ELISA—absorbance values were at most 0.155 (directly coated TeNT and biotinylated SDAs or mAbs) or 0.072 (other ELISAs). Thus, absorbance values above 0.2 are indicative of antigen binding. The ELISAs with biotinylated SDAs or mAbs on directly coated TeNT or captured TeNT were generally consistent with similar ELISAs using unlabelled SDAs or mAbs. None of the biotinylated SDAs or mAbs were negative in an ELISA where its unlabelled counterpart was positive. This shows that biotinylation never abrogated antigen binding. Often biotinylated SDAs gave slightly higher absorbance values on captured TeNT (e.g. the three CDR3 group B SDAs SVT06L, SVT08L and SVT31L). Notable exceptions are mAbs B417M and 11n185 that generally give lower absorbance values and >50-fold higher EC when biotinylated, indicating that biotinylation was either less effective or affected antigen binding by these mAbs. In case of mAb B417M the presence of 0.5% HSA as a stabilising agent could have decreased its biotinylation efficiency.

In general the ELISA binding of the yeast-produced SVT SDAs is consistent with the ELISA binding of their *E. coli* produced counterparts (example 3; Table 2). As noted earlier in example 3, with exception of SVT02L and SVT03L, all SDAs bind to rTTC. As noted earlier, the failure to detect binding of SVT02 and SVT03 to rTTC could be due to direct coating of rTTC since these SDAs also fail to bind directly coated TeNT while they do bind to captured TeNT. Furthermore, as earlier observed, the three CDR3 group B SDAs SVT06L, SVT08L and SVT31L as well as SVT05L only partially inhibit TeNT-GT1b interaction with minimal absorbance values of about 0.5 and relatively high EC values. Furthermore, as observed earlier, SDA SVT03L does not inhibit TeNT-GT1b interaction. However, yeast produced clone SVT02L also shows partial TeNT-GT1b inhibition with an EC value of >1000 ng/ml while its *E. coli* produced counterpart did not show any inhibition. This difference could simply be due to the use of a too low SDA concentration in case of the *E. coli* produced SDA that was used at tenfold *E. coli* supernatant dilution with unknown SDA concentration. The observed binding of biotinylated yeast produced SVT03L to directly coated TeNT only at the highest SDA concentration analysed was also not observed earlier and can similarly be explained by the higher SDA concentration used (see example 11).

The three mutant SDAs of SVT15L, SVT20L and SVT34L have similar maximal absorbance values and EC values as their wildtype counterparts in the ELISAs using biotinylated SDAs and in the GT1b-TeNT inhibition ELISA. This suggests that the framework 4 mutations introduced to increase antigen binding do not affect TeNT binding. Here, the EC values are determined at the absorbance value corresponding to 50% inhibition of TeNT-GT1b inhibition ($IC_{50}$). The $IC_{50}$ values vary from 34 to 986 ng/ml. Clones from CDR3 group B show higher $IC_{50}$ values (317-986 ng/ml) than clones from CDR3 groups A, C and D (34-133 ng/ml). Clones from the same CDR3 group differ in $IC_{50}$ value with at most a factor 4.

Six mAbs were included in the analysis. mAb 11n185 was selected because it binds TeNT light chain. The further five mAbs were selected because they neutralize TeNT in a mouse bioassay. The mAbs bind in the different ELISAs as follows:

1. mAbs 14F5 and 6F55 bind less efficiently to directly coated TeNT as compared to captured TeNT, similar to SVT02L and SVT03L.
2. Only mAbs 6E7 and 6F57 inhibit TeNT-GT1b interaction in ELISA. They have an IC50 that is considerably higher than the $IC_{50}$ of most SDAs.
3. Whereas most SDAs bind to rTTC, only two out of six mAbs bind rTTC. This suggests that the neutralization of TeNT by three mAbs is not based on inhibition of TeNT-GT1b interaction.

11. SDAs Characterized for Binding to Fragment C of TeNT (rTTC Binding).

Two SDAs (SVT02L and SVT03L) do not bind to directly coated TeNT and therefore their binding to the directly coated fragment C (rTTC) of TeNT (named also Hc or TTC) is inconclusive with respect to particle specificity since passive adsorption could have abrogated antigen binding (example 10). the binding of these SDAs to rTTC captured with mAb 6E7 was therefore analysed in a similar manner as described in example 10. Six wells of a 96-well plate were coated with TeNT (0.75 µg/ml) and 18 wells with mAb 6E7

(1 µg/ml). Six mAb 6E7 coated wells were subsequently incubated with 2 µg/ml rTTC, six further wells with 0.75 µg/ml TeNT whereas the remaining six wells with mAb 6E7 coating were incubated with ELISA buffer (negative control). Subsequently six SDAs were incubated in the four wells with different antigens coated at 2 µg/ml SDA concentration. Bound SDA was detected by incubation with anti-myc mAb PO-conjugate.

The results (Table 11) show that:
Negative controls SVA12L and mAb 6E7 coating without captured antigen are negative (absorbance <0.07).
Capture of TeNT or rTTC with mAb 6E7 or direct coating of TeNT is successful as it is detected by SVT16L (high absorbance) and SVT15-3FW4M (lower absorbance).
SVT02L and SVT03L are functional as they bind to captured TeNT.
SVT03L does bind to directly coated TeNT, although with lower A450 than captured TeNT, whereas SVT02L does not bind to directly coated TeNT at all.
SVT02L and SVT03L do not bind to rTTC captured with mAb 6E7. Since they recognize another antigenic site than mAb 6E7 (example 13) this is not due to use of mAb 6E7 for capture.
Therefore, SVT02L and SVT03L bind another TeNT part than present in rTTC. This observation is consistent with the inability of these SDAs to inhibit TeNT-GT1b interaction (example 10).

12. Western Blot Analysis of TeNT Binding of SVT SDAs

Binding of SVT clones to TeNT light or heavy chain was analysed by Western blotting (FIG. 4) as done previously [19] using 2.5 µg authentic TeNT per gel and using 0.5 µg/ml biotinylated SDA (example 6) and 0.1 µg/ml streptavidin PO conjugate (Jackson Immunoresearch Laboratories) for immunoblotting. SDA SVA12L was used as a negative control. Most SDAs did not show binding to either light or heavy chain in Western blot. This could be due to those SDAs recognizing conformational epitopes. However, SDAs SVT06 and SVT08 bind a polypeptide of about 100 kDa that must represent TeNT heavy chain. These clones belong to the same CDR3 group (group B) and recognize the same antigenic site (Table 12). Both SDAs also bind to rTTC (Tables 2 and 10), that is derived from the heavy chain. Therefore, binding in Western blot to TeNT heavy chain of SDAs SVT06 and SVT08 is consistent with earlier observations.

13. Tetanus Toxin Antigen Mapping by SDAs (SVT)

The antigenic sites of SVT SDAs and six anti-TeNT mAbs were mapped by blocking/competition ELISA using biotinylated SDAs and mAbs. If possible, two representatives of each CDR3 group were used for this purpose. SDAs were primarily selected based on their $IC_{50}$ value in TeNT-GT1b interaction. However, SVT29L was yeast-produced at only 0.07 mg/L and therefore replaced by SVT15L-3FW4M. Competition/blocking ELISAs were done using similar ELISA procedures as described in the previous example, but using 0.5 µg/ml TeNT for direct coating. A biotinilyated SDA or mAb concentration was used that resulted in almost maximal absorbance value and competed/blocked this SDA or mAb with 5 µg/ml of various unlabelled SDAs or mAbs. TeNT coated plates were first incubated with the unlabelled SDA or mAb in 90 µl/well for 30 min (blocking step). Then 10 µl 50 µg/ml biotinylated SDA or mAb was added and incubated for another 30 min (competition step). In case of biotinylated SVT02 and SVT04 TeNT was captured with cAb-TT2 since these SDAs only bind to captured TeNT but not to directly coated TeNT. In all other cases directly coated antigens were used. A control without antigen coating and a control without biotinylated SDA were included. The % inhibition of antigen binding due to a competing/blocking SDA was then calculated as 100-100*([A450 with competing SDA or mAb]—[A450 without Ag coating])/([A450 without competing SDA or mAb]—[A450 without Ag coating]). All SDAs and mAbs blocked the binding of their biotinylated counterpart by at least 75%, indicating that the assay was valid.

At least five independent antigenic sites indicated by letters A-E were identified (Tables 12 and 13). As expected, SDAs from the same CDR3 group are always part of the same antigenic site. SVT02L, mAb 14F5 and mAb 6F55 form antigenic site A. These three SDAs or mAbs also show other similar characteristics in other ELISAs. Most notable is their more efficient binding to captured TeNT as compared to directly coated TeNT. This suggests that their binding is highly dependent on the correct TeNT tertiary conformation. SVT03L is a single SDA forming antigenic site B. SVT15L and its mutant derivative SVT15L-3FW4M form antigenic site C. SVT06L, SVT08L, mAb 6E7 and mAb 6F57 form antigenic site D. These SDAs are expected to be less dependent on the correct conformation of the antigenic site since they also bind to TeNT in Western blot (example 12).

Consistent with this notion partial competition by clones from other antigenic sites does not occur for these four SDAs or mAbs. The SDAs SVT13, SVT16, SVT22 and SVT34, representing two CDR3 groups, form antigenic site E.

The results of the SVT clones are summarized in Table 12. In general the results are consistent with the general view on Ag specificity of SDAs and antigenic structure of TeNT:
SDAs of the same CDR3 group fall into the same antigenic site.
SDAs or mAbs of the same antigenic site show similar antigen binding specificity:
SDAs or mAbs of antigenic site A bind an epitope that is conformationally sensitive since they show reduced binding upon direct coating of TeNT.
SDAs of antigenic site D bind TeNT Hc in Western blot.
SDAs and mAbs of antigenic sites C, D and E all inhibit TeNT-GT1 b interaction, whereas SDAs or mAbs of antigenic sites A and B do not.
SDAs or mAbs that inhibit TeNT-GT1b interaction all bind to rTTC.

Of note is that clone SVT02 is now shown to bind the same antigenic site as two mAbs reported to neutralize TeNT in a mouse bioassay. This strongly suggests that SVT02 could also neutralize TeNT although it did not inhibit TeNT-GT1b interaction. TeNT neutralizing mAbs that do not inhibit GT1b interaction have been described earlier [68]. Similarly, clones SVT06 and SVT08 probably neutralize TeNT (example 17) since they compete with two neutralizing mAbs. Clone SVT06 is most suitable for further work since it produced at a higher level. The SDAs from antigenic sites C and E do not compete with any of the neutralizing mAbs. However, these SDAs do inhibit TeNT-GT1b interaction. Therefore, they are likely to neutralize TeNT, only to be proven in in vivo assays (example 17). SDAs SVT02L, SVT06L, SVT15L-3FW4M and SVT16L are therefore recommended building blocks for generation of multimeric SDAs (Table13).

14. Yeast Production of Multimeric SDAs

Multimeric SDAs were produced by making stable MIRY integrants [75] using plasmid pRL44 [69] in yeast strain SU50 [70] in order to increase SDA production levels. Such MIRY integrants on average have a fivefold increased production level of SDAs as compared to 2 micron based plasmids. Twelve plasmids were generated that encode multimeric SDAs (Table 14) composed of fusions of TeNT binding SVT-SDAs with either Alb binding SVA12 SDA (5 plasmids), IgG binding SVG06 SDA (2 plasmids) or IgG binding SVG13 SDA (5 plasmids). The elements from which these multimeric SDAs were made are as follows:

GS3: $(G4S)_3$ linker described earlier [27]

GS2: $(G4S)_2$ linker derived from pRL144 plasmid [19]

H6: his6 tag, double stop codon and HindIII site as in pRL188 [2]

SVG06M4: SVG06 with four mutations: Q1E, Q5V, E120Q, L123Q

SVG13M4: SVG13 with four mutations: Q1E, Q5V, K120Q, L123Q

SVA12M2: SVA12 with two mutations: Q1E, Q5V

SVT15-3FW4M: SVT15 without internal Sac site and 3 mutations: K120Q, 1122T, L123Q SVT16-L123Q: SVT16 with silently restored BstEII site and L123Q mutation Synthetic SacI-HindIII fragments were produced and subsequently subcloned into plasmid pRL44 [69] using SacI and HindIII sites, resulting in plasmids pRL482 to pRL501 (Table 14).

Baker's yeast strain SU50 (MATa; cir°; leu2-3,-112; his4-519; can1; [70]) was transformed with HpaI-linearized plasmids pRL482 to pRL501 by electroporation [71] and leu+ auxotrophs were selected. A single colony-purified transformant was induced for SDA expression at 0.5 L scale in shaker flasks and SDA was purified from spent culture supernatant by IMAC [58]. SDA was subsequent further purified by cation exchange chromatography on an SP sepharose column as earlier described [44] with slight modifications. SP sepharose Fast Flow (GE Healthcare, Piscataway, NJ) and 25 mM sodium acetate pH 4.7 buffer was used for SDA binding to the column. Bound SDA was eluted with a step gradient of 0.1, 0.2, 0.4, 0.6, 0.8 and 1 M NaCl in binding buffer. Bound SDA generally eluted between 0.4 and 0.8 M NaCl (Table 14). It was concentrated and buffer exchanged to PBS using 3-kDa molecular weight cutoff centrifugal concentration devices. The SDA concentration was determined using the bicinchonic acid assay (BCA, Pierce cat.no, 23212) and a bovine serum albumin standard (Thermo Scientific, Rockford, IL). Based on purified SDA yield the production level of the multimeric SDAs in yeast was calculated (Table 14). Mono and multimeric SDAs were analysed by reducing SDS PAGE using NuPage Novex 4%-12% Bis-Tris gels with MOPS running buffer (Invitrogen) and staining with Gelcode Blue reagent (Thermo Scientific). In contrast to the multimeric SDAs the monomeric SDAs contain a myc tag in addition to the his6 tag. The monomeric SDAs which contained a myc tag yielded an additional molecule with an about a 2-kDa higher molecular mass that is not observed with most multimeric SDAs which lack the myc tag (FIGS. 5A and B). This additional molecule presumably represents partial O-glycosylation that is dependent on the presence of the myc tag. Such molecules have been observed earlier [44]. The SVT15-3FW4M SDA in addition to this presumed O-glycosylated variant produces a molecule with about 2-kDa lower molecular mass that presumably represents degraded SDA (FIG. 5B).

SDS PAGE analysis of two SVG06M4 containing multimeric SDAs (FIG. 5A) reveals a double band at the position of SDA2s that is not observed with multimeric SDAs containing SVA12M2 or SVG13M4 SDAs (FIG. 5B). Since this SDA is always placed C-terminal in the multimeric SDAs it is most likely degradation at the C-terminus of SVG06M4. This could be due to the introduction of mutations E120Q and L123Q at the C-terminus of SVG06M4 in multimeric SDAs. It would imply loss of the his6 tag in such SDAs. Since SDAs were initially purified by IMAC, this would mean that such degradation occurred after IMAC purification.

All SVG13M4-as well as all SVA12M2-containing multimeric SDAs migrated at positions expected based on their predicted molecular mass (FIG. 5B). The monomeric SVG13L SDA migrates slightly faster than SVA12L SDA, consistent with the about 1 kDa lower molecular weight of SVA12L. Such a pattern is also seen when comparing SVG13L and SVA12L containing multimeric SDAs composed of either two (SDA2) or three (SDA3) SDA domains.

15. Bispecific or Bivalent Antigen Binding of Multimeric SDAs

The several target antigen binding capacities of the various multimeric yeast-produced SDAs was amongst others evaluated in ELISA. Controls of monovalent SDAs that formed the building blocks of these multimeric SDAs were included. ELISAs were basically done as described in earlier examples. Seven different types of ELISA were done (Tables 15 and 16). The GT1b-TeNT inhibition ELISA was earlier described in examples 3 and 10. Three further ELISAs served to measure monovalent SDA binding to passively adsorbed TeNT (0.75 μg/ml), Alb (5 μg/ml) or IgG (5 μg/ml), where both an anti-his tag mAb and a polyclonal anti-SDA serum was used for SDA detection. For measuring bispecific binding to TeNT and IgG or Alb or bivalent TeNT binding TeNT and horse Alb were also biotinylated using Sulfo-NHS-LC-biotin (Pierce, Rockford, IL) with a weight ratio of protein to biotin of 5 as described earlier [72]. They were used in three ELISAs to measure:

bispecific binding to coated dog IgG or Alb (5 μg/ml) and biotinylated TeNT (0.25 μg/ml)

bispecific binding to TeNT (0.75 μg/ml) that was captured with passively adsorbed cAb-TT2 (1 μg/ml) and biotinylated horse Alb (1 μg/ml)

bivalent binding to coated TeNT (0.75 μg/ml) and biotinylated TeNT (0.25 μg/ml)

Polystyrene 96-well plates were coated with the required antigens dissolved in either PBS (TeNT) or 50 mM $NaHCO_3$ pH 9.2 (all further antigens) overnight at 4° C. at 100 μl/well. All subsequent incubations were done, after washing plates using 100 μl/well in ELISA buffer (1% skimmed milk; 0.05% Tween-20; 0.5 M NaCl; 2.7 mM KCl; 2.8 mM KH2PO4; 8.1 mM Na2HPO4; pH 7.4), for 1 h at RT. cAb-TT2 coated plates were subsequently incubated with TeNT in ELISA buffer. Then plates were incubated with twofold SDA dilution series starting at 1 μg/ml SDA concentration over twelve wells. In some ELISAs bound SDAs were detected directly using 1000-fold diluted anti-his6 clone BMG-his-1 mAb PO conjugate (hisPO; Roche Applied Science) or 10,000-fold diluted goat anti-llama Ig PO conjugate (GALPO; Bethyl Laboratories). In other ELISAs plates with bound SDAs were incubated with biotinylated TeNT or biotinylated horse Alb. Biotinylated antigens were then detected with 0.5 μg/ml of a streptavidin PO conjugate (StrepPO; Jackson Immunoresearch Laboratories). Bound PO was then detected by staining with 3,3',5,5' tetramethylbenzidine. After stopping the reaction by addition of 0.5 M sulfuric acid (50 μl per well) the absorbance at 450 nm was measured using a spectrophotometer. Absorbance data were evaluated using an Excel® spreadsheet template (Microsoft Corporation, Redmond, USA). This was used to calculate the maximal A450 value. A four-parameter logistic curve was fitted to absorbance and SDA concentrations using appropriate computer software. This curve was used to interpolate the Effective Concentration (EC) resulting in a particular absorbance value for each SDA in each ELISA. The exact absorbance value used for interpolation of SDA concentration (see Table 14) varied between different ELISAs, dependent on background absorbance values in the absence of SDA and maximal absorbance values observed with different SDAs.

The results of the various ELISAs are presented as both maximal absorbance reached (minimal absorbance for TeNT-GT1b inhibition ELISA; Table 15) and Effective Concentration of SDA (Table 16). From these ELISAs it can be concluded that:

- The GT1b-TeNT inhibition ELISA shows that all SVT02 containing SDAs as well as monomeric SVA and SVG SDAs do not inhibit whereas all further monomeric and multimeric SDAs do inhibit. This is consistent with earlier observations on monomeric SDAs SVT06L, SVT15L and SVT16L (Example 10).
- The ELISA with TeNT and biotin-TeNT has high maximal absorbance values of 1.63 and 1.72 with multimeric SDAs, as expected, but lower absorbance values of at most 1.12 with some bispecific multimeric SDAs and slightly increased absorbance values of at most 0.35 with some monomeric SDAs, which is not expected. Background absorbance is about 0.14. Possible there is bridging due to IgG or Alb present in milk that is used as a blocking agent. Nevertheless these results indicate bivalent TeNT binding by the two bivalent and bispecific SDAs.
- As observed earlier, multimeric SDAs containing an SVT02 SDA domain never bind to directly coated TeNT.
- In ELISA with cAb-TT2 captured TeNT and biotinylated horse Alb the monomeric SVA12L SDA does not bind and all multimeric SDAs containing SVA12 SDA do bind, including SVT02-GS2-SVA12M2-H6 that did not bind to directly coated TeNT.
- The SVT15-3FW4M SDA and SVT15-3FW4M-GS2-SVG06M4-H6 SDA seem to be inefficiently recognized by anti-his6 mAb PO-conjugate, but is well detected with GALPO or in GT1b-TeNT inhibition ELISA. This is consistent with C-terminal proteolytic degradation of the his6 tag that was also observed in SDS-PAGE (example 14).
- SVT02-GS2-SVG06M4-H6 (example 14) showed degradation in SDS-PAGE that could indicate loss of the his6 tag from most SDA molecules, which can explain the low absorbance value in an ELISA on dog IgG using anti-his6 mAb for SDA detection. For this particular bispecific SDA this cannot be confirmed by demonstrating binding to TeNT using GALPO or in the GT1b-TeNT inhibition ELISA since SVT02 does not bind to directly coated TeNT nor inhibit in the GT1b-TeNT ELISA.
- All multimeric SDAs, including SVT02-GS2-SVG06M4-H6 and SVT15-3FW4M-GS2-SVG06M4-H6 bind to both TeNT and either Alb or IgG as demonstrated by the ELISA using dog IgG or dog Alb coating and biotinylated TeNT. Monomeric SDAs do not show binding in these ELISAs.
- STV02-GS2-SVG13M4-H6 gives a maximal absorbance value on dog IgG of 0.18 that is much lower than the other multimeric SDAs containing SVG13M4 but comparable to the value of 0.16 for monomeric SVG13L and clearly above the background values of 0.05-0.06 observed for a specific monomeric SVT-SDAs. This indicates that STVO2-GS2-SVG13M4-H6 binds dog IgG. This is confirmed by the higher absorbance values using biotinylated TeNT for STVO2-GS2-SVG13M4-H6 detection bound to plates coated with dog IgG.

Taken together, all multimeric SDAs show bispecific binding to TeNT and either IgG or Alb but some SDAs do not show strong binding in specific ELISAs since they do not bind to directly coated TeNT (SVT02 containing SDAs), or they do not inhibit GT1b-TeNT interaction (SVT02 containing SDAs) or they have lost the C-terminal his-tag (SVT02-GS2-SVG06M4-H6 and SVT15-3FW4M-GS2-SVG06M4-H6).

To confirm the bispecific/bivalent nature of the multimeric SDAs a second and completely different assay system was used. Biolayer interferometry (BLI) was used as an analytical technique to measure the interactions between TeNT (holotoxin), Albumin (horse) and several SDAs. BLI is an optical technique that analyses the interference pattern of waves of light reflected from two surfaces. Changes in the number of molecules bound to the biosensor causes a spectral shift in the interference wavelength pattern that is measured (real time) and reported in nanometer (nm) shift. The Octet® platform provides herewith the means to obtain accurate information about the rate of biomolecular complex formation between SDAs and target antigens. The Octet Red96 instrument (ForteBio) was equipped with Streptavidin (SAX) biosensors. For measurements 10 µg/ml of biotinylated TeNT (bio-T, Table 17a) or biotinylated horse Albumin (bio-Ah, Table 17b), called the ligand, was coupled to SAX sensors for 10 minutes. The sensors (loaded with the respective target antigen) where than transferred into a solution that contained a specific SDA (mono or multimeric) at 100 nM, and it was measured if interaction occurred for 4 minutes. In a next step the sensors, now with bound with mono or multimeric SDA, were transferred in a solution and allowed to react with a second analyte either the non-labeled toxin (TeNT, at 100 nM) or horse Albumin (Ah, at 100 nM) for 5 minutes. The interaction (nm shift) between sensor and analyte was again monitored. The results were analyzed and Tables 17a and 17b below shows the results for different SDAs (mono and multimeric).

From the results it can be concluded that:
- SDA SVT06-GS3-SVT16-L123Q-GS2-SVA12M2-H6 demonstrates bivalent binding to two TeNT-TeNT molecules.
- SDA SVT06-GS3-SVT16-L123Q-GS2-SVA12M2-H6 and SVT06-GS2-SVA12M2-H6 demonstrate bispecific binding to TeNT and horse albumin in two different test setups.
- SVT16-L123Q-GS2-SVG13M4-H6 and SVT16L were able to bind to TeNT.
- SVT16-L123Q-GS2-SVG13M4-H6 and SVG13L was as expected not able to interact with horse albumin.

16. Analysis of Multimeric SDA Serum Half-Life in Swine

Several in vitro assays (examples 4, 5, 7, 8, 9, 15 and 18) with mono and multimeric SDAs have demonstrated that these SDAs can bind to blood components of several species (e.g. Equine, Canine, Feline and Swine). To evaluate the in vivo characteristics of some of the SDAs with regard to prolongation of serum half-life an animal experiment was performed. The animal experiment was performed in swine, being a true cross species since the SDAs were generated by use of Equine and Canine proteins only. For this purpose 24 about 6 weeks old piglets consisting of 12 males and 12 females were used. They were weighed 10 days before multimeric SDA inoculation and allocated into four groups of 6 piglets each with equal distribution of gender, preferably equal average body weights and preferably equal distribution of piglets according to sow origin. Groups (Table 18) are indicated by the name of the plasmid encoding the bispecific SDAs (pRL489, pRL490, pRL495 and pRL499) to be injected intramuscularly. Three piglets of group pRL489, two males and one female, also received a second bispecific SDA encoded by plasmid pRL276 called M8ggsVI4q6e [44]. This bispecific SDA contains the same IgG binding SDA domain as SDA2 K609ggsVI-4q6e that was earlier used for measuring half-life [19], but a different fused SDA domain that is specific for foot-and-mouth disease virus (FMDV) antigen.

Piglets were weighed one day before SDA inoculation (day-1). Based on these body weights the dosing of the multimeric SDAs was calculated (Table 18). Dosages increased from 0.2, 0.3 to 0.5 mg/kg for each group. Filter sterilized SDAs diluted in PBS were injected intramuscularly at a single site into the hind thigh in a volume of about 5 ml. Blood samples for serum preparation were collected from the vena jugularis immediately prior to SDA inoculation and 1, 2, 4, 8, 11, 14, 21 and 28 days after SDA inoculation. The body weight of the piglets was also determined at the end of the experiment at day 28 in order to compensate serum half-life for growth of animals.

SDA levels in sera were determined by ELISA using either TeNT holotoxin or FMDV and an anti-tag mAb PO-conjugate. For this purpose 96-well polystyrene plates coated with either TeNT holotoxin at 2 μg/ml in PBS or SDA M23F specific for FMDV 01 manisa [2] dissolved in coating buffer (50 mM $NaHCO_3$ pH 9.2 buffer) overnight at 4° C. at 100 μl/well. All subsequent incubations were done, after washing plates with buffer, for 1 hr at RT. M23F coated plates were subsequently incubated with 5 μg/ml 146S of FMDV 01 Manisa in ELISA buffer. Then plates were incubated with twofold SDA dilution series over eight wells starting at both 1 μg/ml and 0.1 μg/ml SDA standard in two series and fivefold diluted piglet sera. Sera of piglets inoculated with SVT06 or SVT16 containing multimeric SDAs were incubated on TeNT-coated plates whereas sera from piglets inoculated with M8ggsVI4q6e were incubated on FMDV-coated plates. TeNT-coated plates were subsequently incubated with anti-his6 mAb-PO conjugate and FMDV coated plates with anti-myc mAb-PO conjugate. Bound PO was then detected by staining with 3,3',5,5' tetramethylbenzidine. After stopping the reaction by addition of 0.5 M sulfuric acid the absorbance at 450 nm was measured using a spectrophotometer. A four-parameter logistic curve was fitted to absorbance and SDA concentrations of standards. This curve was used to interpolate the SDA concentration resulting in a particular absorbance value for each serum sample in each ELISA. Calculated serum SDA concentrations were exported to an Excel® spreadsheet template (Microsoft Corporation, Redmond, USA).

Piglet weight increased from about 10 kg to about 25 kg during the 4 weeks period of serum collection. We compensated for body weight increase in serum half-life measurement as follows. For each piglet we assumed that the body weight increase per hour depends on the initial body weight and fits to the formula $BW(t)=BW(0)*T^t$, that can be rewritten as $T=10^{\wedge}(log\ 10(BW(t)/BW(0))/t)$, where t is time in hours, where $BW(t)$ is body weight at time t, $BW(0)$ is body weight at time 0, T is fraction weight gain per hour. This allows the calculation of factor T from the piglets weights at day −1 and day 28. At intermediate time points between day −1 and day 28 we then compensated for body weight increase by multiplying the VHH concentration measured with $T^t$.

Terminal serum half-life was calculated according to the formula: $SDA(t)=SDA(0)*(0.5^{\wedge}(t/T\frac{1}{2}\beta))$, where t is time in hrs, where $SDA(0)$ is the SDA concentration at first time point used, for half-life calculation that is compensated for body weight increase, $SDA(t)$ is than the SDA concentration at time t, $T\frac{1}{2}\beta$ is the terminal half-life.

Since the day 28 samples contained a lower SDA level as revealed by absorbance values that were often less than 3 times the background absorbance value these data were omitted from analysis. The serum half-life was calculated from the day 4 to day 21 samples. The Solver function of Microsoft Excel was used to fit SDA concentrations against time according to the above formula for each individual piglet. Average and standard deviation of $T\frac{1}{2}\beta$ were then calculated.

The biodistribution volume of intravenous injected IgG in humans is 60 ml/kg body weight according to references in [73]. Therefore, the initial (day 1-2) concentration of SDA in blood is expected to be a bit less than 1/0.06=16.67 times the injected dose since most SDA is initially in the blood. This fits nicely for the three Alb binding SDAs and control SDA M8ggsVI-4q6e that have initial SDA concentrations above 2 mg/L (FIG. 6) but is considerably lower for SVT16-L123Q-GS2-SVG13M4-H6, consistent with its low half-life.

The $T\frac{1}{2}\beta$ of SDAs starting from day 4 (96 h.) was calculated, including bodyweight compensation, these are summarized in Table 18. The $T\frac{1}{2}\beta$ of M8ggsVI-4q6e is lower than $T\frac{1}{2}\beta$ of K609ggsVI-4q6e measured earlier [19]. This could be due to the different SDA fused or a difference between the two animal experiments.

All three Alb binding multimeric SDAs showed a $T\frac{1}{2}\beta$ ranging from 111 to 135 hr, with low standard deviations. This is higher than the $T\frac{1}{2}\beta$ of 82 hr of the positive control SDA M8ggsVI-4q6e. All these three multimeric SDAs contained the Alb binding SDA domain SVA12M2, fused to either SVT06, SVT16-L123Q or fused to both these SVT SDA domains into a multimeric SDA. Apparently the half-life driven by SVA12M2 is not affected by the specific SVT SDA fused to it, nor by the number of SDAs fused to it.

The $T\frac{1}{2}\beta$ of SVT16-L123Q-GS2-SVG13M4-H6 containing the SVG13 SDA directed against IgG is only 20 hr. The $T\frac{1}{2}\beta$ is clearly increased as compared to a control monomer SDA K609ggsK812 that does not bind serum proteins and has a 1.8 hours $T\frac{1}{2}\beta$ [19], indicating that half-life extension did occur. Nevertheless this is much lower than the $T\frac{1}{2}\beta$ of the Alb binding multimeric SDAs. The binding of SVG13L to porcine IgG in ELISA resulted in lower maximal absorbance values and lower EC values for swine IgG when compared to Feline, Equine, Canine and human IgG (Table 8). This suggests that the binding of SVG13L to other IgG than porcine IgG is of higher affinity and leads consequently to a more prolonged serum half-life in these species.

The affinity of SVA12L to Equine, Canine and Feline Albumin varies between $10^{-270}$ nM, and was approximately 159 nM for swine Albumin (example 18). Therefore a similar or even better serum half-life of SVA12 when included in multimeric SDAs can be expected in vivo in Equine, Canine and Felines.

The positive control M8ggsVI-4q6e contains the SDA domain VI-4 as also contained in VI-4L (example 9). The SDAs VI-4L, V18L, V111L and V114L have an affinity ($K_D$) of 1-33 nM to porcine IgG [19,44]. The SDA SVG13 gave comparable EC values to Equine, Canine and Feline IgG as the SDAs VI4L, VI8L, VilL and V114L demonstrated against swine IgG (Table 8). Therefore a similar serum half-life of SVG13 can be expected in vivo in Equine, Canine and Feline species.

17. Analysis of SDA for Tetanus Toxin Neutralizing Capacity in a Mouse Model

In vitro assays (examples 3, 10, 11, 12, 13, 15 and 18) with mono and multimeric SVT based SDAs demonstrated that these SDAs can efficiently bind to tetanus holotoxin in several experimental test settings. To evaluate the in vivo characteristics of some of these SDAs an animal experiment was performed to assess their tetanus toxin neutralising capacity. Six candidate SDA samples (see Table 19) were tested for anti-tetanus toxin potency using the mouse toxin neutralisation test. One monomeric SDA (SVT03L), four bispecific SDAs (SVT02-GS2-SVG13M4-H6, SVT06-GS2-SVG13M4-H6, SVT153FW4M-GS2-SVG13M4-H6, SVT16L123Q-GS2-SVG13M4-H6), and one bispecific (for albumin and tetanus) and bivalent (for tetanus toxin) SDA (SVT06-GS3-SVT16-L123Q-GS2-SVA12M2-H6) were evaluated in the mouse toxin neutralisation test (TNT). It was performed following a method similar to as described in the European Pharmacopoeia monograph 0091 for tetanus antitoxin. The assay was performed using a level of sensitivity higher than the method described in the Ph Eur monograph 0091, allowing for detection of lower amounts of toxin neutralising antibodies in order to accurately determine the neutralizing endpoints of the SDAs. The tetanus toxin (NIBSC: AWX 4664, diluted 1/100) dose level of the assay performed was at Lp/200. A reference tetanus antitoxin TE3 (prediluted 1/400 to 0.025 IU/ml in the first dilution) was included (one group of 4 mice) in each study which allowed determination of the potency for each test sample. Each time a fixed volume of 0.35 ml toxin was mixed with 2.15 ml of prediluted SDA test sample and left to stand for 30 minutes prior to injection into mice (0.5 ml s.c., left thigh). Each prediluted sample was serially diluted with buffer to create a two-fold or four-fold dilution series. Each SDA dilution had n=4 mice. Animals were observed for 96 hr for signs of tetanus paresis. In each assay the reference TE3 was diluted (two fold or fourfold) with buffer.ln each study (1, 2 and 3) female NIH mice, 16-20 g, age 5-6 weeks were used. In total 3 consecutive studies were performed.

In study 1 the SDA samples were diluted such that the starting concentration of each SDA in the assay mixture was 1000 nM for all candidates, except for SVT06-GS3-SVT16-L123Q-GS2-SVA12M2-H6 where the amount in the mixture was 100 nM. Each candidate was then serially diluted to create a two-fold dilution series of 5 or 6 dilutions in total (see table 19). Each dilution was mixed with a fixed amount of tetanus toxin and left to stand for 30 minutes prior to injection into mice (0.5 ml s.c., left thigh). Each dilution group had n=4 mice. Animals were observed for 96h for signs of tetanus paresis. The proportion of mice protected at each dilution is shown in table 19. No in vivo tetanus toxin neutralising effect, at 1000 nM level, was noted for the SDAs SVT02-GS2-SVG13M4-H6, SVT03L and SVT16-L123Q-GS2-SVG13M4-H6.

The SDAs SVT06-GS2-SVG13M4-H6 and SVT15-3FW4M-GS2-SVG13M4-H6 both provided protection, at the 1000 nM and 500 nM concentration. Both SDAs were able to neutralize the tetanus toxin effectively when tested in this in vivo model.

The SVT06-GS3-SVT16-L123Q-GS2-SVA12M2-H6 SDA provided full protection at all 6 dilutions. Although given at a 10-fold lower concentration this bivalent (i.e. to TeNT) SDA was more potent than all other bispecific SDAs. In addition, the SVA12L SDA fused to the two fused SVT SDAs (SVT06-GS3-SVT16-L123Q) does (in vitro) not bind to mouse albumin. Therefore this multimeric SDA neutralises the tetanus toxin very efficient in the 30 minutes incubation time that is given. Based on the concentration of the reference antitoxin TE3 (prediluted 1/400 to 0.025 IU/ml in the first dilution) at end-point (mid-way between dilution steps 2 and 3), the potency for each test sample can be expressed in IU/ml. Note that where no end-point was obtained, the potency is expressed as <(if 0% protection at all dilutions) or >(if 100% protection at all dilutions). The data are shown in table 20.

The end-point for the reference antitoxin was midway between dilutions 2 and 3=1.3 ml in the assay mixture (0.0325 IU in the assay mixture). For the unknown samples, at end-point there is 0.0325 IU in the assay mixture=0.0325 IU in 2.15 ml which=0.0151 IU/ml. This value can then be multiplied by the respective total dilution factor of the relevant SDA.

The trivalent SDA SVT06-GS3-SVT16-L123Q-GS2-SVA12M2-H6 has the highest potency (protection at lower than 3.1 nM) of all samples tested. It is a trivalent SDA, with one SDA (SVA12), out of three linked SDAs, that binds to the albumin of several species. The other two SDAs (SVT06 and SVT16) bind with high affinity (low $K_D$ value to the tetanus toxin and each bind to a different domain (example 13, 15, 18).

Subsequently, another TNT had to be performed (study 2) to determine the endpoint of protection for SVT06-GS3-SVT16-L123Q-GS2-SVA12M2-H6. In addition, in the literature [7,42] it is described that mixing mouse monoclonal antibodies directed against different epitopes can provide a synergistic effect towards the level of tetanus toxin neutralisation. A similar effect was observed for scFvs that can neutralise tetanus toxin [67]. Others [24] have published that a bivalent anti tetanus toxin nanobody did not lead to a strong improved efficacy when compared to the monomeric form. Therefore, in addition in this second test it was evaluated whether combinations of these different multimeric SDAs when mixed together in a solution would show a stronger toxin neutralisation effect (synergistic effect) than when tested single, see Table 21 for the scheme tested. The assay was performed as described above.

The results of the 2nd mouse toxin neutralisation test are shown in Table 22a and 22b and 23. The end-point for the reference antitoxin was the same as in study 1, midway between dilutions 2 and 3=1.3 ml in the assay mixture (0.0325 IU in the assay mixture). The same potency calculation (based on the relevant concentrations at the first dilution) could therefore be followed for group 7 (single SDA) as shown in study 1. For the SDA combinations it is not possible to provide an estimate for the potency of each SDA in the mixture as the relative contribution of each SDA is unknown. The potency of the mixture can however be described as the lowest concentration (nM) at which the SDA mixture provided a 100% protection (Table 22b).

The multimeric SDAs SVT15-3FW4M-GS2-SVG13M4-H6 and SVT16-L123Q-GS2-SVG13M4-H6 when mixed with SVT06-GS2-SVG13M4-H6 at 62.5 nM (group 1 and 3) provided protection at least at a >125 fold higher level, final concentration of both SDAs was 3.91 nM in total, than when SVT06-GS2-SVG13M4-H6 was tested as single molecule (500 nM). Thus clear evidence of a strong synergistic effect between these SDAs (see Table 21a+21b) was demonstrated.

The mice in Group 5 were unprotected, this shows that in this mixture, and at these concentrations of the relevant SDAs, no synergistic effect was found for SVT15-3FW4M-GS2-SVG13M4-H6 and SVT16-L123Q-GS2-SVG13M4-H6.

The SDA SVT06-GS3-SVT16-L123Q-GS2-SVA12M2-H6 again provided full protection at all dilutions. The final dilution at which full protection was found had an amount of SDA equal to 0.2 nM (Table 23). The potency of this SDA consequently is >1478 IU/mg.

From the data in study 2 it cannot be excluded whether the SDAs SVT02-GS2-SVG13M4-H6 and SVT03L can have a synergistic effect since the synergistic effect of the other SDAs in the mixtures alone is present at the final dilution. The final concentrations of in group 2 and 4 of the individual SDAs SVT15-3FW4M-GS2-SVG13M4-H6 and SVT16-L123Q-GS2-SVG13M4-H6 when mixed with SVT06-GS2-SVG13M4-H6 was however two-fold lower than that of the same SDAs in group 1 and 3. At the lowest concentration (0.97 nM in the final dilution step) full protection was found. Subsequently a third study was performed to determine the endpoint of potency of candidate SVT06-GS3-SVT16-L123Q-GS2-SVA12M2-H6 (see Table 24 below). In this study it was decided to implement a 4-fold dilution per step. In addition, in order to investigate whether the single multimeric SDA SVT06-GS3-SVT16-L123Q-GS2-SVA12M2-H6 alone was more potent than when the two SDAs SVT06-GS2-SVG13M4-H6 and SVT16-L123Q-GS2-SVG13M4-H6 molecules were mixed and diluted in the same manner this group was included as well.

To investigate whether SVT15-3FW4M-GS2-SVG13M4-H6 could further increase the potency of the single SDA SVT06-GS3-SVT16-L123Q-GS2-SVA12M2-H6 the mixture of both was tested as well in a separate group.

In study 3 the endpoint for the reference antitoxin (TE-3) was slightly different to that obtained in study1 and study 2 with only 75% of animals protected in dilution 2 (Table 24). Using the Spearman-Karber method to calculate the 50% protective dose, the concentration of antitoxin at end point is calculated as 0.034 IU in the assay mixture (in phase 1 and 2, the end point for the reference was midway between dilutions 2 and 3=0.0325 IU in the assay mixture).

For SDA SVT06-GS3-SVT16-L123Q-GS2-SVA12M2-H6, which was tested individually, the end point is dilution 1 (50% of animals protected) and dilution 1 contains 0.034 IU in the assay mixture (=0.034 IU in 2.15 ml of test sample and 0.0158 IU/ml). A neutralising titre can be calculated by multiplying the total dilution factor for the sample by the concentration of antitoxin at end point as shown in Table 25.

The very high tetanus toxin neutralising capacity for SDA SVT06-GS3-SVT16-L123Q-GS2-SVA12M2-H6 was again confirmed. The potency of the master stock for this particular multimeric SDA was calculated from the results of this particular assay at 11,474 IU/ml which would equate to more than 1500 IU/per mg protein. In another assay with smaller dilutions steps from 0.2 nM onwards the neutralising capacity of this SDA can be determined even more precisely.

Notably, SVA12L does not bind to mouse Alb and therefore is unlikely to give half-life elongation in mice and contribute to the measured potency (example 7) after administering it to the mice. Indication of a synergistic effect of combining SVT06-GS3-SVT16-L123Q-GS2-SVA12M2-H6 and SVT15-3FW4M-GS2-SVG13M4-H6 was demonstrated at 0.4 nM of total SDA providing full protection.

No protection was seen in this assay for the combination of candidate SVT06-GS2-SVG13M4-H6 and SVT16-L123Q-GS2-SVG13M4-H6. Therefore based on the results shown above it can be concluded that the total concentration of this SDA pair required to give full protection would be in the range 0.4-4 nM, resulting in an amount of 0.2-2 nM or lower for the individual SDAs in the mixture.

Therefore the three studies performed show that the single bivalent and bispecific multimeric SDA SVT06-GS3-SVT16-L123Q-GS2-SVA12M2-H6 provides a very high level of protection against the extremely potent tetanus toxin. Furthermore, it outperformed the strong synergistic effect seen after mixing the two single bispecific SDAs SVT06-GS2-SVG13M4-H6 and SVT16-L123Q-GS2-SVG13M4-H6. The SVG13L SDA has shown to bind to mouse IgG (example 8) which may have contributed to the potency of these bispecific SDAs after administration of the mixture to mice. The bivalent bispecific SDA SVT06-GS3-SVT16-L123Q-GS2-SVA12M2-H6 has as a single molecule more potency than suprasynergistic tetanus toxin neutralising properties shown of the mixture, this is a remarkable feature.

18. Affinity Determination of Different SDAs Against TeNT, Albumin and Immunoglobulin Several SDAs were tested for their target (TeNT, albumin and immunoglobulin of different species) binding characteristics. The tetanus toxin binding characteristics are of importance in the capacity of each SVT SDA to neutralise the tetanus toxin in vivo (example 17). The SVA and SVG SDAs once fused to the SVT SDAs serve to prolong the terminal serum half-life of the SVT SDAs. Thus for the SVA and SVG SDAs binding characteristics [19, 22, 23, 25] to the different blood components are of importance. For veterinary purposes it is in addition of importance to address the species differences between such blood components. For certain cross species disease targets (e.g. Tetanus) it would be preferred to use a single SDA for therapeutic use in several species instead of developing for each species a separate therapeutic SDA.

Here, the biolayer interferometry (BLI) technique was used to measure the interactions between TeNT, albumin of different species and immunoglobulin of different species and several mono and multimeric SDAs. BLI is an optical analytical technique that analyses the interference patterns between waves of light. Changes in the number of molecules (analyte) bound to the biosensor (coated with ligand) causes a spectral shift (nm shift) in the interference wavelength pattern (=signal) that is measured in real time. $K_D$ is the affinity constant, or equilibrium dissociation constant, which is a measure for how tightly the ligand binds to its analyte. It represents the ratio of the on-rate to the off-rate and can be calculated using $k_a$ and $k_{dis}$. $K_D$ is expressed in molar units (M). The $K_D$ corresponds to the concentration of analyte at which 50% of ligand binding sites are occupied at equilibrium, or the concentration at which the number of ligand molecules with analyte bound equals the number of ligand molecules without analyte bound. There is an inverse relationship between Ko and affinity a smaller affinity constant indicates a tighter interaction, or greater affinity of analyte to ligand.

To measure the interactions between the targets and SDAs the Octet Red96 instrument (Pall Life Sciences) was equipped with either Streptavidin (SA/SAX), Anti-Penta-HI (HIS1 K) or for example Ni-NTA (NTA) Dip and Read™ biosensors (FortéBio).

To determine the binding affinity of SDAs to tetanus toxin 2 μg/ml of biotinylated (see example 3) TeNT was coupled to SA sensors. The SDAs were diluted in PBS buffer (PBS 10×Fischer scientific, cat BP399-1 and WFI, Hyclone, cat #SH3022110) containing 0.02% Tween 20 (ACROS ORGANICS, CAT #233362500) (PBSTween) in a twofold dilution series from 100 nM to 1.56 nM (SVT02-GS2-

SVG13M4-H6, SVT03L, SVT15-3FW4M-GS2-SVG13M4-H6 and SVT16L123Q-GS2-SVG13M4-H6), or a twofold dilution series from 10 nM to 0.156 nM (SVT06-GS2-SVG13M4-H6, SVT06-GS2-SVA12M2-H6 and SVT06-GS3-SVT16-L123Q-GS2-SVA12M2-H6). The SDA dilution series were incubated with TeNT-coupled sensors for 5 minutes (100 nM start concentration) or 10 minutes (10 nM start concentration) followed by a dissociation step in PBS-Tween for another 10 minutes (SVT02-GS2-SVG13M4-H6, SVT03L, SVT15-3FW4M-GS2-SVG13M4-H6 and SVT16L123Q-GS2-SVG13M4-H6) or 60 minutes (SVT06-GS2-SVG13M4-H6, SVT06-GS2-SVA12M2-H6 and SVT06-GS3-SVT16-L123Q-SVA1212M2-H6).

To determine the binding affinity of the SDAs SVT06L, SVT15L and SVT16L to tetanus toxin, 5 µg/ml of the respective biotinylated SDA was coupled to SA sensors and the tetanus toxin, in a twofold dilution series from 75 nM to 4.69 nM were incubated with the SDA-coupled sensors for 5 minutes followed by a dissociation step in PBS-Tween for another 30 minutes.

The results were then analyzed using ForteBio Data Analysis software to determine the affinity constant ($K_D$, which is $k_{diss}/k_a$). Table 27 shows affinity data for several purified SDAs.

The bispecific and monomeric SDAs (SVT02-GS2-SVG13M4-H6, SVT06-GS2-SVG13M4-H6, SVT06-GS2-SVA12M2-H6, SVT15-3FW4M-GS2-SVG13M4-H6, SVT06L, SVT15L, SVT16L, SVT16L123Q-GS2-SVA12M2-H6, SVT16L123Q-GS2-SVG13M4-H6) bound with sub-nanomolar to picomolar affinities to TeNT. For TeNT neutralisation capacity this is a pivotal characteristic. A quick association and a strongly delayed dissociation of the SVT based SDAs prevent the toxin from exerting its activity in a rapid and durable manner at low toxin concentrations that are normally found in intoxicated animals.

Especially the stability of the complex of tetanus toxin and SDA is important as it will prevent for example the uptake of the toxin in the neuron. Very low dissociation (Kdis) values were found for the SDAs SVT03L, SVT15-3FW4M-GS2-SVG13M4-H6, SVT06-GS3-SVT15-3FW4M-GS2-SVG06M4-H6 and SVT06-GS3-SVT16-L123Q-GS2-SVA12M2-H6.

For three out of four of these fragment C binding SDAs SVT06-GS2-SVG13M4-H6, SVT15-3FW4M-GS2-SVG13M4-H6 and SVT06-GS3-SVT16-L123Q-GS2-SVA12M2-H6 excellent toxin neutralising properties were demonstrated when tested as single SDA (at <4 µg/ml and <30 ng/ml levels) and mixed together (at <30 ng/ml levels, see example 17) in an in vivo TNT.

The avidity ($K_D$) for TeNT of the three SDAs containing two SVT domains, SVT06-GS3-SVT02-GS2-SVG06M4-H6, SVT06-GS3-SVT16-L123Q-GS2-SVA12M2-H6 and SVT06-GS3-SVT16-L123Q-GS2-SVA12M2-H6 is in the picomolar range. For SDA SVT06-GS3-SVT16-L123Q-GS2-SVA12M2-H6 the measured avidity is 13 picomolar and this SDA has shown excellent tetanus toxin neutralising properties in the in vivo toxin neutralisation model (example 17).

This SDA has an about tenfold higher affinity (lower $K_D$ value) than the affinities of comparable monomeric SDAs or multimeric VHHs containing only one corresponding TeNT binding SDA domain (SVT06 or SVT16), suggesting that both SDA domains present in SVT06-GS3-SVT16-L123Q-GS2-SVA12M2-H6 are capable of simultaneous antigen binding.

For determining the binding affinity of SDAs to serum albumin several assays were performed. Firstly 1.0 (SVA06L) or 1.5 (SVA12L, SVA16L) microgram/ml of SDA was coupled to Ni-NTA sensors (loading time 15 min). The Equine, Canine or Feline albumin was added as analyte, in a twofold dilution series from 76.9 nM to 4.81 nM (Horse or Dog or Cat albumin) for SVA06L. For SVA12L a twofold dilution series from 307.7 nM to 19.2 nM (Horse or Dog albumin), or 615.4 nM to 38.5 nM (Cat albumin) was used. For SVA16L a twofold dilution series from 100 nM to 3.1 nM (Horse, Dog and Cat albumin) was used. Albumins were reacted on the SDA (SVA06L and SVA12L) coated sensors for 1 minute followed by a dissociation step in PBSTween for another 2 minutes, for SVA16L the intervals were 3 and 5 minutes respectively.

To determine the affinity of SVA12L to Swine albumin a twofold dilution series of 250 to 15.6 nM was used, here a one minute association and dissociation step was used.

The results were then analyzed using ForteBio Data Analysis software. Table 28 shows the data for the tested SDAs.

Several SDAs that bind to the Fc part of Equine or Canine immunoglobulin were also tested for their binding characteristics. Firstly, to determine the affinity of SDAs SVG03L, SVG23L and SVG24L when binding to Equine IgG (Fc) (Fitzgerald, cat #31C-CH0804), a setup was used were 0.5 µg/ml of the SDA was coupled to NTA sensors. The scout assay showed that SVG23L did not bind to the Equine Fc protein used. The Equine IgG (Fc) was diluted in PBSTween in a twofold dilution series from 50 nM to 3.13 nM for SDA SVG03L. The Equine IgG (Fc) was diluted in PBSTween in a twofold dilution series from 100 nM to 6.25 nM for SDA SVG24L. The Fc dilution series were incubated with SDA-coupled sensors for 3 minutes (association phase) followed by a dissociation step in PBSTween for 10 minutes.

To determine the affinity of SDAs SVG03L, SVG23L and SVG24L when binding to Canine IgG (Fc) (Rockland, cat #004-0103), a setup was used were 1 µg/ml of the SDA was coupled to NTA sensors. The scout assay showed that SVG03L did not bind to the Canine Fc protein used. The Canine IgG (Fc) was diluted in PBSTween in a twofold dilution series from 40 nM to 2.5 nM for SDA SVG23L. The Canine IgG (Fc) was diluted in PBSTween in a twofold dilution series from 400 nM to 18.80 nM for SDA SVG24L. The Fc dilution series were incubated with SDA-coupled sensors for 70-100 seconds (association phase) followed by a dissociation step in PBSTween for 5 minutes.

The results were then analysed using ForteBio Data Analysis software. Table 35 shows the data for the tested SDAs against the Fc part of Equine or Canine immunoglobulin.

Since albumin and immunoglobulin are abundant serum proteins the affinity of SDAs for albumin or immunoglobulin does not need to be very high in order to have most SDAs molecules bind these targets. Consistent with this notion, it has been observed that serum half-life extension of protein therapeutics using genetically engineered bacterial albumin binding domains was mostly not dependent on the affinity for albumin. If $K_D$ values were lower than 100 nM (increased binding affinity) then serum half-life was not affected by affinity. Only when $K_D$ values became close to 1 µM was serum half-life slightly decreased [36,37].

For the SDAs SVA06L, SVA12L and SVA16L the affinity to albumin of Porcine, Equine, Canine or Feline origin varied between 1-275 nM and all were below 1000 nM. For the multimeric SDA SVT06-GS3-SVT16-L123Q-GS2-SVA12M2-H6 a serum half-life of approximately $110^{-145}$ hours was estimated in young swine. At 21 days after administration the SDAs SVT06-GS3-SVT16-L123Q-GS2-SVA12M2-H6 (0.3 mg/kg), SVT06-GS2-SVA12M2-H6 (0.2 mg/kg) and SVT16-L123Q-GS2-SVA12M2-H6 (0.5 mg/kg) were still detectable in the serum of swine. Thus for SDA SVA12L the dosage given, the amount of SDAs fused to it and the type of SDA did not influence significantly the half-life in swine. Since all the SVA SDAs were generated with Equine and Canine albumin a similar half-life profile can be expected for these SDAs in Equines, Canines and Felines.

For the SDAs SVG03L, SVG23L and SVG24L the affinity constant Ko to the Fc part of the immunoglobulin of Equine or Canine origin varied between 0.1-4 nM and all were below 10 nM. The use of these binders may be of benefit in interfering with different immunological processes (a.o. activation of the complement pathway, type I hypersensitivity reactions, allergy, atopy).

19. Construction and Production of Further Multimeric SDAs Against TeNT

Two more multimeric SDAs (SVT06-GS3-SVT15-3FW4M-GS2-SVA12M2-H6 and SVT15-3FW4M-GS3-SVT06-GS2-SVG13M5-H6) were produced by making stable MIRY integrants [75] using plasmid pRL44 [69] in yeast strain SU50 [70]. The elements from which these multimeric SDAs were made are as follows:

GS3: (G4S)$_3$ linker described earlier [27]
GS2: (G4S)$_2$ linker derived from pRL144 plasmid [19]
H6: his6 tag, double stop codon and Hindlll site as in pRL188 [2]
SVG13M5: SVG13 with five mutations: Q1E, Q5V, W118R, K120Q, L123Q
SVA12M2: SVA12 with two mutations: Q1E, Q5V
SVT15-3FW4M: SVT15 without internal Sac site and 3 mutations: K120Q, I122T, L123Q
SVT16-L123Q: SVT16 with silently restored BstEII site and L123Q mutation
Synthetic Sacl-Hindill fragments were produced and subsequently subcloned into plasmid pRL44 [69] using Sac and Hindlll sites, resulting in plasmids pRL505 and pRL506 (Table 34).

Baker's yeast strain SU50 (MATa; cir°; leu2-3,-112; his4-519; can1; [70]) was transformed with Hpal-linearized plasmids pRL505 and pRL506 by electroporation [71] and leu+ auxotrophs were selected. A single colony-purified transformant was induced for SDA expression at 0.5 L scale and SDA was purified from spent culture supernatant by IMAC [58]. SDA was subsequent further purified by cation exchange chromatography on an SP sepharose column as earlier described [44] with slight modifications. SP sepharose Fast Flow (GE Healthcare, Piscataway, NJ) and 25 mM sodium acetate pH 4.7 buffer was used for SDA binding to the column. Bound SDA was eluted with a step gradient of 0.1, 0.2, 0.4, 0.6, 0.8 and 1 M NaCl in binding buffer. Bound SDA generally eluted between 0.4 and 0.6 M NaCl (Table 34). It was concentrated and buffer exchanged to PBS using 3-kDa molecular weight cutoff centrifugal concentration devices. The SDA concentration was determined using the bicinchonic acid assay (BCA, Pierce cat.no, 23212) and a bovine serum albumin standard (Thermo Scientific, Rockford, IL). Based on purified SDA yield the production level of the multimeric SDAs in yeast was calculated (Table 34).

Multimeric SDAs were analysed by reducing SDS PAGE using NuPage Novex 4%-12% Bis-Tris gels with MOPS running buffer (Invitrogen) and staining with Gelcode Blue reagent (Thermo Scientific). Both multimeric SDAs migrated at positions expected based on their predicted molecular mass. From the stocks a sample was biotinylated (Sulfo-NHS-LC-biotin, Pierce, Cat. No. 21335, lot No. OE185235A) with an appropriate weight ratio of protein to biotin.

20. Further Bindings Characteristics of Several SDAs Against TeNT,

Further assays were performed to study the binding of a selection of SDAs when compared to cAb-TT1 and cAb-TT2 [46] when using the Octet Red96 instrument (Pall Life Sciences) when equipped with Streptavidin (SA) biosensors. For this purpose the binding affinity of the SDAs SVT06L, SVT15L and SVT06-GS3-SVT16-L123Q-GS2-SVA12M2-H6, cAb-TT1 and cAb-TT2 to tetanus toxin was evaluated.

To determine the binding affinity to tetanus toxin, the biotinylated SDAs were coupled to SA sensors (see example 18). A twofold dilution series of the tetanus toxin was prepared, for assay details see table 29. After further assay optimisation the SDAs were incubated with the different dilutions of the tetanus toxin, the association step (2-8 minutes), followed by a dissociation step in PBS-Tween (2-10 minutes). The results were then analysed using ForteBio Data Analysis software to determine the affinity constant ($K_D$), table 29 shows the affinity data for each SDA.

The earlier test results (see Table 27) of SVT06L, SVT15L and SVT06-GS3-SVT16-L123Q-GS2-SVA12M2-H6 were repeated in this assay setup and confirm the high affinity to tetanus toxin. For cAb-TT1 and cAb-TT2 the lower affinity as published was confirmed. Especially the fast dissociation of both cAb-TT1 and cAb-TT2 is remarkable. However, this is in line with the results from a mouse toxin neutralisation test, as described in WO96/34103, where after application of 4 μg of cAb-TT2 75% of the mice had died after 4 days. In contrast, SVT06-GS3-SVT16-L123Q-GS2-SVA12M2-H6 has protected mice when used at low nanogram levels (20-30 ng/ml) in several sequentially performed TNTs against a 5× higher lethal dose of the tetanus toxin.

To determine the affinity of 2 additional multimeric SDAs (SVT06-GS3-SVT15-3FW4M-GS2-SVA12M2-H6 and SVT15-3FW4M-GS3-SVT06-GS2-SVG13M5-H6) when binding to tetanus toxin, a setup was used were 4 μg/ml of biotinylated TeNT was coupled to SA sensors. The SDAs (incl. SVT06-GS3-SVT16-L123Q-GS2-SVA12M2-H6) were diluted in PBS buffer containing 0.02% Tween 20 (PBSTween) in a twofold dilution series from 10 nM to 0.62 nM. The SDA dilution series were incubated with TeNT-coupled sensors for 3 minutes (association phase) followed by a dissociation step in PBS-Tween for another 15 minutes. The results were then analysed using ForteBio Data Analysis software to determine the affinity constant ($K_D$) for each SDA.

From this study the bispecific (binding to tetanus toxin, and albumin or IgG) and bivalent (for tetanus toxin) SDAs bound with sub-nanomolar to picomolar affinities to TeNT, see Table 30. It is expected that these SDAs (SVT06-GS3-SVT15-3FW4M-GS2-SVA12M2-H6 and SVT15-3FW4M-GS3-SVT06-GS2-SVG13M5-H6) will provide effective neutralisation of tetanus toxin in vivo at low nanogram levels based on the results provided in example 17.

21. Further Bindings Characteristics of Several Multimeric SDAs Against Equine, Human or Canine Albumin, In order to determine the binding affinity of a selection of bivalent and bispecific (multimeric) SDAs to Equine, Canine and Human serum albumin additional assays were performed.

To determine the affinity of 3 multimeric SDAs (SVT06-GS3-SVT16-L123Q-GS2-SVA12M2-H6, SVT06-GS3-

SVT15-3FW4M-GS2-SVA12M2-H6 and SVT15-3FW4M-GS3-SVT06-GS2-SVG13M5-H6) when binding to Equine albumin, after optimisation a setup was used were 2.5 microgram/ml of biotinylated (Sulfo-NHS-LC-biotin, Pierce, Cat. No. 21335, lot No. OE185235A, at an appropriate weight ratio of protein to biotin) Equine or 5.0 microgram of Human albumin was coupled to SA sensors. After further optimisation two of these SDAs (SVT06-GS3-SVT16-L123Q-GS2-SVA12M2-H6, SVT06-GS3-SVT15-3FW4M-GS2-SVA12M2-H6) were diluted in PBS buffer containing 0.02% Tween 20 (PBSTween) in a twofold dilution series from 10 nM to 0.62 nM. The SDA dilution series were incubated with Equine albumin-coupled sensors for 6-10 minutes (association phase) followed by a dissociation step in PBS-Tween for another 10 minutes. For SVT15-3FW4M-GS3-SVT06-GS2-SVG13M5-H6 a concentration of 100 nM was chosen.

The monomer SDA SVA12L and all 3 multimeric SDAs were evaluated for affinity binding characteristics to human albumin at a concentration of 100 nM.

To determine the affinity of the 3 multimeric SDAs (SVT06-GS3-SVT16-L123Q-GS2-SVA12M2-H6, SVT06-GS3-SVT15-3FW4M-GS2-SVA12M2-H6 and SVT15-3FW4M-GS3-SVT06-GS2-SVG13M5-H6) when binding to Canine albumin, after optimisation a setup was used were 1.25 microgram/ml of biotinylated multimeric SDA (see example 19) was coupled to SA sensors. The Canine albumin was diluted in PBS buffer containing 0.02% Tween 20 (PBSTween) in a twofold dilution series from 500 nM to 16 nM. The albumin dilution series were incubated with the respective SDA coupled sensors for 4-5 minutes (association phase) followed by a dissociation step in PBS-Tween for another 5-10 minutes.

The results were then analyzed using ForteBio Data Analysis software. Table 31a and Table 31b show the data for the tested SDAs. None of the mono or multimeric SDAs was found to bind to human albumin, as expected. The multimeric SDA_SVT15-3FW4M-GS3-SVT06-GS2-SVG13M5-H6 was found not to bind to Equine, Human or Canine albumin, as expected.

For the multimeric SDAs SVT06-GS3-SVT16-L123Q-GS2-SVA12M2-H6 and SVT06-GS3-SVT15-3FW4M-GS2-SVA12M2-H6 the affinity constant Kn to albumin of Equine or Canine origin varied between 0.5-1.5 nM and 250-400 nM, respectively. For the multimeric SDA SVT06-GS3-SVT16-L123Q-GS2-SVA12M2-H6 a serum half-life of approximately $110^{-145}$ hours (4.5-6 days) was found in Porcine (see example 16) and a serum half-life of approximately 510 hours (21.25 days) was found in Equines (see example 23). Based on the affinity data one can expect a similar half-life for SVT06-GS3-SVT15-3FW4M-GS2-SVA12M2-H6 in Porcine and Equine.

22. The Affinity of Several SDAs to TeNT as Determined by a Another Methodology (Creoptix WAVE System).

For several SDAs the affinity constant to the target TeNT was in the μM range as determined by the Octet Red96 instrument. In order to confirm these findings an additionally technology, the Creoptix™ sensors proprietary Grating-Coupled Interferometry (GCI) methodology [76], was used. GCI is a method based on waveguide interferometry to monitor and characterize molecular interactions and to determine kinetic rates, affinity constants and concentrations of the interacting analytes. Waveguide Interferometry like other optical label-free methods, such as Surface Plasmon Resonance (SPR), detect refractive index changes within an evanescent field near a sensor surface due to changes in mass by complex formation of the interacting molecules. The combination of two very sensitive methods, namely interferometry and planar optical waveguide sensing leads to very low limits of detection.

Affinity (KD) experiments of several mono and multimeric SDAs with TeNT as target were performed with the Creoptix WAVE instrument (Creoptix A G, Waedenswil, Switzerland), at 30° C. The protocols in the WAVE control software for conditioning of the chip (4PCP-S), immobilization of proteins and performing kinetics experiments were followed. Standard chemicals were used. Biotinylated tetanus toxin (10 microgram/ml) was immobilized on the PCH-streptavidin chip with 10 microliter/min injection and 120 s injection duration over the relevant channels. All experiments were run with PBS buffer containing 0.02% Tween 20 (PBSTween) as running buffer. The binding characteristics were evaluated for several SDAs (mono and multimeric) at five concentrations (100-1.2 nM, 3-fold dilution steps). The association phase for the evaluated SDAs was 4 minutes. For SVT 03L, SVT06-GS3-SVT16-L123Q-GS2-SVA12M2-H6 and SVT15-3FW4M-GS3-SVT06-GS2-SVG13M5-H6 the dissociation period was 6000 seconds. For SVT06-SVT16-L123Q-GS2-SVG13M4-H6 and SVT15-3FW4M-GS2-SVG13M4-H6 the dissociation duration was set at 1000 and 12000 seconds, respectively. The results were then analysed using the Creoptix Data Analysis software to determine the affinity constant ($K_D$), results are shown in Table 32.

The results confirm the earlier findings with regard to the slow dissociation and fast association of each of the SDAs tested. The $K_D$ of the SDAs tested varied between 1.0-25 μM.

23. Analysis of the Serum Half-Life of a Multimeric SDA in Equines.

For SDA SVT06-GS3-SVT16-L123Q-GS2-SVA12M2-H6 the determination of the serum half-life was also performed in Equines. A relevant target species since the SDAs were generated by use of Equine and Canine albumin proteins only. For this purpose three 4.5-6.5 yr old ponies (females) were used. They were weighed before intramuscularly inoculation. Based on the body weights the needed amount of the multimeric SDA was calculated (dosage at 0.17 mg/kg) per animal. Filter sterilized SDA, dissolved in PBS, was injected intramuscularly at a single site into the hind thigh in a volume of about 2.5 ml. Blood samples for serum preparation were collected from the vena jugularis immediately prior to and at 1, 2, 4, 7, 10, 13, 17 and 21 days after SDA inoculation. SDA levels in sera were determined by ELISA using TeNT holotoxin and an anti-tag mAb PO-conjugate. For this purpose 96-well polystyrene plates coated with TeNT holotoxin at 2 μg/ml in PBS dissolved in coating buffer (50 mM $NaHCO_3$ pH 9.2 buffer) overnight at 40C at 100 μl/well. All subsequent incubations were done, after washing plates with ELISA buffer (1% skimmed milk; 0.05% Tween-20; 0.5 M NaCl; 2.7 mM KCl; 2.8 mM $KH_2PO_4$; 8.1 mM $Na_2HPO_4$; pH 7.4, 100 μl/well), for 1 hr at RT. TeNT coated plates were incubated with twofold dilution series over eight wells, per column, starting at both 1 microgram/ml and 0.1 microgram/ml with an SDA standard, a null serum spiked with 1 microgram/ml SDA in column 3 and the nine collected sera of an animal in columns 4-12. Sera were initially diluted fivefold and further twofold diluted over eight wells. After washing, TeNT-coated plates were subsequently incubated with an anti-his6 mAb-PO conjugate (1/1000, Roche, Cat. No. 11965085001). Bound PO was then detected by staining with 3,3',5,5' tetramethylbenzidine (Surmodics; Cat. No. TMBW-1000-01). After stopping the reaction by addition of 0.5 M sulfuric acid the absorbance at 450 nm was measured using a spectrophotometer. Absorbance data were evaluated using a suitable commercial software program. A four-parameter logistic curve was fitted to absorbance and SDA concentrations of standards. This curve was used to interpolate the SDA concentration resulting in a particular absorbance value for each serum sample in each ELISA. Calculated serum SDA concentrations were exported to an Excel® spreadsheet template (Microsoft Corporation, Redmond, USA).

Terminal serum half-life was calculated according to the formula:

SDA(t)=SDA(0)*(0.5^(t/T1/2ß)), where t is time in hrs, where SDA(0) is the SDA concentration at first time point used, for half-life calculation that is compensated for body weight increase, SDA(t) is than the SDA concentration at time t, T1/2ß is the terminal half-life.

The serum half-life was calculated from the data retrieved from the day 2 to day 21 samples. The Solver function of Microsoft Excel was used to fit SDA concentrations against time according to the above formula for each individual animal. Average and standard deviation of T % R were then calculated (see Table 33).

The animals inoculated with the (Equine) albumin binding bivalent and bispecific multimeric SDA SVT06-GS3-SVT16-L123Q-GS2-SVA12M2-H6 showed an average T1/2ß of 510 hr. This multimeric SDA contained the albumin binding SDA domain SVA12M2, linked to the SVT06 and SVT16-L123Q SDA domains into a multimeric SDA. At 21 days after administration of the SDA a serum level of 0.4-0.6 microgram/ml was measured for three animals, thus based on the data shown in example 17 all animals would have been protected against tetanus are levels far above the minimum level required (0.1 IU/ml). As expected, the calculated serum half-life for the SDA SVT06-GS3-SVT16-L123Q-GS2-SVA12M2-H6 in Equines exceeds that measured and calculated for Porcines. This supports calculations predicting that a similar long serum half-life can be expected for Canines.

TABLE 2

Phage display selection and binding in ELISA of *E. coli*-produced TeNT binding SDAs.

| | Phage display selection conditions | | | | | | Absorbance at 450 nm in ELISA | | | |
|---|---|---|---|---|---|---|---|---|---|---|
| | Antigen in first round | | Antigen in second round | | | | | | | |
| SDA | Concentration (µg/ml) | Antigen | Concentration (µg/ml) | Antigen | IEP[e] | CDR3 Group | GT1b-TeNT inhibition | directly coated TeNT | cAb-TT2 captured TeNT | directly coated rTTC |
| None | NA[a] | NA | NA | NA | NA | NA | 1.302 | 0.053 | 0.058 | 0.054 |
| None | NA | NA | NA | NA | NA | NA | 1.257 | 0.056 | 0.059 | 0.054 |
| SVT20 | 0.1 | TeNT | 1 | TeNT | 9.5 | A | 0.132 | 1.076 | 0.685 | 0.165 |
| SVT34 | 0.1 | TeNT | 1 | rTTC | 9.4 | A | 0.117 | 1.433 | 0.483 | 0.160 |
| SVT16 | 1 | rTTC | 1 | TeNT | 8.9 | A | 0.120 | 1.039 | 0.736 | 0.151 |
| SVT25 | 0.1 | TeNT | 1 | rTTC | 9.2 | A | 0.139 | 1.135 | 0.427 | 0.211 |
| SVT06 | 1 | TeNT | 0.1 | TeNT | 4.7 | B | 0.720 | 1.037 | 0.683 | 0.105 |
| SVT31 | 1 | rTTC | 1 | rTTC | 5.0 | B | 0.105 | 1.379 | 1.095 | 0.218 |
| SVT08 | 0.1 | TeNT | 0.1 | TeNT | 5.0 | B | 0.746 | 1.067 | 0.510 | 0.130 |
| SVT15 | 1 | TeNT | 1 | rTTC | 7.0 | C | 0.190 | 1.026 | 0.680 | 0.099 |
| SVT29 | 1 | TeNT | 1 | TeNT | 7.1 | C | 0.152 | 1.282 | 0.868 | 0.111 |
| SVT13 | 0.1/1[c] | cAb-TT2-TeNT | 1/1 | cAb-TT2-TeNT | 7.8 | D | 0.196 | 0.762 | 0.165 | 0.128 |
| SVT22 | 1 | rTTC | 1 | TeNT | 7.8 | D | 0.137 | 1.082 | 0.299 | 0.138 |
| SVT02 | 1/1[b] | cAb-TT2-TeNT[d] | 1/1 | cAb-TT2-TeNT | 9.5 | E | 1.338 | 0.078 | 0.511 | 0.060 |
| SVT03 | 1/1 | mAb TT10-TeNT[d] | 1/1 | mAb TT10-TeNT | 8.7 | F | 1.286 | 0.091 | 0.534 | 0.061 |
| SVT05 | 1 | rTTC | 0.1 | TeNT | 5.0 | G | 0.985 | 1.037 | 0.548 | 0.108 |

[a]NA, not applicable
[b]1/1 indicates that both capture antibody and TeNT were used at 1 µg/ml
[c]0.1/1 indicates that capture antibody was used at 0.1 µg/ml and TeNT at 1 µg/ml
[d]TeNT was captured with directly coated cAb-TT2 or mAb TT10.
[e]Predicted from mature SDA sequence ending at IMGT residue 128 using web.expasy.orq/compute_pi/, resolution is average.

TABLE 3

Phage display selection history and binding in ELISA of *E. coli*-produced IgG binding SDAs.

| | Phage display selection conditions | | | | | | | | | | | | | |
|---|---|---|---|---|---|---|---|---|---|---|---|---|---|---|
| | Antigen in round 1 | | Antigen in round 2 | | Absorbance at 450 nm in ELISA | | | | | | | | | |
| SDA | Concentration (µg/ml) | IgG Origin | Concentration (µg/ml) | IgG Origin | Dog IgG | Horse IgG | Human IgG | Swine IgG | Pig IgG | Bovine IgG | Guinea Horse Fc | Horse Fab | Dog Fab | None |
| None | NA[a] | NA | NA | NA | 0.062 | 0.255 | 0.074 | 0.073 | 0.062 | 0.060 | 0.065 | 0.055 | 0.054 | 0.060 |
| None | NA | NA | NA | NA | 0.068 | 0.261 | 0.074 | 0.072 | 0.082 | 0.073 | 0.067 | 0.053 | 0.057 | 0.053 |
| SVG13 | 1 | Horse | 1 | Horse | 0.693 | 0.436 | 0.524 | 0.195 | 0.579 | 0.272 | 0.097 | 0.222 | 0.590 | 0.051 |
| SVG18 | 1 | Dog | 1 | Horse | 1.003 | 0.478 | 0.096 | 0.097 | 0.174 | 0.124 | 0.072 | 0.320 | 1.365 | 0.050 |
| SVG19 | 1 | Horse | 1 | Dog | 1.018 | 0.681 | 0.309 | 0.146 | 0.435 | 0.453 | 0.079 | 0.472 | 1.223 | 0.069 |
| SVG06 | 1 | Horse | 1 | Dog | 0.277 | 0.325 | 0.365 | 0.131 | 0.204 | 0.172 | 0.073 | 0.089 | 0.178 | 0.059 |
| SVG23 | 1 | Dog | 1 | Dog | 1.735 | 0.260 | 0.073 | 0.092 | 0.068 | 0.062 | 0.072 | 0.056 | 0.061 | 0.090 |
| SVG24 | 1 | Horse | 1 | Dog | 1.741 | 0.765 | 0.084 | 0.341 | 0.068 | 0.075 | 1.669 | 0.060 | 0.074 | 0.063 |

TABLE 3-continued

Phage display selection history and binding in ELISA of *E. coli*-produced IgG binding SDAs.

| | Phage display selection conditions | | | | Absorbance at 450 nm in ELISA | | | | | | | | | |
|---|---|---|---|---|---|---|---|---|---|---|---|---|---|---|
| | Antigen in round 1 | | Antigen in round 2 | | | | | | | | | | | |
| SDA | Concentration (µg/ml) | IgG Origin | Concentration (µg/ml) | IgG Origin | Dog IgG | Horse IgG | Human IgG | Swine IgG | Pig IgG | Bovine IgG | Guinea Horse Fc | Horse Fab | Dog Fab | None |
| SVG03 | 1 | Horse | 1 | Horse | 0.070 | 1.102 | 0.076 | 0.075 | 0.063 | 0.061 | 0.476 | 0.057 | 0.054 | 0.051 |
| SVG07 | 1 | Horse | 1 | Dog | 0.479 | 0.401 | 0.170 | 0.103 | 0.249 | 0.121 | 0.099 | 0.152 | 0.454 | 0.060 |

[a]NA, not applicable

TABLE 4

Phage display selection history and binding in ELISA of *E. coli*-produced Alb binding SDAs.

| | Phage display selection conditions | | | | Absorbance at 450 nm in ELISA | | | |
|---|---|---|---|---|---|---|---|---|
| | Antigen round 1 | | Antigen round 2 | | | | | |
| SDA | Concentration (µg/ml) | Alb Origin | Concentration (µg/ml) | Alb Origin | Horse | Dog | Human | None |
| None | NA[a] | NA | NA | NA | 0.087 | 0.115 | 0.083 | 0.135 |
| None | NA | NA | NA | NA | 0.064 | 0.081 | 0.057 | 0.080 |
| SVA16 | 1 | Horse | 1 | Dog | 2.110 | 2.020 | 0.083 | 0.064 |
| SVA04 | 1 | Dog | 1 | Horse | 2.013 | 1.533 | 0.085 | 0.151 |
| SVA06 | 1 | Horse | 1 | Dog | 1.655 | 1.987 | 0.067 | 0.108 |
| SVA12 | 1 | Dog | 1 | Horse | 1.999 | 1.775 | 0.057 | 0.058 |
| SVA02 | 1 | Dog | 1 | Dog | 1.904 | 1.873 | 0.065 | 0.066 |
| SVA07 | 1 | Horse | 1 | Horse | 1.455 | 0.059 | 0.062 | 0.060 |

[a]NA, not applicable

TABLE 5

Yeast production of SDAs.

| SDA | Yeast Strain | SDA Sub-fam. (designation according to [52]) | ml[c] | Total SDA Yield (mg) | Production Level (mg/L) | Ratio SU51/ W303-1a Production Level | Ratio Mutant/ Wildtype Production Level |
|---|---|---|---|---|---|---|---|
| SVT02L | W303-1a | 1 | 500 | 0.868 | 1.74 | ND | ND |
| SVT03L | W303-1a | 1 | 500 | 0.222 | 0.44 | ND | ND |
| SVT05L | W303-1a | X | 500 | 0.076 | 0.15 | ND | ND |
| SVT06L | W303-1a | X | 500 | 2.208 | 4.42 | ND | ND |
| SVT08L | W303-1a | X | 500 | 1.024 | 2.05 | ND | ND |
| SVT13L | W303-1a | 3 | 500 | 1.276 | 2.55 | ND | ND |
| SVT15L | W303-1a | 1 | 500 | 0.202 | 0.40 | ND | ND |
| SVT15L | W303-1a | 1 | 50 | 0.016 | 0.32 | ND | ND |
| SVT15L-3FW4M | W303-1a | 1 | 50 | 0.093 | 1.87 | ND | 5.2 |
| SVT16L | W303-1a | 1 | 500 | 1.043 | 2.09 | ND | ND |
| SVT20L | W303-1a | 1 | 50 | 0.022 | 0.43 | ND | ND |
| SVT20L | W303-1a | 1 | 500 | 0.126 | 0.25 | ND | ND |
| SVT20L-L123Q | W303-1a | 1 | 50 | 0.061 | 1.22 | ND | 3.6 |
| SVT22L | W303-1a | 3 | 500 | 0.310 | 0.62 | ND | ND |
| SVT25L | W303-1a | 1 | 500 | 0.023 | 0.05 | ND | ND |
| SVT29L | W303-1a | 1 | 500 | 0.037 | 0.07 | ND | ND |
| SVT31L | W303-1a | X | 500 | 0.177 | 0.35 | ND | ND |
| SVT34L | W303-1a | 1 | 500 | 0.218 | 0.44 | ND | ND |
| SVT34L | W303-1a | 1 | 50 | 0.037 | 0.73 | ND | ND |
| SVT34L-L123Q | W303-1a | 1 | 50 | 0.076 | 1.52 | ND | 2.6 |
| SVG03L | W303-1a | 1 | 50 | 0.015 | 0.29 | ND | ND |
| SVG06L | W303-1a | C | 50 | 0.090 | 1.81 | ND | ND |
| SVG07L | W303-1a | C | 50 | 0.007 | 0.15 | ND | ND |
| SVG13L | W303-1a | C | 50 | 0.079 | 1.59 | ND | ND |

TABLE 5-continued

Yeast production of SDAs.

| SDA | Yeast Strain | SDA Sub-fam. (designation according to [52]) | ml[c] | Total SDA Yield (mg) | Production Level (mg/L) | Ratio SU51/ W303-1a Production Level | Ratio Mutant/ Wildtype Production Level |
|---|---|---|---|---|---|---|---|
| SVG18L | W303-1a | C | 50 | 0.015 | 0.30 | ND | ND |
| SVG19L | W303-1a | C | 50 | 0.082 | 1.65 | ND | ND |
| SVG23L | W303-1a | 1 | 50 | 0.021 | 0.41 | ND | ND |
| SVG24L | W303-1a | 1 | 50 | 0.049 | 0.99 | ND | ND |
| SVA02L | W303-1a | 1 | 50 | 0.011 | 0.22 | ND | ND |
| SVA04L | W303-1a | 1 | 50 | 0.009 | 0.18 | ND | ND |
| SVA06L | W303-1a | 1 | 50 | 0.011 | 0.21 | ND | ND |
| SVA07L | W303-1a | 1 | 50 | 0.141 | 2.82 | ND | ND |
| SVA12L | W303-1a | 1 | 50 | 0.192 | 3.85 | ND | ND |
| SVA16L | W303-1a | 1 | 50 | 0.037 | 0.73 | ND | ND |
| SVT13L | SU51 | 3 | 50 | 0.320 | 6.39 | 2.5 | ND |
| SVT15L | SU51 | 1 | 50 | 0.047 | 0.94 | 2.6 | ND |
| SVT20L | SU51 | 1 | 50 | 0.190 | 3.79 | 11.1 | ND |
| SVT34L | SU51 | 1 | 50 | 0.397 | 7.93 | 13.6 | ND |

TABLE 6

ELISA binding of SVA clones to different antigens.

| | Albumin from different species | | | | | | | | | |
|---|---|---|---|---|---|---|---|---|---|---|
| SDA | Horse | Dog | Mouse | Swine | Cat | Human | Sheep | Bovine | Chicken | None |
| | Maximal absorbance value at 450 nm | | | | | | | | | |
| SVA16L | 1.822 | 1.761 | 0.066 | 0.079 | 0.083 | 0.056 | 0.060 | 0.051 | 0.053 | 0.052 |
| SVA04L | 0.190 | 0.069 | 0.107 | 0.080 | 0.087 | 0.052 | 0.052 | 0.050 | 0.052 | 0.050 |
| SVA06L | 0.483 | 0.921 | 0.360 | 0.288 | 0.158 | 0.050 | 0.052 | 0.052 | 0.054 | 0.051 |
| SVA12L | 1.950 | 1.674 | 0.057 | 1.371 | 0.202 | 0.056 | 0.054 | 0.055 | 0.055 | 0.051 |
| SVA02L | 0.809 | 0.579 | 0.191 | 0.085 | 0.089 | 0.078 | 0.061 | 0.054 | 0.059 | 0.057 |
| SVA07L | 0.550 | 0.056 | 0.079 | 0.084 | 0.086 | 0.060 | 0.055 | 0.056 | 0.057 | 0.054 |
| SVT06L | 0.056 | 0.053 | 0.073 | 0.080 | 0.099 | 0.065 | 0.060 | 0.051 | 0.057 | 0.051 |
| No SDA | 0.074 | 0.086 | 0.097 | 0.085 | 0.060 | 0.124 | 0.104 | 0.069 | 0.068 | 0.065 |
| | SDA Effective Concentration (ng/ml) resulting in $A_{450}$ nm = $0.2^a$ | | | | | | | | | |
| SVA16L | 3.6 | 6.4 | >1000 | >1000 | >1000 | >1000 | >1000 | >1000 | >1000 | >1000 |
| SVA04L | >1000 | >1000 | >1000 | >1000 | >1000 | >1000 | >1000 | >1000 | >1000 | >1000 |
| SVA06L | 235 | 51 | 180 | 344 | >1000 | >1000 | >1000 | >1000 | >1000 | >1000 |
| SVA12L | 3.7 | 9.1 | >1000 | 21 | 673 | >1000 | >1000 | >1000 | >1000 | >1000 |
| SVA02L | 149 | 171 | >1000 | >1000 | >1000 | >1000 | >1000 | >1000 | >1000 | >1000 |
| SVA07L | 238 | >1000 | >1000 | >1000 | >1000 | >1000 | >1000 | >1000 | >1000 | >1000 |
| SVT06L | >1000 | >1000 | >1000 | >1000 | >1000 | >1000 | >1000 | >1000 | >1000 | >1000 |
| No SDA | >1000 | >1000 | >1000 | >1000 | >1000 | >1000 | >1000 | >1000 | >1000 | >1000 |

[a]>1000 indicates that absorbance is below 0.2 at highest SDA concentration analysed

TABLE 7

ELISA binding of SVG clones to different antigens

| | Purified IgG or antibody fragments derived thereof | | | | | | |
|---|---|---|---|---|---|---|---|
| | Horse | Horse | Horse | Horse | Dog | Dog | Dog |
| | | | | A450 nm for EC | | | |
| SDA | IgG[b] 0.4 | Fab$_2$ 0.2 | Fab 0.2 | Fc 0.2 | IgG 0.2 | Fc 0.2 | Fab 0.2 |
| | Maximal absorbance value at 450 nm (background subtracted)[b] | | | | | | |
| SVG03L | 1.393 | 0.132 | 0.096 | 1.438 | 0.080 | 0.146 | 0.083 |
| SVG06L | 0.284 | 0.330 | 0.333 | 0.096 | 1.297 | 0.109 | 1.308 |
| SVG07L | 0.074 | 0.100 | 0.085 | 0.066 | 0.242 | 0.073 | 0.210 |
| SVG13L | 0.533 | 0.826 | 0.853 | 0.094 | 1.611 | 0.089 | 1.603 |
| SVG18L | 0.127 | 0.149 | 0.144 | 0.064 | 0.743 | 0.071 | 1.168 |

TABLE 7-continued

ELISA binding of SVG clones to different antigens

| | | | | | | | |
|---|---|---|---|---|---|---|---|
| SVG19L | 0.253 | 0.299 | 0.303 | 0.068 | 0.876 | 0.073 | 1.216 |
| SVG23L | 0.056 | 0.078 | 0.074 | 0.063 | 0.618 | 1.400 | 0.065 |
| SVG24L | 0.088 | 0.089 | 0.194 | 1.184 | 0.847 | 1.446 | 0.089 |

SDA Effective Concentration (ng/ml) resulting in indicated absorbance values[a]

| | | | | | | | |
|---|---|---|---|---|---|---|---|
| SVG03L | 16 | >1000 | >1000 | 35 | >1000 | >1000 | >1000 |
| SVG06L | 237 | 184 | 184 | >1000 | 12 | >1000 | 20 |
| SVG07L | >1000 | >1000 | >1000 | >1000 | 441 | >1000 | 818 |
| SVG13L | 45 | 37 | 44 | >1000 | 9.7 | >1000 | 13 |
| SVG18L | >1000 | >1000 | >1000 | >1000 | 37 | >1000 | 29 |
| SVG19L | 212 | 215 | 305 | >1000 | 29 | >1000 | 26 |
| SVG23L | >1000 | >1000 | >1000 | >1000 | 252 | 78 | >1000 |
| SVG24L | >1000 | >1000 | >1000 | 109 | 50 | 28 | >1000 |

Purified IgG from different animal species

| | Mouse | Swine | Cat | Human | Sheep | Bovine | Chicken | Guinea Pig |
|---|---|---|---|---|---|---|---|---|
| | | | | A450 nm for EC | | | | |
| | GG | IgG | GG | GG | GG[b] | IgG | GG[b] | IgG |
| SDA | 0.2 | 0.2 | 0.2 | 0.2 | 0.3 | 0.2 | 0.4 | 0.2 |

Maximal absorbance value at 450 nm (background subtracted)[b]

| | Mouse | Swine | Cat | Human | Sheep | Bovine | Chicken | Guinea Pig |
|---|---|---|---|---|---|---|---|---|
| SVG03L | 0.093 | 0.105 | 0.088 | 0.193 | 0.180 | 0.083 | 0.079 | 0.114 |
| SVG06L | 0.708 | 0.402 | 1.609 | 1.301 | 0.328 | 0.721 | 0.070 | 1.075 |
| SVG07L | 0.073 | 0.103 | 0.116 | 0.164 | 0.114 | 0.108 | 0.074 | 0.137 |
| SVG13L | 1.002 | 0.436 | 1.633 | 1.255 | 0.277 | 0.704 | 0.164 | 1.309 |
| SVG18L | 0.075 | 0.100 | 0.233 | 0.142 | 0.131 | 0.101 | 0.470 | 0.146 |
| SVG19L | 0.136 | 0.114 | 0.583 | 0.249 | 0.162 | 0.322 | 0.397 | 0.318 |
| SVG23L | 0.068 | 0.089 | 0.071 | 0.121 | 0.101 | 0.077 | 0.064 | 0.076 |
| SVG24L | 0.091 | 0.132 | 0.108 | 0.139 | 0.144 | 0.087 | 0.069 | 0.094 |

SDA Effective Concentration (ng/ml) resulting in indicated absorbance values[a]

| | Mouse | Swine | Cat | Human | Sheep | Bovine | Chicken | Guinea Pig |
|---|---|---|---|---|---|---|---|---|
| SVG03L | >1000 | >1000 | >1000 | >1000 | >1000 | >1000 | >1000 | >1000 |
| SVG06L | 58 | 71 | 7.5 | 8.6 | 258 | 19 | >1000 | 19 |
| SVG07L | >1000 | >1000 | >1000 | >1000 | >1000 | >1000 | >1000 | >1000 |
| SVG13L | 19 | 54 | 7.8 | 12 | 391 | 19 | >1000 | 9.3 |
| SVG18L | >1000 | >1000 | 683 | >1000 | >1000 | >1000 | 45 | >1000 |
| SVG19L | >1000 | >1000 | 58 | 223 | >1000 | 127 | 65 | 126 |
| SVG23L | >1000 | >1000 | >1000 | >1000 | >1000 | >1000 | >1000 | >1000 |
| SVG24L | >1000 | >1000 | >1000 | >1000 | >1000 | >1000 | >1000 | >1000 |

[a]>1000 indicates that at highest SDA concentration analysed absorbance is below required value.
[b]To compensate for high background the abs value of the individual SDAs was subtracted with a value of 0.2 (Horse IgG and chicken GG) or 0.1 (sheep GG). The absorbance value where effective concentrations are calculated are increased with these subtracted values for these three ELISAs.

TABLE 8

Binding of monovalent yeast-produced SDAs to IgG of eight species.

| SDA | bovine | cat | dog | horse | human | mouse | sheep | swine |
|---|---|---|---|---|---|---|---|---|

Maximal A450 on IgG from different species

| | | | | | | | | |
|---|---|---|---|---|---|---|---|---|
| SVG13L | 0.71 | 1.32 | 1.34 | 1.05 | 1.16 | 1.13 | 0.66 | 0.74 |
| VI-4L | 0.14 | 0.10 | 0.11 | 0.30 | 0.17 | 0.11 | 0.25 | 1.62 |
| VI-8L | 0.11 | 0.11 | 0.10 | 0.29 | 0.14 | 0.11 | 0.23 | 1.75 |
| VI-11L | 0.14 | 0.11 | 0.09 | 0.57 | 0.13 | 0.10 | 0.31 | 1.86 |
| VI-14L | 0.15 | 0.12 | 0.11 | 0.31 | 0.18 | 0.13 | 0.21 | 1.83 |
| None | 0.14 | 0.10 | 0.08 | 0.27 | 0.14 | 0.10 | 0.18 | 0.12 |

$EC_{A450=0.3}$ (ng/ml) on IgG from different species[a]

| | | | | | | | | |
|---|---|---|---|---|---|---|---|---|
| SVG13L | 49 | 8 | 7 | 5 | 14 | 17 | 145 | 51 |
| VI-4L | >1000 | >1000 | >1000 | >1000 | >1000 | >1000 | >1000 | 10 |
| VI-8L | >1000 | >1000 | >1000 | >1000 | >1000 | >1000 | >1000 | 5 |
| VI-11L | >1000 | >1000 | >1000 | 226 | >1000 | >1000 | 980 | 3 |
| VI-14L | >1000 | >1000 | >1000 | 875 | >1000 | >1000 | >1000 | 4 |
| None | >1000 | >1000 | >1000 | >1000 | >1000 | >1000 | >1000 | >1000 |

[a]>1000 indicates absorbance of 0.3 is not reached at highest SDA concentration analysed.

TABLE 9 mAbs against TeNT.

| mAb | Supplier | Cat. No. | TeNT Neutralization in mouse Bioassay | Western Blotting |
|---|---|---|---|---|
| 6E7[a] | ThermoFisher | HYB 278-17-02 | Yes | unknown |
| 14F5[a] | ThermoFisher | HYB 278-14-02 | Yes | unknown |
| 6F55[b] | US Biological | T2962-33 | Yes | unknown |
| 6F57[b] | US Biological | T2962-35 | Yes | unknown |
| 11n185[c] | US Biological | T2962-01E | unknown | Yes (Lc) |
| B417M | Antibodies Online | ABIN349738 | Yes | Yes |
| TT10[d] | NIBSC | 10/134 | Yes | Yes (Hc) |

[a]mAbs 6E7 and 14F5 bind independent antigenic sites according to manufacturer
[b]mAbs 6F55 and 6F57 bind independent antigenic sites according to manufacturer
[c]mAb 11n185 binds to TeNT light chain according to manufacturer
[d]References: [48, 62].

TABLE 11

Binding to rTTC of two SVT clones that do not bind directly coated TeNT and three control SDAs.

| | Absorbance at 450 nm | | | |
|---|---|---|---|---|
| | Coating: | | | |
| | TeNT | 6E7 | 6E7 | 6E7 |
| | | Capture step: | | |
| SDA | none | rTTC | none | TeNT |
| SVA12L | 0.048 | 0.059 | 0.059 | 0.059 |
| SVT02L | 0.062 | 0.062 | 0.067 | 1.189 |
| SVT03L | 0.331 | 0.061 | 0.070 | 1.325 |
| SVT15L-3FW4M | 0.477 | 0.528 | 0.063 | 0.236 |
| SVT16L | 1.269 | 1.377 | 0.063 | 1.131 |

TABLE 10

Antigen binding of different SVT clones and mAbs.

| | | Antigen: | | | | | | | | | | |
|---|---|---|---|---|---|---|---|---|---|---|---|---|
| | | TeNT | TeNT | TeNT[a] | rTTC | None | TeNT | TeNT | TeNT | TeNT | TeNT[a] | TeNT | TeNT |
| | | — | cAbTT2 | GT1b | — | — | — | cAb-TT2 | — | cAbTT | GT1b | — | cAb-TT2 |
| | | | | | | | | SDA/mAb biotinilation: | | | | |
| | | No | No | No | No | No | Yes | Yes | No | No | No | Yes | Yes |
| SDA or mAb | CDR3 Group | Max. absorbance value (Min.forGT1b-TeNT inhibition)[b] | | | | | | | EC (ng/ml) resulting in indicated A450 | | | |
| | | | | | | | | | 0.2 | 0.15 | 0.59 | 0.4 | 0.2 |
| SVT16L | A | 1.575 | 0.363 | 0.129 | 1.011 | 0.05 | 1.423 | 0.971 | 1.1 | 3.2 | 47 | 0.52 | 1.6 |
| SVT20L | A | 1.536 | 0.327 | 0.117 | 0.967 | 0.05 | 1.204 | 0.535 | 1.2 | 3.1 | 39 | 2.1 | 4.5 |
| SVT20L-L123Q | A | 0.857 | 0.098 | 0.096 | 0.265 | 0.06 | 1.328 | 0.698 | 4 | >1000 | 38 | 1.4 | 2.8 |
| SVT25L | A | 1.559 | 0.362 | 0.106 | 0.936 | 0.05 | 0.985 | 0.302 | 3.6 | 6.4 | 133 | 43 | 84 |
| SVT34L | A | 1.537 | 0.335 | 0.103 | 0.886 | 0.06 | 1.293 | 0.669 | 1 | 3.2 | 46 | 1.7 | 3.5 |
| SVT34L-L123Q | A | 1.011 | 0.178 | 0.137 | 0.559 | 0.05 | 1.209 | 0.518 | 2 | 5.9 | 34 | 2 | 3.2 |
| SVT06L | B | 1.392 | 0.409 | 0.481 | 0.543 | 0.06 | 1.507 | 1.204 | 1.7 | 2.6 | 317 | 0.39 | 0.37 |
| SVT08L | B | 1.367 | 0.360 | 0.486 | 0.502 | 0.05 | 1.574 | 1.200 | 2.2 | 3.6 | 411 | 0.4 | 0.52 |
| SVT31L | B | 1.318 | 0.270 | 0.568 | 0.483 | 0.05 | 1.430 | 1.033 | 2.4 | 4.3 | 986 | 0.98 | 1.5 |
| SVT15L | C | 1.337 | 0.477 | 0.140 | 0.528 | 0.05 | 1.401 | 0.825 | 2.8 | 5.7 | 72 | 2.8 | 5.7 |
| SVT15L3FW4M | C | 0.817 | 0.195 | 0.127 | 0.206 | 0.05 | 1.372 | 0.697 | 3.8 | 9.8 | 39 | 2 | 3.5 |
| SVT29L | C | 1.516 | 0.429 | 0.135 | 0.580 | 0.05 | 1.128 | 0.596 | 2.6 | 6.3 | 114 | 6.9 | 14 |
| SVT13L | D | 1.544 | 0.487 | 0.126 | 1.105 | 0.05 | 1.484 | 1.056 | 1.9 | 4.1 | 82 | 0.57 | 1.3 |
| SVT22L | D | 1.593 | 0.318 | 0.107 | 0.981 | 0.06 | 1.337 | 0.799 | 2 | 5.4 | 105 | 1.3 | 2.6 |
| SVT02L | E | 0.077 | 0.196 | 0.576 | 0.057 | 0.05 | 0.191 | 0.530 | >1000 | 36 | >1000 | >1000 | 11 |
| SVT03L | F | 0.104 | 0.304 | 0.903 | 0.053 | 0.05 | 0.233 | 0.493 | >1000 | 1.9 | >1000 | >1000 | 2.8 |
| SVT05L | G | 1.292 | 0.375 | 0.655 | 0.604 | 0.05 | 1.260 | 0.622 | 0.51 | 0.86 | >1000 | 0.98 | 1.7 |
| SVA12L | | 0.071 | 0.056 | 0.711 | 0.057 | 0.05 | 0.155 | 0.072 | >1000 | >1000 | >1000 | >1000 | >1000 |
| mAb B417M | | 1.646 | 1.393 | 0.833 | 0.052 | 0.05 | 0.630 | 0.299 | 3.3 | <0.49 | >1000 | 124 | 27 |
| mAb 6E7 | | 1.832 | 1.375 | 0.420 | 1.794 | 0.06 | 1.656 | 1.566 | 1.2 | 1 | 1410 | 1.4 | 1.2 |
| mAb 14F5 | | 0.318 | 1.240 | 0.979 | 0.051 | 0.05 | 0.461 | 1.259 | 81 | 3.2 | >1000 | 406 | 8.1 |
| mAb 6F57 | | 1.765 | 1.354 | 0.568 | 1.764 | 0.04 | 1.259 | 0.965 | 3.4 | 4.1 | 1590 | 24 | 18 |
| mAb 6F55 | | 0.217 | 0.956 | 0.974 | 0.048 | 0.05 | 0.226 | 0.630 | 504 | 18 | >1000 | >100 | 134 |
| mAb 11n185 | | 1.841 | 0.061 | 0.945 | 0.048 | 0.04 | 0.294 | 0.100 | 2.3 | >1000 | >1000 | >100 | >1000 |

[a]In the GT1b-TeNT inhibition ELISA the maximal absorbance value in the absence of SDA is 0.999.
[b]For the GT1b-TeNT inhibition ELISA absorbance values below 0.7 are considered positive. For all further ELISAs absorbance values above 0.2 are considered indicative of antigen binding.

TABLE 12

Epitope binning (competition/blocking) ELISAs of SVT SDAs and anti-TeNT mAbs.

| | % inhibition of binding of biotinylated SDA or mAb[a] | | | | | | | | |
|---|---|---|---|---|---|---|---|---|---|
| SDA or mAb[b] | SVT02L | mAb 14F5 | mAb 6F55 | SVT03L | SVT15L | SVT15L-3FW4M | SVT06L | SVT08L | mAb 6E7 |
| SVT02L | 96 | 97 | 94 | 9 | 6 | 12 | 2 | 16 | 8 |
| mAb 14F5 | 81 | 78 | 54 | 28 | 6 | 16 | 12 | 22 | -16 |
| mAb 6F55 | 72 | 85 | 78 | 10 | 4 | 41 | 16 | 30 | 29 |
| SVT03L | 10 | -8 | 35 | 97 | 12 | 10 | 10 | 10 | -12 |
| SVT15L | 6 | 7 | -2 | -5 | 96 | 96 | 1 | 15 | 6 |
| SVT15L-3FW4M | 10 | 2 | -4 | -8 | 96 | 95 | 7 | 6 | 6 |
| SVT06L | 11 | 11 | 4 | -3 | 14 | 12 | 96 | 97 | 67 |
| SVT08L | 7 | 3 | 1 | 0 | 6 | 12 | 95 | 96 | 66 |
| mAb 6E7 | 12 | 8 | 1 | 4 | 4 | 7 | 18 | 35 | 75 |
| mAb 6F57 | 4 | 3 | -1 | -3 | -1 | 10 | 45 | 49 | 88 |
| SVT13L | 7 | 5 | 1 | 1 | -19 | 8 | 1 | 13 | 2 |
| SVT22L | 4 | 0 | -2 | 5 | 2 | 11 | 6 | 1 | 8 |
| SVT16L | 13 | 6 | -3 | -1 | 12 | 17 | -8 | 2 | 6 |
| SVT34L | 2 | 4 | -3 | 0 | 3 | 14 | -2 | -4 | 10 |
| mAb B417M | -220 | -23 | -44 | 7 | 66 | 33 | 11 | -56 | 66 |
| mAb 11n185 | -43 | -24 | -17 | 19 | 18 | 3 | 5 | -4 | 19 |

| | % inhibition of binding of biotinylated SDA or mAb[a] | | | | | | | |
|---|---|---|---|---|---|---|---|---|
| SDA or mAb[b] | mAb 6F57 | SVT13L | SVT16L | SVT22L | SVT34L | mAb B417M | mAb 11n185 | Anti-genic site |
| SVT02L | 19 | 21 | 26 | 3 | -16 | -11 | 19 | A |
| mAb 14F5 | 9 | 42 | 0 | -28 | 20 | 35 | 14 | A |
| mAb 6F55 | -24 | 39 | 17 | 10 | 12 | 33 | 27 | A |
| SVT03L | 17 | 23 | 18 | 10 | -4 | 0 | -26 | B |
| SVT15L | 4 | 2 | 5 | 2 | 10 | 5 | 0 | C |
| SVT15L-3FW4M | 6 | -5 | 3 | 4 | 3 | -9 | -1 | C |
| SVT06L | 53 | 7 | -3 | 3 | 11 | 4 | 5 | D |
| SVT08L | 50 | 5 | 8 | 6 | 8 | 0 | 4 | D |
| mAb 6E7 | 64 | -3 | -2 | 1 | 7 | 0 | 6 | D |
| mAb 6F57 | 85 | -4 | 0 | 7 | 11 | 1 | -3 | D |
| SVT13L | 0 | 95 | 91 | 92 | 91 | 4 | 2 | E |
| SVT22L | 10 | 95 | 92 | 94 | 93 | -2 | 3 | E |
| SVT16L | 2 | 96 | 95 | 96 | 95 | -1 | -2 | E |
| SVT34L | 13 | 93 | 93 | 94 | 95 | -2 | 2 | E |
| mAb B417M | 65 | 6 | -56 | 66 | -43 | 79 | -146 | — |
| mAb 11n185 | 16 | 1 | -14 | 38 | -11 | 15 | 84 | — |

[a]Values above or equal to 50 are indicated in grey background colour.
[b]Biotinylated SDA or mAb is in rows and unlabelled SDA or mAb in columns.

TABLE 13

Overview of SVT clones most suitable for multimeric SPA construction and reference mAbs.

| Biotinylated SDA or mAb | CDR3 Group | TeNT-GT1b Inhibition (IC$_{50}$ in ng/ml)[a] | rTTC Binding[b] | Neutralizing TeNT in Mouse bioassay[c] | Binding in Western blot[d] | Anti-genic site | Binding directly coated TeNT[e] | Yeast strain W303-1a SDA production level (mg/L)[f] |
|---|---|---|---|---|---|---|---|---|
| SVT02L | E | >1,000 | No | unknown | — | A | No | 1.74 |
| mAb 14F5 | — | >10,000 | No | Yes | ND | A | Reduced | — |
| mAb 6F55 | — | >10,000 | No | Yes | ND | A | Reduced | — |
| SVT03L | F | >1,000 | No | unknown | — | B | Reduced | 0.44 |
| SVT15L | C | 72 | Yes | unknown | — | C | Good | 0.40 |
| SVT15L-3FW4M | C | 39 | Yes | unknown | — | C | Good | 1.87 |
| SVT06L[g] | B | 317 | Yes | unknown | Hc | D | Good | 4.42 |
| SVT08L[g] | B | 411 | Yes | unknown | Hc | D | Good | 2.05 |
| mAb 6E7 | — | 1,410 | Yes | Yes | ND | D | Good | — |
| mAb 6F57 | — | 1,590 | Yes | Yes | ND | D | Good | — |
| SVT13L | D | 82 | Yes | unknown | — | E | Good | 2.55 |
| SVT22L | D | 105 | Yes | unknown | — | E | Good | 0.62 |
| SVT16L | A | 47 | Yes | unknown | — | E | Good | 2.09 |

TABLE 13-continued

Overview of SVT clones most suitable for multimeric SPA construction and reference mAbs.

| Biotinylated SDA or mAb | CDR3 Group | TeNT-GT1b Inhibition (IC$_{50}$ in ng/ml)$^a$ | rTTC Binding$^b$ | Neutralizing TeNT in Mouse bioassay$^c$ | Binding in Western blot$^d$ | Antigenic site | Binding directly coated TeNT$^e$ | Yeast strain W303-1a SDA production level (mg/L)$^f$ |
|---|---|---|---|---|---|---|---|---|
| SVT34L | A | 46 | Yes | unknown | — | E | Good | 0.44 |
| mAb B417M | — | >10,000 | No | Yes | ND | — | Good | — |
| mAb 11n185 | — | >10,000 | No | unknown | Lc$^c$ | — | Good | — |

$^a$From Table 10.
$^b$From Table 10. Absorbance value above 0.2 is considered positive binding (Yes).
$^c$According to manufacturer.
$^d$Hc, heavy-chain; Lc, light-chain; dashes indicate no binding is detectable in Western blot; ND, not determined.
$^e$Reduced indicates maximal A450 value is higher on cAb-TT2-captured TeNT than on directly coated TeNT (Table 10).
$^f$From Table 5, 500-ml cultures of wild-type SDAs.
$^g$Unusual VEDG sequence insertion after IMGT position 50.

TABLE 14

Multimeric SPA production in yeast using MIRY type transformants.

| Plasmid | Multimeric SDA | IEP$^a$ | Elutes in SP-seph. Fractions (M NaCl) | SDA production Level$^b$ (mg/L) |
|---|---|---|---|---|
| pRL482 | SVT02-GS2-SVG06M4-H6 | 9.1 | 0.4-0.6 | 11 |
| pRL484 | SVT15-3FW4M-GS2-SVG6M4-H6 | 6.9 | 0.4-0.6 | 2.6 |
| pRL489 | SVT06-GS2-SVA12M2-H6 | 5.8 | 0.4-0.6 | 11 |
| pRL490 | SVT06-GS3-SVT16-L123Q-GS2-SVA12M2-H6 | 6.4 | 0.4-0.6 | 10 |
| pRL493 | SVT02-GS2-SVA12M2-H6 | 9.1 | 0.4-0.6 | 0.97 |
| pRL494 | SVT15-3FW4M-GS2-SVA12M2-H6 | 6.8 | 0.4-0.6 | 34 |
| pRL495 | SVT16-L123Q-GS2-SVA12M2-H6 | 8.6 | 0.4-0.6 | 99 |
| pRL496 | SVT02-GS2-SVG13M4-H6 | 8.8 | 0.4-0.6 | 17 |
| pRL497 | SVT06-GS2-SVG13M4-H6 | 5.5 | 0.6-0.8 | 0.93 |
| pRL498 | SVT15-3FW4M-GS2-SVG13M4-H6 | 6.3 | 0.6-0.8 | 41 |
| pRL499 | SVT16-L123Q-GS2-SVG13M4-H6 | 7.8 | 0.4-0.6 | 97 |
| pRL501 | SVT06-SVT16-L123Q-GS2-SVG13M4-H6 | 6.0 | 0.4-0.6 | 0.2 |

$^a$Predicted from mature multimeric SDA sequence using web.expasy.org/cgi-bin/compute_pi/pi_tool.
$^b$The production level in yeast strain SU50 was calculated from the yield of purified SDA from 0.5 L cultures.

TABLE 15

Functional analysis of multimeric yeast-produced SDAs by ELISA: absorbance values.

| Plasmid | SDA | Antigen Captured with Detection Ab or biotinylated antigen PO-Conjugate | IgG/Alb$^a$ TeNT StrepPO | TeNT TeNT StrepPO | TeNT cAb-TT2 Alb StrepPO | IgG/Alb$^a$ hisPO | TeNT hisPO | TeNT GALPO | TeNT GT1b L9237$^c$ GALPO |
|---|---|---|---|---|---|---|---|---|---|
| | | Maximal absorbance value (Minimal for GT1b-TeNT inhibition) | | | | | | | |
| PSVA12L | SVA12L | | 0.26 | 0.24 | 0.22 | 1.47 | 0.13 | 0.14 | 0.89 |
| pRL489 | SVT06-GS2-SVA12M2-H6 | | 1.56 | 0.66 | 1.47 | 1.67 | 1.59 | 1.21 | 0.18 |
| pRL490 | SVT06-GS3-SVT16-L123Q-GS2-SVA12M2-H6 | | 1.55 | 1.62 | 1.45 | 1.51 | 1.72 | 1.41 | 0.13 |
| pRL493 | SVT02-GS2-SVA12M2-H6 | | 1.29 | 0.18 | 1.10 | 1.91 | 0.10 | 0.09 | 0.66 |
| pRL494 | SVT15-3FW4M-GS2-SVA12M2-H6 | | 1.34 | 0.64 | 1.34 | 1.55 | 1.35 | 1.36 | 0.15 |
| pRL495 | SVT16-L123Q-GS2-SVA12M2-H6 | | 1.28 | 0.78 | 1.37 | 1.78 | 1.67 | 1.39 | 0.15 |
| pRL482 | SVT02-GS2-SVG06M4-H6 | | 1.00 | 0.14 | ND$^b$ | 0.06 | 0.06 | 0.10 | 0.82 |
| pRL484 | SVT15-3FW4M-GS2-SVG06M4-H6 | | 1.30 | 0.29 | ND | 0.07 | 0.37 | 1.23 | 0.12 |
| pRL496 | SVT02-GS2-SVG13M4-H6 | | 1.32 | 0.19 | ND | 0.18 | 0.06 | 0.09 | 0.77 |
| pRL497 | SVT06-GS2-SVG13M4-H6 | | 1.61 | 0.98 | ND | 1.18 | 1.44 | 1.20 | 0.22 |
| pRL498 | SVT15-3FW4M-GS2-SVG13M4-H6 | | 1.47 | 0.78 | ND | 1.00 | 1.51 | 1.16 | 0.13 |
| pRL499 | SVT16-L123Q-GS2-SVG13M4-H6 | | 1.50 | 1.12 | ND | 0.69 | 1.45 | 1.22 | 0.13 |
| pRL501 | SVT06-SVT16-L123Q-GS2-SVG13M4-H6 | | 1.69 | 1.73 | ND | 0.78 | 1.62 | 1.37 | 0.13 |
| pSVG06L | SVG06L | | 0.11 | 0.14 | ND | 0.56 | 0.05 | 0.07 | 0.80 |
| pSVG13L | SVG13L | | 0.11 | 0.17 | ND | 0.16 | 0.08 | 0.09 | 0.72 |
| pSVT02L | SVT02L | | 0.10 | 0.16 | ND | 0.06 | 0.06 | 0.08 | 0.77 |
| pSVT06L | SVT06L | | 0.12 | 0.35 | ND | 0.05 | 1.44 | 0.32 | 0.27 |

TABLE 15-continued

Functional analysis of multimeric yeast-produced SDAs by ELISA: absorbance values.

| Plasmid | Antigen<br>Captured with<br>Detection Ab or biotinylated antigen<br>PO-Conjugate<br>SDA | IgG/Alb[a]<br><br>TeNT<br>StrepPO | TeNT<br><br>TeNT<br>StrepPO | TeNT<br>cAb-TT2<br>Alb<br>StrepPO | IgG/Alb[a]<br><br><br>hisPO | TeNT<br><br><br>hisPO | TeNT<br><br><br>GALPO | TeNT<br>GT1b<br>L9237[c]<br>GALPO |
|---|---|---|---|---|---|---|---|---|
| | | Maximal absorbance value (Minimal for GT1b-TeNT inhibition) | | | | | | |
| pSVT15L-3FW4M | SVT15L-3FW4M | 0.14 | 0.20 | ND | 0.05 | 0.19 | 0.35 | 0.19 |
| pSVT16L | SVT16L | 0.19 | 0.18 | ND | 0.06 | 1.56 | 0.44 | 0.18 |
| | No SDA | 0.09 | 0.15 | ND | 0.06 | 0.06 | 0.08 | 0.88 |

[a]SVA12 containing SDAs wells were coated with dog Alb, for all other SDAs wells were coated with dog IgG, biotinylated Equine Alb was used
[b]ND, not determined
[c]Llama serum of animal L9237 (49 dpi), diluted 1:1000 (see example 1)

TABLE 16

Functional analysis of multimeric yeast-produced SDAs by ELISA: Effective Concentration of SDA.

| Plasmid | Antigen<br>Captured with<br>Detection antibody or biotinylated antigen<br>PO-Conjugate<br>A450 for EC value<br>SDA | IgG/Alb[a]<br><br>TeNT<br>StrepPO<br>0.3 | TeNT<br><br>TeNT<br>StrepPO<br>0.3 | TeNT<br>cAb-TT2<br>Alb[b]<br>StrepPO<br>0.7 | IgG/Alb[a]<br><br><br>hisPO<br>0.2 | TeNT<br><br><br>hisPO<br>0.15 | TeNT<br><br><br>GALPO<br>0.15 | TeNT<br>GT1b<br>L9237[d]<br>GALPO<br>0.56 |
|---|---|---|---|---|---|---|---|---|
| | | Effective SDA Concentration (ng/ml) | | | | | | |
| PSVA12L | SVA12L | >1000[c] | >1000 | >1000 | 50 | >1000 | >1000 | >1000 |
| pRL489 | SVT06-GS2-SVA12M2-H6 | 0.8 | 19 | 1.5 | 39 | 3.5 | 1.1 | 55 |
| pRL490 | SVT06-GS3-SVT16-L123Q-GS2-SVA12M2-H6 | 1.5 | 5.4 | 1.8 | 71 | 3.8 | 1.1 | 49 |
| pRL493 | SVT02-GS2-SVA12M2-H6 | 14 | >1000 | 11 | 13 | >1000 | >1000 | >1000 |
| pRL494 | SVT15-3FW4M-GS2-SVA12M2-H6 | 11 | 33 | 3.9 | 76 | 8 | 2 | 78 |
| pRL495 | SVT16-L123Q-GS2-SVA12M2-H6 | 4.3 | 15 | 2.5 | 34 | 2.9 | 1 | 45 |
| pRL482 | SVT02-GS2-SVG06M4-H6 | 26.5 | >1000 | ND[e] | >1000 | >1000 | >1000 | >1000 |
| pRL484 | SVT15-3FW4M-GS2-SVG06M4-H6 | 8.3 | >1000 | ND | >1000 | 37 | 4.3 | 131 |
| pRL496 | SVT02-GS2-SVG13M4-H6 | 9.1 | >1000 | ND | >1000 | >1000 | >1000 | >1000 |
| pRL497 | SVT06-GS2-SVG13M4-H6 | <0.49 | 9.6 | ND | 46 | 3.4 | 2 | 93 |
| pRL498 | SVT15-3FW4M-GS2-SVG13M4-H6 | 2.2 | 23 | ND | 63 | 4.9 | 2 | 77 |
| pRL499 | SVT16-L123Q-GS2-SVG13M4-H6 | 2.6 | 13 | ND | 127 | 8 | 3 | 73 |
| pRL501 | SVT06-SVT16-L123Q-GS2-SVG13M4-H6 | 1.2 | 5.3 | ND | 134 | 11 | 4 | 35 |
| pSVG06L | SVG06L | >1000 | >1000 | ND | 164 | >1000 | >1000 | >1000 |
| pSVG13L | SVG13L | >1000 | >1000 | ND | >1000 | >1000 | >1000 | >1000 |
| pSVT02L | SVT02L | >1000 | >1000 | ND | >1000 | >1000 | >1000 | >1000 |
| pSVT06L | SVT06L | >1000 | 64 | ND | >1000 | 4.9 | 14 | 33 |
| pSVT15L-3FW4M | SVT15L-3FW4M | >1000 | >1000 | ND | >1000 | 26 | 6 | 31 |
| pSVT16L | SVT16L | >1000 | >1000 | ND | >1000 | 1.4 | 5 | 21 |
| | No SDA | >1000 | >1000 | ND | >1000 | >1000 | >1000 | >1000 |

[a]SVA12 containing SDAs wells were coated with dog Alb, whereas for all further SDAs wells were coated with dog IgG
[b]biotinylated horse Alb was used
[c]>1000, at the highest SDA concentration used the absorbance for calculating the EC value is not reached
[d]Llama serum of animal L9237 (49 dpi) diluted 1:1000 (see example 1)
[e]ND, not determined TABLE 17a Functional analysis of multimeric SDAs by biolayer interferometry to TeNT and horse Albumin (TeNT loaded)

| Ligand Loaded | 1st sample analyte (SDA) | 1st test Signal[d] (nm) | 2nd sample analyte | 2nd test Signal(nm) | Bivalent TeN-TeNT or bispecificTeNT-Ah binding |
|---|---|---|---|---|---|
| bio-T[b] | SVA12L | 0.01 | TeNT | 0.02 | no |
| bio-T | SVG13L | 0.02 | TeNT | 0.03 | no |
| bio-T | SVT16L | 0.11 | TeNT | 0.01 | no |
| bio-T | SVT16-GS2-SVA12M2-H6 | 0.19 | TeNT | 0.02 | no |
| bio-T | SVT16-L123Q-GS2-SVG13M4-H6 | 0.18 | TeNT | 0.03 | no |
| bio-T | SVT06-GS3-SVT16-L123Q-GS2-SVA12M2-H6 | 0.32 | TeNT | 0.15 | yes |
| bio-T | M8ggsVI4q6e | 0.02 | TeNT | 0.03 | no |
| bio-T | PBST[a] | 0.01 | TeNT | 0.03 | no |

TABLE 17a-continued

Functional analysis of multimeric SDAs by biolayer interferometry to TeNT and horse Albumin (TeNT loaded)

| Ligand Loaded | $1^{st}$ sample analyte (SDA) | $1^{st}$ test Signal[d] (nm) | $2^{nd}$ sample analyte | $2^{nd}$ test Signal(nm) | Bivalent TeN-TeNT or bispecificTeNT-Ah binding |
|---|---|---|---|---|---|
| bio-T | SVA12L | 0.02 | Ah | 0.01 | no |
| bio-T | SVG13L | 0.02 | Ah | 0.01 | no |
| bio-T | SVT16L | 0.11 | Ah | 0.01 | no |
| bio-T | SVT16-GS2-SVA12M2-H6 | 0.19 | Ah | 0.17 | yes |
| bio-T | SVT16-L123Q-GS2-SVG13M4-H6 | 0.18 | Ah | 0.00 | no |
| bio-T | SVT06-GS3-SVT16-L123Q-GS2-SVA12M2-H6 | 0.33 | Ah | 0.26 | yes |
| bio-T | M8ggsVI4q6e[c] | 0.02 | Ah | 0.01 | no |
| bio-T | PBST | 0.01 | Ah | 0.01 | no |

[a]Buffer, negative control.
[b]Average signal after loading TeNT was 2.05 nm
[c]SDA negative control, bispecific SDA [44]
[d]A shift (nm) in the interference wavelength pattern caused by binding of the analyte TABLE 17b Functional analysis of multimeric SDAs by Biolayer interferometry to TeNT (Equine Albumin loaded)

| Ligand Loaded | $1^{st}$ sample analyte (SDA) | $1^{st}$ test Signal[d] (nm) | $2^{nd}$ sample analyte | $2^{nd}$ test Signal (nm) | Bispecific binding Ah-TeNT |
|---|---|---|---|---|---|
| bio-Ah[b] | SVA12L | 0.08 | TeNT | 0.01 | no |
| bio-Ah | SVG13L | 0.01 | TeNT | 0.02 | no |
| bio-Ah | SVT16L | 0.02 | TeNT | 0.01 | no |
| bio-Ah | SVT16-GS2-SVA12M2-H6 | 0.17 | TeNT | 0.47 | yes |
| bio-Ah | SVT16-L123Q-GS2-SVG13M4-H6 | 0.02 | TeNT | 0.02 | no |
| bio-Ah | SVT06-GS3-SVT16-L123Q-GS2-SVA12M2-H6 | 0.21 | TeNT | 0.53 | yes |
| bio-Ah | M8ggsVI4q6e[c] | 0.01 | TeNT | 0.02 | no |
| bio-Ah | PBST | 0.00 | TeNT | 0.02 | no |

[a] Buffer, background control.
[b]Average signal after loading horse albumin was 0.78 nm
[c]SDA negative control, bispecific SDA [44]
[d]A shift (nm) in the interference wavelength pattern caused by binding of the analyte

TABLE 18

Terminal serum half-life of multimeric SDAs in swine

| Plasmid | SDA | SDA Dosing (mg/kg) | Curve Fitting Region (hours) | T½β[c] (hours) |
|---|---|---|---|---|
| pRL489 | SVT06-GS2-SVA12M2-H6 | 0.2 | 96-504 | 135 ± 19 |
| pRL490 | SVT06-GS3-SVT16-L123Q-GS2-SVA12M2-H6 | 0.3 | 96-504 | 122 ± 13 |
| pRL495 | SVT16-L123Q-GS2-SVA12M2-H6 | 0.5 | 96-504 | 111 ± 13 |
| pRL499 | SVT16-L123Q-GS2-SVG13M4-H6 | 0.5 | 24-96 | 21[b] ± 3.8 |
| pRL276 | M8ggsVI-4q6e[a] | 0.5 | 96-504 | 82 ± 4.5 |

[a]see reference [19]
[b]Estimate based on assuming that levels have decreased to detection level in 96 h sample.
[c]Mean and standard deviation (including bodyweight increase).

TABLE 19

SDAs inoculated, concentration of stock solution, and proportion of mice protected (as a %) at end of test (study 1).

| SDA/Reference | Proportion (%) of mice (n = 4) protected at end of test | | | | | | |
|---|---|---|---|---|---|---|---|
| | 1[a] | 2 | 4 | 8 | 16 | 32 | 64 |
| SVT02-GS2-SVG13M4-H6 | 0 | 0 | 0 | 0 | 0 | 0 | 0 |
| SVT03L | 0 | 0 | 0 | 0 | 0 | 0 | ND[c] |
| SVT06-GS2-SVG13M4-H6 | 100 | 75 | 0 | 0 | 0 | 0 | 0 |
| SVT15-3FW4M-GS2-SVG13M4-H6 | 100 | 100 | 0 | 0 | 25 | 0 | 0 |
| SVT16-L123Q-GS2-SVG13M4-H6 | 0 | 0 | 0 | 0 | 0 | 0 | 0 |
| SVT06-GS3-SVT16-L123Q-GS2-SVA12M2-H6 | 100 | 100 | 100 | 100 | 100 | 100 | ND |
| Reference antitoxin (TE3[b]) | 100 | 100 | 0 | 0 | 0 | 0 | ND |

[a]Dilution factor, starting concentration at dilution 1 of all SDAs is 1000 nM, except for the SDA3 it is 100 nM.
[b]Human Tetanus Immunoglobulin; it has a fixed amount tetanus toxin neutralising capacity (International Units), here a 10 IU/ml stock solution was used that was prediluted 1/400 to 0.025 IU/ml.
[c]ND = not determined

TABLE 20

Summary of end points for SDAs and potency in IU/mg

| SDA | Endpoint dilution factor | SDA concentration providing full protection (nM) | Potency[c] IU/mg |
|---|---|---|---|
| SVT02-GS2-SVG13M4-H6 | <1 | >1000[d] | — |
| SVT03L | <1 | >1000 | — |
| SVT06-GS2-SVG13M4-H6 | 2.4[a] | 1000[e] | 1.04 |
| SVT15-3FW4M-GS2-SVG13M4-H6 | 2.8[b] | 500 | 1.21 |
| SVT16-L123Q-GS2-SVG13M4-H6 | <1 | >1000 | — |
| SVT06-GS3-SVT16-L123Q-GS2-SVA12M2-H6 | >32 | 3.1 | >93.1 |

[a]Spearman-Kaerber method used for calculation (100% at dilution 1.75% at dilution 2 and 0% at dilution 3)
[b]geomean of 2 (dilution number 2) and 4 (dilution number 3)
[c]Tetanus antitoxin potency (International Units/mg) of master stock solution
[d]No protection at 1000 nM level
[e]Full protection at the concentration tested

TABLE 21

Scheme of the SDAs evaluated in different mixtures (or single) in the TNT (study 2)

| SDA | Group | | | | | | |
|---|---|---|---|---|---|---|---|
| | 1 | 2 | 3 | 4 | 5 | 6 | 7[b] |
| SVT02-GS2-SVG13M4-H6 | | 31.25 | | 31.25 | | | |
| SVT03L | | 31.25 | | 31.25 | | | |
| SVT06-GS2-SVG13M4-H6 | 62.5[a] | 31.25 | 62.5 | 31.25 | | | |
| SVT15-3FW4M-GS2-SVG13M4-H6 | | | 62.5 | 31.25 | 62.5 | 62.5 | |
| SVT16-L123Q-GS2-SVG13M4-H6 | 62.5 | 31.25 | | | 62.5 | | |
| SVT06-GS3-SVT16-L123Q-GS2-SVA12M2-H6 | | | | | | 6.25 | 6.25 |
| Total nM per group | 125 | 125 | 125 | 125 | 125 | 68.75 | 6.25 |

[a]Amount (nM) of each SDA in the mixture at starting point
[b]Only group containing a single SPA TABLE 22a Proportion of mice protected (as a %) at end of test of mixture evaluation (study 2).

| Group | Total nM[a] | 1[b] | 2 | 4 | 8 | 16 | 32 |
|---|---|---|---|---|---|---|---|
| 1 | 125 | 100[c] | 100 | 100 | 100 | 100 | 100 |
| 2 | 125 | 100 | 100 | 100 | 100 | 100 | 100 |
| 3 | 125 | 100 | 100 | 100 | 100 | 100 | 100 |
| 4 | 125 | 100 | 100 | 100 | 100 | 100 | 100 |
| 5 | 125 | 0 | 0 | 0 | 0 | 0 | 0 |
| 6 | 68.75 | 100 | 100 | 100 | 100 | 100 | 100 |
| 7 | 6.25 | 100 | 100 | 100 | 100 | 100 | 100 |
| Reference TE3[d] | | 100 | 100 | 0 | 0 | 0 | 0 |

[a]At dilution 1
[b]Dilution tested, two-fold dilution steps follow
[c]Total amount of mice per dilution is 4
[d]Prediluted to 0.025 IU/ml

TABLE 22b

Summary of end points for mixed SDAs

| Group | Total amount of SDA in 1st dilution (nM) | SDA(s) concentration providing full protection (nM) | Protection at this concentration |
|---|---|---|---|
| 1 | 125 | ≤3.91 | Yes |
| 2 | 125 | ≤3.91 | Yes |
| 3 | 125 | ≤3.91 | Yes |
| 4 | 125 | ≤3.91 | Yes |
| 5 | 125 | >125 | No |
| 6 | 68.75 | ≤2.15 | Yes |

TABLE 23

Summary of end points and potency in IU/ml for single samples

| Group | SDA | Dilution factor | End point Dilution No. | End point Dil. Factor | Total dilution factor | Potency[a] IU/mg |
|---|---|---|---|---|---|---|
| 7 | SVT06-GS3-SVT16-L123Q-GS2-SVA12M2-H6 | 23,240 | >6 | >32 | 743,680 | >1478 |

[a]Tetanus antitoxin potency (International Units/mg)

TABLE 24

Proportion of mice (n = 4) protected (as a %) at end of test (study 3).

| Group | Total nM[a] | 1[b] | 4 | 16 | 64 | 256 | 1024 |
|---|---|---|---|---|---|---|---|
| SVT06-GS3-SVT16-L123Q-GS2-SVA12M2-H6 | 1 | 0.2 | 50[c] | 0 | 0 | 0 | 0 | 0 |
| SVT06-GS2-SVG13M4-H6 + SVT16-L123Q-GS2-SVG13M4-H6 | 2 | 0.4 | 0 | 0 | 0 | 0 | 0 | 0 |
| SVT06-GS3-SVT16-L123Q-GS2-SVA12M2-H6 + SVT15-3FW4M-GS2-SVG13M4-H6 | 3 | 0.4 | 100 | 0 | 0 | 0 | 0 | 0 |
| Reference TE-3 prediluted to 0.025 IU/ml | | | 100 | 75 | 0 | 0 | 0 | 0 |

[a]At dilution 1
[b]First dilution with starting concentration as shown, four-fold dilution steps follow
[c]Total amount of mice per dilution is 4

TABLE 25

| Summary of end points and potency in IU/ml for single samples | | | | | | |
|---|---|---|---|---|---|---|
| Group | SDA | Dilution factor | End point Dilution No. | End point Dil. Factor | Total dilution factor | Potency[a] IU/mg |
| 1 | SVT06-GS3-SVT16-L123Q-GS2-SVA12M2-H6 | 726,222 | 1 | 1 | 726,222 | 1509.7 |

[a]Tetanus antitoxin potency (International Units/mg) calculated on 4-fold dilution step study 3 results of TE-3 reference.

TABLE 26

| Summary of end points for mixed SDAs | | | |
|---|---|---|---|
| Group | Total SDA (nM) in 1st dilution | Lowest concentration (nM) providing full protection | Protection at this concentration |
| 2 | 0.4 | >0.4 | No |
| 3 | 0.4 | 0.4-0.1 | Yes |

TABLE 27

TeNT binding affinity/avidity determination of several purified mono- and multimeric SDAs

| SDA | $K_D$ (M) | $k_a$ (1/Ms) | $k_{dis}$ (1/s) | R-square |
|---|---|---|---|---|
| SVT02-GS2-SVG13M4-H6 | 9.87E−11 | 1.23E+06 | 1.21E−04 | 0.992 |
| SVT03L | <1.0E−12[a] | 5.65E+06 | <1.0E−07 | 0.914 |
| SVT06-GS2-SVG13M4-H6 | 1.23E−10 | 6.7E+05 | 8.24E−05 | 0.998 |
| SVT06-GS2-SVA12M2-H6 | 1.51E−10 | 5.91E+05 | 8.90E−05 | 0.992 |
| SVT15-3FW4M-GS2-SVG13M4-H6 | 1.58E−11 | 4.29E+05 | 6.77E−06 | 0.998 |
| SVT06L | 5.35E−10 | 1.17E+05 | 6.27E−05 | 0.999 |
| SVT15L | 4.13E−10 | 9.36E+04 | 3.87E−05 | 0.998 |
| SVT16L | 3.39E−10 | 9.16E+05 | 3.11E−04 | 0.996 |
| SVT16-L123Q-GS2-SVA12M2-H6 | 2.24E−10 | 8.86E+05 | 1.99E−04 | 0.998 |
| SVT16-L123Q-GS2-SVG13M4-H6 | 2.27E−10 | 6.65E+05 | 1.84E−04 | 0.999 |
| SVT06-GS3-SVT02-GS2-SVG06M4-H6[b] | 1.30E−10 | 3.29E+05 | 4.27E−05 | 0.998 |
| SVT06-GS3-SVT15-3FW4M-GS2-SVG06M4-H6[b] | <1.0E−12[a] | 6.91E+04 | <1.0E−07 | 0.997 |
| SVT06-GS3-SVT16-L123Q-GS2-SVA12M2-H6[b] | 1.33E−11 | 9.89E+05 | 1.32E−05 | 0.998 |

[a] $K_D$ was not calculated because the SDA did not dissociate from the tetanus toxin within the time course studied. In case for the $k_{dis}$ value the value 1.0E−07 is chosen for both SDAs the $K_D$ value for SVT03L is estimated at 1.77E−14 and for SVT06-GS3-SVT15-3FW4M-GS2-SVG06M4-H6 would be 1.45E−12.
[b] Bivalent for TeNT therefore avidity measurement

TABLE 28

Affinity data for purified SDAs against Alb (Equine, Porcine, Canine and Feline)

| SDA | Albumin species | $K_D$ (M) | $k_a$ (1/Ms) | $k_{dis}$ (1/s) | R square |
|---|---|---|---|---|---|
| SVA12L | Swine | 1.59E−07 | 1.50E+05 | 2.38E−02 | 0.990 |
| SVA06L | Swine | | | | |
| SVA16L | Swine | | | | |
| SVA12L | Horse | 1.07E−08 | 1.01E+05 | 1.09E−03 | 0.999 |
| SVA06L | Horse | 1.35E−08 | 7.26E+05 | 9.77E−03 | 0.971 |
| SVA16L | Horse | 1.06E−08 | 2.29E+05 | 2.42E−03 | 0.999 |
| SVA12L | Dog | 2.71E−07 | 4.59E+04 | 1.25E−02 | 0.990 |
| SVA06L | Dog | 3.16E−09 | 7.11E+05 | 2.24E−03 | 0.998 |
| SVA16L | Dog | 1.11E−08 | 4.35E+05 | 4.83E−03 | 0.997 |
| SVA12L | Cat | 1.90E−08 | 3.88E+04 | 7.37E−04 | 0.999 |
| SVA06L | Cat | 1.20E−09 | 7.29E+05 | 8.78E−04 | 0.996 |
| SVA16L | Cat | 1.95E−09 | 1.47E+05 | 2.87E−04 | 0.976 |

TABLE 29

TeNT binding affinity/avidity determination of several purified mono- and multimeric SDAs.

| SDA (Ligand) | Ligand loading concentration (µg/ml) | Analyte (TeNT) Concentration (nM) | $K_D$ (M) | $k_a$ (1/Ms) | $k_{dis}$ (1/s) | R-square |
|---|---|---|---|---|---|---|
| SVT06L | 0.6 | 0.94-15 | 2.24E−10 | 5.03E+05 | 1.13E−04 | 1 |
| SVT15L | 0.3 | 2.5-20 | 7.72E−10 | 1.11E+05 | 8.57E−05 | 0.998 |
| SVT06-GS3-SVT16-L123Q-GS2-SVA12M2-H6[a] | 0.3 | 2.5-20 | 1.10E−11 | 3.98E+05 | 4.39E−06 | 0.999 |
| cAb-TT1 | 0.6 | 25-400 | 4.31E−08 | 4.91E+04 | 2.12E−03 | 0.951 |
| cAb-TT2 | 0.3 | 0.75-12 | 6.01E−09 | 8.41E+05 | 5.05E−03 | 0.998 |

[a] Bivalent for TeNT therefore avidity measurement

TABLE 30

TeNT binding affinity/avidity determination of 3 multimeric SDAs

| SDA (Analyte) | Ligand (TeNT) loading concentration (µg/ml) | Analyte (SDA) Concentration (nM) | $K_D$ (M) | $k_a$ (1/Ms) | $k_{dis}$ (1/s) | R-square |
|---|---|---|---|---|---|---|
| SVT06-GS3-SVT16-L123Q-GS2-SVA12M2-H6[b] | 4 | 0.63-10 | <1.0E−12 | 5.38E+05 | <3.18E−07 | 0.999 |
| SVT06-GS3-SVT15-3FW4M-GS2-SVA12M2-H6[b] | 4 | 0.63-10 | <1.0E−12[a] | 9.40E+05 | <3.2E−07 | 0.999 |

TABLE 30-continued

TeNT binding affinity/avidity determination of 3 multimeric SDAs

| SDA (Analyte) | Ligand (TeNT) loading concentration (µg/ml) | Analyte (SDA) Concentration (nM) | $K_D$ (M) | $k_a$ (1/Ms) | $k_{dis}$ (1/s) | R-square |
|---|---|---|---|---|---|---|
| SVT15-3FW4M-GS3-SVT06-GS2-SVG13M5-H6[b] | 4 | 0.63-10 | <1.0E-12[a] | 4.84E+05 | <1.99E-07 | 0.999 |

[a] $K_D$ was not calculated because the SDA did not dissociate from the tetanus toxin within the time course studied.. If for SVT06-GS3-SVT16- L123Q-GS2-SVA12M2-H6, SVT06-GS3-SVT15-3FW4M-GS2-SVA12M2-H6 and SVT15-3FW4M-GS3-SVT06-GS2-SVG13M5 for the $k_{dis}$ value the value 3.18E−07, 3.2E−07 and 1.99E−07 is chosen, respectively, the $K_D$ values would be 5.91E−13, 3.4E−13 and 4.1E−13 respectively.

[b]Bivalent for TeNT therefore avidity measurement

TABLE 31a

The binding affinity of multimeric SDAs to Equine or Human serum albumin

| SDA (Analyte) | Albumin Species | Ligand (Alb) loading concentration (μg/ml) | Analyte SDA) Concentration (nM) | $K_D$ (M) | $k_a$ (1/Ms) | $k_{dis}$ (1/s) | R-square |
|---|---|---|---|---|---|---|---|
| SVT06-GS3-SVT16-L123Q-GS2-SVA12M2-H6 | Equine | 2.5 | 0.63-10 | 6.46E−10 | 2.16E+05 | 1.39E−04 | 1 |
| SVT06-GS3-SVT15-3FW4M-GS2-SVA12M2-H6 | Equine | 2.5 | 0.63-10 | 1.34E−09 | 1.1E+05 | 1.51E−04 | 1 |
| SVT15-3FW4M-GS3-SVT06-GS2-SVG13M5-H6[a] | Equine | 2.5 | 100 | No Signal | | | |
| SVA12L | Human | 5 | 100 | No Signal | | | |
| SVT06-GS3-SVT16-L123Q-GS2-SVA12M2-H6 | Human | 5 | 100 | No Signal | | | |
| SVT06-GS3-SVT15-3FW4M-GS2-SVA12M2-H6 | Human | 5 | 100 | No Signal | | | |
| SVT15-3FW4M-GS3-SVT06-GS2-SVG13M5-H6[a] | Human | 5 | 100 | No Signal | | | |

[a]SVG13M5 binds to for example Equine, or Human IgG Fab fragment

TABLE 31b

The binding affinity of multimeric SDAs to serum Canine serum albumin

| SDA (Ligand) | Albumin Species | Ligand (SDA) loading concentration (μg/ml) | Analyte (Alb) Concentration (nM) | $K_D$ (M) | $k_a$ (1/Ms) | $k_{dis}$ (1/s) | R-square |
|---|---|---|---|---|---|---|---|
| SVT06-GS3-SVT16-L123Q-GS2-SVA12M2-H6 | Canine | 1.25 | 16-500 | 2.68E−07 | 2.3E+04 | 6.20E−03 | 0.998 |
| SVT06-GS3-SVT15-3FW4M-GS2-SVA12M2-H6 | Canine | 1.25 | 16-500 | 3.75E−07 | 1.6E+04 | 6.16E−03 | 0.998 |
| SVT15-3FW4M-GS3-SVT06-GS2-SVG13M5-H6[a] | Canine | 1.25 | 16-500 | No Signal | | | |

[a]SVG13M5 binds to for example Canine IgG Fab fragment

TABLE 32

TeNT binding affinity/avidity of multimeric SDAs when evaluated with the Creoptix ™ WAVE system

| SDA (analyte) | Ligand (TeNT) captured (pg/mm$^2$) | Analyte flow (μl/min) | Analyte (SDA) Concentration (nM) | $K_D$ (M) | $k_a$ (1/Ms) | $k_{dis}$ (1/s) | R-max (pg/mm$^2$) |
|---|---|---|---|---|---|---|---|
| SVT03L | 252.7 | 54 | 1.2-100 | 1.4E−12 | 4.62E+06 | 6.64E−06 | 14.5 |
| SVT15-3FW4M-GS2-SVG13M4-H6 | 216.6 | 60 | 1.2-100 | 20.9E−12 | 3.90E05 | 8.15E−06 | 30.4 |
| SVT06-SVT16-L123Q-GS2-SVG13M5-H6[a, b] | 181.1 | 60 | 1.2-100 | 15.9E−12 | 4.17E+05 | 6.61E−06 | 37.5 |
| SVT06-GS3-SVT16-L123Q-GS2-SVA12M2-H6[a] | 239.6 | 54 | 1.2-100 | 8.86E−12 | 1.14E+06 | 1.01E−05 | 44.7 |
| SVT15-3FW4M-GS3-SVT06-GS2-SVG13M5-H6[a] | 176.5 | 60 | 1.2-100 | 22.9E−12 | 1.19E+06 | 2.73E−05 | 27.6 |

[a]Bivalent for TeNT therefore avidity measurement

[b]Bivalent, with two SVT SDA's fused without linker in between

TABLE 33

Terminal serum half-life of SVT06-GS3-SVT16-L123Q-GS2-SVA12M2-H6 (pRL490) in Equines (i.m. dose 0.17 mg/kg)

| Animal | Measured concentration (milligram/liter) Time (hrs) | | | | | | | | | Curve Fitting Region | $T\frac{1}{2}\beta^a$ |
|---|---|---|---|---|---|---|---|---|---|---|---|
| | 0 | 24 | 48 | 96 | 168 | 240 | 312 | 408 | 504 | | |
| | Time (days) | | | | | | | | | | |
| # | 0 | 1 | 2 | 4 | 7 | 10 | 13 | 17 | 21 | (days) | (hours) |
| 2 | <0.09 | 1.014 | 1.164 | 0.997 | 0.807 | 0.806 | 0.733 | 0.661 | 0.605 | 2-21 | 510 ± 107 |
| 5 | <0.10 | 0.519 | 0.736 | 0.664 | 0.483 | 0.549 | 0.488 | 0.486 | 0.395 | | |
| 6 | <0.09 | 1.08 | 1.32 | 1.21 | 1.04 | 1.01 | 0.795 | 0.708 | 0.593 | | |

$^a$Mean and standard deviation.

TABLE 34

Multimeric SPA production in yeast using MIRY type transformants.

| Plasmid | Multimeric SDA | $IEP^a$ | Elutes in SP-seph. Fractions (M NaCl) | SDA production Level$^b$ (mg/L) |
|---|---|---|---|---|
| pRL505 | SVT06-GS3-SVT15-3FW4M-GS2-SVA12M2-H6 | 5.94 | 0.4-0.6 | 3.2 |
| pRL506 | SVT15-3FW4M-GS3-SVT06-GS2-SVG13M5-H6 | 5.80 | 0.4-0.6 | 4.8 |

$^a$Predicted from mature multimeric SDA sequence using web.expasy.org/cgi-bin/compute_pi/pi_tool.
$^b$The production level in yeast strain SU50 was calculated from the yield of purified SDA from 0.5 L cultures.

TABLE 35

Affinity of several SDAs to Equine and Canine IgG

| SDA | IgG (Fc) species | $K_D$ (M) | $k_a$ (1/Ms) | $k_{dis}$ (1/s) | Full R^2 |
|---|---|---|---|---|---|
| SVG03L$^a$ | Horse Fc | 4.30E−10 | 1.14E+06 | 4.91E−04 | 0.987 |
| SVG23L$^a$ | Horse Fc | no affinity | | | |
| SVG24L$^a$ | Horse Fc | 3.45E−09 | 1.02E+05 | 3.53E−04 | 0.996 |
| SVG03L | Dog Fc | no affinity | | | |
| SVG23L | Dog Fc | 2.15E−10 | 2.43E+06 | 5.21E−04 | 0.991 |
| SVG24L | DogFc | 2.22E−09 | 1.55E+05 | 3.44E−04 | 0.992 |

$^a$Fc fragment binding SDA

REFERENCES

[1] Hamers-Casterman C et a. Nature. 1993; 363:446-8.
[2] Harmsen M M et al. Vet Microbiol. 2007; 120:193-206.
[3] Harmsen M M et al. J Immunoassay Immunochem. 2012; 33:234-51.
[4] Rossetto 0 et al. Tetanus neurotoxin. Toxicon. 2013; 66:59-63.
[5] Herreros J et al. Biochem J. 2000; 347 Pt 1:199-204.
[6] Fitzsimmons S P et al. Vaccine. 2000; 19:114-21.
[7] Yousefi M et al. Human vaccines & immunotherapeutics. 2014; 10:344-51.
[8] Scott N et al. Mol Immunol. 2010; 47:1931-41.
[9] Sagt C M et al. Appl Environ Microbiol. 2000; 66:4940-4.
[10] Liu L. J Pharm Sci. 2015; 104:1866-84.
[11] Gorlani A et al. Protein Eng Des Sel. 2012; 25:39-46.
[12] Liu J L et al. Microbial cell factories. 2015; 14:158.
[13] Goldman E R et al. Protein Expr Purif. 2014; 95:226-32.
[14] Van de Laar T et al. Biotechnol Bioeng. 2007; 96:483-94.
[15] Batra S K et al. Curr Opin Biotechnol. 2002; 13:603-8.
[16] Iznaga-Escobar N et al. Methods Find Exp Clin Pharmacol. 2004; 26:123-7.
[17] Kontermann RE. Curr Opin Biotechnol. 2011; 22:868-76.
[18] Klooster R et al. J Immunol Methods. 2007; 324:1-12.
[19] Harmsen M M et al. Vaccine. 2005; 23:4926-34.
[20] Coppieters K et al. Arthritis Rheum. 2006; 54:1856-66.
[21] Holliger P et al. Nat Biotechnol. 1997; 15:632-6.
[22] Holt L J et al. Protein Eng Des Sel. 2008; 21:283-8.
[23] Hutt M et al. J Biol Chem. 2012; 287:4462-9.
[24] Rossotti M A et al. mAbs. 2015; 7:820-8.
[25] Walker A et al. Protein Eng Des Sel. 2010; 23:271-8.
[26] Terryn S et al. PLoS ONE. 2014; 9:e109367.
[27] Huston J S et al. Proc Natl Acad Sci. 1988; 85:5879-83.
[28] Mukherjee J et al. PLoS ONE. 2012; 7:e29941.
[29] Sepulveda J et al. Infect Immun. 2010; 78:756-63.
[30] Vance D J et al. J Biol Chem. 2013; 288:36538-47.
[31] Klein J S et al. Protein Eng Des Sel. 2014; 27:325-30.
[32] Trinh R et al. Mol Immunol. 2004; 40:717-22.
[33] Beirnaert E. Improved nanobodies$^T$M against tumor necrosis factor-alpha. 2006.
[34] WO2011064382
[35] Conrath K E et al. J Biol Chem. 2001; 276:7346-50.
[36] Hopp J et al. Protein Eng Des Sel. 2010; 23:827-34.
[37] Jacobs S A et al. Protein Eng Des Sel. 2015; 28:385-93.
[38] Fridy P C et al. Nat Methods. 2014; 11:1253-60.
[39] Chaudhury C et al. J Exp Med. 2003:197:315-22.
[40] Nagel J et al. J Immunol. 1973; 110:1388-95.
[41] Mizuguchi J et al. Naturwissenschaften. 1982; 69:597-8.
[42] Volk W A et al. Infect Immun. 1984; 45:604-9.
[43] Harmsen M M et al. Appl Microbiol Biotechnol. 2009; 84:1087-94.
[44] Harmsen M M et al. Vet Microbiol. 2008; 132:56-64.
[45] Frenken LGJ et al. J Biotechnol. 2000; 78:11-21.
[46] Arbabi-Ghahroudi M et al. FEBS Lett. 1997; 414:521-6.
[47] Xing D K et al. Biologicals. 1996; 24:57-65.
[48] Coombes L et al. Biologicals. 2012; 40:466-72.
[49] McCafferty J, Johnson KS. In: Phage display of peptides and proteins. 1996. p. 79-111.
[50] Lou J et al. J Immunol Methods. 2001; 253:233-42.
[51] Lefranc MP, Methods Mol Biol. 2004; 248:27-49.
[52] Harmsen M M et al. Mol Immunol. 2000; 37:579-90.
[53] Butler JE. Methods. 2000; 22:4-23.
[54] Arbabi-Ghahroudi M et al. Protein engineering, design & selection: PEDS. 2009; 22:59-66.

[55] de Wildt R M et al. J Mol Biol. 1999; 294:701-10.
[56] Desmyter A et al. J Biol Chem. 2001; 276:26285-90.
[57] Deschacht N et al. J Immunol. 2010; 184:5696-704.
[58] Van der Vaart JM in Methods Mol Biol. Totowa, NJ: Humana Press; 2002. p. 359-66.
[59] Harmsen M M et al. Appl Microbiol Biotechnol. 1996; 46:365-70.
[60] Harmsen M M et al. Appl Microbiol Biotechnol. 2002; 60:449-54.
[61] Harmsen M M et al. Appl Microbiol Biotechnol. 2007; 77:13-22.
[62] Sheppard A J et al. Infect Immun. 1984; 43:710-4.
[63] Emsley P et al. J Biol Chem. 2000; 275:8889-94.
[64] Fotinou C et al. J Biol Chem. 2001; 276:32274-81.
[65] Chen C, Baldwin M R, Barbieri J T. Biochemistry. 2008; 47:7179-86.
[66] Chen C, Fu Z, Kim J J, Barbieri J T, Baldwin MR. J Biol Chem. 2009; 284:26569-77.
[67] Wang H, Yu R, Fang T, Yu T, Chi X, Zhang X, et al. Toxins. 2016; 8.
[68] Kenimer J G et al. Infect Immun. 1983; 42:942-8.
[69] Harmsen M M et al. Vet Microbiol. 2005; 111:89-98.
[70] Giuseppin M L et al. Appl Environ Microbiol. 1993; 59:52-9.
[71] Becker DM, Guarente L. Methods Enzymol. 1991; 194:182-7.
[72] Harmsen M M et al. Vaccine. 2011; 29:2682-90.
[73] Van Oers J W, Tilders FJ. Endocrinology. 1991; 128: 496-503.
[74] Verheesen & Laeremans. Methods Mol Biol 2012; 911: 81-104.
[75] Gorlani A et al. Methods Mol Biol. 2012; 911:277-86
[76] Kozma, F. et al. Biosensors and Bioelectronics 2014, 58:287-307.

The invention claimed is:

1. A single domain antibody (SDA) capable of binding to tetanus neurotoxin (TeNT), wherein the SDA has an overall amino acid sequence identity of at least 80% with a sequence selected from the group consisting of SEQ ID NO: 17, 13, 14, 15, 16, 18, 19, 20, 21, 22, 23, 24, 25 and 26 with the proviso that the amino acid sequence identities of CDR1, CDR2 and CDR3 are at least 90%.

2. The SDA according to claim 1, wherein the SDA has an overall amino acid sequence identity of at least 90% with a sequence selected from the group consisting of SEQ ID NO: 17, 13, 14, 15, 16, 18, 19, 20, 21, 22, 23, 24, 25 and 26, with the proviso that the amino acid sequence identities of CDR1, CDR2 and CDR3 are at least 90%.

3. The SDA according to claim 1, wherein the amino acid sequence identities of CDR1, CDR2 and CDR3 are at least 95%.

4. A polypeptide construct comprising at least one SDA capable of binding to TeNT according to claim 1 and at least one SDA capable of binding to a serum protein.

5. The polypeptide construct according to claim 4, wherein the serum protein is serum albumin or an immunoglobulin.

6. The polypeptide construct according to claim 5, wherein the SDA capable of binding to serum albumin has an overall amino acid sequence identity of at least 70% with a sequence selected from the group consisting of SEQ ID NO: 40, 37, 38, 39, 41 and 42, with the proviso that amino acid sequence identities of CDR1, CDR2 and CDR3 are at least 75%.

7. The polypeptide construct according to claim 5, wherein the immunoglobulin is immunoglobulin G (IgG).

8. The polypeptide construct according to claim 5, wherein the SDA capable of binding to the immunoglobulin has an overall amino acid sequence identity of at least 70% with a sequence selected from the group consisting of SEQ ID NO: 30, 27, 28, 29, 31, 32, 33 and 34, with the proviso that the amino acid sequence identities of CDR1, CDR2 and CDR3 are at least 75%.

9. The polypeptide construct according to claim 4, wherein the polypeptide construct comprises at least two SDAs capable of binding to TeNT wherein each of the at least two SDAs capable of binding to TeNT has an overall amino acid sequence identity of at least 70% with a sequence selected from selection A; SEQ ID NO: 24, or selection B; SEQ ID NO: 25, or selection C; SEQ ID NO: 20, or selection D; SEQ ID NO: 17 or 19 or selection E; SEQ ID NO: 22, 15, 23 or 14, with the proviso that the at least two SDAs do not comprise a sequence from the same selection and with the proviso that the amino acid sequence identities of CDR1, CDR2 and CDR3 are at least 75%.

10. A DNA fragment encoding an SDA according to claim 1 or a polypeptide construct comprising at least one SDA capable of binding to TeNT wherein the SDA has an overall amino acid sequence identity of at least 70% with a sequence selected from the group consisting of SEQ ID NO: 17, 13, 14, 15, 16, 18, 19, 20, 21, 22, 23, 24, 25 and 26 with the proviso that the amino acid sequence identities of CDR1, CDR2 and CDR3 are at least 75% and at least at least one SDA capable of binding to a serum protein.

11. The SDA according to claim 1, wherein the amino acid sequence identities of CDR1, CDR2 and CDR3 are 100%.

12. The SDA according to claim 1, wherein the CDR regions are identified according to the IMGT numbering system.

* * * * *